(12) United States Patent
Bird et al.

(10) Patent No.: US 8,372,340 B2
(45) Date of Patent: Feb. 12, 2013

(54) APPARATUS AND METHODS FOR INTEGRATED SAMPLE PREPARATION, REACTION AND DETECTION

(75) Inventors: Dylan Hilmer Bird, San Francisco, CA (US); Jesus Ching, Saratoga, CA (US); Bruce A. Johnson, San Jose, CA (US); Keith E. Moravick, Mountain View, CA (US); Bruce Richardson, Los Gatos, CA (US)

(73) Assignee: Luminex Corporation, Austin, TX (US)

( * ) Notice: Subject to any disclaimer, the term of this patent is extended or adjusted under 35 U.S.C. 154(b) by 169 days.

(21) Appl. No.: 13/033,129

(22) Filed: Feb. 23, 2011

(65) Prior Publication Data
US 2011/0236960 A1    Sep. 29, 2011

Related U.S. Application Data

(63) Continuation-in-part of application No. 12/789,831, filed on May 28, 2010, now Pat. No. 8,124,024, which is a continuation of application No. 11/582,651, filed on Oct. 17, 2006, now Pat. No. 7,727,473, application (Continued)

(51) Int. Cl.
*B01J 19/00* (2006.01)
(52) U.S. Cl. .......... 422/63; 422/68.1; 422/64; 435/91.2; 435/287.2; 435/288.6; 435/259; 436/177; 436/178; 436/53
(58) Field of Classification Search .............. 435/288.5, 435/206.1, 306.1, 91.2, 287.2, 255.6, 259; 436/53, 177, 178; 422/500–509, 537, 539, 422/540, 541, 542
See application file for complete search history.

(56) References Cited

U.S. PATENT DOCUMENTS

| | | | |
|---|---|---|---|
| 3,607,094 | A | 9/1971 | Beer |
| 3,802,782 | A | 4/1974 | Natelson |
| 4,004,150 | A | 1/1977 | Natelson |
| 4,201,478 | A | 5/1980 | Gerlier et al. |
| 4,439,039 | A | 3/1984 | Suovaniemi |
| 4,448,534 | A | 5/1984 | Wertz et al. |
| 4,495,149 | A | 1/1985 | Iwata et al. |
| 4,626,684 | A | 12/1986 | Landa |
| 4,762,420 | A | 8/1988 | Bowley |
| 5,035,505 | A | 7/1991 | Tsukada et al. |

(Continued)

FOREIGN PATENT DOCUMENTS

| | | |
|---|---|---|
| DE | 3441179 | 5/1986 |
| JP | 11-271227 | 10/1999 |

(Continued)

OTHER PUBLICATIONS

Office Action for Japanese Patent Application No. 2008-536791, mailed Oct 3, 2011.

(Continued)

*Primary Examiner* — In Suk Bullock
*Assistant Examiner* — Sharon Pregler
(74) *Attorney, Agent, or Firm* — Fulbright & Jaworski L.L.P.

(57) ABSTRACT

Cartridges for the isolation of a biological sample and downstream biological assays on the sample are provided. In one embodiment, a nucleic acid sample is isolated from a biological sample and the nucleic acid sample is amplified, for example by the polymerase chain reaction. The cartridges provided herein can also be used for the isolation of non-nucleic acid samples, for example proteins, and to perform downstream reactions on the proteins, for example, binding assays. Instruments for carrying out the downstream biological assays and for detecting the results of the assays are also provided.

24 Claims, 77 Drawing Sheets

Related U.S. Application Data

No. 13/033,129, which is a continuation-in-part of application No. 12/821,446, filed on Jun. 23, 2010, now Pat. No. 7,910,062, which is a continuation of application No. 12/005,860, filed on Dec. 27, 2007, now Pat. No. 7,754,148.

(60) Provisional application No. 60/728,569, filed on Oct. 19, 2005, provisional application No. 60/753,622, filed on Dec. 22, 2005, provisional application No. 60/753,618, filed on Dec. 22, 2005, provisional application No. 60/882,150, filed on Dec. 27, 2006, provisional application No. 61/307,281, filed on Feb. 23, 2010.

(56) References Cited

U.S. PATENT DOCUMENTS

| | | | |
|---|---|---|---|
| 5,073,029 | A | 12/1991 | Eberly et al. |
| 5,139,745 | A | 8/1992 | Barr et al. |
| 5,188,455 | A | 2/1993 | Hammerstedt |
| 5,234,665 | A | 8/1993 | Ohta et al. |
| 5,242,660 | A | 9/1993 | Hsei |
| 5,242,837 | A | 9/1993 | Slovacek et al. |
| 5,283,624 | A | 2/1994 | Tsukada et al. |
| 5,290,513 | A | 3/1994 | Berthold et al. |
| 5,307,144 | A | 4/1994 | Hiroshi et al. |
| 5,333,675 | A | 8/1994 | Mullis et al. |
| 5,348,853 | A | 9/1994 | Wang et al. |
| 5,389,524 | A | 2/1995 | Larsen et al. |
| 5,397,709 | A | 3/1995 | Berndt |
| 5,411,876 | A | 5/1995 | Bloch et al. |
| 5,415,839 | A | 5/1995 | Zaun et al. |
| 5,436,718 | A | 7/1995 | Fernandes |
| 5,475,610 | A | 12/1995 | Atwood et al. |
| 5,494,646 | A | 2/1996 | Seymour |
| 5,508,197 | A | 4/1996 | Hansen et al. |
| 5,525,300 | A | 6/1996 | Danssaert et al. |
| 5,525,466 | A | 6/1996 | Slovacek et al. |
| 5,538,849 | A | 7/1996 | Uematsu et al. |
| 5,541,072 | A | 7/1996 | Wang et al. |
| 5,576,197 | A | 11/1996 | Arnold |
| 5,578,818 | A | 11/1996 | Kain et al. |
| 5,580,523 | A | 12/1996 | Bard |
| 5,585,242 | A | 12/1996 | Bouma et al. |
| 5,589,136 | A | 12/1996 | Northrup et al. |
| 5,616,301 | A | 4/1997 | Moser et al. |
| 5,627,041 | A | 5/1997 | Shartle |
| 5,639,423 | A | 6/1997 | Northrup et al. |
| 5,639,668 | A | 6/1997 | Neel et al. |
| 5,645,801 | A | 7/1997 | Bouma et al. |
| 5,656,493 | A | 8/1997 | Mullis et al. |
| 5,657,118 | A | 8/1997 | Lee |
| 5,665,975 | A | 9/1997 | Kedar |
| 5,674,743 | A | 10/1997 | Ulmer |
| 5,686,300 | A | 11/1997 | Berndt |
| 5,705,628 | A | 1/1998 | Hawkins |
| 5,738,825 | A | 4/1998 | Rudigier et al. |
| 5,746,978 | A | 5/1998 | Bienhaus et al. |
| 5,759,784 | A | 6/1998 | Asp et al. |
| 5,811,312 | A | 9/1998 | Hasegawa et al. |
| 5,825,478 | A | 10/1998 | Wilcox et al. |
| 5,827,480 | A | 10/1998 | Haff et al. |
| 5,837,144 | A | 11/1998 | Bienhaus et al. |
| 5,861,124 | A | 1/1999 | Hosoi et al. |
| 5,882,903 | A | 3/1999 | Andrevski et al. |
| 5,897,783 | A | 4/1999 | Howe et al. |
| 5,904,899 | A | 5/1999 | Hayashi |
| 5,935,522 | A | 8/1999 | Swerdlow et al. |
| 5,989,499 | A | 11/1999 | Catanzariti et al. |
| 6,004,512 | A | 12/1999 | Titcomb et al. |
| 6,015,674 | A | 1/2000 | Woudenberg et al. |
| 6,027,945 | A | 2/2000 | Smith et al. |
| 6,043,506 | A | 3/2000 | Heffelfinger et al. |
| 6,050,719 | A | 4/2000 | Winkler et al. |
| 6,057,163 | A | 5/2000 | McMilan |
| 6,061,128 | A | 5/2000 | Zweig et al. |
| 6,071,748 | A | 6/2000 | Modlin et al. |
| 6,096,272 | A | 8/2000 | Clark et al. |
| 6,211,989 | B1 | 4/2001 | Wulf et al. |
| 6,222,619 | B1 | 4/2001 | Herron et al. |
| 6,228,634 | B1 | 5/2001 | Blumenfeld et al. |
| 6,232,608 | B1 | 5/2001 | Giebeler |
| 6,281,008 | B1 | 8/2001 | Komai et al. |
| 6,296,810 | B1 | 10/2001 | Ulmer |
| 6,297,018 | B1 | 10/2001 | French et al. |
| 6,353,475 | B1 | 3/2002 | Jensen et al. |
| 6,358,387 | B1 | 3/2002 | Kopf-Sill et al. |
| 6,369,893 | B1 | 4/2002 | Christel et al. |
| 6,429,007 | B1 | 8/2002 | Kluttz et al. |
| 6,431,476 | B1 | 8/2002 | Taylor et al. |
| 6,440,725 | B1 | 8/2002 | Pourahmadi et al. |
| 6,451,258 | B1 | 9/2002 | Malmqvist |
| 6,468,810 | B1 | 10/2002 | Korpela et al. |
| 6,492,162 | B1 | 12/2002 | Sakurai et al. |
| 6,517,778 | B1 | 2/2003 | Kumar et al. |
| 6,520,197 | B2 | 2/2003 | Deshmukh et al. |
| 6,545,758 | B1 | 4/2003 | Sandstrom |
| 6,565,815 | B1 | 5/2003 | Chang et al. |
| 6,569,631 | B1 | 5/2003 | Pantoliano et al. |
| 6,576,459 | B2 | 6/2003 | Miles et al. |
| 6,597,450 | B1 | 7/2003 | Andrews et al. |
| 6,645,758 | B1 | 11/2003 | Schnipelsky et al. |
| 6,657,169 | B2 | 12/2003 | Brown |
| 6,672,458 | B2 | 1/2004 | Hansen et al. |
| 6,699,713 | B2 | 3/2004 | Benett et al. |
| 6,730,501 | B2 | 5/2004 | Eyre et al. |
| 6,730,883 | B2 | 5/2004 | Brown et al. |
| 6,739,531 | B2 | 5/2004 | Taylor |
| 6,764,859 | B1 | 7/2004 | Kreuwel et al. |
| 6,783,934 | B1 | 8/2004 | McMillan et al. |
| 6,787,338 | B2 | 9/2004 | Wittwer et al. |
| 6,814,934 | B1 | 11/2004 | Higuchi |
| 6,818,185 | B1 | 11/2004 | Petersen et al. |
| 6,838,680 | B2 | 1/2005 | Maher et al. |
| 6,852,284 | B1 | 2/2005 | Holl et al. |
| 6,875,602 | B2 | 4/2005 | Gutierrez |
| 6,890,742 | B2 | 5/2005 | Ammann et al. |
| 6,893,879 | B2 | 5/2005 | Petersen et al. |
| 6,908,759 | B2 | 6/2005 | Jang |
| 6,927,852 | B2 | 8/2005 | Reel |
| 6,955,589 | B2 | 10/2005 | Kordonski et al. |
| 6,982,431 | B2 | 1/2006 | Modlin et al. |
| 6,986,848 | B2 | 1/2006 | Ikeda et al. |
| 7,008,789 | B2 | 3/2006 | Gambini et al. |
| 7,027,683 | B2 | 4/2006 | O'Connor et al. |
| 7,078,224 | B1 | 7/2006 | Bitner et al. |
| 7,108,472 | B2 | 9/2006 | Norris et al. |
| 7,148,043 | B2 | 12/2006 | Kordunsky et al. |
| 7,171,863 | B2 | 2/2007 | Tamura et al. |
| 7,223,949 | B2 | 5/2007 | Deka et al. |
| 7,236,237 | B2 | 6/2007 | Schmilovitch et al. |
| 7,284,900 | B2 | 10/2007 | Mayer |
| 7,294,466 | B2 | 11/2007 | McMillan et al. |
| 7,301,628 | B2 | 11/2007 | Cunningham et al. |
| 7,329,488 | B2 | 2/2008 | Roh et al. |
| 7,341,691 | B2 | 3/2008 | Tamura et al. |
| 7,344,894 | B2 | 3/2008 | Greenstein et al. |
| 7,358,078 | B2 | 4/2008 | Chen et al. |
| 7,373,253 | B2 | 5/2008 | Eyre |
| 7,387,891 | B2 | 6/2008 | Boege et al. |
| 7,394,547 | B2 | 7/2008 | Tan et al. |
| 7,423,750 | B2 | 9/2008 | Hoshizaki et al. |
| 7,459,302 | B2 | 12/2008 | Reid et al. |
| 7,498,164 | B2 | 3/2009 | Oldham et al. |
| 7,507,575 | B2 | 3/2009 | Bedingham et al. |
| 7,521,179 | B2 | 4/2009 | Bachi |
| 7,584,019 | B2 | 9/2009 | Feingold et al. |
| 7,585,663 | B2 | 9/2009 | Shigeura et al. |
| 7,682,565 | B2 | 3/2010 | Linton et al. |
| 7,699,979 | B2 | 4/2010 | Li et al. |
| 7,718,072 | B2 | 5/2010 | Safar et al. |
| 7,718,421 | B2 | 5/2010 | Chen et al. |
| 7,727,473 | B2 | 6/2010 | Ching et al. |

| | | |
|---|---|---|
| 7,754,148 B2 | 7/2010 | Yu et al. |
| 7,910,062 B2 | 3/2011 | Yu et al. |
| 8,048,386 B2 | 11/2011 | Dority et al. |
| 8,133,703 B2 | 3/2012 | Ching et al. |
| 2003/0016352 A1 | 1/2003 | Goldman et al. |
| 2003/0073110 A1 | 4/2003 | Aritomi et al. |
| 2003/0129739 A1 | 7/2003 | Jones |
| 2003/0170686 A1 | 9/2003 | Hoet et al. |
| 2003/0203491 A1 | 10/2003 | Andrevski et al. |
| 2004/0126783 A1 | 7/2004 | Bortolin et al. |
| 2004/0200909 A1 | 10/2004 | McMillan et al. |
| 2004/0209266 A1 | 10/2004 | Squirrell |
| 2004/0222395 A1 | 11/2004 | Yee |
| 2005/0244837 A1 | 11/2005 | McMillan et al. |
| 2006/0011539 A1 | 1/2006 | Lee et al. |
| 2006/0019379 A1 | 1/2006 | Taylor et al. |
| 2006/0030038 A1 | 2/2006 | Taylor et al. |
| 2006/0094108 A1 | 5/2006 | Yoder et al. |
| 2006/0194264 A1 | 8/2006 | Sheppard, Jr. et al. |
| 2006/0205085 A1 | 9/2006 | Handique et al. |
| 2006/0246490 A1 | 11/2006 | Anderson et al. |
| 2006/0257991 A1 | 11/2006 | McDevitt et al. |
| 2006/0269922 A1 | 11/2006 | Sagner et al. |
| 2006/0276972 A1 | 12/2006 | Light, II et al. |
| 2007/0036026 A1 | 2/2007 | Laibinis et al. |
| 2007/0054293 A1 | 3/2007 | Liu et al. |
| 2007/0054349 A1 | 3/2007 | Hickey |
| 2007/0077646 A1 | 4/2007 | Okamoto |
| 2007/0087431 A1 | 4/2007 | Ching et al. |
| 2007/0099289 A1 | 5/2007 | Irimia et al. |
| 2007/0125942 A1 | 6/2007 | Kido |
| 2007/0212698 A1 | 9/2007 | Bendele et al. |
| 2007/0248958 A1 | 10/2007 | Jovanovich et al. |
| 2007/0281288 A1 | 12/2007 | Belkin et al. |
| 2008/0003649 A1 | 1/2008 | Maltezos et al. |
| 2008/0050781 A1 | 2/2008 | Oldham et al. |
| 2008/0153096 A1 | 6/2008 | Witty et al. |
| 2008/0280285 A1 | 11/2008 | Chen et al. |
| 2008/0316482 A1 | 12/2008 | Hoshizaki et al. |
| 2009/0023201 A1 | 1/2009 | Hongo et al. |
| 2009/0142745 A1 | 6/2009 | Breidenthal et al. |
| 2009/0155838 A1 | 6/2009 | Hale |
| 2009/0186344 A1 | 7/2009 | Farinas |
| 2009/0186357 A1 | 7/2009 | Mauk et al. |
| 2009/0269841 A1 | 10/2009 | Wojciechowski et al. |
| 2009/0291507 A1 | 11/2009 | Clemmens et al. |
| 2010/0112567 A1 | 5/2010 | Adolfsen et al. |
| 2010/0239471 A1 | 9/2010 | Ching et al. |
| 2011/0158849 A1 | 6/2011 | Yu et al. |
| 2012/0003631 A1 | 1/2012 | Yu et al. |

FOREIGN PATENT DOCUMENTS

| | | |
|---|---|---|
| JP | 2001-108684 | 4/2001 |
| WO | WO 01/13096 A1 | 2/2001 |
| WO | WO 2004/005553 A1 | 1/2004 |
| WO | WO 2004/080597 A2 | 9/2004 |

OTHER PUBLICATIONS

Office Action for Japanese Patent Application No. 2008-536791, mailed Jul. 17, 2012.

International Search Report and Written Opinion for PCT/US2006/40835, mailed Dec. 4, 2007, 13 pages.

Office Action for U.S. Appl. No. 12/005,860 mailed Nov. 3, 2009.

Office Action for U.S. Appl. No. 12/821,446 mailed Sep. 1, 2010.

Office Action for U.S. Appl. No. 12/789,831 mailed Nov. 23, 2010.

International Search Report and Written Opinion for PCT/US11/25871, mailed May 5, 2011.

Final Office Action for U.S. Appl. No. 12/789,831, mailed May 28, 2010.

Office Action for Chinese Patent Application No. 200680043554.3, mailed Mar. 30, 2011.

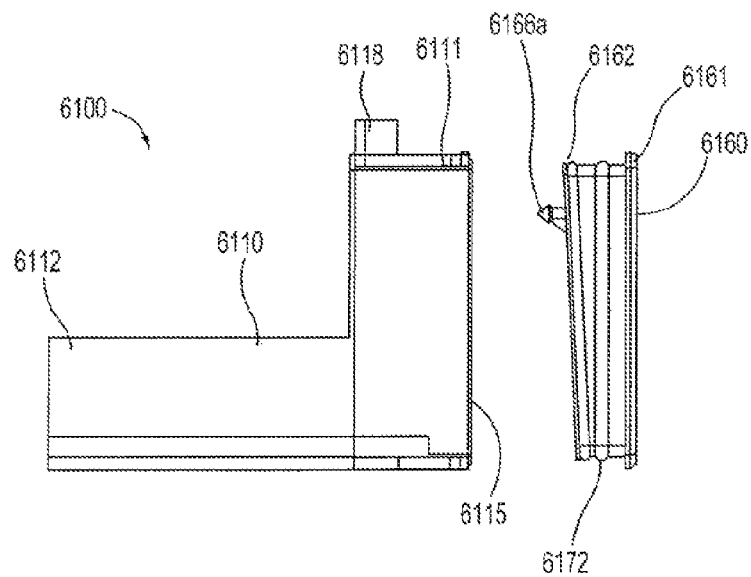
FIG. 11
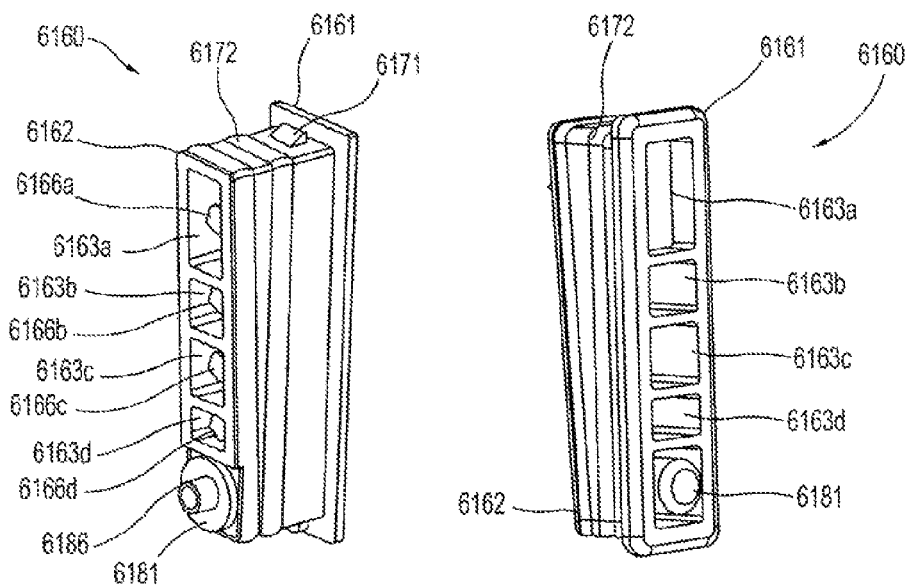
FIG. 12
FIG. 13

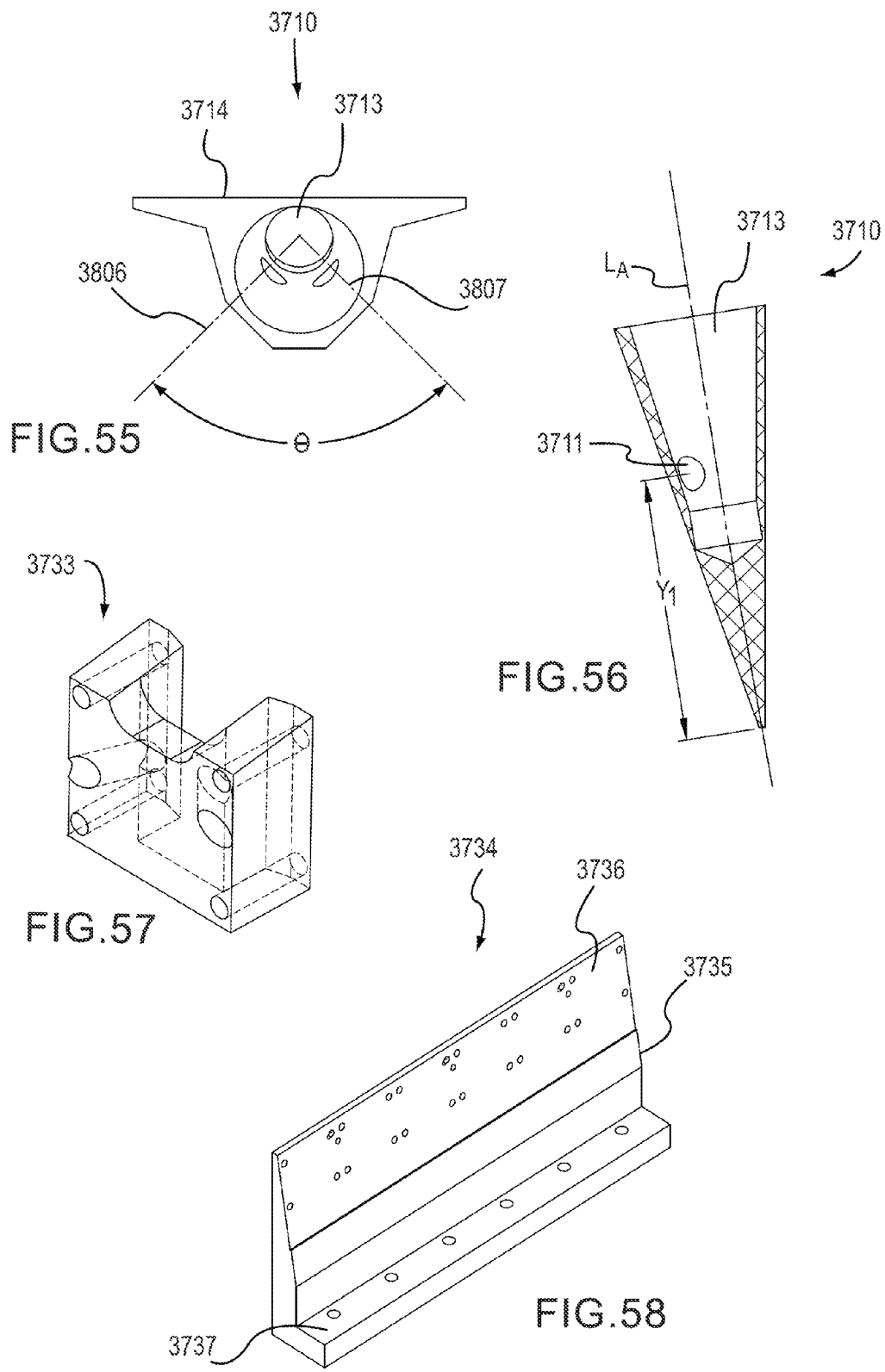

APPARATUS AND METHODS FOR INTEGRATED SAMPLE PREPARATION, REACTION AND DETECTION

CROSS-REFERENCE TO RELATED APPLICATIONS

This application is a continuation-in-part of U.S. patent application Ser. No. 12/789,831, entitled "CASSETTE FOR SAMPLE PREPARATION," filed May 28, 2010, which is a continuation of U.S. application Ser. No. 11/582,651, entitled "CASSETTE FOR SAMPLE PREPARATION," filed Oct. 17, 2006, which claims the benefit of U.S. Provisional Application No. 60/728,569, entitled "METHOD AND APPARATUS FOR ISOLATING NUCLEIC ACID," filed Oct. 19, 2005; U.S. Provisional Application No. 60/753,622, entitled "CASSETTE FOR SAMPLE PREPARATION," filed Dec. 22, 2005; and, U.S. Provisional Application No. 60/753,618, filed Dec. 22, 2005, entitled "CASSETTE FOR SAMPLE PREPARATION," each of which is incorporated herein by reference in its entirety. This application is also a continuation-in-part of U.S. patent application Ser. No. 12/821,446, entitled "INSTRUMENT FOR CASSETTE FOR SAMPLE PREPARATION," filed Jun. 23, 2010, which is a continuation of U.S. patent application Ser. No. 12/005,860, entitled "INSTRUMENT FOR CASSETTE FOR SAMPLE PREPARATION," filed Dec. 27, 2007, which claims priority to U.S. Provisional Application Ser. No. 60/882,150, entitled "INSTRUMENT FOR CASSETTE FOR SAMPLE PREPARATION," filed Dec. 27, 2006, each of which is incorporated herein by reference in its entirety. This application claims priority to U.S. Provisional Application Ser. No. 61/307,281, entitled "CASSETTE AND INSTRUMENT FOR INTEGRATED NUCLEIC ACID ISOLATION AND AMPLIFICATION," filed Feb. 23, 2010, which is incorporated herein by reference in its entirety.

BACKGROUND

The embodiments described herein relate to apparatus and methods for sample preparation, reaction and analysis. More particularly, the embodiments described herein relate to a cartridge and instrument within which the isolation, amplification and analysis of nucleic acid can be performed in an integrated process.

Some known diagnostic procedures include the isolation and analysis of nucleic acids, such as DNA or RNA. Known methods for isolating nucleic acids within a sample often include several steps, such as: (1) removing the proteins within the sample by adding a protease (e.g., Proteinase K); (2) breaking down the remaining bulk sample to expose the nucleic acids contained therein (also referred to as cell lysing); (3) precipitating the nucleic acid from the sample; and (4) washing and/or otherwise preparing the nucleic acid for further analysis.

In certain instances, amplification of the isolated nucleic acid (e.g., replication of the nucleic acid to increase its volume) is desired for further analysis. The polymerase chain reaction (PCR) process is a known technique for amplifying portions of a nucleic acid molecule. During a PCR, an input sample containing the target DNA is mixed with reagents, which include the DNA polymerase (e.g., Taq polymerase). The input sample can be, for example, the isolated nucleic acid sample produced by the procedure described above. The sample is then thermally cycled multiple times within an isolated chamber to complete the reaction. The temperatures and time periods of the thermal cycling are carefully controlled to ensure accurate results. After the DNA sequence is sufficiently amplified, it can be analyzed using various optical techniques.

Some known systems for performing nucleic acid isolation and amplification include different portions (e.g., an isolation portion and an amplification portion) between which the samples must be transferred using human intervention and/or processes that can compromise the integrity of the sample. Some known systems for performing nucleic acid isolation and amplification include complex control systems requiring significant preparation and/or calibration by an experienced laboratory technician. Accordingly, such known systems are not well suited for "bench top" applications, high-volume diagnostic programs and/or use in a wide variety of laboratory settings.

In certain applications, multiple stages of reactions may be desired, with one or more later stages requiring the addition reagents between stages of the reaction. For example, in a Reverse Transcription PCR, a reverse transcription reaction is generally completed before a PCR process is performed, with the PCR process requiring additional reagents. In some known systems, the additional reagents required for a later stage of reaction are often transferred into the reaction chamber with human intervention and/or processes that can compromise the integrity of the sample. Accordingly, such known processes can induce error and contamination, and can also be costly and/or difficult to implement for high-volume applications.

Although some known systems include chambers that contain reagents, such chambers are often integral to the cartridge and/or the reaction chamber. Accordingly, when such systems and/or cartridges are used in connection with different reactions and/or assays, an entirely different cartridge, cassette or other apparatus is often used to facilitate the use of the particular combination of reagents to conduct the desired reaction process. Thus, such known systems and/or cartridges are often not interchangeably usable for different reaction processes and/or assays.

Although some known systems include optical detection systems to detect one or more different analytes and/or targets within a test sample, such known systems often include the sources of excitation light and/or the detectors of emission light in a portion of the device that is movable relative to the reaction chamber. For example, some known systems are configured to supply an excitation light beam to the reaction chamber via a movable lid. Thus, such known systems are susceptible to detection variability that can result from variation in the location of the excitation and/or detection light paths.

Thus, a need exists for improved apparatus and methods for performing nucleic acid isolation and amplification.

SUMMARY

Cartridges and instruments for performing sample isolation and downstream reactions are described herein. In some embodiments, an apparatus includes an isolation module, which can be used, for example, to isolate a nucleic acid sample, and a reaction module, which can be used, for example, to amplify the nucleic acid sample. The isolation module includes a first housing and a second housing. The first housing defines a first chamber and a second chamber. At least the first chamber is configured to contain a sample, such as, for example, a sample containing a nucleic acid. The second housing includes a side wall and a puncturable member that collectively define a first volume configured to contain a first substance. The first substance can be, for example, a reagent, a wash buffer solution, a mineral oil and/or any other substance to be added to the sample. At least a portion of the second housing is configured to be disposed within the first housing such that the first volume is in fluid communication with the first chamber when a portion of the puncturable member is punctured. The reaction module defines a reaction chamber and a second volume configured to contain a second substance. The reaction module is configured to be coupled to the isolation module such that the reaction chamber and the second volume are each in fluid communication with the second chamber of the first housing.

In some embodiments, a PCR is carried out in the cartridge and/or instrument provided herein. In a further embodiment, the reaction is monitored in real time with the use of a fluorescent probe, for example, a single stranded DNA molecule comprising a minor groove binder (MGB) and a fluorophore at the 5' end, and a non-fluorescent quencher at its 3'-end. In one embodiment, a PCR is carried out on multiple targets, and the progress of the reactions are monitored in real time. In some embodiments, the targets are gene sequences from one or more of the following viruses: influenza A, influenza B, respiratory syncytial virus (RSV), herpes simplex virus 1 (HSV1) or herpes simplex virus 2 (HSV 2). In some embodiments, prior to a PCR, a reverse transcription reaction is carried out in the cartridge and/or instrument provided herein.

BRIEF DESCRIPTION OF THE DRAWINGS

FIG. 11 is a side exploded view of a portion of the cartridge shown in FIG. 8.

FIGS. 12 and 13 are perspective views of a reagent module of the cartridge shown in FIG. 8.

FIGS. 54 and 55 are a front view and a top view, respectively, of the receiving block of the heater assembly shown in FIG. 52.

FIG. 56 is a cross-sectional view of the receiving block of the heater assembly shown in FIG. 52 taken along the line $X_2$-$X_2$ shown in FIG. 54.

FIG. 57 is a perspective view of a clamp of the heater assembly shown in FIG. 52.

FIG. 58 is a perspective view of a mounting block of the heater assembly shown in FIG. 52.

DETAILED DESCRIPTION

Figure 1:
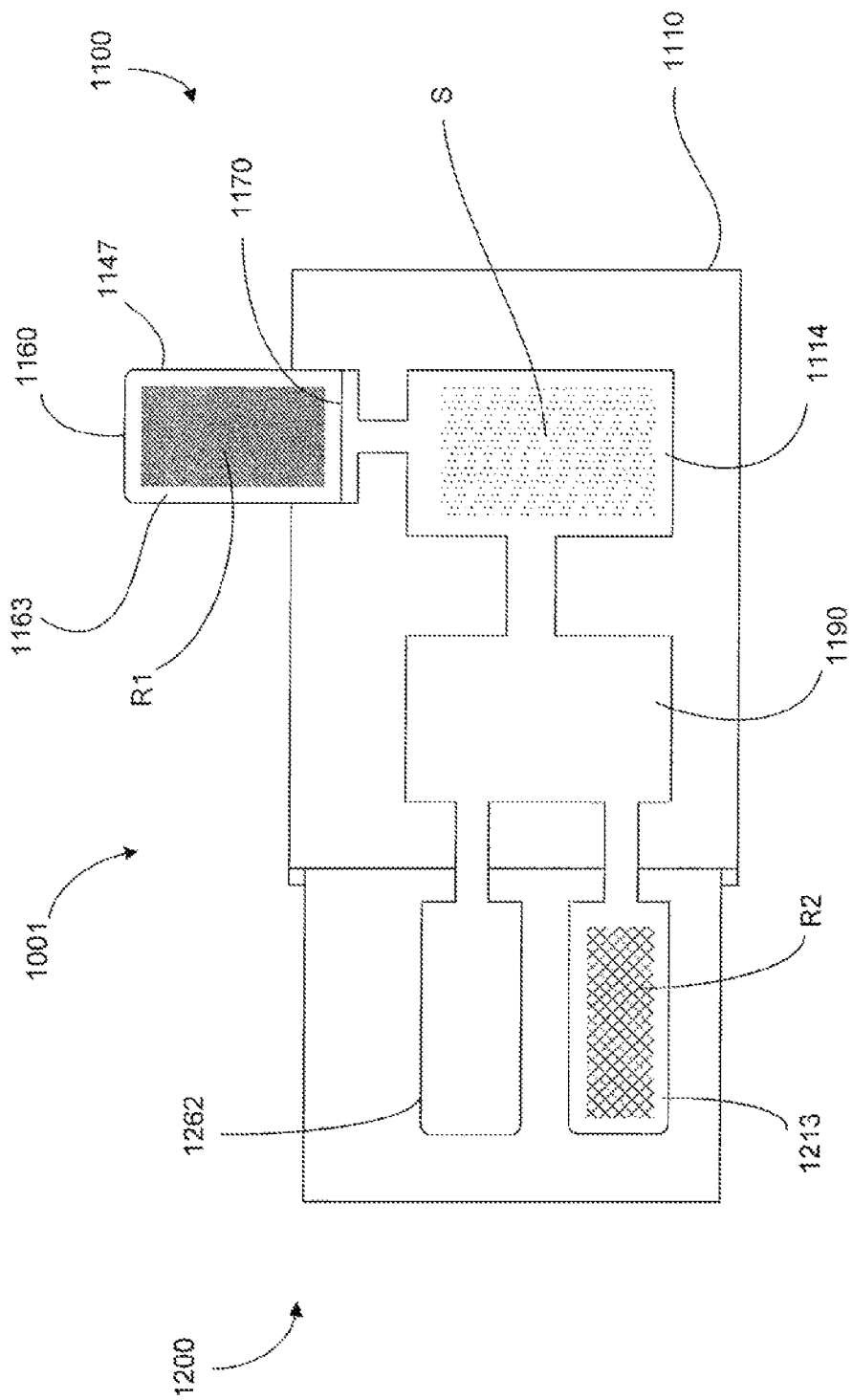
FIGS. 1 and 2 are schematic illustrations of a cartridge according to an embodiment, in a first configuration and a second configuration, respectively.

Cartridges and instruments for performing sample isolation and reaction are described herein. In some embodiments, an apparatus includes an isolation module, which can be used, for example, to isolate a nucleic acid sample or an analyte sample, and a reaction module, which can be used, for example, to amplify the nucleic acid sample, or to test the binding of the analyte to other compounds. The isolation module includes a first housing and a second housing. The first housing defines a first chamber and a second chamber. At least the first chamber is configured to contain a sample, such as, for example, a sample containing a nucleic acid. The second housing includes a side wall and a puncturable member that collectively define a first volume configured to contain a first substance. The first substance can be, for example, a reagent, a wash buffer solution, a mineral oil and/or any other substance to be added to the sample. At least a portion of the second housing is configured to be disposed within the first housing such that the first volume is in fluid communication with the first chamber when a portion of the puncturable member is punctured. The reaction module defines a reaction chamber and a second volume configured to contain a second substance. The reaction module is configured to be coupled to the isolation module such that the reaction chamber and the second volume are each in fluid communication with the second chamber of the first housing.

In some embodiments, an apparatus includes a first module, a second module, and a third module. The first module defines a first chamber and a second chamber. At least the first chamber is configured to contain a sample. The second module defines a first volume configured to contain a first substance. The first substance can be, for example, a reagent, a wash buffer solution, a mineral oil and/or any other substance to be added to the sample. A portion of the second module is configured to be disposed within the first chamber of the first module when the second module is coupled to the first module such that the first volume is configured to be selectively placed in fluid communication with the first chamber. The third module defines a reaction chamber and a second volume. The second volume is configured to contain a second substance. A portion of the third module is disposed within the second chamber of the first module when the third module is coupled to the first module such that the reaction chamber and the second volume are each in fluid communication with the second chamber of the first module.

In some embodiments, an apparatus includes a first module, a second module, and a third module. The first module defines a first chamber and a second chamber. The first module includes a first transfer mechanism configured to transfer a sample between the first chamber and the second chamber while maintaining fluid isolation between the first chamber and the second chamber. The second module defines a volume configured to contain a substance, such as, for example a reagent or the like. A portion of the second module is configured to be disposed within the first chamber of the first module when the second module is coupled to the first module such that the volume is configured to be selectively placed in fluid communication with the first chamber. The third module defines a reaction chamber. The third module is configured to be coupled to the first module such that the reaction chamber is in fluid communication with the second chamber. The third module includes a second transfer mechanism configured to transfer a portion of the sample between the second chamber and the reaction chamber.

In some embodiments, an apparatus includes a first module and second module. The first module includes a reaction vial, a substrate and a first transfer mechanism. The reaction vial defines a reaction chamber, and can be, for example, a PCR vial. The first transfer mechanism includes a plunger movably disposed within a housing such that the housing and the plunger define a first volume that contains a first substance.

The plunger can be moved between a first position and a second position. The first substance can be, for example, a reagent, a mineral oil or the like. The substrate defines at least a portion of a first flow path and a second flow path. The first flow path is configured to be in fluid communication with the reaction chamber, the first volume and an isolation chamber of an isolation module. The second flow path configured to be in fluid communication with the isolation chamber. A portion of the plunger disposed within the first flow pathway such that the first volume is fluidically isolated from the reaction chamber when the plunger is in the first position. The portion of the plunger is disposed apart from the first flow pathway such that the first volume is in fluid communication with the reaction chamber when the plunger is in the second position. The plunger is configured to produce a vacuum within the reaction chamber to transfer a sample from the isolation chamber to the reaction chamber when the plunger is moved from the first position to the second position. The second module includes a second transfer mechanism, and defines a second volume configured to contain a second substance. The second module is configured to be coupled to the first module such that the second volume can be selectively placed in fluid communication with the isolation chamber via the second flow path. The second transfer mechanism is configured to transfer the second substance from the second volume to the isolation chamber when the second transfer mechanism is actuated.

In some embodiments, an instrument for manipulating and/or actuating a cartridge containing a sample can include a block, a first optical member, a second optical member and an optics assembly. The block defines a reaction volume configured to receive at least a portion of a reaction container. The block can include and/or be attached to a mechanism for facilitating, producing, supporting and/or promoting a reaction associated with the sample. In some embodiments, for example, the block can be coupled to a heating element configured to thermally cycle the sample. The first optical member is disposed at least partially within the block such that the first optical member is in optical communication with the reaction volume. The second optical member disposed at least partially within the block such that the second optical member is in optical communication with the reaction volume. The optics assembly includes an excitation module configured to produce a plurality of excitation light beams and a detection module configured to receive a plurality of emission light beams. The optics assembly is coupled to the first optical member and the second optical member such that each of the plurality of excitation light beams can be conveyed into the reaction volume and each of the plurality of emission light beams can be received from the reaction volume.

In some embodiments, an instrument for manipulating and/or actuating a cartridge includes a chassis, an acoustic transducer and an actuation mechanism. The chassis is configured to contain a cartridge having a housing that defines a volume. The volume can receive a portion of a sample, such as for example a sample containing nucleic acids. The acoustic transducer is configured to produce acoustic energy. The actuation mechanism is configured to move at least a portion of the acoustic transducer into contact with a portion of the cartridge. The actuation mechanism is further configured to adjust a force exerted by the portion of the acoustic transducer against the portion of the cartridge.

The term "light beam" is used herein to describe any projection of electromagnetic energy, whether in the visible spectrum or not. For example, a light beam can include collimated projection of electromagnetic radiation in the visible spectrum that is produced by a laser, a light-emitting diode (LED), a flash lamp, or the like. A light beam can be either continuous within a desired time period or discontinuous (e.g., pulsed or intermittent) within the desired time period. In certain situations, a light beam can include and/or be associated with information (i.e., the light beam can be an optical signal), such as an amount of an analyte present in a sample.

The term "parallel" or is used herein to describe a relationship between two geometric constructions (e.g., two lines, two planes, a line and a plane or the like) in which the two geometric constructions are substantially non-intersecting as they extend substantially to infinity. For example, as used herein, a first line is said to be parallel to a second line when the first line and the second line do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The term "normal" is used herein to describe a relationship between two geometric constructions (e.g., two lines, two planes, a line and a plane or the like) in which the two geometric constructions intersect at an angle of approximately 90 degrees within at least one plane. For example, as used herein, a first line is said to be normal to a plane when the line and the plane intersect at an angle of approximately 90 degrees within a plane. Two geometric constructions are described herein as being "normal" or "substantially normal" to each other when they are nominally normal to each other, such as for example, when they are normal to each other within a tolerance. Such tolerances can include, for example, manufacturing tolerances, measurement tolerances or the like.

Figure 2:
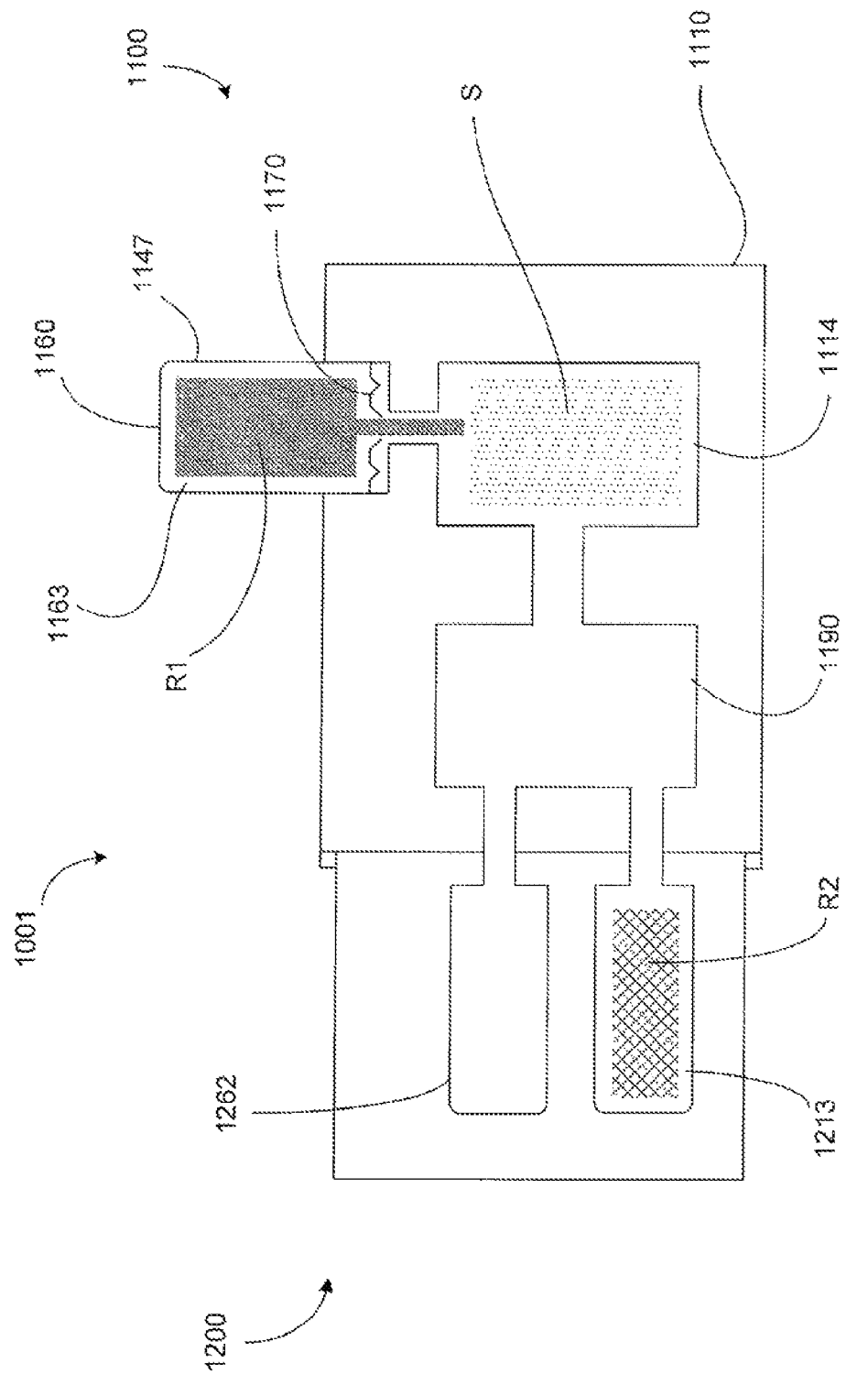

FIGS. 1 and 2 are schematic illustrations of a cartridge 1001 according to an embodiment, in a first configuration and a second configuration, respectively, that includes an isolation module 1100 and a reaction module 1200. The isolation module 1100 and the reaction module 1200 are coupled to each other such that the isolation module 1100 and the reaction module 1200 can be placed in fluid communication with each other. As described herein, the isolation module 1100 and the reaction module 1200 can be coupled together in any suitable manner. In some embodiments, for example, the isolation module 1100 and the reaction module 1200 can be separately constructed and coupled together to form the cartridge 1001. This arrangement between the isolation module 1100 and the reaction module 1200 allows various different configurations of the isolation module 1100 to be used with various different configurations of the reaction module 1200. The different configurations of the isolation module 1100 and/or the reaction module 1200 can include different reagents and/or different structures within the isolation module 1100 and/or the reaction module 1200.

The cartridge 1001 can be manipulated and/or actuated by any of the instruments described herein. In some embodiments, the cartridge 1001 can be used to perform sample preparation, nucleic acid isolation and/or Polymerase Chain Reactions (PCRs) on the sample. In such embodiments, the isolation module 1110 can isolate a target nucleic acid from the sample contained therein. The isolated nucleic acid can then be amplified (e.g., using PCR) in the reaction module 1200, as described further below. The modular arrangement of the cartridge 1001 allows any number of different reaction modules 1200 that each contain, for example, different reagents and/or that are each configured to amplify a different type of sample, to be used with an isolation module 1100, and vice-versa.

The isolation module 1100 includes a first housing 1110 and a second housing 1160. As described in more detail herein, the second housing 1160 is coupled to the first housing 1110 such that the second housing 1160 can be placed in fluid communication with the first housing 1110. In some embodiments, the first housing 1110 and the second housing 1160 are modularly arranged, so that different configurations of the first housing 1110 and the second housing 1160 can be used with each other. The different configurations of the first housing 1110 and the second housing 1160 can include, for example, different chemicals, reagents, samples and/or different internal structures.

The first housing 1110 defines a first chamber 1114 and a second chamber 1190. At least one of the first chamber 1114 or the second chamber 1190 can contain a sample S. The sample S can be any biological sample, for example a biological sample containing one or more target nucleic acids, such as, for example, urine, blood, other materials containing tissue samples or the like. The sample S can be introduced into the first chamber 1114 or the second chamber 1190 via any suitable mechanism, including for example, by pipetting or injecting the sample S into the first chamber 1114 and/or the second chamber 1190 via an opening or a puncturable member in the first housing 1110 (not shown). Although the first chamber 1114 is shown as being in fluid communication with the second chamber 1190, in other embodiments, the first chamber 1114 can be selectively placed in fluid communication with the second chamber 1190. Said another way, in some embodiments, the first housing 1110 can include any suitable mechanism, such as a valve (not shown in FIGS. 1 and 2), that can selectively place the first chamber 1114 in fluid communication with the second chamber 1190. Moreover, in other embodiments, the first housing 1110 can have any suitable flow control and/or transfer mechanism (not shown in FIGS. 1 and 2) to facilitate the transfer and/or control the transfer of a substance between the first chamber 1114 and the second chamber 1190, including for example, valves, capillary flow control device, pumps, or the like. In yet other embodiments, the first chamber 1114 can be fluidically isolated from the second chamber 1190.

The second housing 1160 includes a sidewall 1147 and a puncturable member 1170. The sidewall 1147 and the puncturable member 1170 define a first volume 1163. The first volume 1163 can be fully or partially filled with a substance R1. The substance R1 can be any biological or chemical substance such as, for example, a mineral oil, a wash buffer, a florescent dye, a reagent, or the like. As shown in FIGS. 1 and 2, a portion of the second housing 1160 is disposed within the first housing 1110 such that when the puncturable member 1170 is punctured, broken, severed and/or ruptured, the first volume 1163 is in fluid communication with the first chamber 1114 as shown in FIG. 2. Similarly stated, the isolation module 1110 can be moved from a first configuration (FIG. 1) to a second configuration (FIG. 2) when the puncturable member 1170 is punctured. When the first volume 1163 is in fluid communication with the first chamber 1114 as shown in FIG. 2 (i.e., when the isolation module is in the second configuration), the substance R1 can be transferred from the first volume 1163 into the first chamber 1114. The substance R1 can be transferred from the first volume 1163 into the first chamber 1114 by any suitable mechanism, for example, by gravitational forces, capillary forces or by some actuating mechanism (not shown in FIGS. 1 and 2) acting on the first volume 1163.

The puncturable member 1170 can be constructed from a material that is substantially impermeable to and/or substantially chemically inert from the substance R1. In this manner, the substance R1 can be stored within the first volume 1163 for an extended period of time without compromising the ability to use the second housing 1160 in any desired application, such as any of the embodiments described herein. Moreover, in some embodiments, the puncturable member 1170 can be constructed from a material having certain temperature characteristics such that the desired properties and integrity of the puncturable member 1170 are maintained over a certain temperature range. For example, in some embodiments, it can be desirable to store the second housing 1160 containing the substance R1 in a refrigerated condition, or it can be desirable to manufacture the second housing 1160 by thermally laminating the puncturable member 1170. In such embodiments, the puncturable member 1170 can be selected such that the refrigeration condition and/or the thermal lamination condition do not substantially degrade the desired properties and integrity of the puncturable member 1170 for the intended application. In some embodiments, the puncturable member 1170 can be constructed from a polymer film, such as any form of polypropylene. In some embodiments, the puncturable member 1170 can be constructed from biaxially oriented polypropylene (BOP).

Although FIGS. 1-2 show at least a portion of the second housing 1160 as being disposed within the first housing 1110, in other embodiments, the first housing 1110 and the second housing 1160 can be coupled together by having at least a portion of the first housing 1110 disposed within the second housing 1160, or by having the first housing 1110 and the second housing 1160 coupled together through an interface or fitting without being disposed within each other. The second housing 1160 can be coupled to the first housing 1110 by any suitable mechanism, such as, for example, by an adhesive bond; a weld joint; a snap fit (e.g. an arrangement in which mating protrusions disposed on the first housing are received within and/or retained by corresponding openings defined by the second housing, or vice versa); an interference fit, in which two parts are fastened by friction after being pushed together (e.g., such as a Luer-Slip®); a threaded coupling, including removable coupling such as Luer-Lok®; or a flange connection. The coupling between the first housing 1110 and the second housing 1160 can be fluid-tight, so that when the puncturable member 1170 has been broken or ruptured as shown in FIG. 2, the fluid transfer between the first volume 1163 and the first chamber 1114 does not result in leaks and/or contamination. The fluid-tight coupling between the first housing 1110 and the second housing 1160 can be achieved through the use of a tapered fit of mating components, o-rings, gaskets or the like.

The reaction module 1200 defines a reaction chamber 1262 and a second volume 1213. The second volume 1213 contains substance R2. The substance R2 can be any biological or chemical substance such as a mineral oil, a wash buffer, a reagent, or the like that participates in or otherwise supports a reaction within the reaction chamber 1262 and/or any other portion of the cartridge 1001. The reaction module 1200 is coupled to the isolation module 1100 such that the reaction chamber 1262 and the second volume 1213 can each be placed in fluid communication with the second chamber 1190 of the isolation module 1100. The reaction module 1200 can be coupled to the isolation module 1100 by any suitable mechanism, such as, for example, by an adhesive bond; a weld joint; a snap fit (e.g. an arrangement in which mating protrusions disposed on the first housing are received within and/or retained by corresponding openings defined by the second housing or vice versa); an interference fit, in which two parts are fastened by friction after being pushed together (e.g., such as a Luer-Slip®); a threaded coupling, including removable coupling such as Luer-Lok®; or a flange connection. The coupling between the first housing 1110 and the reaction module 1200 can be fluid-tight so that the fluid transfer between the isolation module 1100 and the reaction module 1200 will not result in leaks and/or contamination. The fluid-tight coupling between the reaction module 1200 and the isolation module 1100 can be achieved using tapered fit of mating components, o-rings, gaskets or the like. In some embodiments, the coupling between the isolation module 1100 and the reaction module 1200 is removable.

This arrangement allows substances to be transferred from the reaction chamber 1262 and/or the second volume 1213 to the second chamber 1190, or vice versa. For example, in use, samples, reagents, and/or other supporting materials, such as one or more of the sample S, the substance R1 or the substance R2 can be transferred into or out of the reaction chamber 1262 in connection with the desired reaction. Fluid transfer between the second chamber 1190, the reaction chamber 1262 and/or the second volume 1213 can be effected through gravitational forces, capillary forces, hydraulic pressure or the like. In some embodiments, the hydraulic pressure can be applied through a piston pump, a baffle pump or any other suitable transfer mechanism. In some embodiments, such fluid transfer mechanism can be either external to the cartridge 1001 or internal to the cartridge 1001 (e.g., disposed at least partially within the isolation module 1100 and/or the reaction module 1200).

In some embodiments, the substance R1 and the sample S, or a portion thereof, can be transferred from the first volume 1163 and the first chamber 1114, through the second chamber 1190, and to reaction chamber 1262 in connection with a reverse transcription process, creating single-stranded complementary deoxyribonucleic acid (cDNA) from a ribonucleic acid (RNA) template by using a reverse transcriptase enzyme. After the completion of the reverse transcription process, the substance R2 can be transferred from the second volume 1213 through the second chamber 1190 to the reaction chamber 1262 to perform a PCR process on the newly synthesized cDNA, or DNA present in the sample S. In such embodiments, the substance R2 can include one or more PCR reagents, including Taq polymerase. In some embodiments, substance R1 and/or substance R2 can include DNA binding dyes (e.g., minor grove binder (MGB), MGB and fluorophore coupled to the 5'-end of a DNA probe, where the DNA probe hybridizes specifically to a target sequence), so the progress of the PCR process can be monitored in real-time by detecting the fluorescence from the fluorescent reporter molecule in the reaction chamber 1262 using any of the instruments and/or methods described herein.

In some embodiments, the cartridge 1001 (FIGS. 1 and 2) is used to both isolate and amplify a nucleic acid sample. For example, isolation may occur in the first chamber 1114 or the second chamber 1190. Substance R1, in one embodiment, includes a reagent for nucleic acid isolation. DNA, RNA and a combination thereof can be isolated by the cartridges provided herein. For example, substance R1, in one embodiment, comprises magnetic beads derivatized with a reagent to isolate either DNA or RNA.

Both individual nucleic acids and total nucleic acids can be isolated in the cartridges provided herein. For example, substance R1 includes, in one embodiment, beads derivatized with a polyA sequence, designed to isolate the total pool of messenger RNA, present in a sample. In another embodiment, substance R1 includes beads derivatized with specific nucleic sequences, designed to isolate only a portion of the nucleic acid in the sample.

Once the nucleic acid is isolated, it can be amplified. In one embodiment, amplification is by PCR. For the purposes of this invention, reference to "PCR" on a nucleic acid sample includes reverse transcription-PCR (RT-PCR). Specifically, when the nucleic acid sample is one or more target RNAs, or a population of RNAs (e.g., total mRNA), RT-PCR will be carried out on the target RNAs. The PCR master mix provided herein can therefore include reagents for reverse transcription. The reverse transcription step can take place in the same chamber or module as the PCR, or a different chamber or module. In one embodiment, reverse transcription and PCR are carried out in the same chamber, by providing an RT-PCR master mix. One of ordinary skill in the art will readily know whether RT-PCR or PCR is necessary, based on the nucleic acid sample that is originally isolated. Any of the cartridges provided herein can be used to isolate DNA and/or RNA, and to perform RT-PCR and/or PCR.

For example, in one embodiment, if RNA is first isolated, a reverse transcriptase reaction is carried out on the isolated sample, for example in the second chamber 1190 or the reaction chamber 1262. If DNA is isolated, it can be amplified by PCR, for example, in the reaction chamber 1262. Similarly, if RNA is first isolated from the sample S, it is subjected to a reverse transcription reaction, for example in reaction chamber 1262, and the product of this reaction is used in a downstream PCR reaction, for example, in reaction chamber 1262. In some embodiments, multiple target nucleic acids are amplified in the PCR, and the PCR reaction is monitored in real time. Amplification of multiple targets is monitored, in one embodiment, by employing individual DNA hybridization probes, specific for each target, where each probe includes a fluorophore that emits light at a different wavelength, or that can be excited at a unique wavelength. The DNA hybridization probe, in one embodiment, is provided in the second volume 1213 as substance R2 (or a portion thereof).

The probe used for monitoring the PCR, in one embodiment, is a DNA oligonucleotide that specifically hybridizes to a DNA target of interest, and includes a non-fluorescent quencher at the 3' end and a fluorophore at the 5'-end. Additionally, in this embodiment, the DNA oligonucleotide includes a MGB at the 5'-end, either directly bound to the oligonucleotide, or bound to the fluorophore (see Lukhtanov et al. (2007). Nucleic Acids Research 35, p. e30). The DNA oligonucleotide probe fluoresces when bound to target, but not while in solution. Therefore, upon the synthesis of product in the PCR, more hybridization will occur, and more fluorescence is generated. The amount of fluorescence is therefore proportional to the amount of target generated.

Real time monitoring of a PCR reaction is not limited to the cartridges shown in FIGS. 1 and 2. Rather, any of the cartridges provided herein can employ real time PCR, for example with the DNA hybridization probes described above.

In some embodiments, the cartridge 1001 can be manipulated by any of the instruments and/or methods described herein to facilitate the occurrence of a PCR process within the reaction chamber 1262. In such embodiments, the reaction module 1200 can be coupled to and/or placed in contact with a heat transfer apparatus to allow for the contents of the reaction chamber 1262 to be thermally cycled in connection with the PCR process. In such embodiments, the reaction module 1200 can be further operatively coupled to an optical apparatus to allow for the real-time monitoring of the PCR process. In other embodiments, the reaction module 1200 and/or the isolation module 1100 can be operatively coupled to other energy sources such as optical energy, ultrasonic energy, magnetic energy, hydraulic energy or the like to facilitate a reaction and/or an isolation process occurring therein.

Although FIGS. 1-2 show the reaction chamber 1262 and the second volume 1213 each to be in fluid communication with the second chamber 1190, in other embodiments, the fluid communication between the reaction chamber 1262, the second volume 1213 and/or the second chamber 1190 of the isolation module can be selective. Said another way, in some embodiments, the reaction module 1200 and/or the isolation module 1100 can include a mechanism, such as a valve, or a puncturable membrane, that can selectively place the second chamber 1190 in fluid communication with the second volume 1213 and/or the reaction chamber 1262. Although the isolation module 1100 is shown as defining one first volume 1163 in some embodiments, the isolation module 1100 can define any number of volumes and/or can contain any number of different substances. Similarly, although the reaction module 1200 is shown as defining one second volume 1213, in some embodiments, the reaction module 1200 can define any number of volumes and can contain any number of different substances.

Figure 3:
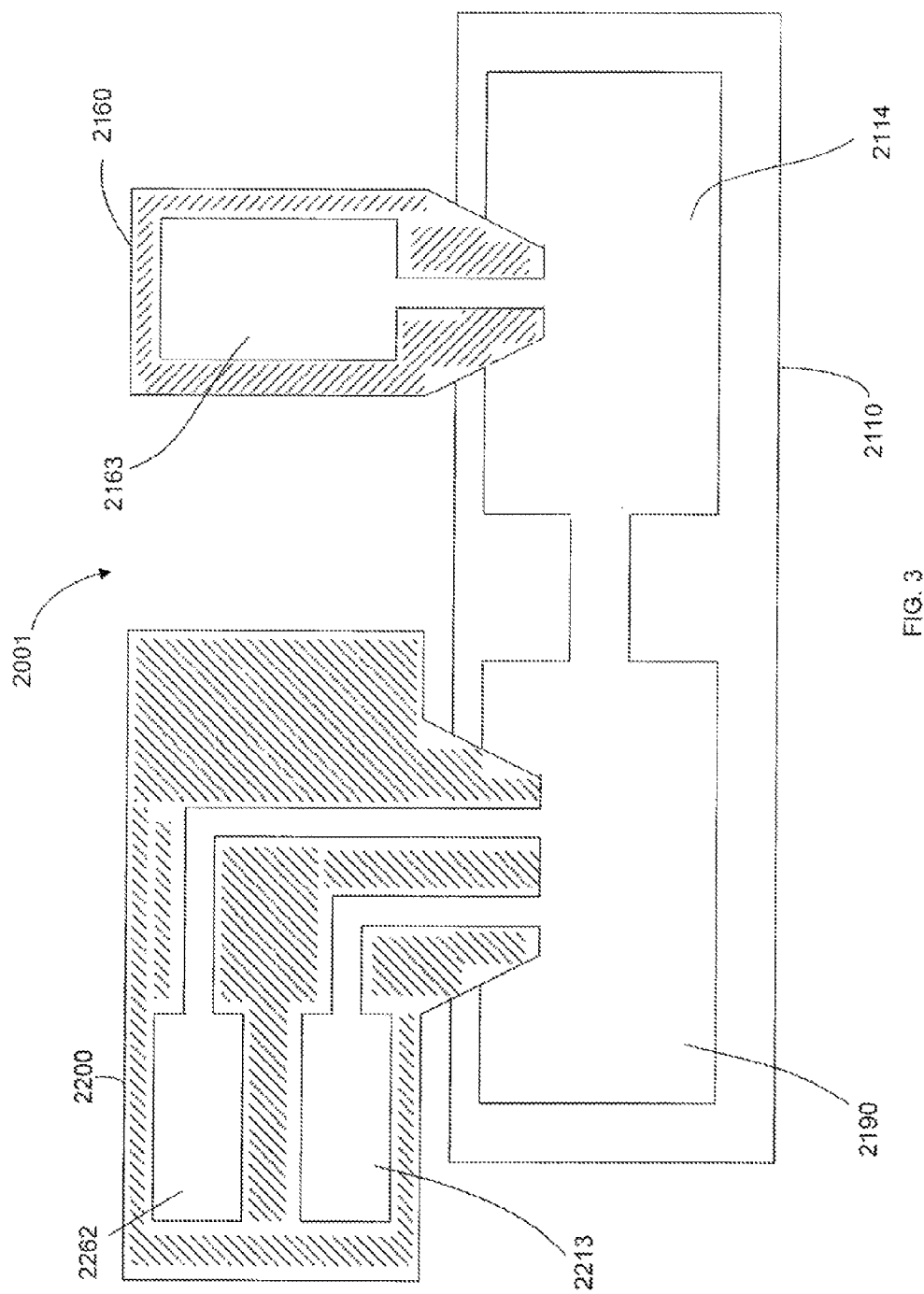
FIG. 3 is a schematic illustration of a cartridge having a first module, a second module and a third module, according to an embodiment.

FIG. 3 is a schematic illustration of a cartridge 2001 according to an embodiment that includes a first module 2110, a second module 2160 and a third module 2200. The first module 2110 defines a first chamber 2114 and a second chamber 2190. The first chamber 2114 and/or the second chamber 2190 can contain any biological sample containing a target nucleic acid, such as, for example, urine, blood, other materials containing tissue samples or the like. Although the first chamber 2114 is shown as being in fluid communication with the second chamber 2190, in other embodiments, the first chamber 2114 can be selectively placed in fluid communication with the second chamber 2190. Said another way, in some embodiments, the first module 2110 can include any suitable mechanism, such as a valve (not shown in FIG. 3), that can selectively place the first chamber 2114 in fluid communication with the second chamber 2190. Moreover, in other embodiments, the first module 2110 can have any suitable flow control and/or transfer mechanism (not shown in FIG. 3) to facilitate the transfer and/or control the transfer of a substance between the first chamber 2114 and the second chamber 2190, including for example, valves, a capillary flow control device, pumps, or the like.

The second module 2160 defines a first volume 2163 that can fully or partially contain any biological or chemical substance. The substance can be, for example, a mineral oil, wash buffer, a reagent, or the like that can participate in and/or otherwise support a reaction within the first chamber 2114 and/or any other portion of the cartridge 2001. In one embodiment, the reaction in the first chamber 2114 is an isolation reaction, for example a nucleic acid or peptide isolation. The second module 2160 can be coupled to the first module 2110 in any suitable manner as described herein. In some embodiments, for example, the first module 2110 and the second module 2160 can be separately constructed and coupled together such that the first module 2110 and the second module 2160 are modularly arranged. In such a modular arrangement, various different configurations of the first module 2110 and the second module 2160 can be used with each other. The different configurations of the first module 2110 and/or the second module 2160 can include different reagents and/or different structures within the first module 2110 and/or the second module 2160. As shown in FIG. 3, a portion of the second module 2160 is disposed within the first chamber 2114 of the first module 2110 such that the first volume 2163 can be placed in fluid communication with the first chamber 2114. In other embodiments, the first volume 2163 can be selectively placed in fluid communication with the first chamber 2114. In some embodiments, for example, the first module 2110 and/or the second module 2160 can include any suitable mechanism, such as a valve and/or any suitable fluid control and/or transfer mechanism as described herein, that can selectively place the first volume 2163 in fluid communication with the first chamber 2114 when the second module 2160 is coupled to the first module 2110. In some embodiments, substances and/or samples can be transferred between the first volume 2163 and the first chamber 2114 using any suitable fluid transfer mechanism as described herein. For example, in use, a sample, isolated sample (e.g., isolated DNA, isolated RNA, isolated peptides, isolated proteins), a reagent (e.g., an isolation reagent), and/or other supporting substances can be transferred into and/or out of the first chamber 2114 in connection with a desired reaction. In yet other embodiments, the first volume 2163 can be fluidically isolated from the first chamber 2114, for example, by a valve, puncturable member, or a selective transfer mechanism as described herein (not shown in FIG. 3).

The third module 2200 defines a reaction chamber 2262 and a second volume 2213. The reaction chamber 2262 and/or the second volume 2213 can fully or partially contain one or more biological or chemical substances such as a mineral oil, wash buffer, one or more PCR reagents, a reagent, or the like that participates in or otherwise supports a reaction within the reaction chamber 2262 and/or any other portion of the cartridge 2001. The third module 2200 can be coupled to the first module 2110 in any suitable manner as described herein. In some embodiments, the first module 2110 is an isolation module 2110, for example, to isolate one or more target nucleic acids from a biological sample. In some embodiments, the first module 2110 is used for RNA isolation and first strand cDNA synthesis. In this embodiment, the first volume 2163 includes an isolation reagent and reagents for a reverse transcription (RT) reaction. In some embodiments, for example, the first module 2110 and the third module 2200 can be separately constructed and coupled together such that the first module 2110 and the third module 2200 are modularly arranged. In such a modular arrangement, different configurations of the first module 2110 and the third module 2200 can be used with each other. The different configurations of the first module 2110 and/or the third module 2200 can include different reagents and/or different structures within the first module 2110 and/or the third module 2200. As shown in FIG. 3, a portion of the third module 2200 is disposed within the second chamber 2190 of the first module 2110 such that the reaction chamber 2262 and the second volume 2213 are each in fluid communication with the second chamber 2190. In other embodiments, the reaction chamber 2262 and/or the second volume 2213 can be selectively placed in fluid communication with the second chamber 2190. Said another way, in some embodiments, the first module 2110 and/or the third module 2200 can include any suitable mechanism, such as a valve and/or any suitable fluid control and/or transfer mechanism as described herein, that can place the reaction chamber 2262 and/or the second volume 2213 in selective fluid communication with the second chamber 2190. In some embodiments, substances and/or samples can be transferred between the second chamber 2190, and the reaction chamber 2262 and/or the second volume 2213 using any suitable fluid transfer mechanism as described herein. For example, in use, samples, reagents, and/or other supporting materials can be transferred into or out of the reaction chamber 2262 in connection with a desired reaction. In yet other embodiments, the reaction chamber 2262 and/or the second volume 2213 can be fluidically isolated from the second chamber 2190, for example, by a puncturable member or a selective transfer mechanism as described herein (not shown).

In some embodiments, the cartridge 2001 can be used to perform sample preparation, nucleic acid isolation and/or Polymerase Chain Reactions (PCRs) on the sample. In such embodiments, a target nucleic acid can be isolated from the sample within the first module 2110. The isolated nucleic acid can be RNA, DNA, or a combination thereof. As described above, if RNA is isolated, prior to PCR, a reverse transcription reaction is carried out in the cartridge 2001, for example in the first chamber 2114 or the second chamber 2190. The isolated nucleic acid (or newly synthesized cDNA if RNA was isolated) can then be amplified (e.g., using PCR) in the third module 2200, as described herein, for example, a real time PCR with a DNA oligonucleotide probe comprising a fluorophore and MGB at the 5'-end and a non-fluorescent quencher at the 3'-end. The modular arrangement of the cartridge 2001 allows any number of different third modules 2200 that each contain, for example, different reagents and/or that are each configured to amplify a different type of sample, to be used with the first module 2110, or vice-versa. In some embodiments, the cartridge 2001 can be manipulated by any of the instruments and/or methods described herein to facilitate the occurrence of a PCR process within the reaction chamber 2262. In such embodiments, the third module 2200 can be coupled to and/or placed in contact with a heat transfer apparatus to allow the contents of the reaction chamber 2262 to be thermally cycled in connection with the PCR process. In such embodiments, the third module 2200 can be further operatively coupled to an optical apparatus to monitor the PCR process. In other embodiments, the third module 2200 and/or the first module 2110 can be operatively coupled to other energy sources such as a source of optical energy, ultrasonic energy, magnetic energy, hydraulic energy or the like to facilitate a reaction and/or an isolation process occurring therein.

Although FIG. 3 shows the integrated cartridge 2001 as defining one first volume 2163 and one second volume 2213, in some embodiments, the integrated cartridge 2001 can define any number of the first volumes 2163 and/or the second volumes 2213 to contain any number of different substances and/or perform additional functionalities. For example, first volumes 2163 and/or second volumes 2213 can contain separate wash buffers, elution buffers, reagents for a reverse transcription reaction, PCR reagents, lysis buffer.

Figure 4:
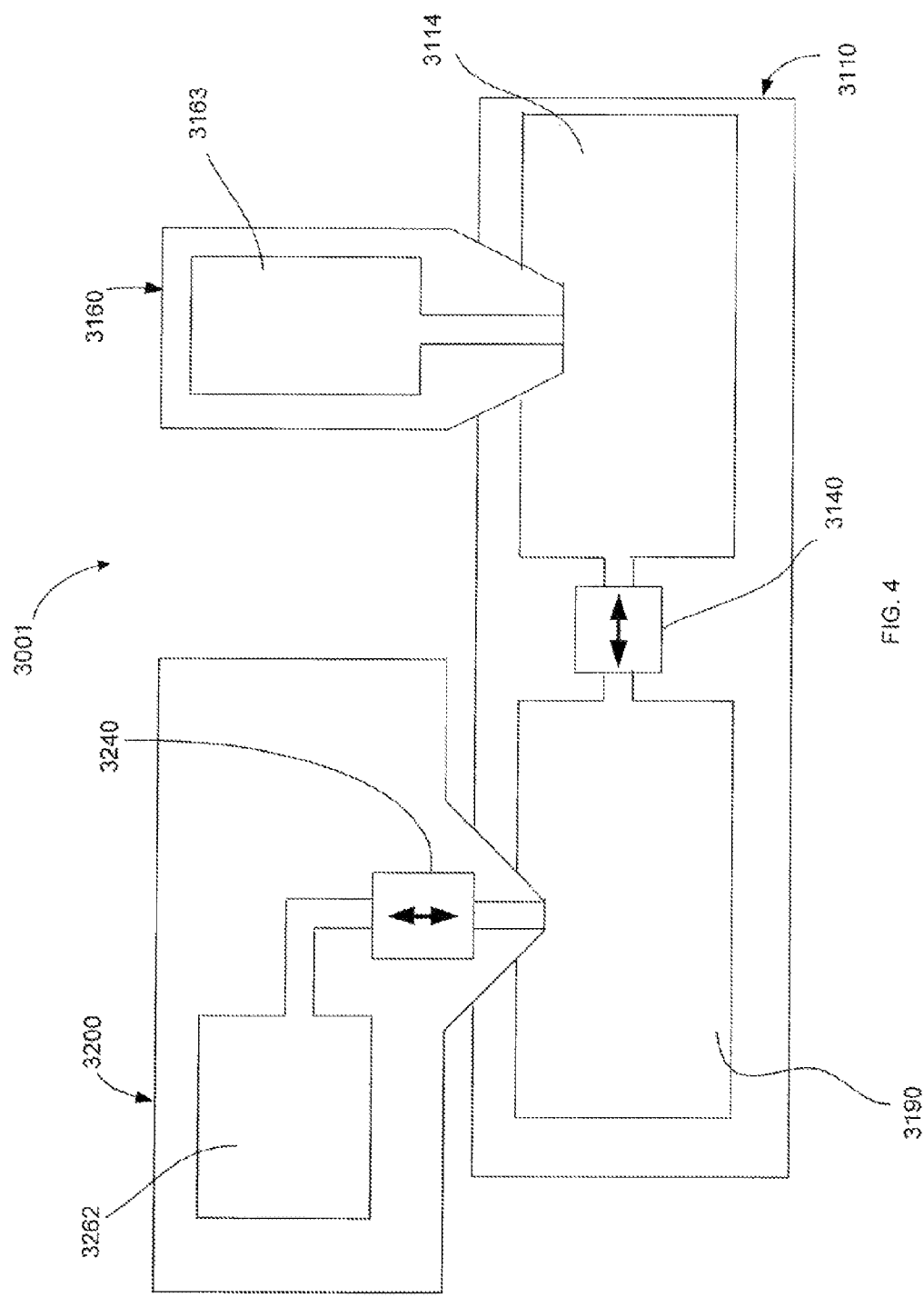
FIG. 4 is a schematic illustration of a cartridge having a first module, a second module and a third module, according to an embodiment.

As described above, in some embodiments, any of the cartridges described herein can include one or more transfer mechanisms configured to transfer a sample between various chambers defined within the cartridge. For example, FIG. 4 is a schematic illustration of a cartridge 3001 according to an embodiment that includes a first module 3110, a second module 3160 and a third module 3200. The first module 3110 defines a first chamber 3114 and a second chamber 3190. In some embodiments, the first module 3110 serves as an isolation module, for example, to isolate one or more target nucleic acids, a population of nucleic acids (e.g., total RNA, total DNA, mRNA), or target peptides or proteins from a biological sample. The first chamber 3114 and/or the second chamber 3190 can contain any biological sample, for example a biological sample containing a target nucleic acid, such as, for example, urine, blood, other materials containing tissue samples or the like. A first transfer mechanism 3140 is disposed between the first chamber 3114 and the second chamber 3190.

In some embodiments, the first transfer mechanism 3140 can be a selective transfer mechanism to selectively transfer samples and/or substances between the first chamber 3114 and the second chamber 3190. In such embodiments, for example, the first transfer mechanism 3140 can transfer samples and/or substances with particular properties between the first chamber 3114 and the second chamber 3190, while limiting and/or preventing the transfer of samples and/or substances having different properties between the first chamber 3114 and/or the second chamber 3190. In some embodiments, the first transfer mechanism 3140 can be an apparatus using magnetic components to transfer samples and/or substances based on the magnetic properties of the samples and/or substances. In other embodiments, the first transfer mechanism 3140 can transfer samples and/or substances based on the electric surface charge of the samples and/or substances, such as, for example, by the use of electrophoresis. In yet other embodiments, the first transfer mechanism 3140 can transfer samples and/or substances based on the sizes of the molecules or ions within the samples and/or substances. In such embodiments, the first transfer mechanism 3140 can include a reverse osmosis mechanism for selectively transferring samples and/or substances. Said another way, in some embodiments, the first transfer mechanism 3140 can rely on and/or produce a force, including for example, a magnetic force, an electrostatic force, a pressure or the like, to act on the targeted samples and/or substances and/or the molecules and/or ions therein. The first transfer mechanism 3140 can also include any suitable structures and/or can combine multiple selective transfer mechanisms (e.g., to impart additional physical motions and/or to provide additional selectivity). In some embodiments, the first transfer mechanism 3140 can selectively transfer certain molecules or ions between the first chamber 3114 and the second chamber 3190, while maintaining substantial fluid isolation between the first chamber 3114 and the second chamber 3190. In some embodiments, the first transfer mechanism 3140 can be a magnetic valve as disclosed in U.S. Pat. No. 7,727,473, entitled "CASSETTE FOR SAMPLE PREPARATION," filed Oct. 17, 2006, which is incorporated herein by reference in its entirety. In yet other embodiments, the first transfer mechanism 3140 can non-selectively transfer the substances and/or samples between the first chamber 3114 and the second chamber 3190.

The second module 3160 defines a first volume 3163 that can fully or partially contain any biological or chemical substance such as, for example, a mineral oil, nucleic acid isolation reagent, reverse transcription reagent, elution buffer, lysis buffer, wash buffer, a reagent, or the like that can participate in and/or otherwise support reaction within the first chamber 3114 and/or any other portion of the cartridge 3001. The second module 3160 can be coupled to the first module 3110 in any suitable manner as described herein. In some embodiments, for example, the first module 3110 and the second module 3160 can be separately constructed and coupled together such that the first module 3110 and the second module 3160 are modularly arranged. In such a modular arrangement, different configurations of the first module 3110 and the second module 3160 can be used with each other. The different configurations of the first module 3110 and/or the second module 3160 can include different reagents and/or different structures within the modules. As shown in FIG. 4, a portion of the second module 3160 is disposed within the first chamber 3114 of the first module 3110 such that the first volume 3163 is in fluid communication with the first chamber 3114. In other embodiments, the first volume 3163 can be selectively placed in fluid communication with the first chamber 3114. Said another way, in some embodiments, the first module 3110 and/or the second module 3160 can include any suitable mechanism, such as a valve and/or any suitable fluid control and/or transfer mechanism as described herein, that can selectively place the first volume 3163 in fluid communication with the first chamber 3114. In some embodiments, substances and/or samples can be transferred using any suitable fluid transfer mechanism as described herein between the first volume 3163 and the first chamber 3114. For example, in use, samples, reagents, and/or other supporting materials can be transferred into or out of the first chamber 3114 in connection with a desired reaction. In yet other embodiments, the first volume 3163 can be fluidically isolated from the first chamber 3114, for example, by a puncturable member or a selective transfer mechanism as described herein (not shown).

The third module 3200 defines a reaction chamber 3262. The reaction chamber 3262 can fully or partially contain any biological or chemical substance such as a mineral oil, reverse transcription reagent, elution buffer, lysis buffer, PCR reagent (e.g., Taq polymerase, primers, DNA oligonucleotide probe for monitoring the reaction, $Mg^{2+}$), wash buffer, a reagent, or the like that participates in or otherwise supports reaction within the reaction chamber 3262 and/or any other portion of the cartridge 3001. The third module 3200 can be coupled to the first module 3110 in any suitable manner as described herein. In some embodiments, for example, the first module 3110 and the third module 3200 can be separately constructed and coupled together such that the first module 3110 and the third module 3200 are modularly arranged. In such a modular arrangement, different configurations of the first module 3110 and the third module 3200 can be used with each other. The different configurations of the first module 3110 and/or the third module 3200 can include different reagents and/or different structures within the modules. As shown in FIG. 4, a portion of the third module 3200 is disposed within the second chamber 3190 of the first module 3110 such that the reaction chamber 3262 can each be in fluid communication with the second chamber 3190 subject to the control of the second transfer mechanism 3240.

The second transfer mechanism 3240 can transfer the substance and/or reagent from the second chamber 3190 to the reaction chamber 3262 or vice versa. In some embodiments, for example, the second transfer mechanism can transfer a predetermined volume of the substance and/or reagent between the second chamber 3190 and the reaction chamber 3262. Similarly stated, in some embodiments, the second transfer mechanism 3240 can transfer the substance and/or reagent between the second chamber 3190 and the reaction chamber 3262 at a predetermined volumetric flow rate. In some embodiments, for example, the second transfer mechanism 3240 can be a pump configured to apply a positive pressure or vacuum on the second chamber 3190 and/or the reaction chamber 3262. In such embodiments, the second transfer mechanism 3240 can be a pump actuated by a plunger using any of the instruments and/or methods described herein. In some embodiments, the second transfer mechanism 3240 can have a puncturable member as described herein, such that the second transfer mechanism 3240 can puncture, break, sever and/or rupture the puncturable member to transfer the substance and/or sample contained in the reaction chamber 3262 into the second chamber 3190 or vice versa. In other embodiments, for example, the second transfer mechanism 3240 can be capillary flow control device. In yet other embodiments, the second transfer mechanism 3240 can be any other selective or non-selective transfer mechanism as described herein.

In some embodiments, the cartridge 3001 can be used to perform sample preparation, nucleic acid isolation, reverse transcription (if RNA is first isolated), and/or Polymerase Chain Reactions (PCRs) on the sample. In such embodiments, a target nucleic acid can be isolated from the sample within the first module 3110. The isolated nucleic acid can then be amplified (e.g., using PCR) in the third module 3200, as described further below. As described herein, PCRs on multiple targets can be monitored in real time with a cartridge of the invention, for example cartridge 3001. In one embodiment, amplification of multiple targets takes place with the DNA oligonucleotide probes disclosed by Lukhtanov et al. (Nucleic Acids Research 35, p. e30, 2007). The modular arrangement of the cartridge 3001 allows any number of different third modules 3200 that each contain, for example, different reagents and/or that are each configured to amplify a different type of sample, to be used with an first module 3110, and vice-versa. In some embodiments, the cartridge 3001 can be manipulated by any of the instruments and/or methods described herein to facilitate the occurrence of a PCR process within the reaction chamber 3262. In such embodiments, the third module 3200 can be coupled to and/or placed in contact with a heat transfer apparatus to allow for the contents of the reaction chamber 3262 to be thermally cycled in connection with the PCR process. In such embodiments, the third module 3200 can be further operatively coupled to an optical apparatus monitor the PCR process. In other embodiments, the third module 3200 and/or the first module 3110 can be operatively coupled to other energy sources such as optical energy, ultrasonic energy, magnetic energy, hydraulic energy or the like to facilitate a reaction and/or an isolation process occurring therein.

Figure 5:
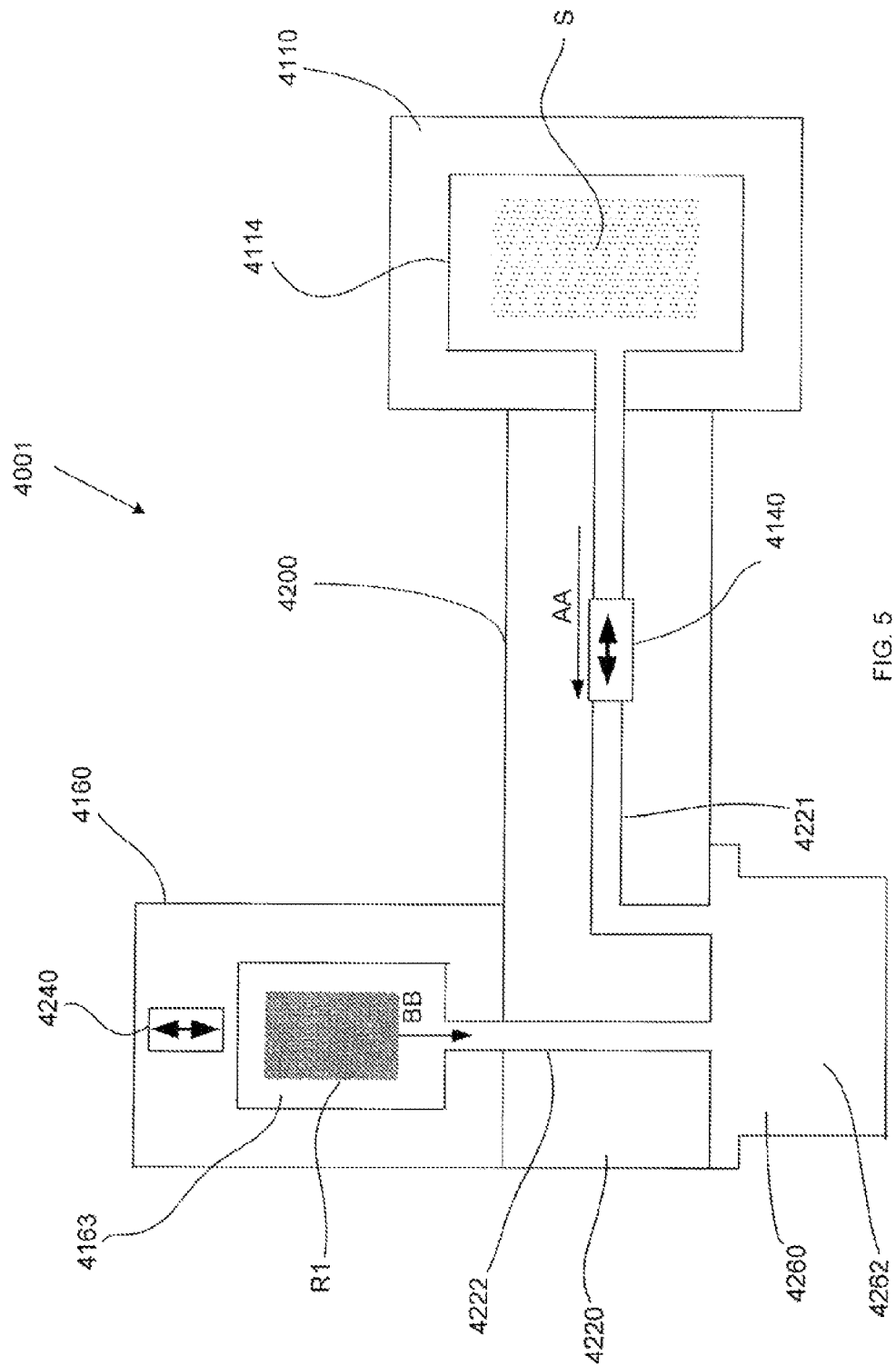
FIG. 5 is a schematic illustration of a cartridge having a first module and a second module, according to an embodiment.

Although in one embodiment, the cartridge 3001 shown and described in relation to FIG. 4 includes a first module, a second module and a third module, in other embodiments, a cartridge can include two modules coupled together. For example, FIG. 5 is a schematic illustration of a portion of a cartridge 4001 according to an embodiment that includes a first module 4200 and a second module 4160. The portion of the cartridge 4001 can be coupled to an isolation module 4110, as shown in FIG. 5. The first module 4200 includes a reaction vial 4260, a substrate 4220, and a first transfer mechanism 4140. The reaction vial 4260 defines a reaction chamber 4262 that can fully or partially contain any biological or chemical sample and/or substance containing a target nucleic acid, such as, for example, urine, blood, other materials containing tissue samples or the like, and/or mineral oil, wash buffer, lysis buffer, reverse transcription reagent, PCR reagent, a reagent, or the like that participates in or otherwise supports reaction within the reaction chamber 4262 and/or any other portion of the cartridge 4001.

The reaction vial 4260 can be any suitable container for containing a sample, e.g., a nucleic acid sample, isolated or otherwise, in a manner that permits a reaction associated with the sample to occur. In some embodiment, the reaction vial 4260 can have a thin wall configured to be received within and/or disposed against a heating element and/or a block (see e.g., block 1710 described below). The reaction vial 4260 can be constructed from any suitable materials with certain properties to be compatible with a desired reaction and/or process. In some embodiments, the reaction vial 4260 can be constructed from a substantially thermally conductive material to allow thermal cycling of the substances and/or samples within the reaction vial 4260. In some embodiments, the reaction vial 4260 can be constructed from a substantially mechanically robust material such that the sidewall of the reaction vial 4260 substantially retains its shape and/or size when a positive pressure or vacuum acts on the volume within the reaction vial 4260. In some embodiments, the reaction vial 4260 can be constructed from a substantially chemically inert material to the reaction within the reaction vial 4260 such that the material forming the reaction vial 4260 would not contaminate or otherwise affect the reaction within the reaction vial 4260.

The reaction vial 4260 can also be any suitable container for containing the sample in a manner that permits the monitoring of such a reaction (e.g., the detection of an analyte within the sample that results from or is associated with the reaction). In some embodiments, for example, the reaction vial 4260 can be a PCR vial, a test tube, a microcentrifuge tube, or the like. Moreover, in some embodiments, at least a portion of the reaction vial 4260 can be substantially transparent to allow optical monitoring of a reaction occurring therein.

In some embodiments, the reaction vial 4260 can be integrally constructed with the substrate 4220. In other embodiments, the reaction vial 4260 and can be coupled to the substrate 4220 by any suitable mechanism as described herein.

The substrate 4220 defines at least a portion of a first flow path 4221 and a second flow path 4222. The first flow path 4221 is configured to be in fluid communication with the reaction chamber 4262 and an isolation chamber 4114 of an isolation module 4110. The first transfer mechanism 4140 is configured to transfer a sample S (or portion thereof), from the isolation chamber 4114 to the reaction chamber 4262 (as shown by the arrow AA) when the first transfer mechanism 4140 is actuated. The substrate 4220 can define the portion of the first flow path 4221 and the second flow path 4222 using any suitable structure, material and/or manufacturing process. In some embodiments, the substrate 4220 can be a single layer. In other embodiments, the substrate 4220 can be constructed from multiple, separate layers of material fabricated and coupled together to define the structure and flow paths. In some embodiments, the substrate 4220 can be constructed using processes, including for example, chemical etching, mechanical and/or ion milling, embossing, lamination, and/or silicon bonding. In some embodiments, at least a portion of substrate 4220 can be configured thereon with, disposed within and/or in contact with a heating element such that in use, the portion of the substrate defining first flow path and/or second flow path can be heated. For example, in some embodiments, the substrate 4220 can be disposed within any of the instruments disclosed herein, and can heat the first flow path 4221 and a second flow path 4222 such that a substance contained therein (e.g., a portion of a sample being transferred between the isolation chamber 4114 and the reaction chamber 4262) can be heated to and/or maintained at a temperature of approximately greater than 50° C. As described in more detail herein, this arrangement facilitates a "hot start" transfer of substances and or reagents associated with a PCR process.

The first transfer mechanism 4140 is at least partially contained within the first module 4200 and is configured to facilitate the transfer of the sample S, from the isolation chamber 4114 to the reaction chamber. In some embodiments, the first transfer mechanism 4140 can facilitate the transfer of the sample S, while maintaining fluid isolation between the first flow path 4221 and regions outside of the first module 4200. For example, in some embodiments, the first transfer mechanism 4140 can be any mechanism that produces a force and/or facilitates the transfer of the sample S without the addition of a substance from a region outside of the first module 4200 (e.g., without the addition of a compressed gas or the like). This arrangement reduces potential contamination, improves process automation and/or otherwise improves the speed and/or the accuracy of the transfer of the sample S. For example, the transfer of the sample S can be programmed to proceed at different time steps, at each time step transferring different quantities of the sample S. Improving the accuracy of the transfer of the sample S can also improve the quality of the PCR analysis. The first transfer mechanism can be any suitable mechanism as described herein. For example, in some embodiments, the first transfer mechanism 4140 can be a selective transfer mechanism to selectively transfer sample S between the isolation chamber 4114 and the reaction chamber 4262. In some embodiments, the first transfer mechanism 4140 can apply magnetic, electrostatic and/or pressure forces to effect the transfer of sample S.

The first module 4200 can be coupled to the isolation module 4110 in any suitable manner as described herein to allow fluid communication between the first module 4200 and the isolation module 4110. In some embodiments, for example, the first module 4200 and the isolation module 4110 can be separately constructed and coupled together such that the first module 4200 and the isolation module 4110 are modularly arranged. In such a modular arrangement, different configurations of the first module 4200 and the isolation module 4110 can be used with each other. The different configurations of the first module 4200 and/or the isolation module 4110 can include different reagents and/or different structures within the modules.

The second module 4160 includes a second transfer mechanism 4240 and defines a volume 4163 configured to contain a substance R1. As used herein, substance R1 and substance R2 can refer to one or more reagents. The substance R1 can be any biological or chemical substance such as, for example, a mineral oil, wash buffer, a florescent dye, lysis buffer, wash buffer, elution buffer, reverse transcription reagent, PCR reagent (e.g., one or more of a Taq polymerase, primers, DNA hybridization probes such as the probes described by Lukhtanov et al. (2007). Nucleic Acids Research 35, p. e30), a reagent or the like. Although FIG. 5 shows the second module 4160 including one volume 4163, in other embodiments the second module 4160 can include any number of volumes 4163 and/or containers within which various substances (including the substance R1 and/or different substances) can be stored. The second module 4160 is configured to be coupled to the first module 4200 such that the volume 4163 can be selectively placed in fluid communication with the reaction chamber 4262 via the second flow path 4222. The second transfer mechanism 4240 is configured to transfer at least a portion of the substance R1 from the volume 4163 to the reaction chamber 4262 (as shown by the arrow BB) when the second transfer mechanism 4240 is actuated.

The second transfer mechanism 4240 can transfer the substance R1 from the second volume 4163 to the reaction chamber 4262 or vice versa. In some embodiments, for example, the second transfer mechanism can transfer a predetermined volume of the substance R1 between the second volume 4163 and the reaction chamber 4262. In some embodiments, for example, the second transfer mechanism can transfer the substance R1 at a predetermined volumetric flow rate between the second volume 4163 and the reaction chamber 4262. In some embodiments, for example, the second transfer mechanism 4240 can be a pump configured to apply a positive pressure or vacuum on the second volume 4163 and/or the reaction chamber 4262. In such embodiments, the second transfer mechanism 4240 can be a pump actuated by a plunger using any of the instruments and/or methods described herein. In some embodiments, the second transfer mechanism 4240 can have a puncturable member as described herein, such that while in use, the second transfer mechanism 4240 can puncture, break, sever and/or rupture the puncturable member and transfer the substance and/or sample contained in the reaction chamber 4262 into the second volume 4163 or vice versa. In some other embodiments, for example, the second transfer mechanism 4240 can be capillary flow control device. In yet other embodiments, the second transfer mechanism 4240 can be any other transfer mechanism as described herein.

In some embodiments, the cartridge 4001 can be used to perform sample preparation, nucleic acid isolation and/or Polymerase Chain Reactions (PCRs) on the sample, or an isolated portion thereof (e.g., an isolated nucleic acid sample). In such embodiments, the isolation module 4110 can isolate a target nucleic acid from the sample contained therein. The isolated nucleic acid can then be amplified (e.g., using PCR) in the reaction chamber 4262, as described further below. Alternatively or additionally, if RNA is isolated, a reverse transcription reaction can be carried out in the reaction chamber 4262. In another embodiment, if RNA is isolated, an integrated reverse transcription-PCR reaction is carried out in one of the reaction chambers, for example reaction chamber 4262. The modular arrangement of the cartridge 4001 allows any number of different second modules 4160 that each contain, for example, different reagents and/or that are each configured to amplify a different type of sample, or isolate a different type of sample, to be used with the first module 4200, and vice versa. In some embodiments, the cartridge 4001 can be manipulated by any of the instruments and/or methods described herein to facilitate the occurrence of an amplification process, e.g., a PCR process, within the reaction chamber 4262. In such embodiments, the reaction vial 4260 can be coupled to and/or placed in contact with a heat transfer apparatus to allow for the contents of the reaction chamber 4262 to be thermally cycled in connection with the PCR process. In such embodiments, the reaction vial 4260 can be further operatively coupled to an optical apparatus to monitor the PCR process. In other embodiments, the reaction vial 4260 and/or the isolation module 4110 can be operatively coupled to other energy sources such as optical energy, ultrasonic energy, magnetic energy, hydraulic energy or the like to facilitate a reaction and/or an isolation process occurring therein.

Figure 6:
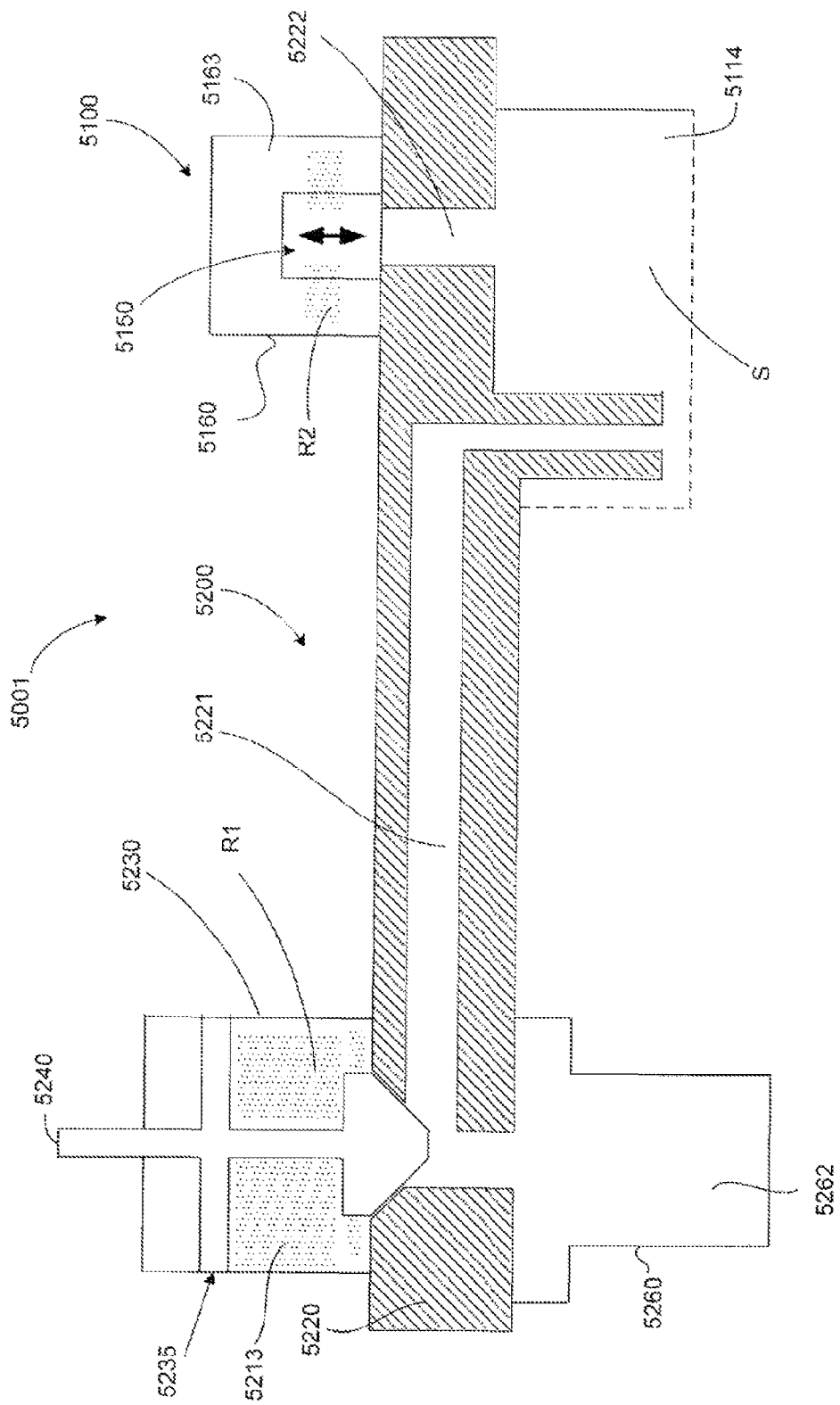
FIGS. 6 and 7 are a schematic illustrations of a portion of a cartridge, according to an embodiment, in a first configuration and a second configuration, respectively.
Figure 7:
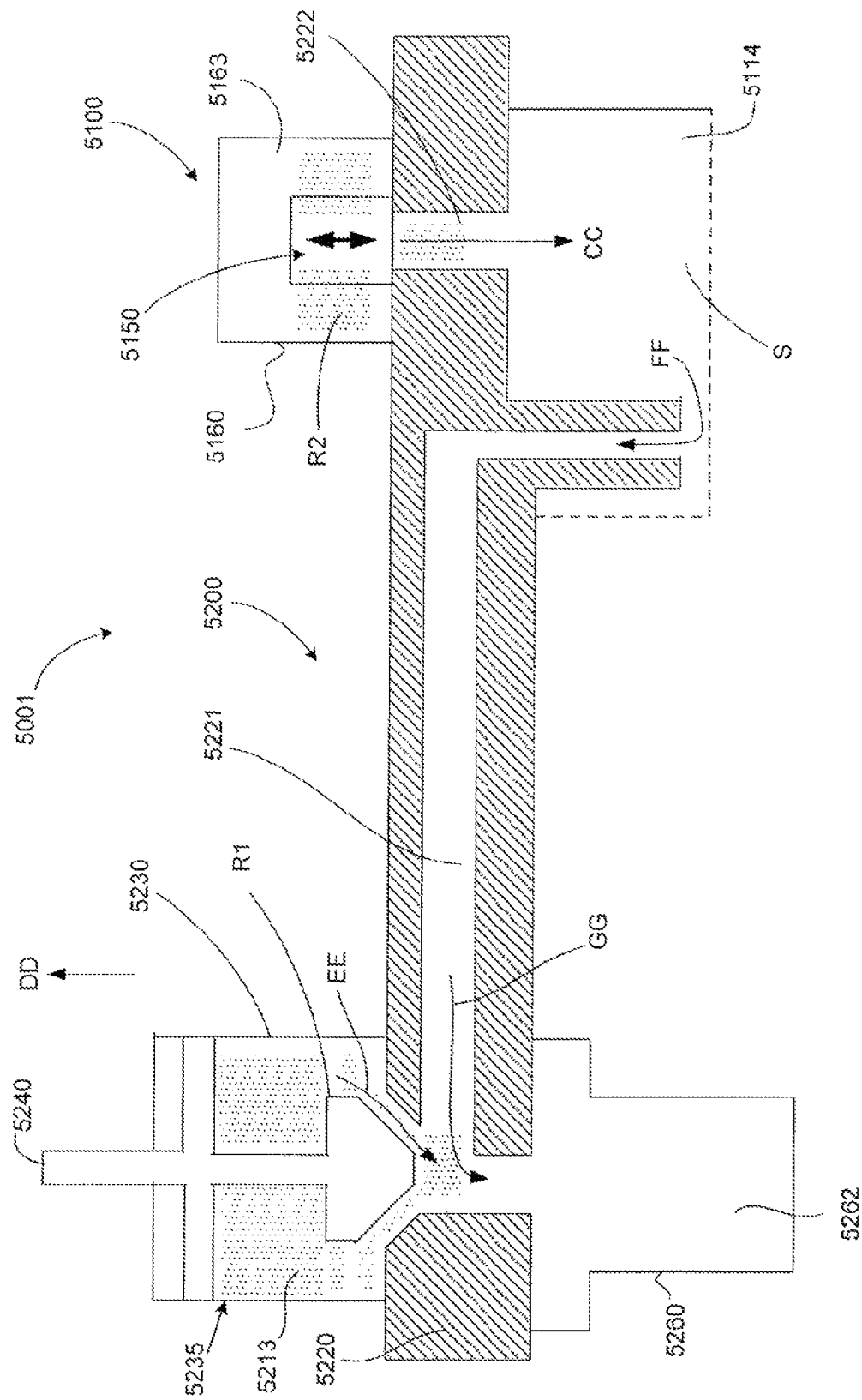

FIGS. 6 and 7 are schematic illustration of a portion of cartridge 5001 according to an embodiment in a first configuration and a second configuration, respectively. The portion of the cartridge 5001 includes a first module 5200 and second module 5100. The first module 5200 includes a reaction vial 5260, a substrate 5220 and a first transfer mechanism 5235. The reaction vial 5260 defines a reaction chamber 5262 that can contain a sample in a manner that permits a reaction associated with the sample S to occur. The reaction vial 5260 can have any suitable shape and/or size, and can be constructed using any suitable materials, as described herein. In some embodiments, for example, the reaction vial 5260 can be a PCR vial, a test tube or the like.

The first transfer mechanism 5235 includes a plunger 5240 movably disposed within a housing 5230 such that the housing 5230 and the plunger 5235 define a first volume 5213. The first volume 5213 contains a first substance R1. The first substance R1 can be, for example, a reagent (e.g., a PCR reagent such as Taq polymerase, primers, DNA hybridization probes such as the ones described above, or a combination thereof), a reverse transcription reagent, a mineral oil or the like. The plunger 5240 can be actuated by any suitable mechanism, such as, for example, any of the instruments described herein.

The substrate 5220 defines at least a portion of a first flow path 5221 and a second flow path 5222. The first flow path 5221 is configured to be in fluid communication with the reaction chamber 5262, the first volume 5213 and an isolation chamber 5114 of an isolation module 5110 (shown in FIG. 6 in dotted line format). The second flow path 5222 is configured to be in fluid communication with the isolation chamber 5114. The isolation chamber 5114 can be any suitable isolation chamber and/or isolation module of the types shown and described herein. Moreover, the isolation chamber 5114 can be coupled to the first module 5200 in any suitable manner as described herein. In some embodiments, the isolation chamber 5114 can be coupled to the first module 5200 and modularly arranged as described herein. The removable coupling between the isolation chamber 5114 and the first module 5200 can be fluid-tight using any suitable mechanism as described herein.

The second module 5100 includes a second transfer mechanism 5150 and defines a second volume 5163 configured to contain a second substance R2. The second module 5100 is configured to be coupled to the first module 5200 such that the second volume 5163 can be selectively placed in fluid communication with the isolation chamber 5114 via the second flow path 5222. The second module 5100 can include any mechanism and/or device configured to selectively place the second volume 5163 in fluid communication with the isolation chamber 5114 and/or the second flow path 5222. For example, in some embodiments, the second module 5100 can include a puncturable member that defines a portion of a boundary of the second volume 5163 and that fluidically isolates the second volume 5163 from the isolation chamber 5114 and/or the second flow path 5222. In other embodiments, the second module 5100 can include a valve configured to selectively place the second volume 5163 in fluid communication with the isolation chamber 5114 and/or the second flow path 5222.

The second transfer mechanism 5150 is configured to transfer at least a portion of the second substance R2 from the second volume 5163 into the isolation chamber 5114 when the second transfer mechanism 5150 is actuated. The second transfer mechanism 5150 can be any suitable transfer mechanism as described herein. For example, in some embodiments, the second transfer mechanism 5150 can apply magnetic, electrostatic and/or pressure forces to effect the transfer of the substance R2 from the second volume 5163 to the isolation chamber 5114. In some embodiments, for example, the second transfer mechanism 5250 can be a pump actuated by a plunger using any of the instruments and/or methods described herein. In some other embodiments, for example, the second transfer mechanism 5250 can be capillary flow control device.

The cartridge 5001 can be moved between at least a first configuration (FIG. 6) and second configuration (FIG. 7) to facilitate a reaction and/or assay involving a sample S, which is initially disposed in the isolation chamber 5114. When the cartridge 5001 is in the first configuration, the plunger 5240 is in a first position within the housing 5230 such that a portion 5246 of the plunger 5240 is disposed within the first flow path 5221. Thus, when the cartridge 5001 is in the first configuration, the first volume 5213 is fluidically isolated from the reaction chamber 5262. In this manner, when the cartridge 5001 is in the first configuration, the first substance R1 is maintained within the first volume 5213 and is prevented from being conveyed into the reaction chamber 5262 (e.g., by leakage, gravity feed, capillary action or the like). Moreover, when the cartridge 5001 is in the first configuration, the second volume 5163 is fluidically isolated from the second flow path 5222 and the isolation chamber 5114. In this manner, when the cartridge 5001 is in the first configuration, the second substance R2 is maintained within the second volume 5163 and is prevented from being conveyed into the isolation chamber 5114 (e.g., by leakage, gravity feed, capillary action or the like).

The cartridge 5001 is moved to the second configuration (FIG. 7) by placing the second volume 5163 in fluid communication with the isolation chamber 5114 via the second flow path 5222, actuating the second transfer mechanism 5150 to convey at least a portion of the second substance R2 into the isolation chamber 5114 (as shown by the arrow CC in FIG. 7), and actuating the first transfer mechanism 5235. More particularly, the second volume 5163 can be placed in fluid communication with the isolation chamber 5114 via the second flow path 5222 by any suitable mechanism, such as, for example by puncturing a puncturable member, actuating a valve or the like. In some embodiments, the second volume 5163 can be placed in fluid communication with the isolation chamber 5114 by actuating the second transfer mechanism 5150. In this manner, the second volume 5163 can be placed in fluid communication with the isolation chamber 5114 and a portion of the second substance R2 can be conveyed into the isolation chamber 5114 in one operation and/or in response to a single actuation event.

The first transfer mechanism 5235 is actuated by moving the plunger 5240 within the housing 5230 as shown by the arrow DD in FIG. 7. Similarly stated, when the first transfer mechanism 5235 is actuated, the plunger 5240 is moved within the housing 5230 from a first position (as shown in FIG. 6) to a second position (as shown in FIG. 7). Thus, when the first transfer mechanism 5235 is actuated, the portion 5246 of the plunger 5240 is at least partially removed from the first flow path 5221, thereby placing the first volume 5213 in fluid communication with the reaction chamber 5262 via the first flow path 5221. In this manner, a portion of the first substance R1 can be conveyed from the first volume 5213 into the reaction chamber 5262, as shown by the arrow EE in FIG. 7.

Moreover, when the plunger 5240 is moved from the first position to the second position, a vacuum is produced within the reaction chamber 5262. This pressure differential within the cartridge 5001 (i.e., between the reaction chamber 5262 and the isolation chamber 5114) results in at least a portion of the contents of the isolation chamber 5114 (i.e., the sample S and/or the second substance R2) to be conveyed into the reaction chamber 5262 via the first flow path 5221, as shown by the arrows FF and GG in FIG. 7. In this manner substances and/or samples can be added, mixed and/or conveyed between the isolation chamber 5114 and the reaction chamber 5262 by actuating the first transfer mechanism 5235 and/or the second transfer mechanism 5150. By performing the mixing of the sample S and the substance R2 within the isolation chamber 5114 instead of transferring the sample S and the substance R2 separately into the reaction chamber 5262, an additional transfer step can be eliminated. Moreover, this arrangement and/or method can improve the mixing of the sample S and the substance R2, thereby improving the accuracy and efficiency of the reaction in the reaction chamber 5262.

Although described as occurring in a particular order, in other embodiments the operations associated with moving the cartridge 5001 from the first configuration to the second configuration can occur in any order. Moreover, in other embodiments, the cartridge 5001 can be placed in any number of different configurations involving any desired combination of the operations.

In some embodiments, the cartridge 5001 can be used to perform Polymerase Chain Reactions (PCRs) on at least a portion of the sample S (which can be, for example, one or more isolated target nucleic acids). In such embodiments, isolated nucleic acids can be amplified (e.g., using PCR) in the reaction chamber 5262, as described herein. In some embodiments, the cartridge 5001 can be manipulated by any of the instruments and/or methods described herein to facilitate the occurrence of a PCR process within the reaction chamber 5262. In such embodiments, the reaction vial 5260 can be coupled to and/or placed in contact with a heat transfer apparatus to allow for the contents of the reaction chamber 5262 to be thermally cycled in connection with the PCR process. In such embodiments, the reaction vial 5260 can be further operatively coupled to an optical apparatus to allow for the real-time monitoring of the PCR process. In other embodiments, the reaction vial 5260 and/or the second module 5100 can be operatively coupled to other energy sources such as optical energy, ultrasonic energy, magnetic energy, hydraulic energy or the like to facilitate a reaction and/or an isolation process occurring therein.

In some embodiments, the first substance R1 can include a mineral oil, wax, or the like such that after the first substance R1 is transferred into the reaction chamber 5262, the first substance R1 can form an layer on the surface of the fluid mixture (i.e., the sample S and the second substance R1) in the reaction chamber 5262. The surface layer of the first substance R1 can reduce the evaporation of the fluid mixture in the reaction chamber 5262 during the reaction process (e.g., during thermal cycling), thereby improving the efficiency, accuracy and/or control of the reaction therein. More particularly, by reducing the evaporation of the fluid mixture in the reaction chamber 5262, the relative concentrations or proportion of the different constituents in the reaction mixture can be more accurately controlled. Additionally, reducing the evaporation of the fluid mixture in the reaction chamber 5262 can also minimize condensation on the walls of the reaction vial 5260, thereby improving the accuracy of the optical monitoring or analysis of the reaction.

The mineral oil can be any mineral oil having suitable properties, such as, for example, the desired physical properties, including for example, density and/or surface tension. The mineral oil or the like can also be selected such that it is chemically inert and physically stable when exposed to the conditions within the reaction chamber 5262.

FIGS. 8-24 are various views of a cartridge 6001 according to an embodiment. In certain views, such as, for example, FIGS. 8 and 9, portions of the cartridge 6001 are shown as semi-transparent so that components and/or features within the cartridge 6001 can be more clearly shown. The cartridge 6001 includes a sample preparation (or isolation) module 6100 and an amplification (or PCR) module 6200 that are coupled together to form an integrated cartridge 6001. One or more cartridges 6001 can be disposed within any suitable instrument of the types disclosed herein (see e.g., instrument 3002 described below) that is configured to manipulate, actuate and/or interact with the cartridge 6001 to perform a nucleic acid isolation, transcription and/or amplification on a test sample contained within the cartridge 6001. The cartridge 6001 allows for efficient and accurate diagnostic testing of samples by limiting the amount of sample handling during and between the isolation, transcription and/or PCR amplification processes. Moreover, the modular arrangement of the isolation module 6100 and the amplification (or PCR) module 6200 allows any number of different PCR modules 6200, each containing different reagents and/or configured to amplify a different type of nucleic acid, to be used with any number of different isolation modules 6100, each containing different reagents and/or configured to isolate a different type of nucleic acid, and vice-versa. This arrangement also allows the isolation module 6100 and the amplification module 6200 to be separately stored. Separate storage can be useful, for example, if the reagents included within the isolation module 6100 have different storage requirements (e.g., expiration dates, lyophilization requirements, storage temperature limits, etc.) than the reagents included within the amplification module 6200.

As shown in FIG. 11, the isolation module 6100 includes a first (or isolation) housing 6110 and a second (or reagent) housing 6160 that is coupled to and/or at least partially within the first housing 6110. The second housing 6160 is not shown in FIGS. 10 and 22 for purposes of clarity. FIGS. 11-14 show the second housing 6160 and certain components contained therein, and FIGS. 15-18 show the second housing 6160 in various different stages of actuation. The second housing 6160 includes a first end portion 6161 and a second end portion 6162, and defines a series of holding chambers 6163a, 6163b, 6163c and 6163d that contain the reagents and/or other substances used in the isolation process. As described in more detail herein, the holding chambers can contain a protease (e.g., Proteinase K), a lysis solution to solubilize the bulk material, a binding solution to magnetically charge the nucleic acid sample resident within the lysing chamber 6114, and a solution of magnetic beads that bind to the magnetically charged nucleic acid to assist in the conveyance of the nucleic acid within the isolation module 6100 and/or the first housing 6110.

Figure 18:
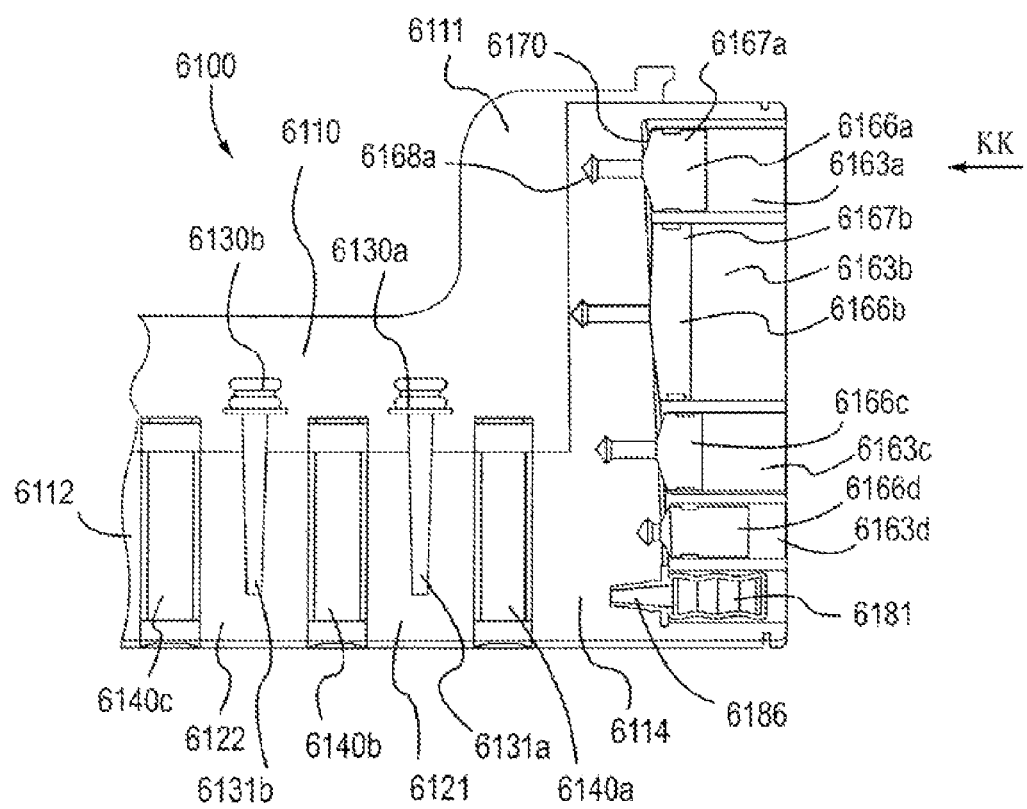
Figure 19:
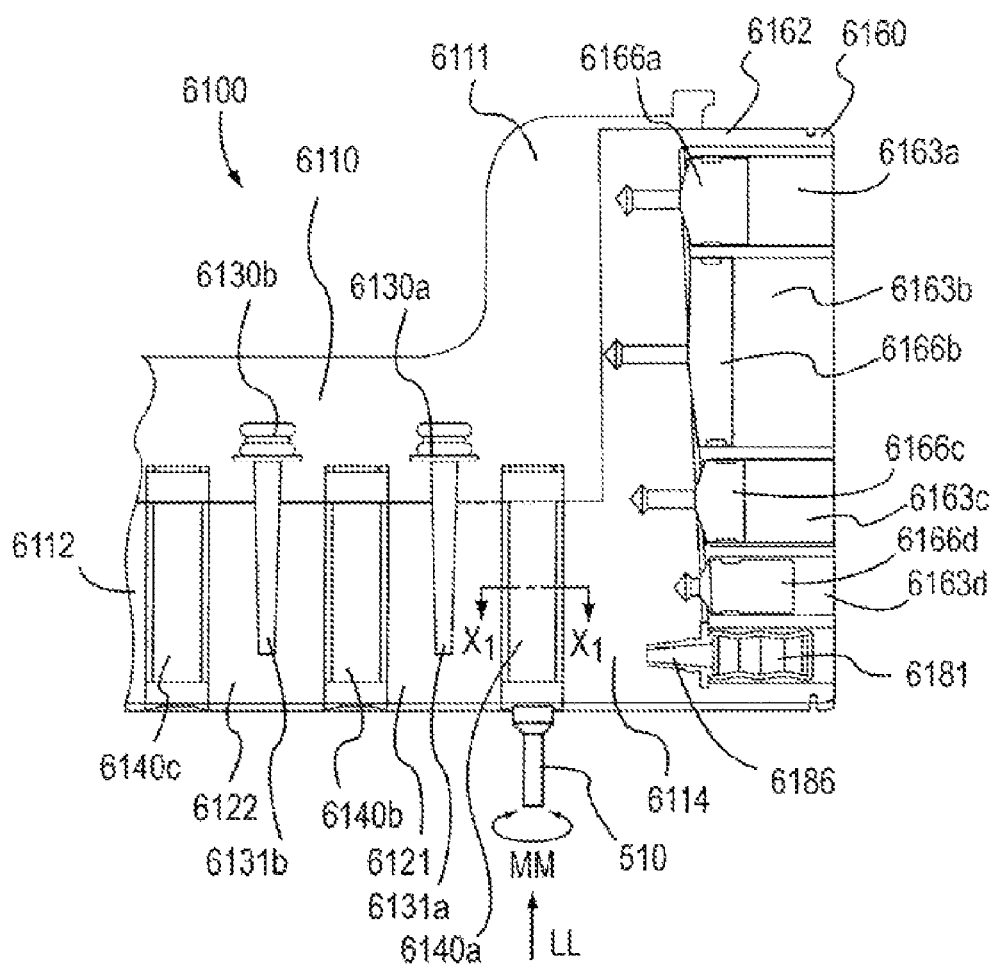
FIG. 19 is a side cross-sectional view of the isolation module of the cartridge shown in FIG. 8.

Each of the holding chambers 6163a, 6163b, 6163c and 6163d includes an actuator 6166 (see e.g., FIG. 14) movably disposed therein. More particularly, as shown in FIG. 18, an actuator 6166a is disposed within the holding chamber 6163a, an actuator 6166b is disposed within the holding chamber 6163b, an actuator 6166c is disposed within the holding chamber 6163c, and an actuator 6166d is disposed within the holding chamber 6163d. As shown in FIG. 15, a puncturable member 6170 is disposed about the second end portion 6162 of the second housing 6160 such that the internal portions of the second housing 6160, the puncturable member 6170 and the actuators 6166a, 6166b, 6166c and 6166d collectively enclose and/or define the holding chambers 6163a, 6163b, 6163c and 6163d. Similarly stated, the internal portions of the second housing 6160, the puncturable member 6170 and the actuators 6166a, 6166b, 6166c and 6166d collectively define fluidically isolated chambers 6163a, 6163b, 6163c and 6163d within which reagents and/or substances can be stored. The puncturable member 6170 can be constructed from any suitable material of the types described herein, such as any form of polypropylene. In some embodiments, the puncturable member 6170 can be constructed from biaxially oriented polypropylene (BOP).

Figure 14:
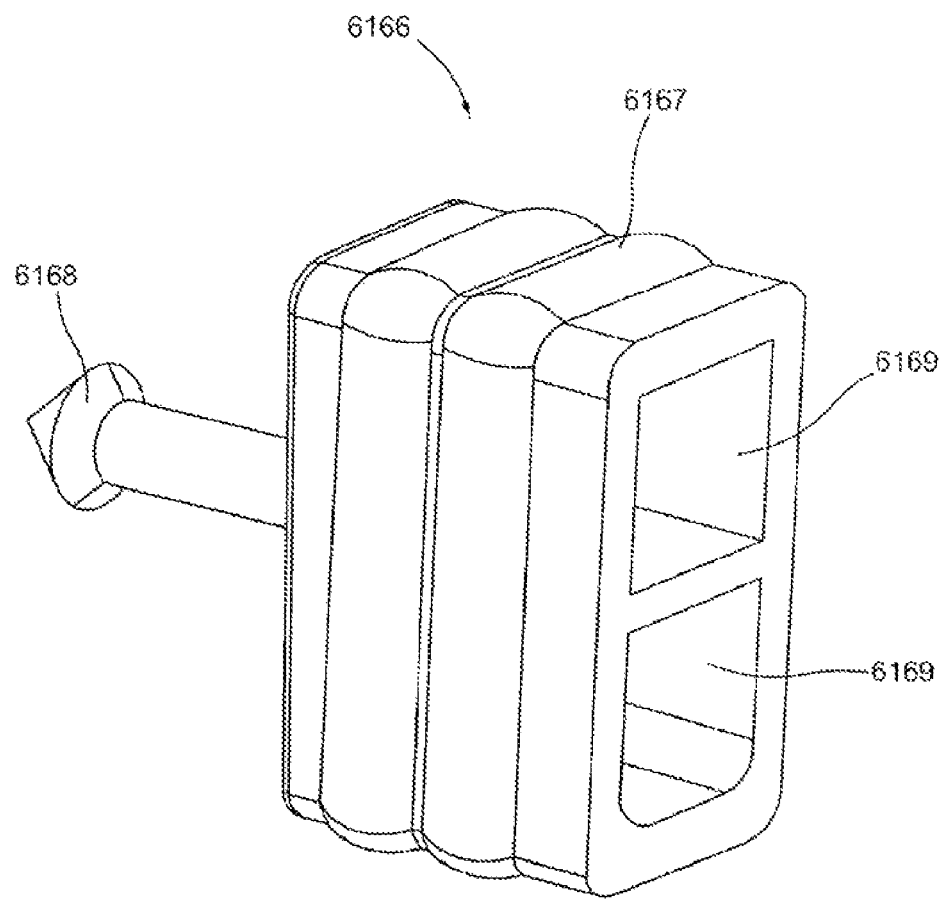
FIG. 14 is a perspective view of a portion of the reagent module shown in FIGS. 12 and 13.
Figure 15:
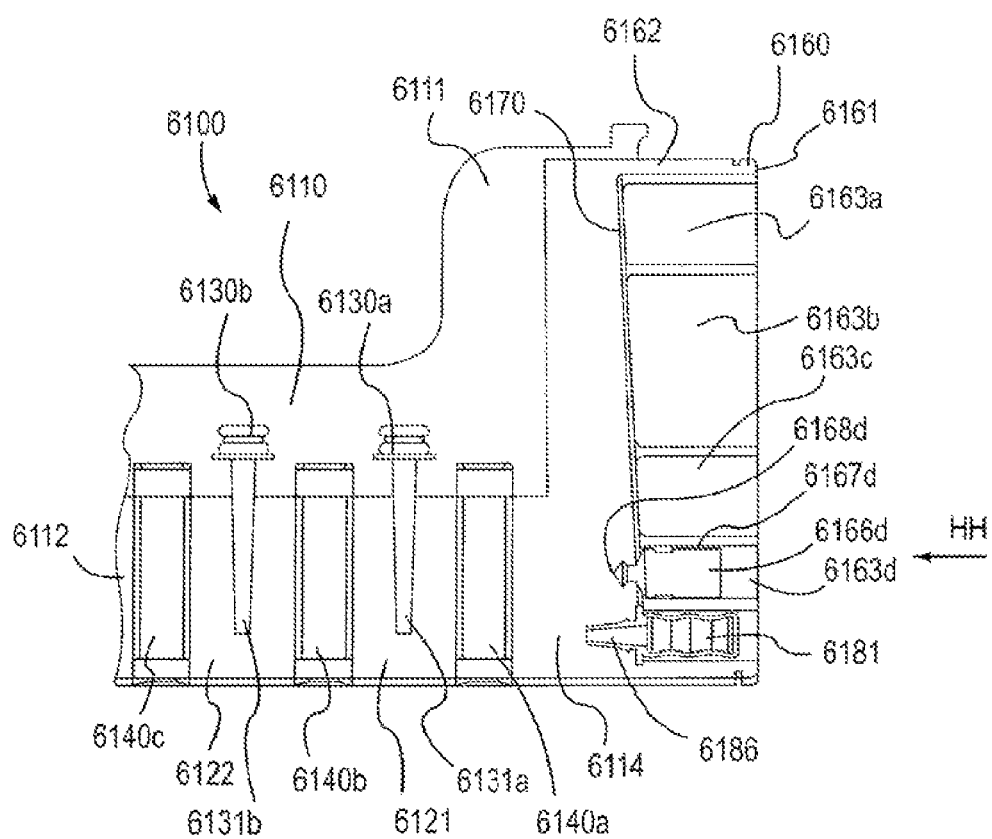
FIGS. 15-18 are side cross-sectional views of an isolation module of the cartridge shown in FIG. 8 in a first configuration, a second configuration, a third configuration and a fourth configuration, respectively.

As shown in FIG. 14, each of the actuators 6166 includes a plunger portion 6167, a piercing portion 6168 and one or more actuator openings 6169. The actuator openings 6169 are configured to receive a portion of an actuator assembly to facilitate movement of the actuator 6166 within the chamber (e.g., chamber 6163a), as described herein. In particular, the actuator openings 6169 can receive a protrusion, such as a protrusion 3446a of an actuator assembly 3400, as described below with respect to FIGS. 37-40. This arrangement allows the plunger 6166 to be actuated from the first end portion 6161 of the second housing 6160. In some embodiments, the actuator 6166 can include a retention mechanism (e.g., a protrusion, a snap ring or the like) configured to retain a protrusion of an actuator assembly (e.g., actuator assembly 3400) to facilitate reciprocal movement of the actuator 6166 by the actuator assembly.

The plunger portion 6167 of the actuator 6166 is configured to engage portion of the second housing 6160 that defines the chamber (e.g., chamber 6163a) within which the actuator 6166 is disposed such that the plunger portion 6167 and the portion of the second housing 6160 form a substantially fluid-tight and/or hermetic seal. Thus, when the actuator 6166 is disposed within the chamber (e.g., chamber 6163a), leakage and/or conveyance of the substance contained within the chamber is minimized and/or eliminated. In this manner, the end face of the plunger portion 6167 defines a portion of the boundary of the chamber (e.g., chamber 6163a). The plunger portion 6167 is also configured such that when a force is exerted on the actuator 6166 (e.g., by the actuator assembly 3400 shown and described below), the actuator 6166 will move within the chamber (e.g., chamber 6163a) to convey the substance contained within the chamber into the lysing chamber 6114, as described below. In this manner, the actuator 6166 can function as a transfer mechanism to convey substances from the chamber (e.g., chamber 6163a) into another portion of the isolation module 6100.

The piercing portion 6168 of the actuator 6166 is configured to puncture, break, sever and/or rupture a portion of the puncturable member 6170 when the actuator 6166 is moved within the chamber (e.g., chamber 6163a) to place the chamber in fluid communication with a region outside of the chamber. In this manner each of the chambers 6163a, 6163b, 6163c and 6163d can be selectively placed in fluid communication with another portion of the isolation module 6100 (e.g., the lysing chamber 6114) to allow transfer of the substance contained within each of the chambers 6163a, 6163b, 6163c and 6163d when each of the actuators 6166a, 6166b, 6166c and 6166d is actuated, as described below.

The second housing 6160 includes a mixing pump 6181, which can be actuated (e.g., by the actuator assembly 3400 of the instrument 3002) to agitate, mix and/or produce a turbulent motion within the sample, reagents and/or other substances contained with a portion (e.g., the lysing chamber 6114) of the isolation module 6100. As shown in FIG. 12, the pump 6181 includes a nozzle 6186 that can direct the flow, increase the pressure of the flow and/or increase the turbulence within the portion of the isolation module 6100 to enhance the mixing therein. Although the mixing pump 6181 is shown as a bellows-style pump, in other embodiments, the mixing pump 6181 can be any suitable mechanism for transferring energy into a solution within the lysing chamber 6114. Such mechanisms can include, for example, a piston pump, a rotating member, or the like. In some embodiments, the second housing 6160 can include any other suitable mechanism for mixing the substances within the isolation chamber 6114 to promote cell lysis of the sample contained therein and/or isolation of the nucleic acids contained therein. In some embodiments, the second housing 6160 can include an ultrasonic mixing mechanism, a thermal mixing mechanism or the like.

As shown in FIG. 11, the second housing 6160 is disposed within an opening 6115 defined by the first end portion 6111 of the first housing 6110. Thus, when the second housing 6160 is disposed within the first housing 6110, a portion of the second housing 6160 defines at least a portion of a boundary of the lysing chamber 6114. More particularly, when the second housing 6160 is disposed within the first housing 6110, the puncturable member 6170 defines a portion of the boundary of the lysing chamber 6114. This arrangement allows the substances contained within the second housing 6160 to be conveyed into the lysing chamber 6114 when a portion of the puncturable member 6170 is pierced, punctured, severed and/or broken (see, e.g., FIG. 15). Although at least a portion of the second housing 6160 is shown as being disposed within the first housing 6110 and/or the lysing chamber 6114, in other embodiments, the second housing 6160 can be coupled to the first housing 6110 without any portion of the second housing being disposed within the first housing. In yet other embodiments, a portion of the of the first housing can be disposed within the second housing when the first housing and the second housing are coupled together.

As shown in FIGS. 12 and 13, the second housing 6160 includes a seal 6172 disposed around the second end portion 6162 such that when the second housing 6160 is coupled to the first housing 6110, the seal 6172 and a portion of the side wall of the first housing 6110 collectively form a substantially fluid-tight and/or hermetic seal between the first housing 6110 and the second housing 6160. Said another way, the seal 6172 fluidically isolates the lysing chamber 6114 from a region outside of the cartridge 6001. In some embodiments, the seal 6172 can also acoustically isolate the second housing 6160 from the first housing 6110.

The first end portion 6161 of the second housing 6160 includes protrusions 6171 configured to be received within corresponding openings 6119 (see e.g., FIG. 10) defined by the first housing 6110. Thus when the second housing 6160 is disposed within the first housing 6110, the protrusions 6171 and the openings 6119 collectively retain the second housing 6160 within the first housing 6110. Similarly stated, the protrusions 6171 and the openings 6119 collectively limit movement of the second housing 6160 relative to the first housing 6110.

The modular arrangement of the first housing 6110 and the second housing 6160 allows any number of second housings 6160 (or reagent housings), each containing different reagents and/or substances to promote nucleic acid isolation, to be used with the first housing 6110 to form the isolation module 6100. This arrangement also allows the first housing 6110 and the second housing 6160 to be separately stored. Separate storage can be useful, for example, if the reagents included within the second housing 6160 have different storage requirements (e.g., expiration dates, lyophilization requirement, storage temperature limits, etc.) from the substances contained within the first housing 6110.

In use, the substances contained within the second housing 6160 can be conveyed into the first housing 6110 to facilitate the isolation process. FIGS. 15-18 show a cross-sectional view of a portion of the isolation module 6100 in various stages of actuation. For example, a Proteinase K can be stored in the chamber 6163*d*, and transferred into the lysing chamber 6114 as shown in FIG. 15. More particularly, the actuator 6166*d* can be moved within the chamber 6163*d* as shown by the arrow HH when actuated by any suitable external force, such as, for example, a force applied by the actuation assembly 3400 of the instrument 3002 described herein. When the actuator 6166*d* moves towards the lysing chamber 6114, the piercing portion 6168*d* contacts and punctures a portion of the puncturable member 6170. In some embodiments, the puncturable member 6170 can include a perforation, stress-concentration riser or other structural discontinuity to ensure that the puncturable member 6170 easily punctures the desired portion of the puncturable member 6170. In this manner, the movement of the actuator 6166*d* places the chamber 6163*d* in fluid communication with the lysing chamber 6114. Continued movement of the actuator 6166*d* transfers the contents of the chamber 6163*d* (e.g., the Proteinase K) into the lysing chamber 6114. In this manner, the actuator 6166*d* functions both as a valve and a transfer mechanism.

In another embodiment, the contents of chamber 6163*d* can include proteinase K (e.g., 10 mg/mL, 15 mg/mL or 20 mg/mL, mannitol, water and bovine serum albumin. In a further embodiment, beads are coated or derivatized with the proteinase K. In another embodiment, the contents of chamber 6163*d* can include a proteinase K, mannitol, water and gelatin. In a further embodiment, beads are coated or derivatized with the proteinase K. In another embodiment, the contents of chamber 6163*d* are lyophilized, for example, as a 50 μL pellet.

In another embodiment, chamber 6163*d* also provides a positive control reagent. The positive control reagent, in one embodiment, is a plurality of beads derivatived with an internal control nucleic acid sequence. In a further embodiment, the beads are provided in a solution of mannitol, BSA and water. In even a further embodiment, the beads and solution are provided as a lyophilized pellet, for example as a 50 μL pellet.

Although specifically described for the chamber 6163*d*, the proteinase K, solution comprising proteinase K and/or positive control reagent, in other embodiments, is present as substance R1 or R2.

Figure 16:
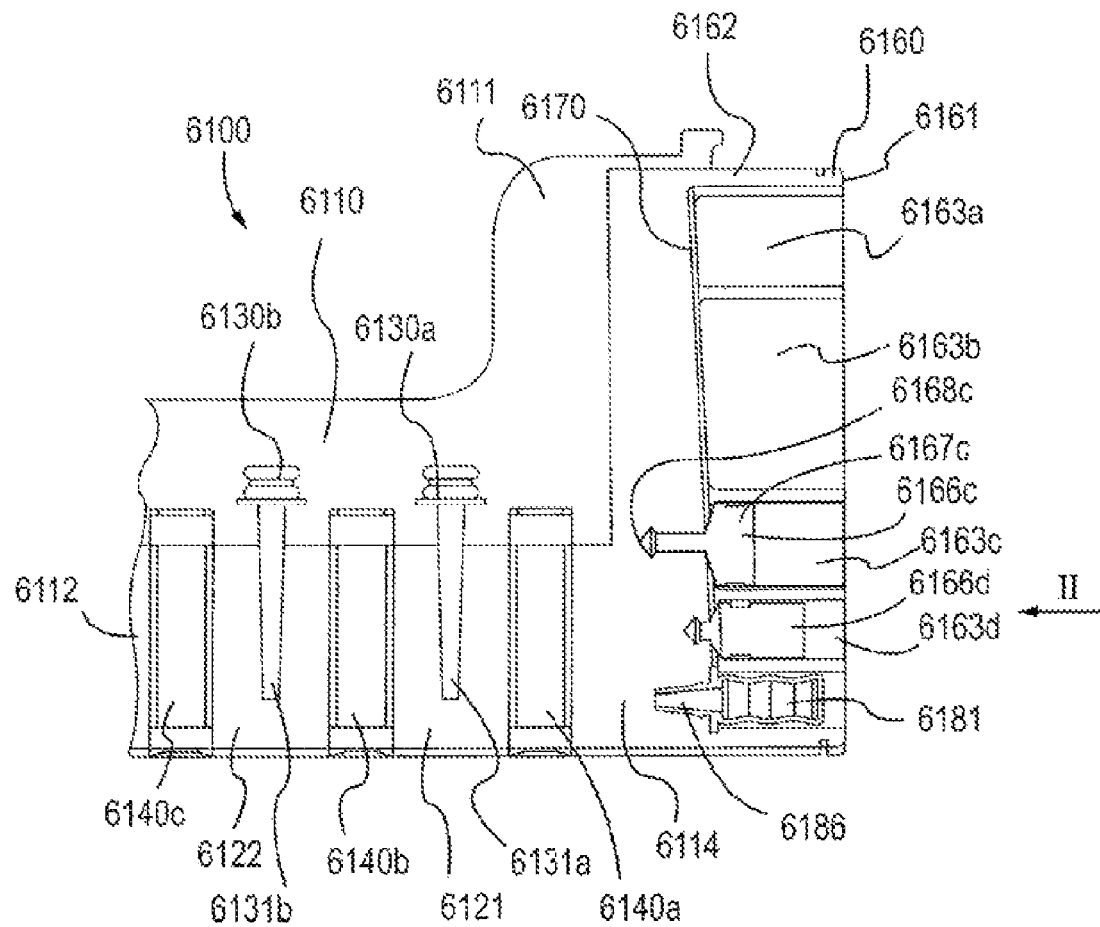

In a similar manner, a lysis solution can be stored in the chamber 6163*c*, and transferred into the lysing chamber 6114 as shown in FIG. 16. More particularly, the actuator 6166*c* can be moved within the chamber 6163*c* as shown by the arrow II when actuated by any suitable external force, such as, for example, a force applied by the actuation assembly 3400 of the instrument 3002 described herein. When the actuator 6166*c* moves towards the lysing chamber 6114, the piercing portion 6168*c* contacts and punctures a portion of the puncturable member 6170. In this manner, the movement of the actuator 6166*c* places the chamber 6163*c* in fluid communication with the lysing chamber 6114. Continued movement of the actuator 6166*c* transfers the contents of the chamber 6163*c* (e.g., the lysing solution) into the lysing chamber 6114. In this manner, the actuator 6166*c* functions both as a valve and a transfer mechanism. In one embodiment, the lysis solution stored in chamber 6163*c*, or another chamber, comprises a filtered solution of guanidine HCl (e.g., 3 M, 4 M, 5 M, 6 M, 7 M or 8 M), Tris HCl (e.g., 5 mM, 10 mM, 15 mM, 20 mM, 25 mM or 30 mM), triton-X-100 (e.g., 1.5%, 2%, 2.5%, 3%, 3.5%, 4%, 4.5% or 5%), NP-40 (e.g., 1.5%, 2%, 2.5%, 3%, 3.5%, 4%, 4.5% or 5%), Tween-20 (e.g., 5%, 10%, 15%, or 20%), $CaCl_2$ (e.g., 1 mM, 1.5 mM, 2 mM, 2.5 mM, 3 mM, 3.5 mM, 4 mM, 4.5 mM or 5 mM), molecular grade water. Although specifically described for the chamber 6163*c*, the lysis solution, in other embodiments, is present as substance R1 or R2.

Figure 17:
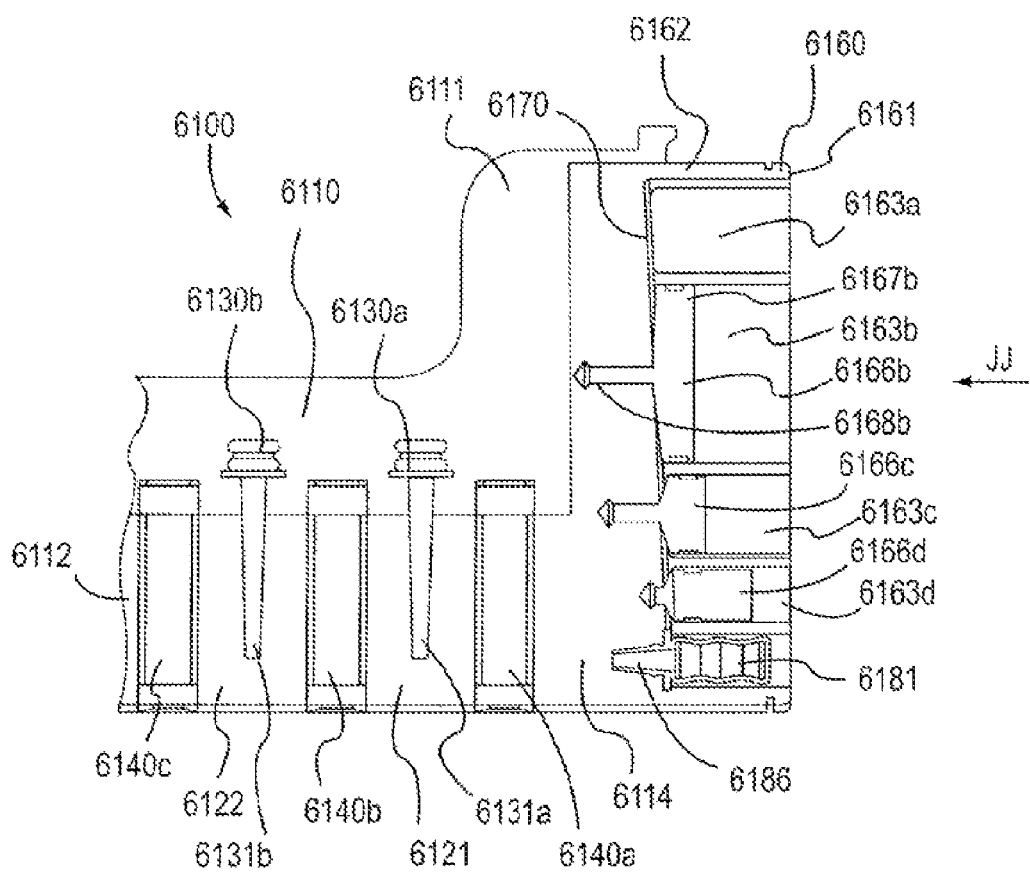

In a similar manner, a binding solution can be stored in the chamber 6163*b*, and transferred into the lysing chamber 6114 as shown in FIG. 17. More particularly, the actuator 6166*b* can be moved within the chamber 6163*b* as shown by the arrow JJ when actuated by any suitable external force, such as, for example, a force applied by the actuation assembly 3400 of the instrument 3002 described herein. When the actuator 6166*b* moves towards the lysing chamber 6114, the piercing portion 6168*b* contacts and punctures a portion of the puncturable member 6170. In this manner, the movement of the actuator 6166*b* places the chamber 6163*b* in fluid communication with the lysing chamber 6114. Continued movement of the actuator 6166*b* transfers the contents of the chamber 6163*b* (e.g., the binding solution) into the lysing chamber 6114. In this manner, the actuator 6166*b* functions both as a valve and a transfer mechanism. In one embodiment, the binding solution comprises isopropanol, for example 100% isopropanol, 90% isopropanol, 80% isopropanol, 70% isopropanol, at a volume of about 50 μL, about 100 μL, about 125 μL, about 150 μL, about 175 μL or about 200 μL. Although specifically described for the chamber 6163*b*, the binding solution, in other embodiments, is present as substance R1 or R2.

In a similar manner, a set of magnetic beads can be stored in the chamber 6163*a*, and transferred into the lysing chamber 6114 as shown in FIG. 18. More particularly, the actuator 6166*a* can be moved within the chamber 6163*a* as shown by the arrow KK when actuated by any suitable external force, such as, for example, a force applied by the actuation assembly 3400 of the instrument 3002 described herein. When the actuator 6166*a* moves towards the lysing chamber 6114, the piercing portion 6168*a* contacts and punctures a portion of the puncturable member 6170. In this manner, the movement of the actuator 6166*a* places the chamber 6163*a* in fluid communication with the lysing chamber 6114. Continued movement of the actuator 6166*a* transfers the contents of the chamber 6163*a* (e.g., the magnetic beads) into the lysing chamber 6114. In this manner, the actuator 6166*a* functions both as a valve and a transfer mechanism. The beads in one embodiment, are paramagnetic. In one embodiment, the beads are magnetic silica beads, and are provided at a concentration of 1.0 mg/mL, or 1.5 mg/mL, 2.0 mg/mL, 2.5 mg/mL, 3.0 mg/mL or 3.5 mg/mL. In a further embodiment, the magnetic silica beads stored in isopropanol, for example about 50% isopropanol, about 55% isopropanol, about 60% isopropanol, about 61% isopropanol, about 62% isopropanol, about 63% isopropanol, about 64% isopropanol, about 65% isopropanol, about 66% isopropanol, about 67% isopropanol, about 68% isopropanol, about 69% isopropanol, about 70% isopropanol, about 75% isopropanol, about 80% isopropanol, or about 85% isopropanol. In one embodiment, the beads are provided as a volume of about 50 μL, about 100 μL, about 125 μL, about 150 μL, about 175 μL or about 200 μL. Although specifically described for the chamber 6163*a*, the beads, in other embodiments, are present as substance R1 or R2.

Figure 10:
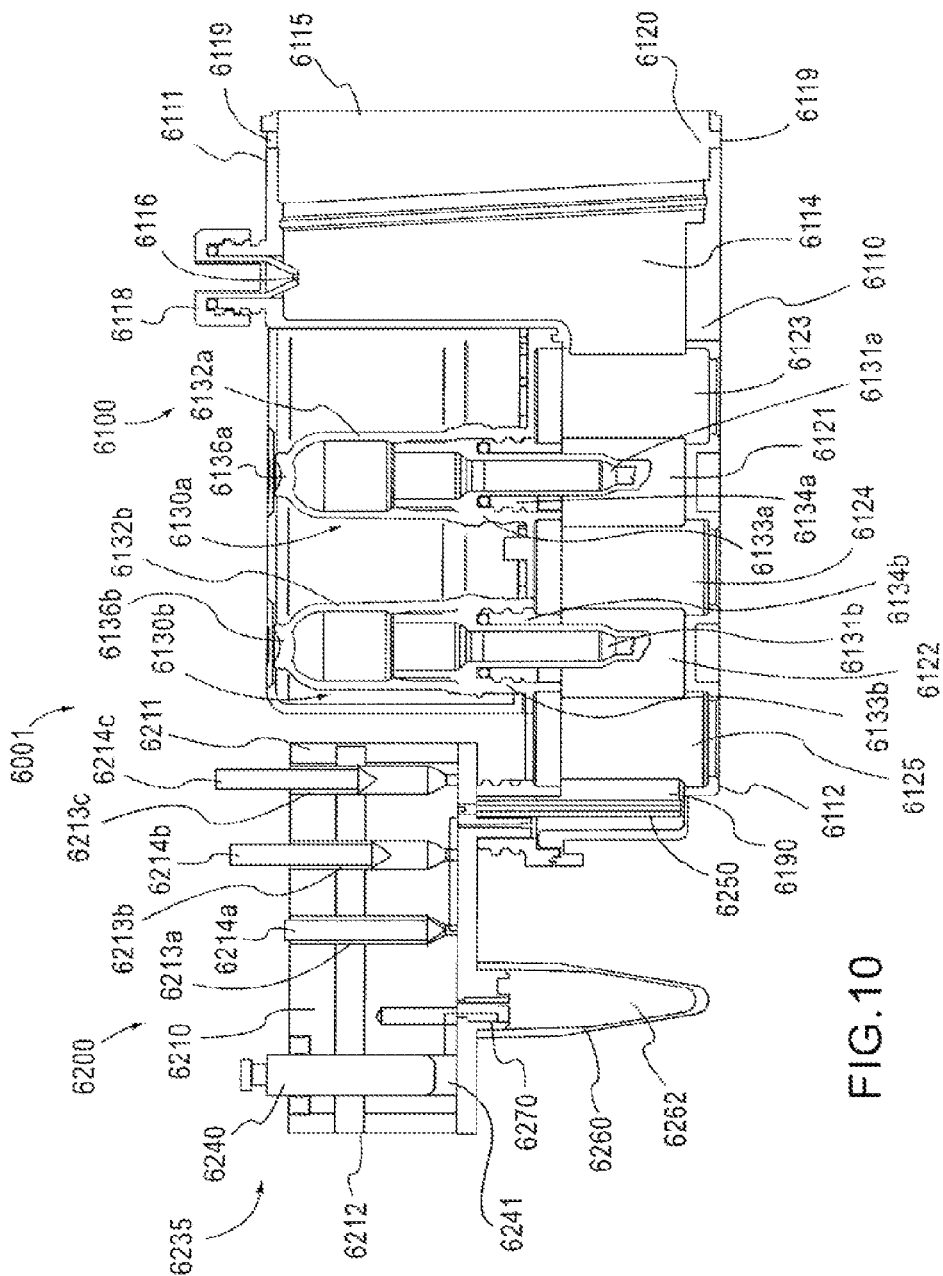
FIG. 10 is a side cross-sectional view of the cartridge shown in FIG. 8.

As shown in FIG. 10, the first housing 6110 includes a first end portion 6111 and a second end portion 6112, and defines the lysing chamber 6114, two wash chambers 6121 and 6122, three transfer assembly lumens 6123, 6124 and 6125, and an elution chamber 6190. The first housing 6110 also defines an opening 6115 adjacent the isolation chamber 6114. As shown in FIG. 11 and described above, the second housing 6160 is disposed within the opening 6115 such that a portion of the second housing 6160 (e.g., the puncturable member 6170) defines at least a portion of a boundary of the isolation chamber 6114.

Figure 8:
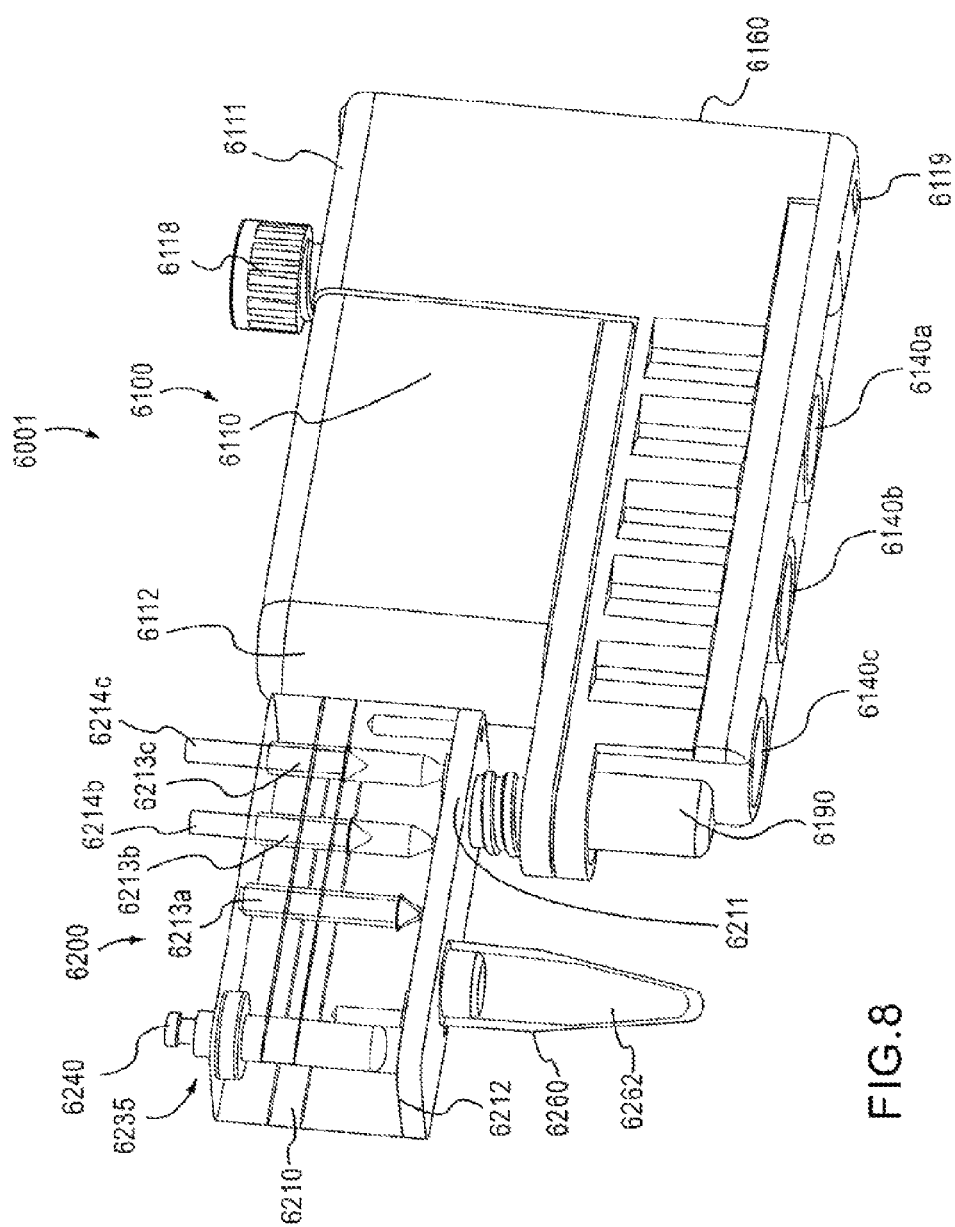
FIG. 8 is a side perspective view of a cartridge according to an embodiment.
Figure 9:
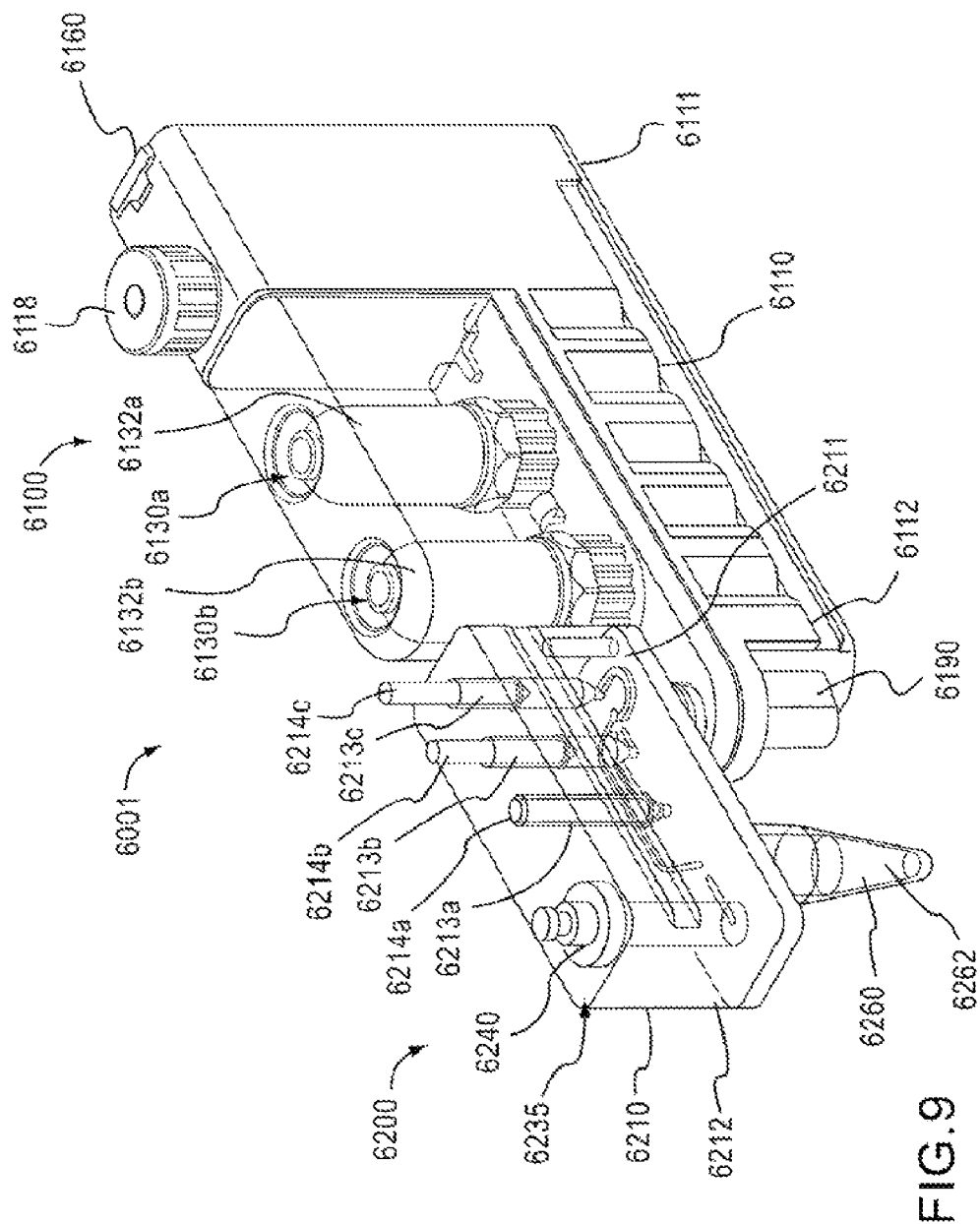
FIG. 9 is top perspective view of the cartridge shown in FIG. 8.

The first end portion 6111 also defines a fill opening 6116 through which the lysing chamber 6114 can be placed in fluid communication with a region outside of the isolation module 6100. As shown in FIGS. 8-10, the isolation module 6100 includes a cap 6118 that is removably coupled to about the fill opening 6116. In use, a sample containing a target nucleic acid, such as, for example, urine, blood and/or other materials containing tissue samples can be conveyed into the lysing chamber 6114 via the fill opening 6116. The sample can be introduced into the lysing chamber 6114 via any suitable mechanism, including for example, by pipetting or injecting the sample into the first chamber 6114 via the fill opening 6116. In some embodiments, a sample filter can be disposed within the fill opening 6116 and/or the fill cap 6118. The filter can be, for example, a hydrophobic filter.

After the sample is disposed into the lysing chamber 6114, reagents and/or substances to facilitate cell lysis can be added to the lysing chamber 6114, as described above. Moreover, the sample can be agitated and/or mixed via the pump 6181 to facilitate the lysing process, as described above. In some embodiments, the contents of the lysing chamber 6144 can be heated (e.g., by the third heating module 3780, as shown and described below with reference to the instrument 3002).

The isolation module 6100 includes a series of transfer assemblies (also referred to as transfer mechanisms), shown in FIGS. 15-19 as transfer assembly 6140*a*, transfer assembly 6140*b* and transfer assembly 6140*c*. As described herein, the transfer assemblies are configured to transfer substances (e.g., portions of the sample including the magnetically charged particles and the isolated nucleic acid attached thereto) between the lysing chamber 6114, the wash chamber 6121, the wash chamber 6122, and the elution chamber 6190. More particularly, the transfer assemblies 6140 are configured to transfer substances between the lysing chamber 6114, the wash chamber 6121, the wash chamber 6122, and the elution chamber 6190 while maintaining the isolation chamber 6114, the wash chamber 6121, the wash chamber 6122, and the elution chamber 6190 substantially fluidically isolated from the other chambers (e.g., the adjacent wash chamber) defined by the first housing 6110.

The transfer assembly 6140*a* is disposed within the transfer assembly lumen 6123, such that the transfer assembly 6140*a* is between the lysing chamber 6114 and the wash chamber 6121. Accordingly, the transfer assembly 6140*a* is configured to transfer substances between the lysing chamber 6114 and the wash chamber 6121.

The transfer assembly 6140*b* is disposed within the transfer assembly lumen 6124, such that the transfer assembly 6140*b* is between the wash chamber 6121 and the wash chamber 6122. Accordingly, the transfer assembly 6140*b* is configured to transfer substances between the wash chamber 6121 and the wash chamber 6122.

The transfer assembly 6140*c* is disposed within the transfer assembly lumen 6125, such that the transfer assembly 6140*c* is between the wash chamber 6122 and the elution chamber 6190. Accordingly, the transfer assembly 6140*c* is configured to transfer substances between the wash chamber 6122 and the elution chamber 6190.

Figure 20:
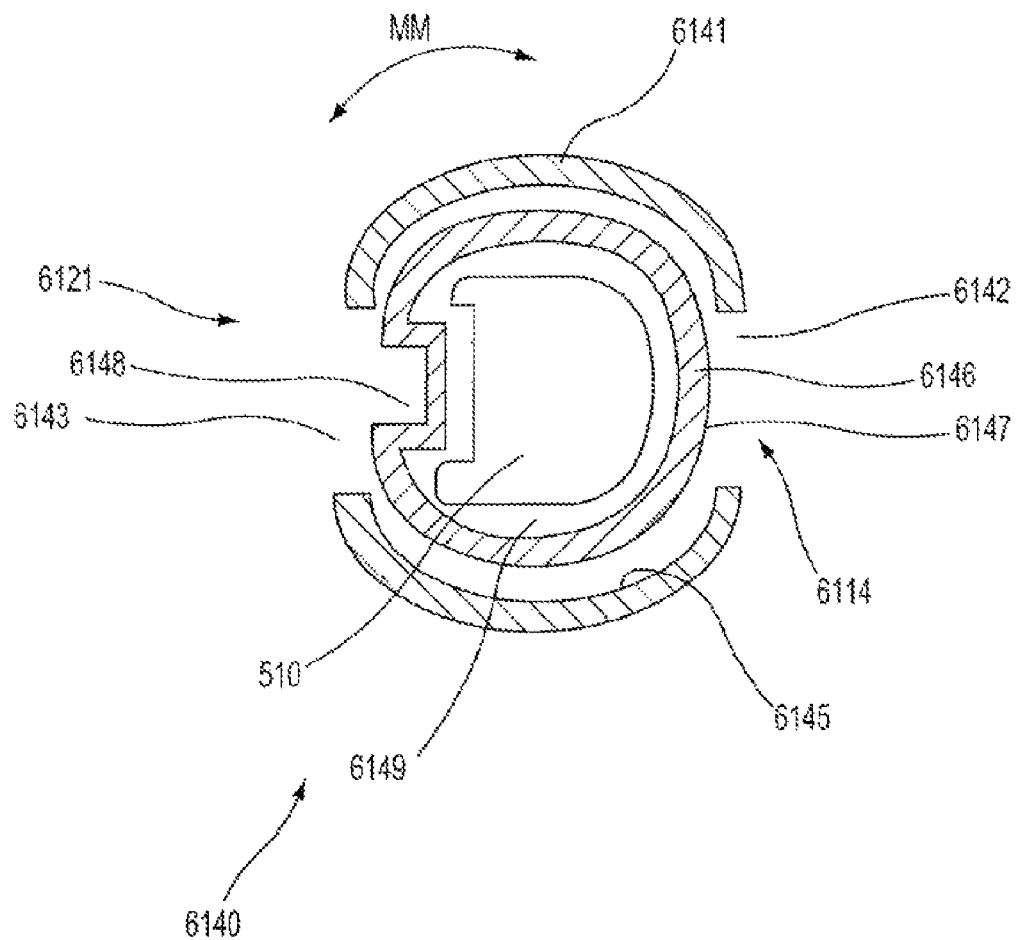
FIG. 20 is a cross-sectional view of a portion of a valve assembly of the isolation module shown in FIG. 19, taken along line $X_1$-$X_1$ in FIG. 19.
Figure 21:
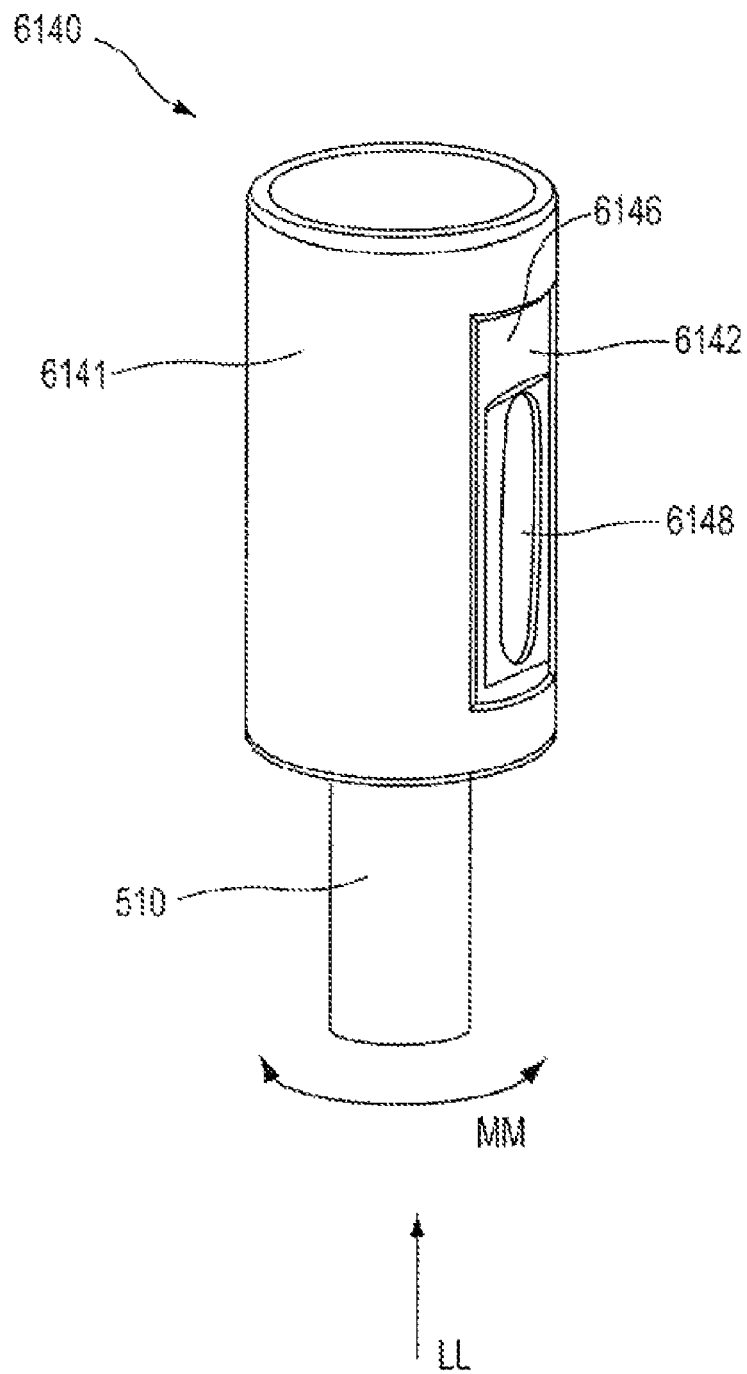
FIG. 21 is a perspective view of a portion of a valve assembly of the isolation module shown in FIG. 19.
Figure 22:
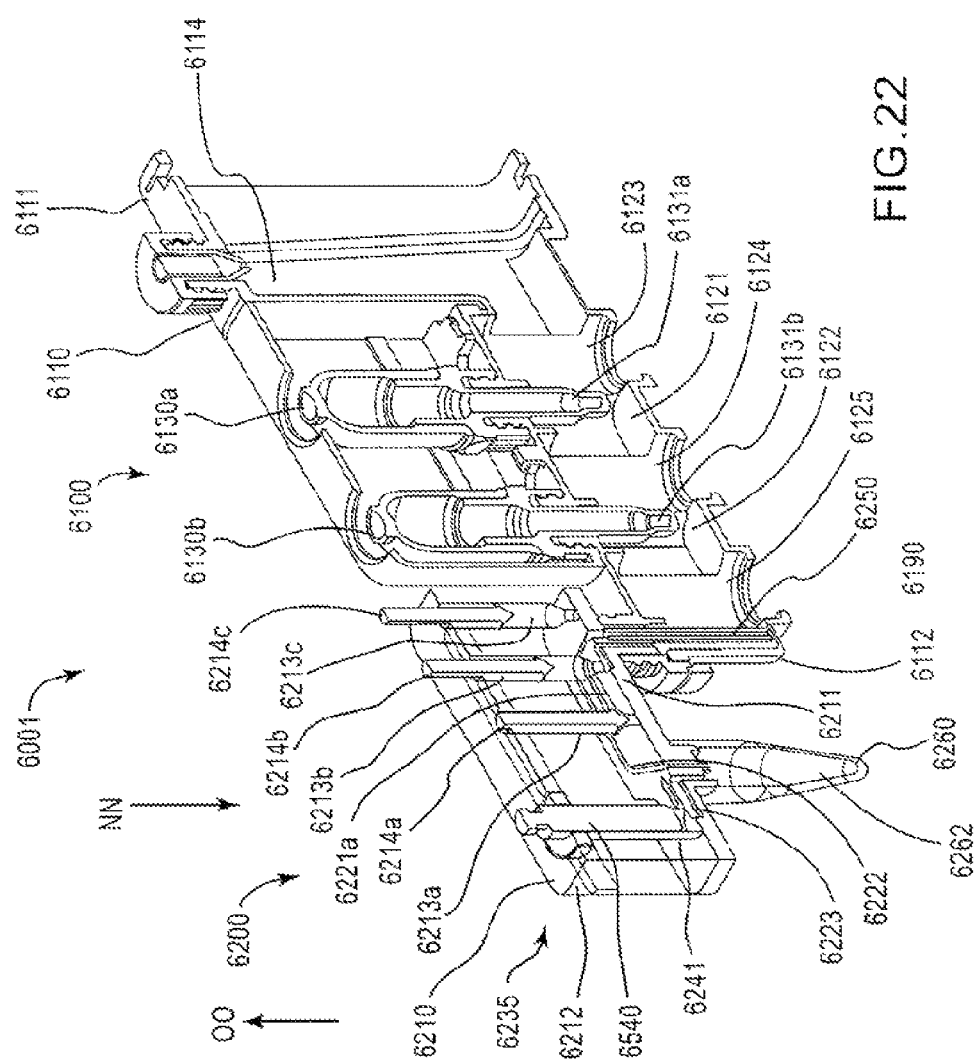
FIG. 22 is perspective cross-sectional view of the cartridge shown in FIG. 8.
Figure 23:
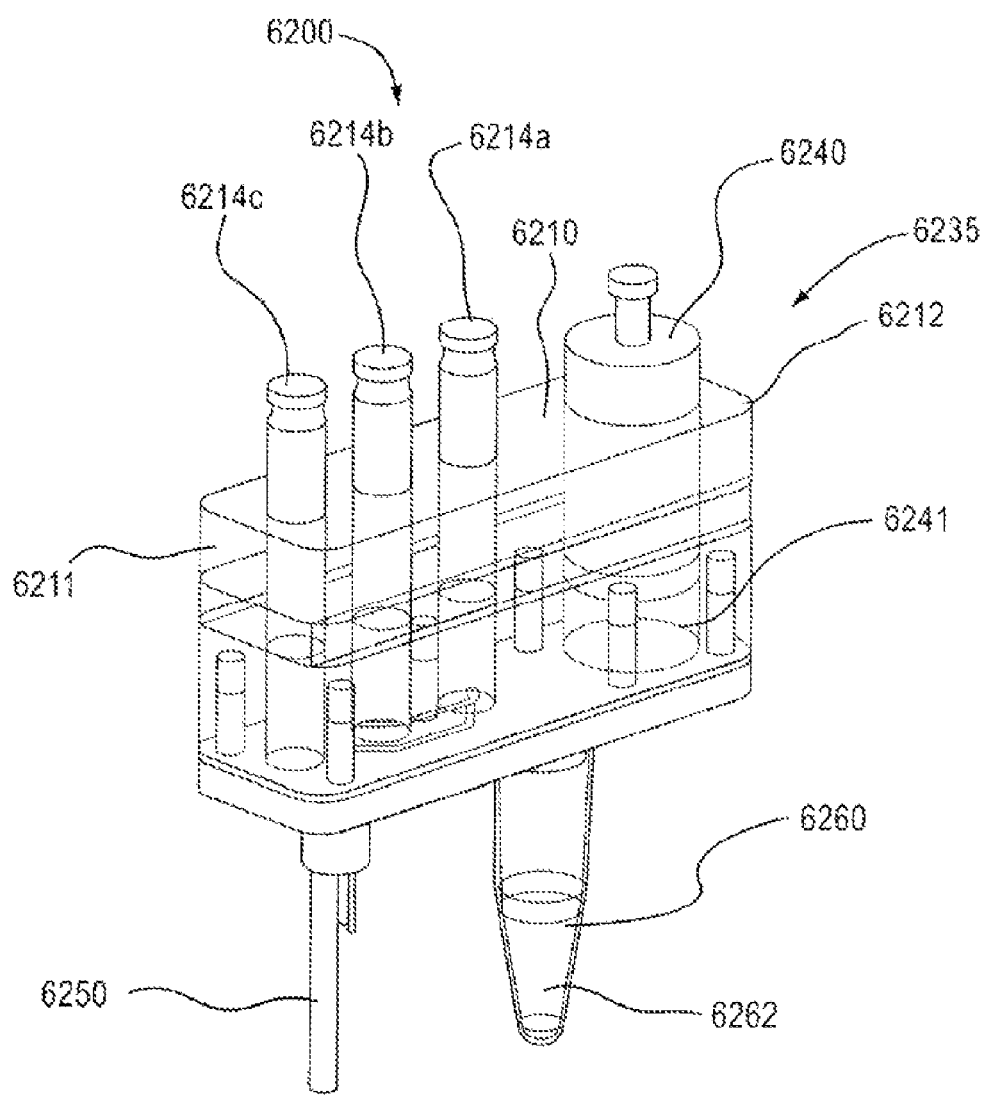
FIG. 23 is a perspective view of a PCR module of the cartridge shown in FIG. 8

Each of the transfer assemblies is described with reference to FIGS. 20 and 21, which shows a representative transfer assembly 6140. The transfer assembly 6140 includes a housing 6141 and a movable member 6146 that is rotatably disposed within the housing 6141. The housing 6141 defines a first opening 6142 and a second opening 6143. When the transfer assembly 6140 is disposed within the transfer assembly lumen (e.g., transfer assembly lumen 6123), the housing 6141 is aligned such that the first opening 6142 is aligned with and/or in fluid communication with a first chamber (e.g., the lysing chamber 6114) and the second opening 6143 is aligned with and/or in fluid communication with a second chamber (e.g., the wash chamber 6121). The housing 6141 can be secured within the transfer assembly lumen (e.g., transfer assembly lumen 6123) by any suitable mechanism, such as for example, by a mechanical fastener or retainer, a chemical bond or adhesive, an interference fit, a weld joint or the like. Moreover, the housing 6141 can include one or more seals (not shown in FIGS. 20 and 21) such that the first chamber (e.g., the lysing chamber 6114) and the second chamber (e.g., the wash chamber 6121) are maintained in fluid isolation from each other. Similarly stated, the housing 6141 and the first housing 6110 can collectively form a substantially fluid-tight and/or hermetic seal to eliminate and/or reduce leakage of substances between the first chamber (e.g., the lysing chamber 6114) and the second chamber (e.g., the wash chamber 6121).

The movable member 6146 includes an outer surface 6147 that defines a recess or cavity 6148. The movable member 6146 is disposed within the housing 6141 such that the movable member 6146 can rotate as shown by the arrow MM in FIGS. 20 and 21. The outer surface 6147 of the movable member 6146 is shown as being spaced apart from the inner surface 6145 of the housing 6141 in FIG. 20 for purposes of clarity. The outer surface 6147 is in sliding contact with the inner surface 6145 of the housing 6141 such that the outer surface 6147 and the inner surface 6145 produce a substantially fluid-tight and/or hermetic seal. In this manner, leakage of substances between the first chamber (e.g., the lysing chamber 6114) and the second chamber (e.g., the wash chamber 6121) via the interface between the housing 6141 and the movable member 6146 is eliminated and/or reduced.

The movable member 6146 further defines a lumen 6149 configured to receive a portion of an actuator 510. The actuator 510 can be any suitable actuator, such as, a shaft 3510 of the transfer actuator assembly 3500 of the instrument 3002 shown and described below with reference to FIGS. 41-46. As shown in FIG. 20, a shape of the actuator 510 can correspond to a shape of the lumen 6149 defined by the movable member 6146 such that rotation of the actuator 510 results in rotation of the movable member 6146. Similarly stated, the actuator 510 can be matingly disposed within the lumen 6149 such that relative rotational movement between the actuator 510 and the movable member 6146 is limited. In some embodiments, the actuator 510 and the lumen 6149 can have a substantially similar hexagonal and/or octagonal shape.

In use, the movable member 6146 can be moved between a first position (not shown) and a second position (FIG. 20) by rotating the movable member 6146 as shown by the arrow MM. When the movable member 6146 is in the first position, the recess or cavity 6148 is aligned with and/or in fluid communication with the first chamber (e.g., the lysing chamber 6114). When the movable member 6146 is in the second position, the recess or cavity 6148 is aligned with and/or in fluid communication with the second chamber (e.g., the wash chamber 6121). Accordingly, one or more substances contained in the first chamber (e.g., the lysing chamber 6114) can be transferred to the second chamber (e.g., the wash chamber 6121) by capturing or disposing a portion of the substance within the cavity 6148 when the movable member 6146 is in the first position, rotating the movable member into the second position and removing the substance from the cavity 6148.

In some embodiments, the substance can be captured, disposed and/or maintained within the cavity 6148 by a magnetic force. For example, in some embodiments, the actuator 510 can include a magnetic portion. In use, the actuator 510 is aligned with the desired transfer assembly 6140 and moved into the lumen 6149, as shown by the arrow LL in FIG. 19. Because the shape of the actuator 510 can correspond to the shape of the lumen 6149, as described above, an alignment operation may be performed in some embodiments to ensure that the actuator 510 will fit within the lumen 6149. When the magnetic portion of the actuator 510 is within the lumen 6149, and when the movable member 6146 is in the first position, a magnetic portion (e.g., the magnetic beads and the nucleic acid attached thereto) of the sample is moved from the first chamber (e.g., the lysing chamber 6114) into the cavity 6148. The actuator 510 is then rotated, as shown by the arrow MM in FIGS. 20 and 21. When the movable member 6146 is in the second position, the actuator 510 can be removed from the lumen 6149, thereby removing the magnetic force that is retaining the magnetic portion of the sample within the cavity 6148. Accordingly, the portion of the sample can then be moved from the cavity 6148 and into the second chamber (e.g., the wash chamber 6121). The portion of the sample can be moved from the cavity 6148 and into the second chamber (e.g., the wash chamber 6121) by any suitable mechanism, such as, for example, by gravity, fluid motion or the like. For example, as described below, in some embodiments, the mixing mechanism 6130*a* can include a nozzle (e.g., nozzle 6131*a*) to direct a pressure jet into and/or adjacent the cavity 6148 to move the portion of the sample from the cavity 6148 and into the second chamber (e.g., the wash chamber 6121).

The use of the transfer mechanism 6140 as described herein can eliminate the need for a separate waste chamber within the first housing 6110 and/or flow paths for conveying waste. Rather, as described above, the target portion of sample is moved between of various chambers (e.g., from the wash chamber 6121 to the wash chamber 6122) while other portions of the sample are maintained in the previous chamber (e.g., the wash chamber 6122). Moreover, because the transfer mechanism 6140 maintains fluidic isolation between the two chambers (e.g., the wash chamber 6121 and the wash chamber 6122) the waste solution is prevented from entering the chamber (e.g., the wash chamber 6122) along with the target portion of the sample. Thus, this arrangement also eliminates the need for filtering mechanisms within the first housing 6110, between the chambers described therein and/or within the flow paths defined by the isolation module 6100.

The use of the transfer mechanism 6140 as described herein also allows the target portion of the sample to be conveyed within the isolation module 6100 while maintaining the pressure within the isolation modules at or near ambient pressure. Similarly stated, the transfer mechanism 6140 as described herein transfers the target portion of the sample without producing a substantial pressure differential within the isolation module 6100. Thus, this arrangement can reduce the leakage of sample from the isolation module.

The isolation module 6100 includes two mixing mechanisms 6130*a* and 6130*b* (also referred to as wash pumps). As described herein, the mixing mechanisms 6130*a* and 6130*b* are configured to produce a fluid flow within the wash chamber 6121 and the wash chamber 6122, respectively, to promote washing and or mixing of the portion of the sample contained therein. Similarly stated, the mixing mechanisms 6130*a* and 6130*b* are configured to transfer energy into the wash chamber 6121 and the wash chamber 6122, respectively.

The mixing mechanism 6130*a* includes an actuator 6132*a* and a nozzle 6131*a*. The mixing mechanism 6130*a* is coupled to the first housing 6110 such that at least a portion of the nozzle 6131*a* is disposed within the wash chamber 6121. In particular, the mixing mechanism 6130*a* includes a coupling portion 6133*a* that is configured to be coupled to a corresponding coupling portion 6134*a* of the first housing 6110. Although the coupling portions 6133*a* and 6134*a* are shown as defining a threaded coupling, in other embodiments, the mixing mechanism 6130*a* can be coupled to the first housing 6110 by any suitable method, such as for example, by a mechanical fastener or retainer, a chemical bond or adhesive, an interference fit, a weld joint or the like.

Similarly, the mixing mechanism 6130*b* includes an actuator 6132*b* and a nozzle 6131*b*. The mixing mechanism 6130*b* is coupled to the first housing 6110 such that at least a portion of the nozzle 6131*b* is disposed within the wash chamber 6122. In particular, the mixing mechanism 6130*b* includes a coupling portion 6133*b* that is configured to be coupled to a corresponding coupling portion 6134*b* of the first housing 6110. Although the coupling portions 6133*b* and 6134*b* are shown as defining a threaded coupling, in other embodiments, the mixing mechanism 6130*b* can be coupled to the first housing 6110 by any suitable method, such as for example, by a mechanical fastener or retainer, a chemical bond or adhesive, an interference fit, a weld joint or the like.

The actuators 6132*a* and 6132*b* each include a top surface 6136*a* and 6136*b*, respectively, that is configured to be contacted and/or actuated by an actuation assembly of an instrument, such as, for example, the actuation assembly 3600 of the instrument 3002 described herein. In use, the actuation assembly can depress and/or move the top surface 6136*a* and 6136*b* of each actuator 6132*a* and 6132*b* to produce a pressure within each mixing mechanism 6130*a* and 6130*b*. The pressure is conveyed into the wash chambers 6121 and 6122 to promote washing, mixing and/or other interaction between and with the sample disposed therein. As described above, in some embodiments, at least one of the nozzles (e.g., the nozzle 6131*a*) can include a tip portion that is angled, bent and/or otherwise shaped to direct the pressure energy and/or flow produced by the actuator (e.g., the actuator 6132*a*) towards a particular region within the wash chamber (e.g., the wash chamber 6121). For example, in some embodiments, the nozzle 6131*a* can be shaped to direct the pressure energy and/or flow produced by the actuator 6132*a* towards the cavity of 6148 of the transfer mechanism 6140.

Although the actuators 6132*a* and 6132*b* are each shown as a bellows-style pump, in other embodiments, the mixing mechanism 6130*a* and/or the mixing mechanism 6130*b* can include any suitable mechanism for producing and/or transferring energy into the wash chambers 6121 and 6122. Such mechanisms can include, for example, a piston pump, a rotating member, or the like. In some embodiments, a mixing mechanism can include an ultrasonic energy source, a thermal energy source or the like.

Although the mixing mechanisms 6130*a* and 6130*b* are shown and described as producing and/or transferring energy into the wash chambers 6121 and 6122, respectively, in other embodiments, a mixing mechanism can also define a volume within which a substance (e.g., a wash buffer solution) can be stored in fluidic isolation from the wash chamber. Thus, when the mixing mechanism is actuated, the substance can be transferred into the wash chamber. In this manner, in some embodiments, a mixing mechanism can also function as a transfer mechanism.

The amplification (or PCR) module includes a housing 6210 (having a first end portion 6211 and a second end portion 6212), a PCR vial 6260 and a transfer tube 6250. The PCR vial 6260 is coupled to the first end portion 6211 of the housing 6210 and defines a volume 6262 within which a sample can be disposed to facilitate a reaction associated with the sample. The PCR vial 6260 can be any suitable container for containing a sample in a manner that permits a reaction associated with the sample to occur. The PCR vial 6260 can also be any suitable container for containing the sample in a manner that permits the monitoring of such a reaction (e.g., the detection of an analyte within the sample that results from or is associated with the reaction). In some embodiments, at least a portion of the PCR vial 6260 can be substantially transparent to allow optical monitoring of a reaction occurring therein be an optical system (e.g., the optics assembly 3800 of the instrument 3002 described herein).

As shown in FIGS. 8, 9, 10 and 22, the amplification module 6200 is coupled to the second end portion 6112 of the first housing 6110 of the isolation module 6100 such that at least a portion of the transfer tube 6250 is disposed within the elution chamber 6190 of the isolation module 6100. In this manner, as described herein, the isolated nucleic acid, any substances and/or any PCR reagents disposed within the elution chamber 6190 can be conveyed from the elution chamber 6190 to the PCR vial 6260 via the transfer tube 6250.

Figure 24:
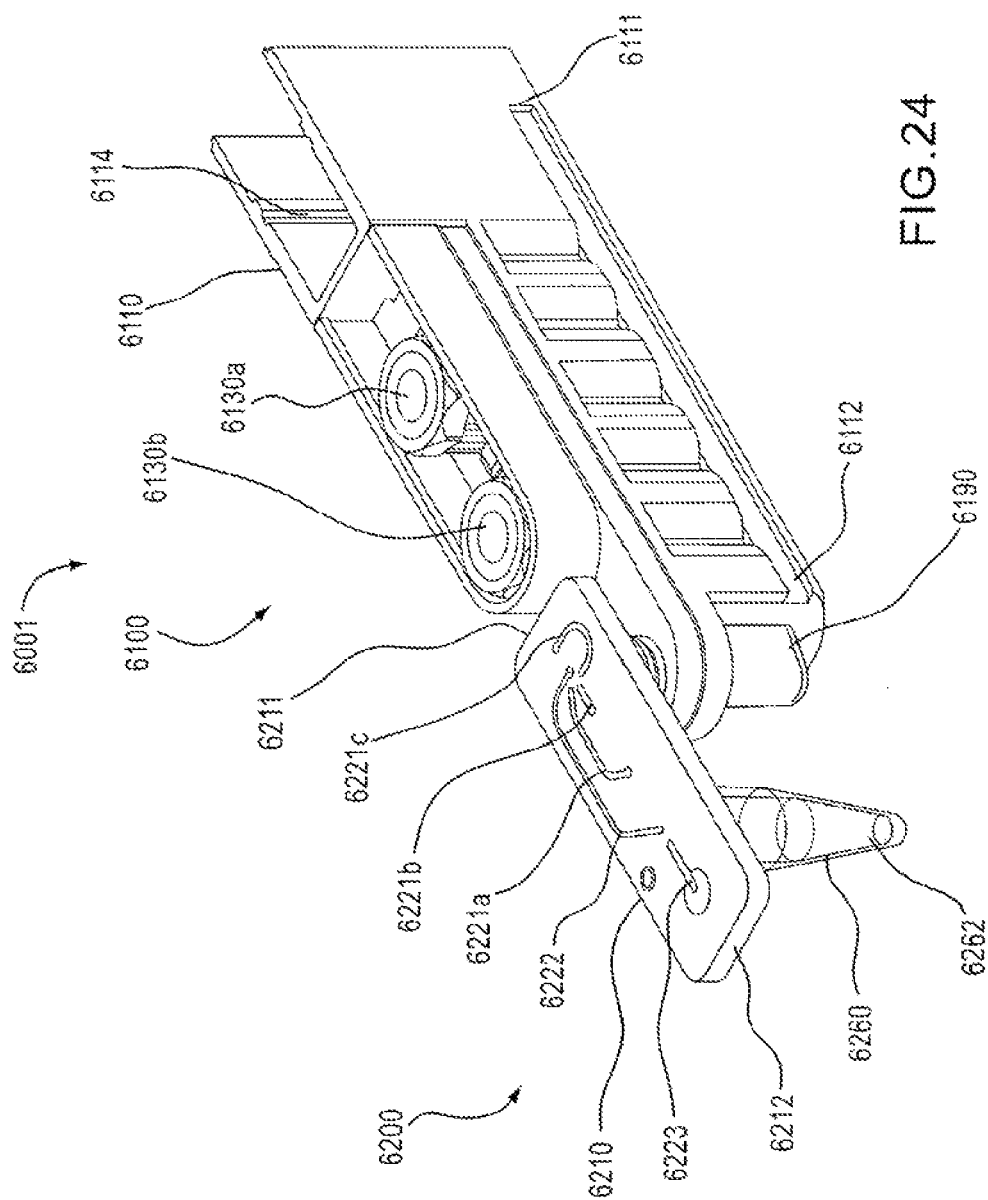
FIG. 24 is perspective cross-sectional view of the cartridge shown in FIG. 8.
Figure 25:
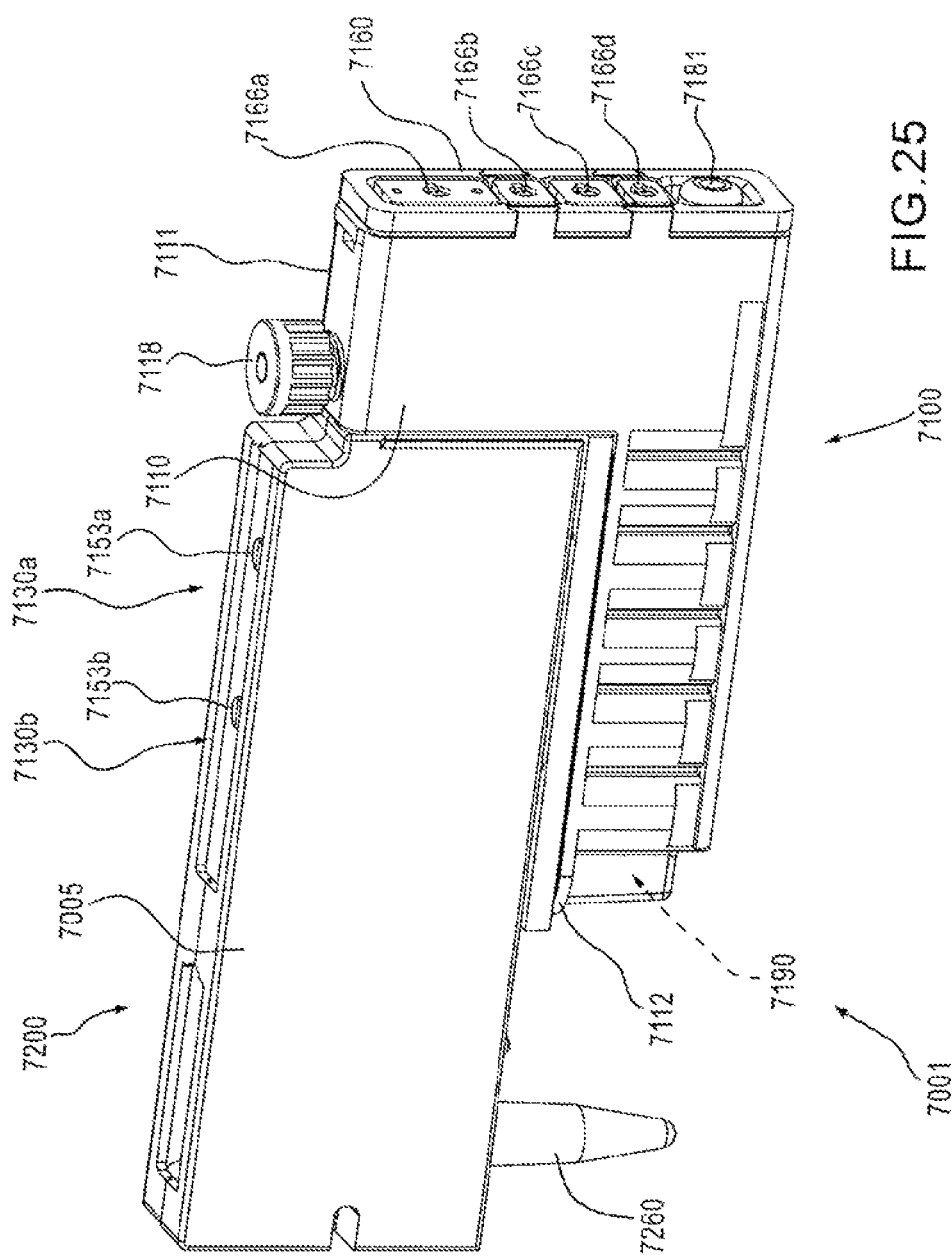
FIG. 25 is a side perspective view of a cartridge according to an embodiment.

The housing 6210 defines a series of reagent chambers 6213*a*, 6213*b*, 6213*c* (see e.g., FIG. 22) and a pump cavity 6241. The reagent chambers 6213*a*, 6213*b*, 6213*c* can contain any suitable substances associated with a reaction and/or process occurring in the PCR vial 6260. The reagent chambers 6213*a*, 6213*b*, 6213*c* can include, for example, an elution fluid, a master mix, probes and/or primers to facilitate the PCR process. As shown in FIG. 24, the housing 6210 defines a series of passageways 6221*a*, 6221*b*, 6221*c* configured to place each of the reagent chambers 6213*a*, 6213*b*, 6213*c* in fluid communication with the elution chamber 6190 of the isolation module 6100. Although not shown in FIG. 22, in some embodiments, a puncturable member can be disposed within any one of the reagent chambers 6213*a*, 6213*b*, 6213*c* and/or within any one of the passageways 6221*a*, 6221*b*, 6221*c* to fluidically isolate the respective reagent chamber from the elution chamber 6190. In a manner similar to that described above with reference to the puncturable member 6170, in such embodiments, the puncturable member can be pierced by the reagent plunger to selectively place the reagent chamber in fluid communication with the elution chamber.

A reagent plunger 6214*a* is movably disposed within the reagent chamber 6213*a*, a reagent plunger 6214*b* is movably disposed within the reagent chamber 6213*b*, and a reagent plunger 6214*c* is movably disposed within the reagent chamber 6213*c*. In this manner, when the reagent plunger (e.g., reagent plunger 6214*a*) is moved, as shown by the arrow NN in FIG. 22, the reagent plunger transfers the contents of the reagent chamber (e.g., the reagent chamber 6213*a*) into the elution chamber 6190 via the associated passageway (e.g., passageway 6221*a*). In this manner, the reagent plunger functions as a transfer mechanism.

The reagent plungers 6214*a*, 6214*b*, 6214*c* can be contacted and/or actuated by an actuation assembly of an instrument, such as, for example, the actuation assembly 3600 of the instrument 3002 described herein. In some embodiments, the reagent plungers 6214*a*, 6214*b*, 6214*c* can include a retention mechanism (e.g., a protrusion, a snap ring or the like) configured to retain a portion of an actuator assembly (e.g., actuator assembly 3400) to facilitate reciprocal movement of the reagent plungers 6214*a*, 6214*b*, 6214*c* by the actuator assembly.

The PCR module includes a transfer mechanism 6235 configured to transfer substances from and/or between the elution chamber 6190 of the isolation module 6100 and the PCR vial 6260 of the PCR module 6200. The transfer mechanism 6235 includes a transfer piston 6240 disposed within the pump cavity 6241. When the transfer piston 6240 is moved within the pump cavity 6241, as shown by the arrow OO in FIG. 22, a vacuum and/or a positive pressure is produced within the PCR volume 6262. This pressure differential between the PCR volume 6262 and the elution chamber 6190 results in at least a portion of the contents of the elution chamber 6190 being transferred into (or from) the PCR volume 6262 via the transfer tube 6250 and the passageway 6222 (see e.g., FIG. 24). In this manner substances and/or samples can be added, mixed and/or conveyed between the elution chamber 6190 and the PCR volume 6262 by actuating the transfer mechanism 6235. The transfer mechanism 6235 can be actuated by any suitable mechanism, such as for example, the actuation assembly 3600 of the instrument 3002 described herein.

The transfer piston 6240 and the pump cavity 6241 can be in any suitable location within the PCR module 6200. For example, although the transfer piston 6240 is shown as being disposed substantially above the PCR vial 6260, in other embodiments, the transfer piston 6240 can be disposed substantially above the elution chamber 6190.

In some embodiments, the housing 6210 defines one or more vent passageways to fluidically couple the elution chamber 6190 and/or the PCR vial 6260 to atmosphere. In some embodiments, any of such vents can include a frit to minimize and/or prevent loss of the sample and/or the reagents from the elution chamber 6190 and/or the PCR vial 6260.

In use, after the nucleic acid is isolated and processed within the isolation module 6100, as described above, it is transferred into the elution chamber 6190 via the transfer assembly 6140*c*. The magnetic beads are then removed (or "washed") from the nucleic acid by an elution buffer, and removed from the elution chamber 6190. Thus, the elution chamber 6190 contains the isolated and/or purified nucleic acid. In some embodiments, the elution buffer is contained within the elution chamber 6190. In other embodiments, the elution buffer is contained in one of the reagent chambers (e.g., reagent chamber 6213*c*) of the PCR module 6200, and is transferred into the elution chamber 6190, as described above. In one embodiment, the elution buffer comprises a filtered solution of molecular grade water, tris HCl (e.g., about 10 mM, about 15 mM, about 20 mM, about 25 mM, about 30 mM, about 35 mM, or about 40 mM), magnesium chloride (e.g., about 1 mM, about 2 mM, about 3 mM, about 4 mM, about 5 mM, about 6 mM, about 7 mM, about 8 mM, about 9 mM, about 10 mM or about 20 mM), glycerol (e.g., about 2%, about 3%, about 4%, about 5%, about 6%, about 7%, about 8%, about 9%, about 10%, about 12%, about 14%, about 16%, about 18%, about 20% or about 25%). In one embodiment, the pH of the elution buffer is about 7.5, about 7.6, about 7.7, about 7.8, about 7.9, about 8.0, about 8.1, about 8.2, about 8.3, about 8.4, about 8.5, about 8.6, about 8.7, about 8.8, about 8.9 or about 9.0). In another embodiment, the elution buffer comprises bactericide, for example, the elution buffer provided above further comprising bactericide. In one embodiment, the elution buffer also serves as a wash buffer. Although specifically described for the elution chamber 6190, the aforementioned elution buffer, in other embodiments, is present as substance R1 or R2.

In some embodiments, the PCR reagents are then conveyed from the PCR module 6200 into the elution chamber 6190. More particularly, the reagent plungers 6214*a*, 6214*b* and/or 6214*c* are actuated (e.g., by the instrument 3002) to introduce the reagents into the elution chamber 6190 via the passageways 6221*a*, 6221*b*, 6221*c*. The PCR sample is then conveyed from the elution chamber 6190 into the PCR vial 6260 via the transfer tube 6250 and the passageway 6222. In particular, the transfer piston 6240 can be actuated to produce a pressure differential within the PCR module 6200 to convey the PCR sample from the elution chamber 6190 into the PCR vial 6260, as described above. In this manner, the PCR sample (the isolated nucleic acid and the PCR reagents) is prepared in the elution chamber 6190. By performing the mixing of the reagents and the nucleic acid sample within the elution chamber 642 (rather than conveying the isolated nucleic acid into the PCR vial 6260 and performing the mixing therein) an additional transfer of the nucleic acid is avoided. This arrangement can result in improved accuracy of the post-PCR analysis, such that, in some instances, the analysis can be semi-quantitative in nature.

In other embodiments, however, the PCR sample (the isolated nucleic acid and the PCR reagents) can prepared in the PCR vial 6260. In such embodiments, for example, the PCR reagents can be stored in the PCR vial 6260, for example, in lyophilized form. The isolated nucleic acid can be conveyed into the PCR vial 6260 and mixed with the lyophilized PCR reagents to reconstitute the reagents within the PCR vial 6260.

After the PCR sample is in the PCR vial 6260, the PCR sample can be thermally cycled (e.g., via the heating assembly 3700 of the instrument 3002) to perform the desired amplification. Upon completion of and/or during the thermal cycling, the PCR sample can be optically analyzed (e.g., via the optics assembly 3800 of the instrument 3002) to analyze the sample. A description of the instrument 3002 is provided below.

FIGS. 25-33 are various views of a cartridge 7001 according to an embodiment. Certain features of the cartridge 7001 are similar to the corresponding features of the cartridge 6001, and are therefore not described below. Where applicable, the discussion presented above for the cartridge 6001 is incorporated into the discussion of the cartridge 7001. For example, although the actuators (e.g., actuator 7163*a*) within the second housing 7160 have a size and/or shape that is different from the size and/or shape of the actuators (e.g., actuator 6163*a*) within the second housing 6160, many aspects of the structure and function of the actuators within the second housing 6160 are similar to that for the actuators within the housing 7160. Accordingly, the description presented above for the actuators (e.g., actuator 6160*a*) is applicable to the actuators (e.g., actuator 7160*a*) described below.

The cartridge 7001 includes a sample preparation (or isolation) module 7100 and an amplification (or PCR) module 7200 that are coupled together to form an integrated cartridge 7001. A cover 7005 is disposed about a portion of the isolation module 7100 and the PCR module 7200. One or more cartridges 7001 can be disposed within any suitable instrument of the types disclosed herein (see e.g., instrument 3002 described below) that is configured to manipulate, actuate and/or interact with the cartridge 7001 to perform a nucleic acid isolation, transcription and/or amplification on a test sample contained within the cartridge 7001.

Figure 26:
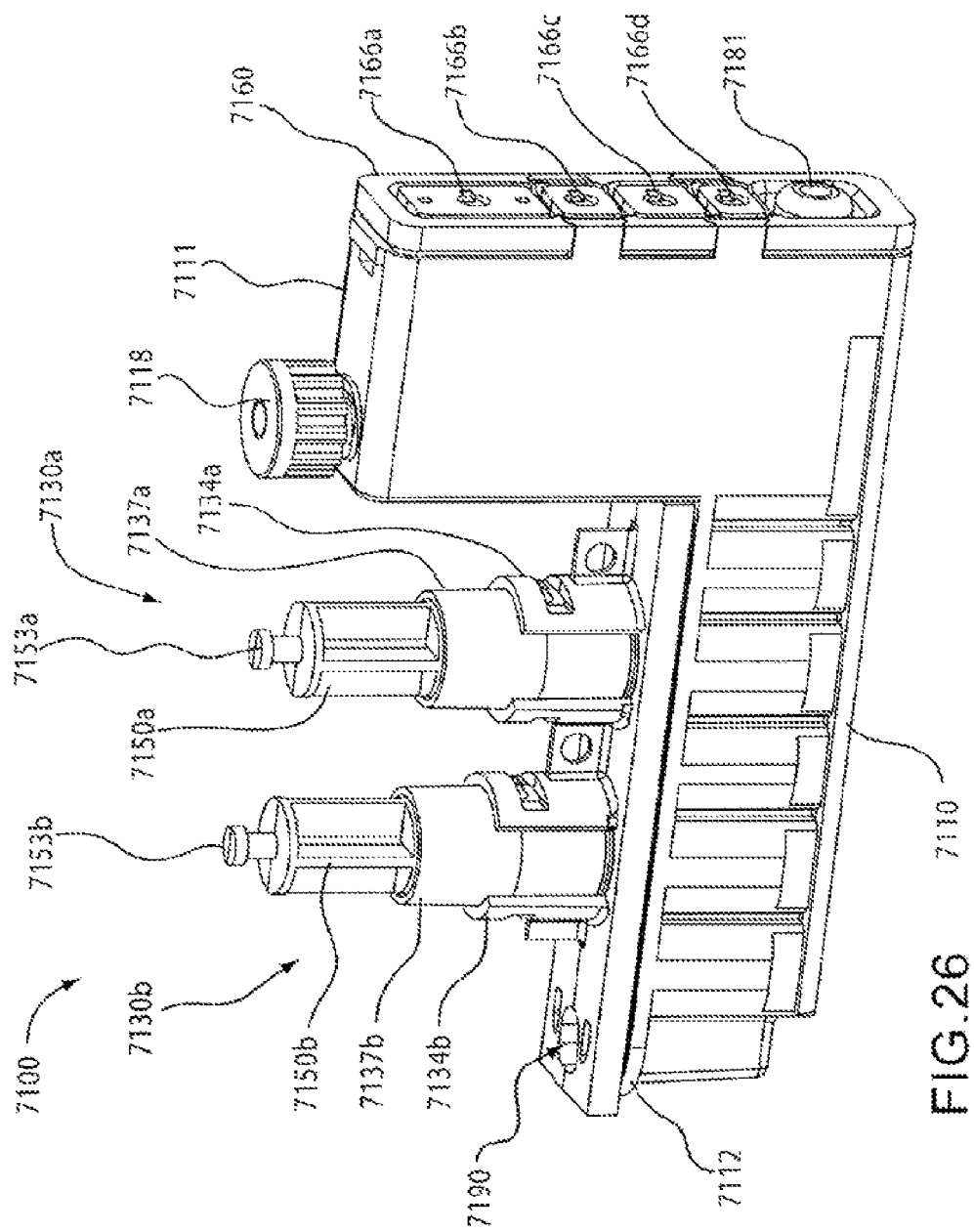
FIG. 26 is a side perspective view of an isolation module of the cartridge shown in FIG. 25, in a first configuration.
Figure 27:
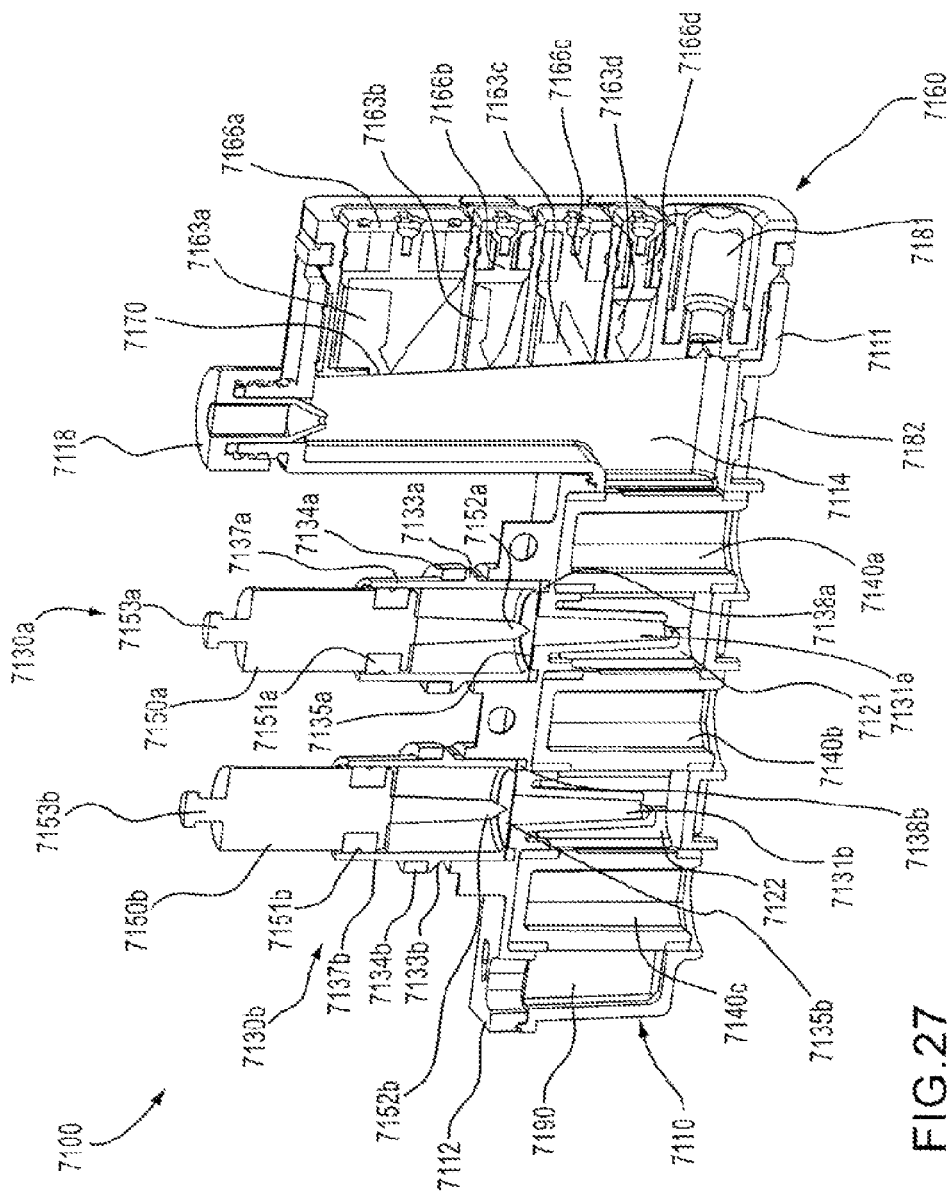
FIG. 27 is a side cross-sectional view of the isolation module shown in FIG. 26, in the first configuration.
Figure 28:
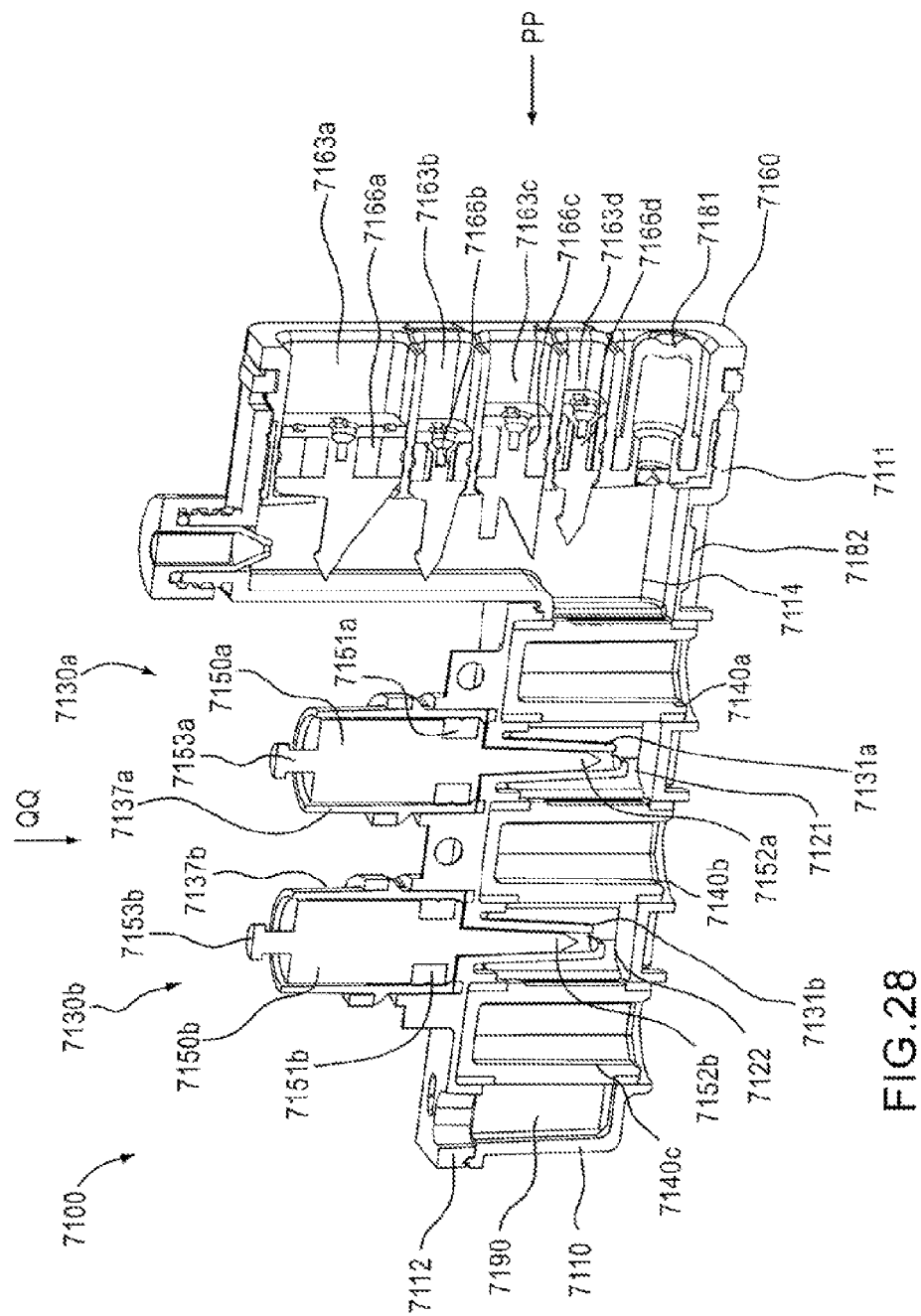
FIG. 28 is a side cross-sectional view of the isolation module shown in FIG. 26, in a second configuration.

As shown in FIGS. 26-28, the isolation module 7100 includes a first (or isolation) housing 7110 and a second (or reagent) housing 7160 that is coupled to and/or at least partially within the first housing 7110. The second housing 7160 defines a series of holding chambers 7163*a*, 7163*b*, 7163*c* and 7163*d* that contain the reagents and/or other substances used in the isolation process. As described herein, the holding chambers can contain a protease (e.g., Proteinase K), a lysis solution to solubilize the bulk material, a binding solution to magnetically charge the nucleic acid sample resident within the lysing chamber 7114, and a solution of magnetic beads that bind to the magnetically charged nucleic acid to assist in the conveyance of the nucleic acid within the isolation module 7100 and/or the first housing 7110. In one embodiment, the aforementioned solutions provided above are used in the cartridge provided in FIGS. 26-28.

Each of the holding chambers 7163*a*, 7163*b*, 7163*c* and 7163*d* includes an actuator movably disposed therein. More particularly, as shown in FIGS. 27 and 28, an actuator 7166*a* is disposed within the holding chamber 7163*a*, an actuator 7166*b* is disposed within the holding chamber 7163*b*, an actuator 7166*c* is disposed within the holding chamber 7163*c*, and an actuator 7166*d* is disposed within the holding chamber 7163*d*. Each of the actuators 7166*a*, 7166*b*, 7166*c* and 7166*d* are similar to the actuator 6166 shown and described above (see e.g., FIG. 14). In particular, each of the actuators 7166a, 7166b, 7166c and 7166d can function as a transfer mechanism to convey substances from the chamber (e.g., chamber 7163a) into another portion of the isolation module 7100 when moved in the direction indicated by the arrow PP in FIG. 28.

As shown in FIG. 27, a puncturable member 7170 is disposed about a portion of the second housing 7160 such that the internal portions of the second housing 7160, the puncturable member 7170 and the actuators 7166a, 7166b, 7166c and 7166d collectively enclose and/or define the holding chambers 7163a, 7163b, 7163c and 7163d. Similarly stated, the internal portions of the second housing 7160, the puncturable member 7170 and the actuators 7166a, 7166b, 7166c and 7166d collectively define fluidically isolated chambers 7163a, 7163b, 7163c and 7163d within which reagents and/or substances can be stored. The puncturable member 7170 can be constructed from any suitable material of the types described herein, such as any form of polypropylene. In some embodiments, the puncturable member 7170 can be constructed from biaxially oriented polypropylene (BOP).

The second housing 7160 includes a mixing pump 7181, which can be actuated (e.g., by the actuator assembly 3400 of the instrument 3002) to agitate, mix and/or produce a turbulent motion within the sample, reagents and/or other substances contained with a portion (e.g., the lysing chamber 7114) of the isolation module 7100.

As shown in FIGS. 26-28, the second housing 7160 is disposed within an opening defined by the first housing 7110. Thus, when the second housing 7160 is disposed within the first housing 7110, a portion of the second housing 7160 defines at least a portion of a boundary of the lysing chamber 7114. More particularly, when the second housing 7160 is disposed within the first housing 7110, the puncturable member 7170 defines a portion of the boundary of the lysing chamber 7114. This arrangement allows the substances contained within the second housing 7160 to be conveyed into the lysing chamber 7114 when a portion of the puncturable member 7170 is pierced, punctured, severed and/or broken. In a similar manner as described above with reference the isolation module 6100, the substances contained within the second housing 7160 can be conveyed into the first housing 7110 when the actuators 7166a, 7166b, 7166c and 7166d are actuated.

As shown in FIGS. 27 and 28, the first housing 7110 includes a first (or top) portion 7112 and a second (or bottom) portion 7111. In some embodiments, the top portion 7112 can be constructed separately from the bottom portion 7111, and can then be coupled to the bottom portion 7111 to form the first housing 7110. The first housing defines the lysing chamber 7114, two wash chambers 7121 and 7122, three transfer assembly lumens (not shown in FIGS. 27 and 28), and an elution chamber 7190. The first housing 7110 also defines an opening adjacent the isolation chamber 7114 within which a portion of the second housing 7160 is disposed.

As shown in FIGS. 26-28, the isolation module 7100 includes a cap 7118 that is removably coupled to the housing 7110. In use, a sample containing a target nucleic acid, such as, for example, urine, blood and/or other materials containing tissue samples can be conveyed into the lysing chamber 7114 via a fill opening 7116 upon removal of the cap 7118. The sample can be introduced into the lysing chamber 7114 via any suitable mechanism, including for example, by pipetting or injecting the sample into the first chamber 7114 via the fill opening 7116.

After the sample is disposed into the lysing chamber 7114, reagents and/or substances to facilitate cell lysis can be added to the lysing chamber 7114, as described above. Moreover, the sample can be agitated and/or mixed via the pump 7181 to facilitate the lysing process, as described above. In some embodiments, the contents of the lysing chamber 7144 can be heated (e.g., by the third heating module 3780, as shown and described below with reference to the instrument 3002). Moreover, the second portion 7111 of the first housing 7110 includes an acoustic coupling portion 7182. Accordingly, in some embodiments, at least a portion of an acoustic transducer (not shown) can be disposed in contact with the acoustic coupling portion 7182. In this manner, the acoustic and/or ultrasonic energy produced by the transducer can be conveyed through the acoustic coupling portion 7182 and the side wall of the first housing 7110, and into the solution within the lysing chamber 7114.

The isolation module 7100 includes a series of transfer assemblies (also referred to as transfer mechanisms), shown in FIGS. 26-28 as transfer assembly 7140a, transfer assembly 7140b and transfer assembly 7140c. As described herein, the transfer assemblies are configured to transfer substances (e.g., portions of the sample including the magnetically charged particles and the isolated nucleic acid attached thereto) between the lysing chamber 7114, the wash chamber 7121, the wash chamber 7122, and the elution chamber 7190. More particularly, the transfer assemblies 7140 are configured to transfer substances between the lysing chamber 7114, the wash chamber 7121, the wash chamber 7122, and the elution chamber 7190 while maintaining the isolation chamber 7114, the wash chamber 7121, the wash chamber 7122, and the elution chamber 7190 substantially fluidically isolated from the other chambers (e.g., the adjacent wash chamber) defined by the first housing 7110. The transfer assemblies 7140a, 7140b and 7140c are similar in structure and function to the transfer assemblies 6140 shown and described above with respect to the isolation module 6100, and are therefore not described in detail below.

The isolation module 7100 includes two wash buffer modules 7130a and 7130b that are each coupled to the upper portion 7112 of the first housing 7110. As described herein, each wash buffer module 7130a and 7130b contains a substance (e.g., a reagent, a wash buffer solution, a mineral oil and/or any other substance to be added to the sample), and is configured to transfer the substance into the wash chamber 7121 and the wash chamber 7122, respectively, when actuated. Moreover, each wash buffer module 7130a and 7130b is configured to produce a fluid flow within the wash chamber 7121 and the wash chamber 7122, respectively, to promote washing and or mixing of the portion of the sample contained therein. Similarly stated, each wash buffer module 7130a and 7130b is configured to transfer energy into the wash chamber 7121 and the wash chamber 7122, respectively. In one embodiment, wash buffer module 7130a and/or 7130b comprises a wash buffer comprising a filtered solution of molecular grade water, tris HCl (e.g., about 10 mM, about 15 mM, about 20 mM, about 25 mM, about 30 mM, about 35 mM, or about 40 mM), magnesium chloride (e.g., about 1 mM, about 2 mM, about 3 mM, about 4 mM, about 5 mM, about 6 mM, about 7 mM, about 8 mM, about 9 mM, about 10 mM or about 20 mM), glycerol (e.g., about 2%, about 3%, about 4%, about 5%, about 6%, about 7%, about 8%, about 9%, about 10%, about 12%, about 14%, about 16%, about 18%, about 20% or about 25%). In one embodiment, the pH of the wash buffer is about 7.5, about 7.6, about 7.7, about 7.8, about 7.9, about 8.0, about 8.1, about 8.2, about 8.3, about 8.4, about 8.5, about 8.6, about 8.7, about 8.8, about 8.9 or about 9.0). In another embodiment, the wash buffer comprises bactericide, for example, the wash buffer provided above further comprising bactericide.

Although specifically described for the chambers 7130a and/or 7130b, the wash buffer described immediately above, in other embodiments, is present as substance R1 and/or R2.

In another embodiment, wash buffer module 7130a and/or 7130b comprises a wash buffer comprising a filtered solution of molecular grade water, guanidine HCl (e.g., about 0.7 mM, about 0.8 mM, about 0.81 mM, about 0.82 mM, about 0.83 mM, about 0.84 mM, about 0.85 mM, about 0.9 mM, about 1.0 mM), tris HCl (e.g., about 10 mM, about 15 mM, about 20 mM, about 25 mM, about 30 mM, about 35 mM, or about 40 mM, and can have a pH of about 7.5, about 8 or about 8.5), triton-X-100 (e.g., about 0.25%, about 0.5%, about 0.75%, about 1%), Tween-20 (e.g., about 0.25%, about 0.5%, about 0.75%, about 1%), EDTA (e.g., about 0.1 mM, about 0.2 mM, about 0.3 mM, about 0.5 mM, about 0.75 mM, about 1 mM, about 2 mM, about 3 mM, about 4 mM, about 5 mM, about 6 mM, about 7 mM, about 8 mM, about 9 mM, about 10 mM or about 20 mM), isopropanol (e.g., about 10%, about 20%, about 30%, about 40%, about 50%, about 60%). In one embodiment, the pH of the elution buffer is about 7.5, about 7.6, about 7.7, about 7.8, about 7.9, about 8.0, about 8.1, about 8.2, about 8.3, about 8.4, about 8.5, about 8.6, about 8.7, about 8.8, about 8.9 or about 9.0). Although specifically described for the chambers 7130a and/or 7130b, the wash buffer described immediately above, in other embodiments, is present as substance R1 and/or R2.

The wash buffer module 7130a includes an actuator 7150a that is movably disposed within a housing 7137a. The housing 7137a is coupled to the upper portion 7112 of the first housing 7110 such that the wash buffer module 7130a is substantially aligned with the wash chamber 7121. In particular, the housing 7137a includes a pair of protrusions 7133a that are configured to be disposed within a corresponding opening defined by a coupling portion 7134a of the upper portion 7112 of the first housing 7110. Although the wash buffer module 7130a is shown as being coupled to the first housing 7110 by a "snap fit," in other embodiments, the wash buffer module 7130a can be coupled to the first housing 7110 by any suitable method, such as for example, by a threaded coupling, a mechanical fastener or retainer, a chemical bond or adhesive, an interference fit, a weld joint or the like.

The actuator 7150a includes a plunger portion 7151a, a piercing portion 7152a and an engagement portion 7153a. The engagement portion 7153a is configured to engage with, be removably coupled to and/or be received within a portion of an actuator assembly to facilitate movement of the actuator 7150a within the housing 7137a, as described herein. The actuator 7150a can be manipulated and/or actuated by any suitable instrument, such as the actuator assembly 3600 described below with respect to FIGS. 47-51.

The plunger portion 7151a of the actuator 7150a is disposed within the housing 7137a. A puncturable member 7135a is disposed about the end portion of the housing 7137a such that end face of the plunger portion 7151a, the housing 7137a and the puncturable member 7135a collectively define a volume within which a substance is disposed. The plunger portion 7151a and the internal surface of the housing 7137a are configured to form a substantially fluid-tight and/or hermetic seal. In some embodiments, the plunger portion 7151a can include a sealing member, an o-ring or the like.

The piercing portion 7152a of the actuator 7150a is configured to puncture, break, sever and/or rupture a portion of the puncturable member 7135a when the actuator 7150a is moved within the housing 7137a in the direction indicated by the arrow QQ in FIG. 28. In this manner, movement of the actuator 7150 places the chamber in fluid communication with the wash chamber 7121. Similarly stated, wash buffer module 7130a can be selectively placed in fluid communication with the wash chamber 7121 when the actuator 7150a is actuated. After the substance within the wash buffer module 7130a is conveyed into the wash chamber 7121, the actuator 7150a can be reciprocated within the housing 7137a to produce a pressure that is conveyed into the wash chamber 7121 to promote washing, mixing and/or other interaction between and with the sample disposed therein. The top portion 7112 of the first housing 7110 includes a nozzle 7131a configured to direct the pressure energy and/or flow produced by the actuator 7150a towards a particular region within the wash chamber 7121.

The wash buffer module 7130b includes an actuator 7150b that is movably disposed within a housing 7137b. The housing 7137b is coupled to the upper portion 7112 of the first housing 7110 such that the wash buffer module 7130b is substantially aligned with the wash chamber 7122. In particular, the housing 7137b includes a pair of protrusions 7133b that are configured to be disposed within a corresponding opening defined by a coupling portion 7134b of the upper portion 7112 of the first housing 7110. Although the wash buffer module 7130b is shown as being coupled to the first housing 7110 by a "snap fit," in other embodiments, the wash buffer module 7130b can be coupled to the first housing 7110 by any suitable method, such as for example, by a threaded coupling, a mechanical fastener or retainer, a chemical bond or adhesive, an interference fit, a weld joint or the like.

The actuator 7150b includes a plunger portion 7151b, a piercing portion 7152b and an engagement portion 7153b. The engagement portion 7153b is configured to engage with, be removably coupled to and/or be received within a portion of an actuator assembly to facilitate movement of the actuator 7150b within the housing 7137b, as described herein. The actuator 7150b can be manipulated and/or actuated by any suitable instrument, such as the actuator assembly 3600 described below with respect to FIGS. 47-51.

The plunger portion 7151b of the actuator 7150b is disposed within the housing 7137b. A puncturable member 7135b is disposed about the end portion of the housing 7137b such that end face of the plunger portion 7151b, the housing 7137b and the puncturable member 7135b collectively define a volume within which a substance is disposed. The plunger portion 7151b and the internal surface of the housing 7137b are configured to form a substantially fluid-tight and/or hermetic seal. In some embodiments, the plunger portion 7151b can include a sealing member, an o-ring or the like.

The piercing portion 7152b of the actuator 7150b is configured to puncture, break, sever and/or rupture a portion of the puncturable member 7135b when the actuator 7150b is moved within the housing 7137b in the direction indicated by the arrow QQ in FIG. 28. In this manner, movement of the actuator 7150b places the chamber in fluid communication with the wash chamber 7122. Similarly stated, wash buffer module 7130b can be selectively placed in fluid communication with the wash chamber 7122 when the actuator 7150b is actuated. After the substance within the wash buffer module 7130b is conveyed into the wash chamber 7122, the actuator 7150b can be reciprocated within the housing 7137b to produce a pressure that is conveyed into the wash chamber 7122 to promote washing, mixing and/or other interaction between and with the sample disposed therein. The top portion 7112 of the first housing 7110 includes a nozzle 7131b configured to direct the pressure energy and/or flow produced by the actuator 7150b towards a particular region within the wash chamber 7122.

Figure 29:
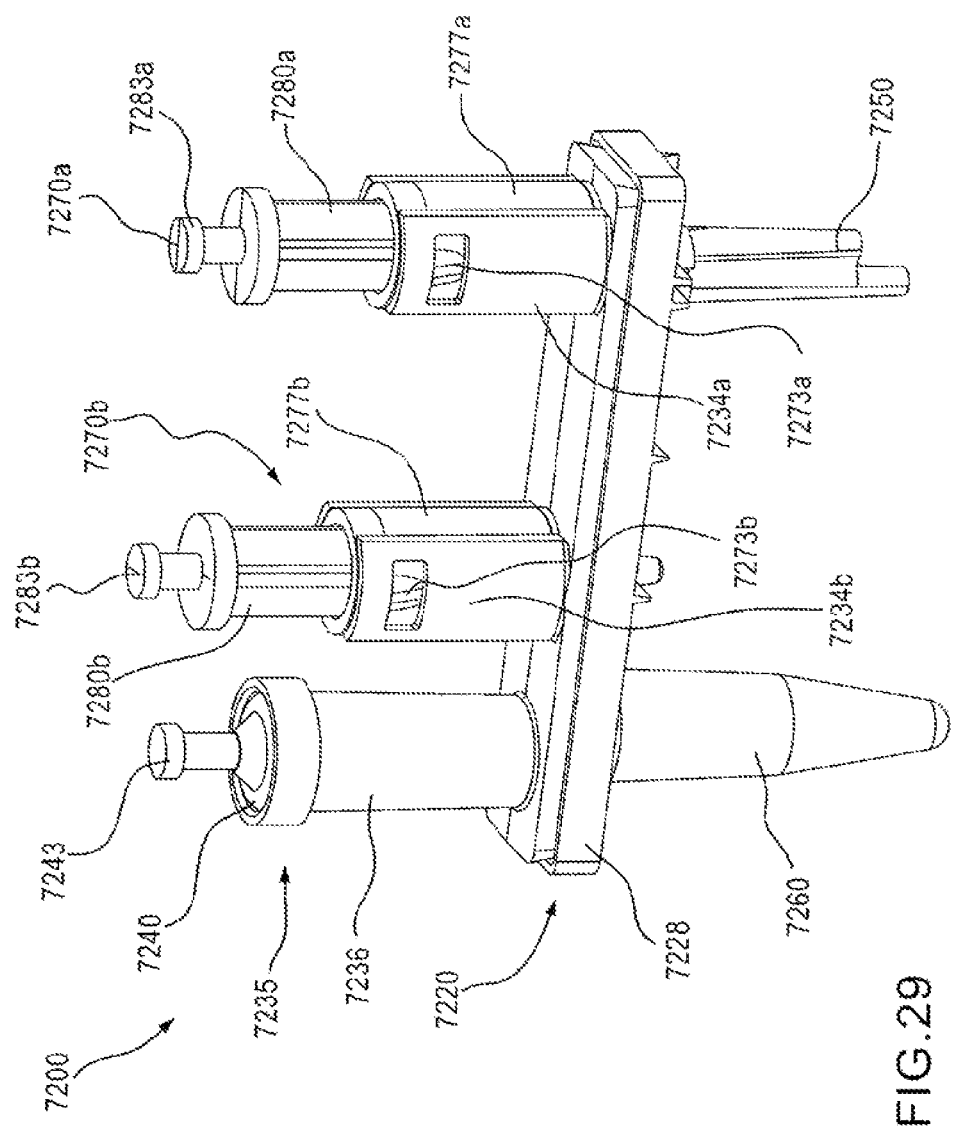
FIG. 29 is a side perspective view of PCR module of the cartridge shown in FIG. 25, in a first configuration.
Figure 30:
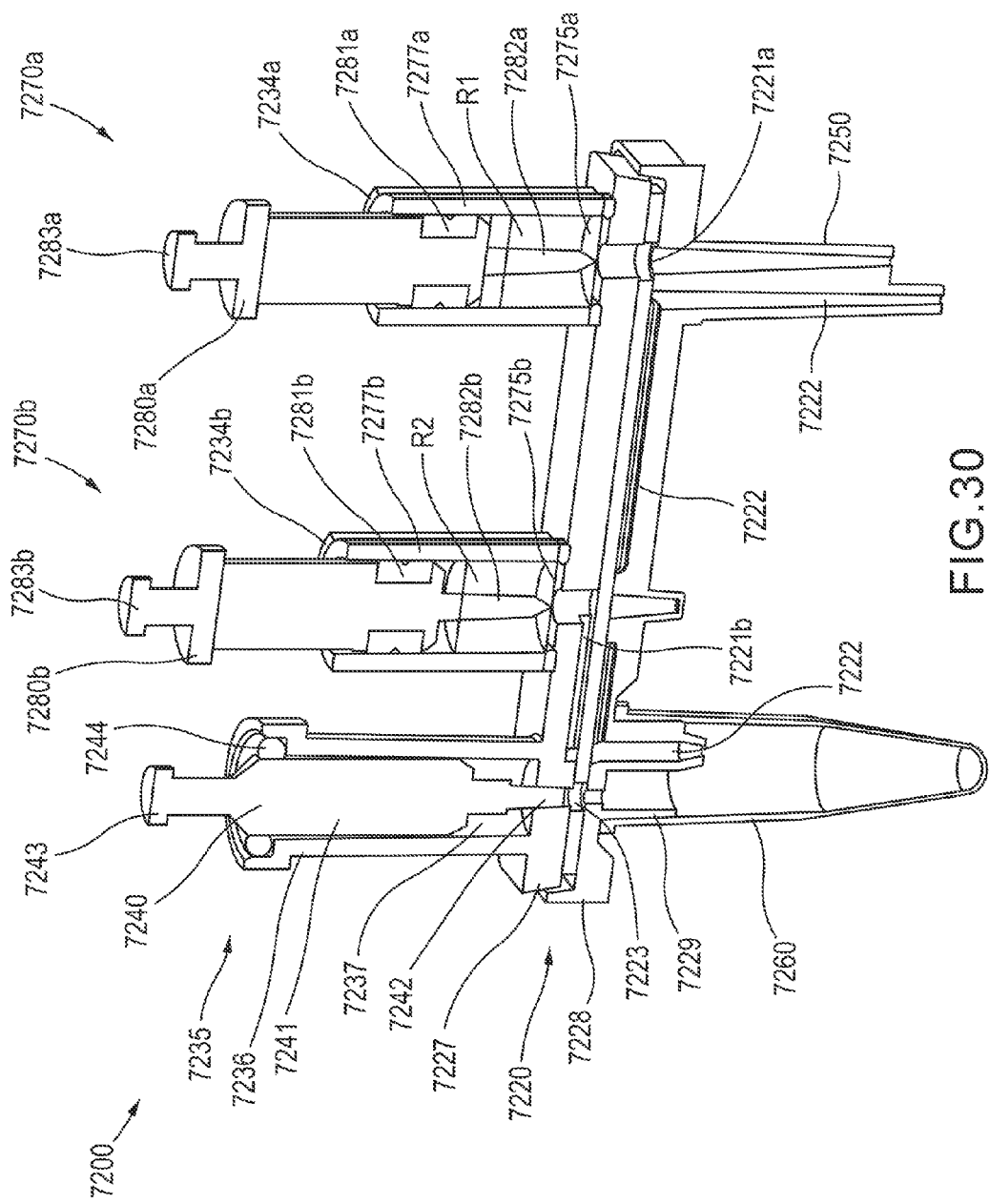
FIG. 30 is a side cross-sectional view of the PCR module shown in FIG. 29, in the first configuration.
Figure 31:
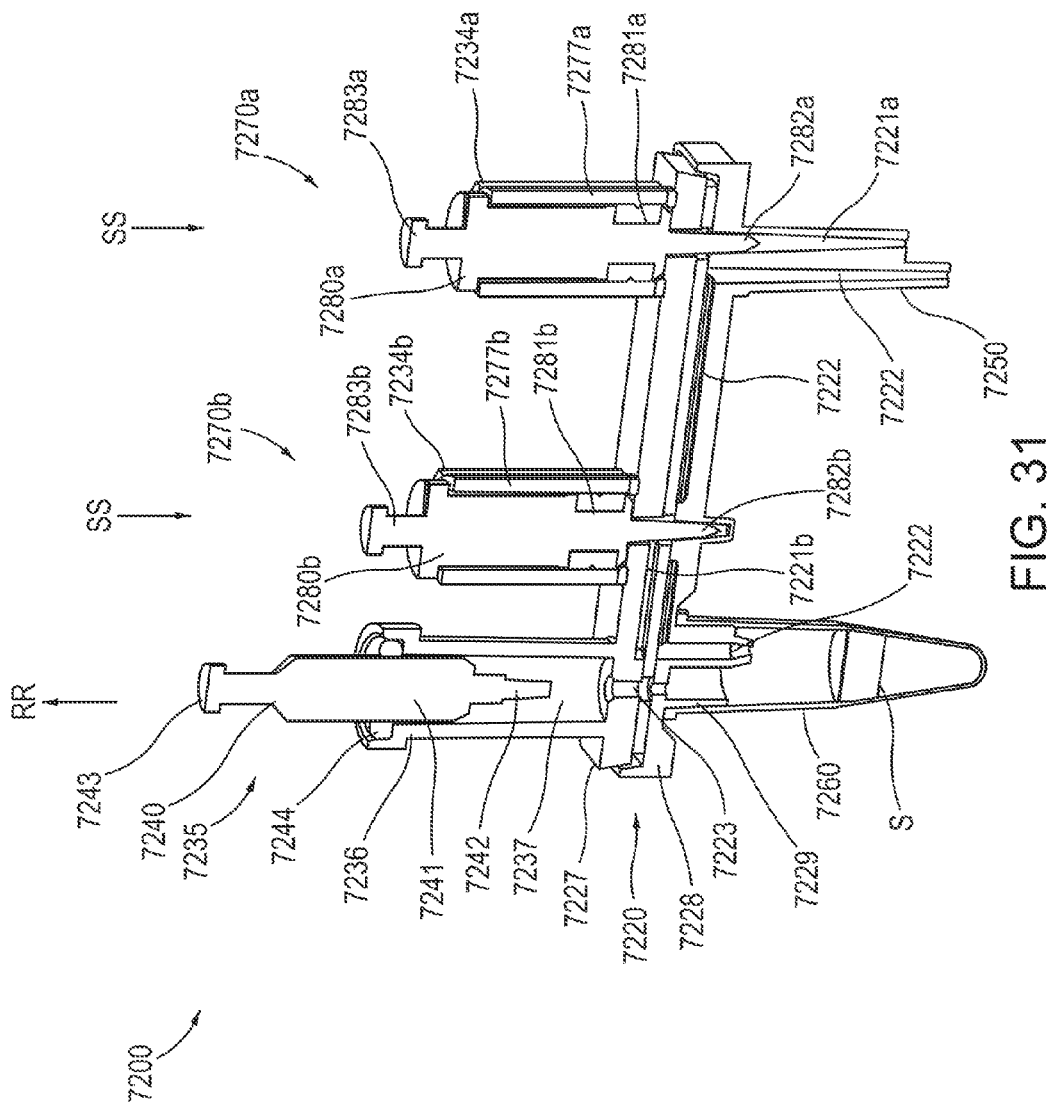
FIG. 31 is a side cross-sectional view of the PCR module shown in FIG. 29, in a second configuration.

As shown in FIGS. 29-31, the amplification (or PCR) module 7200 includes a substrate 7220 that is constructed from a first (or upper) layer 7227 and a second (or bottom) layer 7228. The PCR module 7200 includes a PCR vial 7260 coupled to the second layer 7228, a transfer mechanism 7235, a first reagent module 7270a and a second reagent module 7270b. The PCR vial 7260 is coupled to the first end portion 7211 of the housing 7210 and defines a volume 7262 within which a sample can be disposed to facilitate a reaction associated with the sample. The PCR vial 7260 can be any suitable container for containing a sample in a manner that permits a reaction associated with the sample to occur. The PCR vial 7260 can also be any suitable container for containing the sample in a manner that permits the monitoring of such a reaction (e.g., the detection of an analyte within the sample that results from or is associated with the reaction). In some embodiments, at least a portion of the PCR vial 7260 can be substantially transparent to allow optical monitoring of a reaction occurring therein be an optical system (e.g., the optics assembly 3800 of the instrument 3002 described herein).

Figure 32:
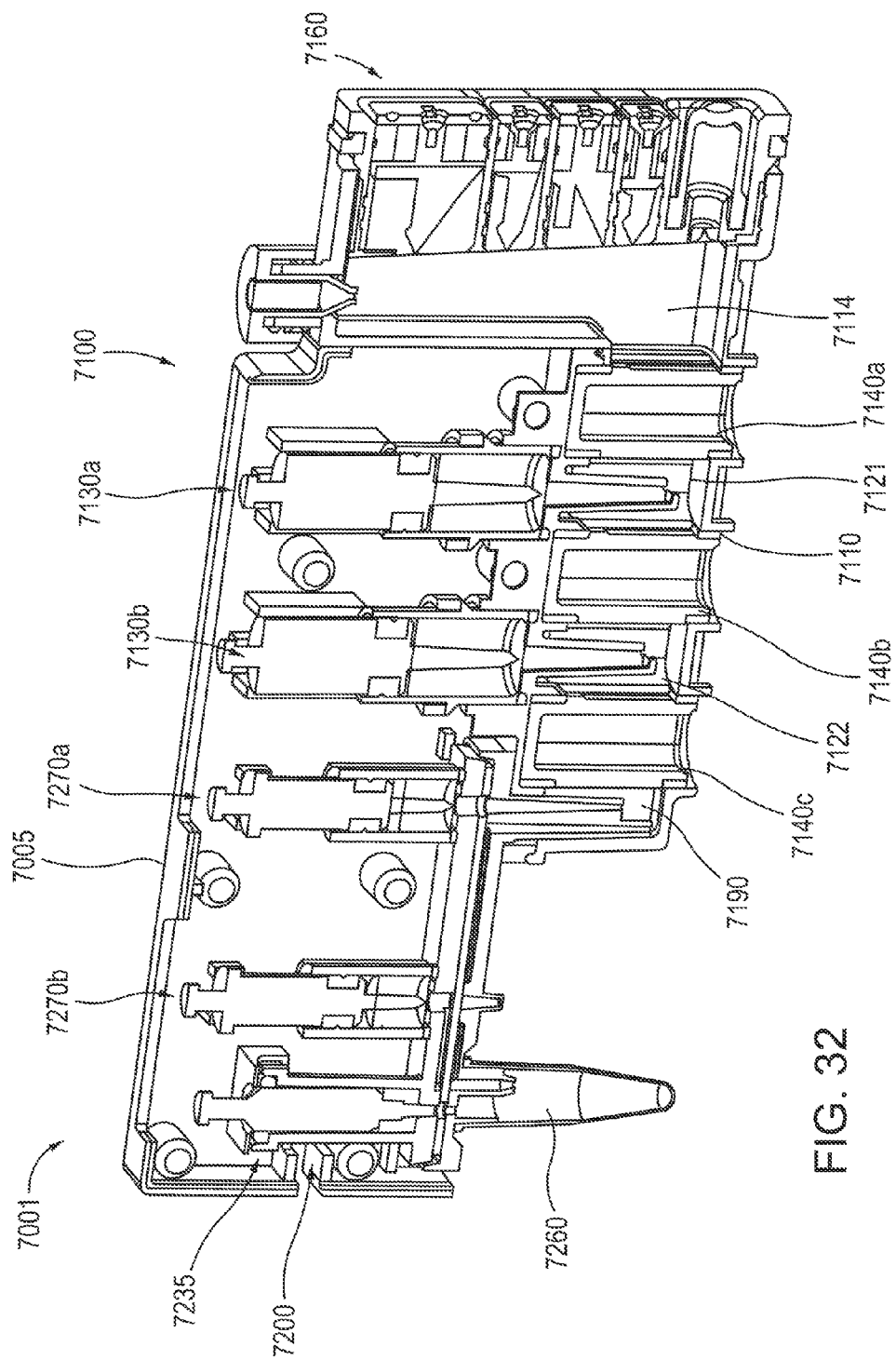
FIGS. 32 and 33 are side cross-sectional views of the cartridge shown in FIG. 25, in a first configuration and a second configuration, respectively.
Figure 33:
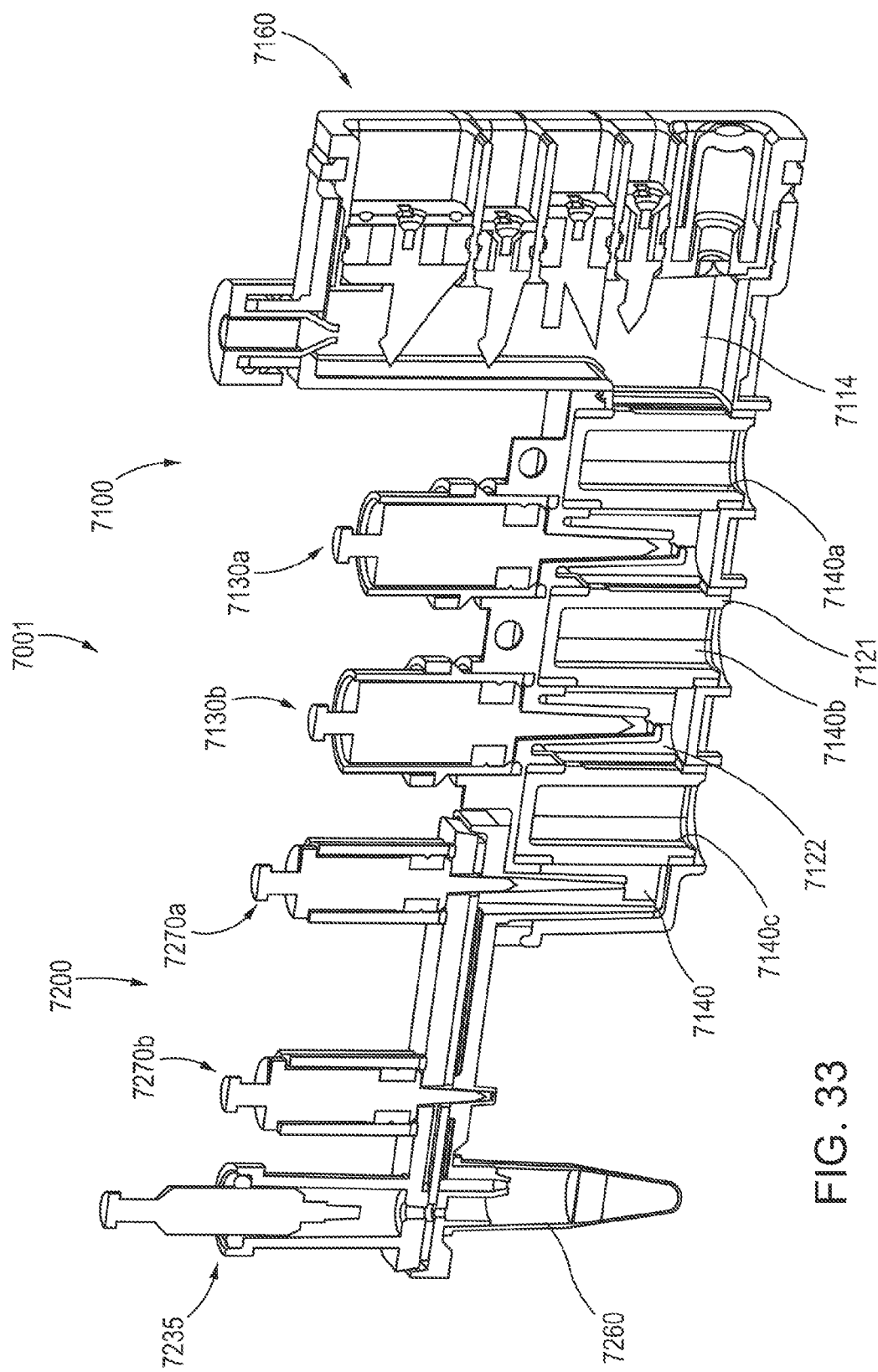

As shown in FIGS. 32 and 33, the amplification module 7200 is coupled to the first housing 7110 of the isolation module 7100 such that at least a portion of a transfer tube 7250 is disposed within the elution chamber 7190 of the isolation module 7100. In this manner, as described herein, the isolated nucleic acid, any substances and/or any PCR reagents disposed within the elution chamber 7190 can be conveyed from the elution chamber 7190 to the PCR vial 7260 via the transfer tube 7250. More particularly, the substrate 7220 defines a flow passageway 7222 that places the PCR vial 7260 in fluid communication with the elution chamber 7190 when the PCR module 7200 is coupled to the isolation module 7100. As shown in FIGS. 30 and 31, portions of the flow passageway 7222 are defined in the transfer tube 7250 and a transfer port 7229 of the second layer 7228 of the substrate 7220. Although the flow passageway 7222 is shown as being defined primarily by the second layer 7228 of the substrate 7220, in other embodiments, the flow passageway 7222 can be defined by the first layer 7227 or in portions of both the first layer 7227 and the second layer 7228.

The substrate 7220 also defines a flow passageway 7223, a flow passageway 7221a and a flow passageway 7221b. As described in more detail herein, the flow passageway 7223 is configured to place a volume 7237 defined within the transfer mechanism 7235 in fluid communication with the PCR vial 7260 via the transfer port 7229. The flow passageway 7221a is configured to place a volume defined by the reagent module 7270a in fluid communication with the elution chamber 7190 via the transfer tube 7250. The flow passageway 7221b is configured to place a volume defined by the reagent module 7270b in fluid communication with the PCR vial 7260 via the transfer port 7229 and/or a portion of the passageway 7222. Any of the flow passageway 7223, the flow passageway 7221a and/or the flow passageway 7221b can be defined by the first layer 7227, the second layer 7228, or in portions of both the first layer 7227 and the second layer 7228.

The PCR module 7200 includes two reagent modules 7270a and 7270b that are each coupled to the upper layer 7227 of the substrate 7220. As described herein, each reagent module 7270a and 7270b contains a substance, R1 and R2, respectively. The reagent module 7270a is configured to convey the substance R1 into the elution chamber 7190 via the flow passageway 7221a, as described herein. The reagent module 7270b is configured to convey the substance R2 into the PCR vial 7260 via the flow passageway 7221b, as described herein. In this manner, each reagent module 7270a and 7270b functions as a reagent storage device and a transfer mechanism.

The substances R1 and R2 can be, for example, a reagent, an elution buffer solution, a wash buffer solution, a mineral oil and/or any other substance to be added to the sample, as described herein. In some embodiments, the substance R1 can include an elution buffer and mineral oil. In some embodiments, the substance R2 can include reaction reagents that facilitate a PCR process within the PCR vial 7260. In some embodiments, a PCR master mix can be disposed within the PCR vial 7260 in a lyophilized state such that the addition of the substance R2 and/or a mixture of the substance R1 and the target sample reconstitutes the lyophilized master mix to facilitate the PCR process.

For example, in one embodiment where HSV is amplified via PCR, the master mix is a lyophilized pellet comprising HSV1 and HSV2 primers specific for a HSV1 and/or HSV2 sequence, detection probe (e.g., a hybridizing oligonucleotide probe comprising a fluorophore and MGB at the 5'-end and a non-fluorescent quencher at the 3' end), and internal control primers and probe, KCl (e.g., about 40 mM, about 50 mM, about 60 mM, about 70 mM), manniol (e.g., about 70 mM, about 80 mM, about 90 mM, about 100 mM, about 110 mM, about 120 mM), BSA (e.g., about 0.1 mg/mL, about 0.5 mg/mL, about 1 mg/mL), dNTPs (e.g., about 0.2 mM, about 0.3 mM, about 0.4 mM, about 0.5 mM, about 1 mM), Taq polymerase (e.g., about 0.1 U/µL, about 0.2 U/µL, about 0.3 U/µL).

In another embodiment, a master mix comprises lyophilized reagents to perform a multiplex PCR on three targets and an internal control. In a further embodiment, the target nucleic acids are a nucleic acid specific for influenza A, a nucleic acid specific for influenza B and a nucleic acid specific for RSV. In even a further embodiment, the multiplex reaction is monitored in real time, for example, by providing a hybridizing oligonucleotide probe, specific for each target sequence, each probe comprising a fluorophore and MGB at the 5'-end and a non-fluorescent quencher at the 3' end.

In another embodiment, the lyophilized master mix comprises reagents for both a PCR and a reverse transcriptase reaction. For example, in one embodiment, the lyophilized master mix includes both the reverse transcriptase and Taq polymerase enzymes, dNTPs, RNase inhibitor, KCl, BSA and primers to carry out first strand cDNA synthesis and PCR.

The master mix comprises different primers and probes, depending on the target to be amplified. Each target will have associated with it a specific primer and probe set, and the primer and probe set can be lyophilized with the other PCR reagents mentioned above, to form a lyophilized master mix. Concentrations of components will also vary depending on the particular target being amplified, and if multiple targets are amplified.

The reagent module 7270a includes an actuator 7280a that is movably disposed within a housing 7277a. The housing 7277a is coupled to the upper layer 7227 of the substrate 7220 such that the reagent module 7270a is substantially aligned with the passageway 7221a, the transfer tube 7250 and/or the elution chamber 7190. As shown in FIG. 29, the housing 7277a includes a pair of protrusions 7273a that are configured to be disposed within a corresponding opening defined by a coupling portion 7234a of the upper layer 7227 of the substrate 7220. Although the reagent module 7270a is shown as being coupled to the substrate 7220 by a "snap fit," in other embodiments, the reagent module 7270a can be coupled to the substrate 7220 by any suitable method, such as for example, by a threaded coupling, a mechanical fastener or retainer, a chemical bond or adhesive, an interference fit, a weld joint or the like.

The actuator 7280*a* includes a plunger portion 7281*a*, a piercing portion 7282*a* and an engagement portion 7283*a*. The engagement portion 7283*a* is configured to engage with, be removably coupled to and/or be received within a portion of an actuator assembly to facilitate movement of the actuator 7280*a* within the housing 7277*a*, as described herein. The actuator 7280*a* can be manipulated and/or actuated by any suitable instrument, such as the actuator assembly 3600 described below with respect to FIGS. 47-51.

The plunger portion 7281*a* of the actuator 7280*a* is disposed within the housing 7277*a*. A puncturable member 7275*a* is disposed about the end portion of the housing 7277*a* such that end face of the plunger portion 7281*a*, the housing 7277*a* and the puncturable member 7275*a* collectively define a volume within which the substance R1 is disposed. The plunger portion 7281*a* and the internal surface of the housing 7277*a* are configured to form a substantially fluid-tight and/or hermetic seal. In some embodiments, the plunger portion 7281*a* can include a sealing member, an o-ring or the like.

The piercing portion 7282*a* of the actuator 7280*a* is configured to puncture, break, sever and/or rupture a portion of the puncturable member 7275*a* when the actuator 7280*a* is moved within the housing 7277*a* in the direction indicated by the arrow SS in FIG. 31. In this manner, movement of the actuator 7280*a* places the volume therein in fluid communication with the passageway 7221*a*, and therefore the elution chamber 7190. Similarly stated, reagent module 7270*a* can be selectively placed in fluid communication with the elution chamber 7190 when the actuator 7280*a* is actuated.

The reagent module 7270*b* includes an actuator 7280*b* that is movably disposed within a housing 7277*b*. The housing 7277*b* is coupled to the upper layer 7227 of the substrate 7220 such that the reagent module 7270*b* is substantially aligned with the passageway 7221*b*. As shown in FIG. 29, the housing 7277*b* includes a pair of protrusions 7273*b* that are configured to be disposed within a corresponding opening defined by a coupling portion 7234*b* of the upper layer 7227 of the substrate 7220. Although the reagent module 7270*b* is shown as being coupled to the substrate 7220 by a "snap fit," in other embodiments, the reagent module 7270*b* can be coupled to the substrate 7220 by any suitable method, such as for example, by a threaded coupling, a mechanical fastener or retainer, a chemical bond or adhesive, an interference fit, a weld joint or the like.

The actuator 7280*b* includes a plunger portion 7281*b*, a piercing portion 7282*b* and an engagement portion 7283*b*. The engagement portion 7283*b* is configured to engage with, be removably coupled to and/or be received within a portion of an actuator assembly to facilitate movement of the actuator 7280*b* within the housing 7277*b*, as described herein. The actuator 7280*b* can be manipulated and/or actuated by any suitable instrument, such as the actuator assembly 3600 described below with respect to FIGS. 47-51.

The plunger portion 7281*b* of the actuator 7280*b* is disposed within the housing 7277*b*. A puncturable member 7275*b* is disposed about the end portion of the housing 7277*b* such that end face of the plunger portion 7281*b*, the housing 7277*b* and the puncturable member 7275*b* collectively define a volume within which the substance R2 is disposed. The plunger portion 7281*b* and the internal surface of the housing 7277*b* are configured to form a substantially fluid-tight and/or hermetic seal. In some embodiments, the plunger portion 7281*a* can include a sealing member, an o-ring or the like.

The piercing portion 7282*b* of the actuator 7280*b* is configured to puncture, break, sever and/or rupture a portion of the puncturable member 7275*b* when the actuator 7280*b* is moved within the housing 7277*b* in the direction indicated by the arrow SS in FIG. 31. In this manner, movement of the actuator 7280*b* places the volume therein in fluid communication with the passageway 7221*b*, and therefore the PCR chamber 7260.

The PCR module 7200 includes a transfer mechanism 7235 configured to transfer substances from and/or between the elution chamber 7190 of the isolation module 7100 and the PCR vial 7260 of the PCR module 7200. As described herein, the transfer mechanism 7235 is also configured to define a volume 7237 within which a substance can be contained, and selectively place the volume 7237 in fluid communication with the PCR vial 7260. In this manner, the transfer mechanism 7235 also acts as a flow control mechanism.

The transfer mechanism 7235 includes an actuator 7240 disposed within a housing 7236. The housing 7236 is coupled to and/or is a portion of the upper layer 7227 of the substrate 7220. The housing 7236 defines a volume 7237 within which a substance, such as, for example, mineral oil, can be stored. Although not shown as including a puncturable member, in other embodiments a portion of the volume 7237 can be surrounded by and/or fluidically isolated by a puncturable member, as described herein.

The actuator 7240 includes a plunger portion 7241, a valve portion 7242 and an engagement portion 7243. The engagement portion 7243 is configured to engage with, be removably coupled to and/or be received within a portion of an actuator assembly to facilitate movement of the actuator 7240 within the housing 7236, as described herein. The actuator 7240 can be manipulated and/or actuated by any suitable instrument, such as the actuator assembly 3600 described below with respect to FIGS. 47-51.

The plunger portion 7241 of the actuator 7240 is disposed within the housing 7236. The plunger portion 7241 and the internal surface of the housing 7236 are configured to form a substantially fluid-tight and/or hermetic seal. In some embodiments, the plunger portion 7241 can include a sealing member, an o-ring or the like. Additionally, a seal 7244 is disposed at the top portion of the housing 7236.

The actuator 7240 is configured to be moved within the housing 7236 between a first position (FIG. 30) and a second position (FIG. 31). When the actuator 7240 is in the first position, the valve portion 7242 of the actuator 7240 is disposed at least partially within the flow passageway 7223 such that volume 7237 is substantially fluidically isolated from the flow passageway 7223 and/or the PCR vial 7260. Similarly stated, when the actuator 7240 is in the first position, a portion of the valve portion 7242 is in contact with the upper layer 7227 to produce a substantially fluid-tight and/or hermetic seal. When the actuator 7250 is moved within the housing 7236 in the direction indicated by the arrow RR in FIG. 31, the valve portion 7242 is spaced apart from the upper layer 7227 and/or is removed from the flow passageway 7223, thereby placing the volume 7237 in fluid communication with the passageway 7223, and therefore the PCR chamber 7260. In this manner, when the actuator 7240 is moved, the substance within the volume 7237 can be conveyed into the PCR volume 7262 defined by the PCR vial 7260.

Moreover, when the actuator 7240 is moved within the housing 7236, as shown by the arrow RR in FIG. 31, a vacuum is produced within the PCR volume 7262 of the PCR vial 7260. This pressure differential between the PCR volume 7262 and the elution chamber 7190 results in at least a portion of the contents of the elution chamber 7190 being transferred into the PCR volume 7262 via the transfer tube 7250 and the passageway 7222 (see e.g., FIG. 24). In this manner substances and/or samples can be added, mixed and/or conveyed between the elution chamber 7190 and the PCR volume 7262 by actuating the transfer mechanism 7235. The transfer mechanism 7235 can be actuated by any suitable mechanism, such as for example, the actuation assembly 3600 of the instrument 3002 described herein.

In use, after the one or more target nucleic acids, or population of nucleic acids is isolated and processed within the isolation module 7100, as described above, it is transferred into the elution chamber 7190 via the transfer assembly 7140c. The reagent module 7270a can then be actuated to convey the substance R1 into the elution chamber 7190. For example, in some embodiments, the reagent module 7270a can be actuated to convey a solution containing an elution buffer and mineral oil into the elution chamber 7190. The magnetic beads are then removed (or "washed") from the nucleic acid by the elution buffer, and removed from the elution chamber 7190 (e.g., by the transfer assembly 7140c). Thus, the elution chamber 7190 contains the isolated and/or purified nucleic acid.

The reagent module 7270b can be actuated to convey the substance R2 into the PCR volume 7262. For example, in some embodiments, the reagent module 7270b can be actuated to convey a solution containing various reaction reagents into the PCR vial 7260. In some embodiments, the PCR vial 7260 can contain additional reagents and/or substances, such as, for example, a PCR master mix, in a lyophilized state. Accordingly, when the substance R2 is conveyed into the PCR vial 7260, the lyophilized contents can be reconstituted in preparation for the reaction.

The target sample S can conveyed (either before or after the actuation of the reagent module 7270b described above) from the elution chamber 7190 into the PCR vial 7260 via the transfer tube 7250 and the passageway 7222. In particular, the actuator 7240 of the transfer mechanism 7235 can be actuated to produce a pressure differential within the PCR module 7200 to convey the PCR sample from the elution chamber 7190 into the PCR vial 7260 via the passageway 7222, as described above. In this manner, the PCR sample (the isolated nucleic acid and the PCR reagents) can be partially prepared in the elution chamber 7190. Moreover, when the transfer mechanism 7235 is actuated, the volume 7237 defined therein is placed in fluid communication with the PCR volume 7262 via the passageway 7223, as described above. Thus, in some embodiments, an additional substance (e.g., a mineral oil) can be added to the PCR vial via the same operation as the sample transfer operation.

After the PCR sample is in the PCR vial 7260, at least a portion of the PCR sample S can be thermally cycled (e.g., via the heating assembly 3700 of the instrument 3002) to perform the desired amplification. Upon completion of and/or during the thermal cycling, the PCR sample can be optically analyzed (e.g., via the optics assembly 3800 of the instrument 3002) to analyze the sample. Alternatively, as described throughout, the PCR sample can be optically analyzed during the PCR, for example, with DNA hybridization probes, each conjugated to an MGB and fluorophore. A description of the instrument 3002, and other suitable instruments for manipulating the cartridge, is provided below.

Any of the cartridges described herein can be manipulated and/or actuated by any suitable instrument to perform an isolation process and/or reaction on a sample contained within the cartridge. For example, in some embodiments, any of the cartridges described herein can be manipulated and/or actuated by an instrument to perform real-time nucleic acid isolation and amplification on a test sample within the cartridge. In this manner, the system (e.g., the cartridge or a series of cartridges and an instrument) can be used for many different assays, such as, for example, the rapid detection of influenza (Flu) A, Flu B, and respiratory syncytial virus (RSV) from nasopharyngeal specimens.

Figure 34:
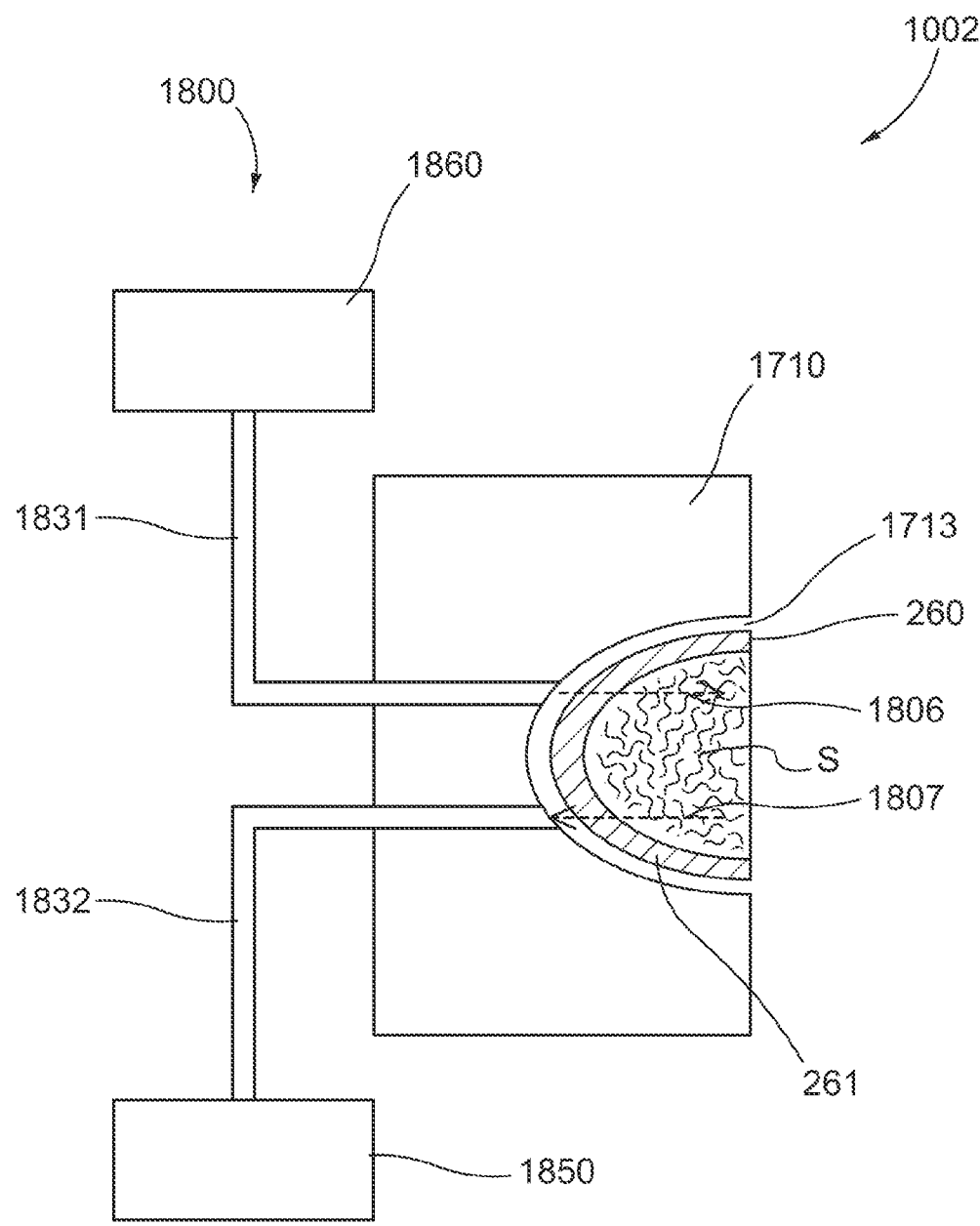
FIG. 34 is a schematic illustration of a portion of an instrument according to an embodiment.

In some embodiments, an instrument can be configured to facilitate, produce, support and/or promote a reaction in a sample contained in a reaction chamber defined by a cartridge of the types shown and described herein. Such an instrument can also include an optics assembly to detect one or more different substances and/or analytes within the sample before, during and/or after the reaction. For example, FIG. 34 is a schematic illustration of an instrument 1002 according to an embodiment. The instrument 1002 includes a block 1710, a first optical member 1831, a second optical member 1832 and an optics assembly 1800. The block 1710 defines a reaction volume 1713 configured to receive at least a portion 261 of a reaction container 260 that contains a sample S. The reaction container 260 can be any suitable container for containing the sample S in a manner that permits a reaction associated with the sample S to occur. The reaction container 260 can also be any suitable container for containing the sample S in a manner that permits the monitoring of such a reaction (e.g., the detection of an analyte within the sample S that results from or is associated with the reaction). In some embodiments, for example, the reaction container 260 can be a PCR vial, a test tube or the like. Moreover, in some embodiments, at least the portion 261 of the reaction container 260 can be substantially transparent to allow optical monitoring of a reaction occurring therein.

The block 1710 can be any suitable structure for and/or can be coupled to any suitable mechanism for facilitating, producing, supporting and/or promoting a reaction associated with the sample S in the reaction container 260. For example, in some embodiments, the block 1710 can be coupled to and/or can include a mechanism for cyclically heating the sample S in the reaction container 260. In this manner, the block 1710 can produce a thermally-induced reaction of the sample S, such as, for example, a PCR process. In other embodiments, the block 1710 can be coupled to and/or can include a mechanism for introducing one or more substances into the reaction container 260 to produce a chemical reaction associated with the sample S.

The reaction volume 1713 can have any suitable size and/or shape for containing the portion 261 of the reaction chamber 260. In some embodiments, for example, the shape of the reaction volume 1713 can substantially correspond to the shape of the portion 261 of the reaction chamber 260 (e.g., as shown in FIG. 34). In other embodiments, however, the shape of the reaction volume 1713 can be dissimilar to the shape of the portion 261 of the reaction chamber 260. Although the portion 261 of the reaction chamber 260 is shown in FIG. 34 as being spaced apart from the side wall of the block 1710 that defines the reaction volume 1713, in other embodiments, the portion 261 of the reaction chamber 260 can be in contact with a portion of the block 1710. In yet other embodiments, the reaction volume 1713 can contain a substance (e.g., a salt water solution, a thermally conductive gel or the like) disposed between the portion 261 of the reaction chamber 260 and portion (e.g., a side wall) of the block 1710.

Although the block 1710 is shown in FIG. 34 as containing only the portion 261 of the reaction chamber 260 within the reaction volume 1713, in other embodiments, the block 1710 can be configured such the entire reaction chamber 260 is received within the reaction volume 1713. In some embodiments, for example, the block 1710 can include a cover or other mechanism (not shown in FIG. 34) that retains substantially the entire reaction chamber 260 within the reaction volume 1713. Moreover, in some embodiments, the block 1710 can substantially surround the entire reaction chamber 260. In other embodiments, the block 1710 can substantially surround the portion 261 of the reaction chamber 260 disposed within the reaction volume 1713.

As shown in FIG. 34, the first optical member 1831 is disposed at least partially within the block 1710 such that the first optical member 1831 is in optical communication with the reaction volume 1713. In this manner, a light beam (and/or an optical signal) can be conveyed between the reaction volume 1713 and a region outside of the block 1710 via the first optical member 1831. The first optical member 1831 can be any suitable structure, device and/or mechanism through which or from which a light beam can be conveyed. In some embodiments, the first optical member 1831 can be any suitable optical fiber to convey a light beam, such as, for example, a multi-mode fiber or a single-mode fiber. In other embodiments, the first optical member 1831 can include a mechanism configured to modify and/or transform a light beam, such as, for example, an optical amplifier, an optical signal converter, a lens, an optical filter or the like. In yet other embodiments, the second optical member 1832 can include a light-emitting diode (LED), a laser or other device configured to produce a light beam.

The second optical member 1832 is disposed at least partially within the block 1710 such that the second optical member 1832 is in optical communication with the reaction volume 1713. In this manner, a light beam (and/or an optical signal) can be conveyed between the reaction volume 1713 and a region outside of the block 1710 via the second optical member 1832. The second optical member 1832 can be any suitable structure, device and/or mechanism through which or from which a light beam can be conveyed. In some embodiments, the second optical member 1832 can be any suitable optical fiber to convey a light beam, such as, for example, a multi-mode fiber or a single-mode fiber. In other embodiments, the second optical member 1832 can include a mechanism configured to modify and/or transform a light beam, such as, for example, an optical amplifier, an optical signal converter, a lens, an optical filter or the like. In yet other embodiments, the second optical member 1832 can include a photodiode or other device configured to receive and/or detect a light beam.

The optics assembly 1800 includes an excitation module 1860 and a detection module 1850. The excitation module 1860 is configured to produce a series excitation light beams (and/or optical signals, not shown in FIG. 34). Accordingly, the excitation module 1860 can include any suitable device and/or mechanism for producing the series of excitation light beams, such as, for example, a laser, one or more light-emitting diodes (LEDs), a flash lamp, or the like. In some embodiments, each light beam produced by the excitation module 1860 can have substantially the same characteristics (e.g., wavelength, amplitude and/or energy) as each of the other light beams produced by the excitation module 1860. In other embodiments, however, a first light beam produced by the excitation module 1860 can have characteristics (e.g., wavelength, amplitude and/or energy) different from one of the other light beams produced by the excitation module 1860. In some embodiments, for example, the excitation module 1860 can include a series of LEDs, each configured to produce a light beam having a different wavelength than the light beams produced by the other LEDs.

The detection module 1850 is configured to receive a series emission light beams (and/or optical signals, not shown in FIG. 34). Accordingly, the detection module 1850 can include any suitable photodetector, such as for example, an optical detector, a photoresistor, a photovoltaic cell, a photo diode, a phototube, a CCD camera or the like. The emission light beams can be produced by any suitable source, such as, for example, by the excitation of a constituent of the sample S. In some embodiments, the detection module 1850 can be configured to selectively receive each emission light beam regardless of the whether each light beam has the same characteristics (e.g., wavelength, amplitude and/or energy) as each of the other emission light beams. In other embodiments, however, the detection module 1850 can be configured to selectively receive each emission light beam based on the particular characteristics (e.g., wavelength, amplitude and/or energy) of the light beam. In some embodiments, for example, the detection module 1850 can include a series of photodetectors, each configured to receive a light beam having a different wavelength than the light beams received by the other photodetectors.

As shown in FIG. 34, the first optical member 1831 and the second optical member 1832 are coupled to the optics assembly 1800. In this manner, each of the series of excitation light beams can be conveyed into the reaction volume 1713 and/or the portion 261 of the reaction container 260, and each of the series of emission light beams can be received from the reaction volume 1713 and/or the portion 261 of the reaction container 260. More particularly, the first optical member 1831 is coupled to the excitation module 1860 such that the series of excitation light beams produced by the excitation module 1860 can be conveyed into the reaction volume 1713 and/or the portion 261 of the reaction container 260. Similarly, the second optical member 1832 is coupled to the detection module 1850 such that each of the plurality of emission light beams can be received from the reaction volume 1713 and/or the portion 261 of the reaction container 260.

The series of light beams produced by the excitation module 1860 is conveyed into the reaction volume 1713 and/or the portion 261 of the reaction container 260 by the first optical member 1831, and along a first light path 1806. Thus, each of the series of light beams produced by the excitation module 1860 is conveyed into the reaction volume 1713 and/or the portion 261 of the reaction container 260 at a substantially constant location. Similarly, the series of light beams received by the detection module 1850 is received from the reaction volume 1713 and/or the portion 261 of the reaction container 260 by the second optical member 1832, and along a second light path 1807. Thus, each of the series of light beams received by the detection module 1850 is received from the reaction volume 1713 and/or the portion 261 of the reaction container 260 at a substantially constant location. By conveying and receiving the excitation light beams and the emission light beams, respectively, at a constant location within the reaction volume 1713, detection variability within a multi-channel analysis associated with conveying excitation light beams from multiple different locations and/or receiving emission light beams from multiple different locations can be reduced.

Moreover, by including the first optical member 1831 and the second optical member 1832 within the block 1710, the position of the first optical member 1831 (and the first light path 1806) and/or the position of the second optical member 1832 (and the second light path 1807) relative to the reaction volume 1713 is constant. This arrangement can also reduce the test-to-test detection variability associated with the light paths and/or optical members by minimizing and/or eliminating relative movement between the first optical member 1831, the second optical member 1832 and/or the reaction volume 1713.

In some embodiments, the series of excitation light beams can be sequentially conveyed into the reaction volume 1713 and the series of emission light beams can be sequentially received from the reaction volume 1713. For example, in some embodiments, the excitation module 1860 can produce a series of light beams, each having a different wavelength, in a sequential (or time-phased) manner. Each light beam is conveyed into the reaction volume 1713, where the light beam can, for example, excite the sample S contained within the reaction container 260. Similarly, in such embodiments, the emission light beams are produced (as a result of the excitation of certain analytes and/or targets within the sample S) in a sequential (or time-phased) manner. Thus, the detection module 1850 can receive a series of light beams, each having a different wavelength, in a sequential (or time-phased) manner. In this manner, the instrument 1802 can be used to detect multiple different analytes and/or targets within the sample S.

Although the portion of the first optical member 1831 disposed within the block 1710 and the portion of the second optical member 1832 disposed within the block 1710 are shown in FIG. 34 as being substantially parallel and/or within the same plane, in other embodiments, a block can include a first optical member that is at any position and/or orientation relative to a second optical member. Similarly stated, although the first light path 1806 is shown in FIG. 34 as being substantially parallel to and/or within the same plane as the second light path 1807, in other embodiments, an instrument can be configured to produce a first light path that is at any position and/or orientation relative to a second light path.

Figure 35:
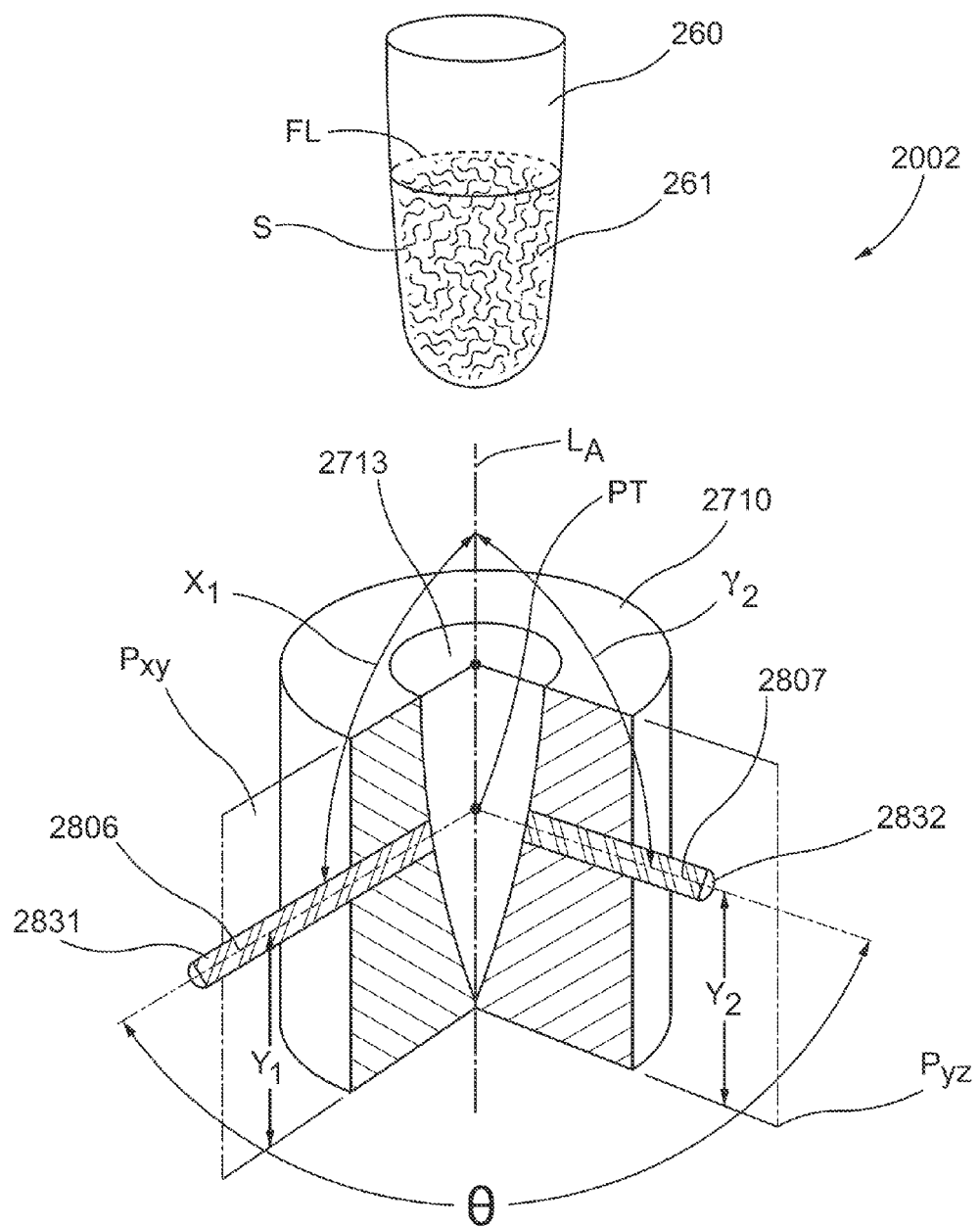
FIG. 35 is a perspective, cross-sectional schematic illustration of an instrument according to an embodiment.

For example, FIG. 35 shows a partial cross-sectional, schematic illustration of a portion of an instrument 2002 according to an embodiment. The instrument 2002 includes a block 2710, a first optical member 2831, a second optical member 2832 and an optics assembly (not shown in FIG. 35). The block 2710 defines a reaction volume 2713 configured to receive at least a portion 261 of a reaction container 260 that contains a sample S. The reaction container 260 can be any suitable container for containing the sample S in a manner that permits a reaction associated with the sample S to occur, and that permits the monitoring of such a reaction, as described herein. In some embodiments, for example, the reaction container 260 can be a PCR vial, a test tube or the like. Moreover, in some embodiments, at least the portion 261 of the reaction container 260 can be substantially transparent to allow optical monitoring of a reaction occurring therein.

The block 2710 can be any suitable structure for and/or can be coupled to any suitable mechanism for facilitating, producing, supporting and/or promoting a reaction associated with the sample S in the reaction container 260. For example, in some embodiments, the block 2710 can be coupled to and/or can include a mechanism for cyclically heating the sample S in the reaction container 260. In this manner, the block 2710 can produce a thermally-induced reaction of the sample S, such as, for example, a PCR process. In other embodiments, the block 2710 can be coupled to and/or can include a mechanism for introducing one or more substances into the reaction container 260 to produce a chemical reaction associated with the sample S.

The reaction volume 2713 can have any suitable size and/or shape for containing the portion 261 of the reaction chamber 260. As shown in FIG. 35, the reaction volume 2713 defines a longitudinal axis $L_A$ and substantially surrounds the portion 261 of the reaction chamber 260 when the portion 261 is disposed within the reaction volume 2713. In this manner, any stimulus (e.g., heating or cooling) provided to the sample S by the block 2710 or any mechanisms attached thereto can be provided in a substantially spatially uniform manner.

As shown in FIG. 35, the first optical member 2831 is disposed at least partially within the block 2710 such that the first optical member 2831 defines a first light path 2806 and is in optical communication with the reaction volume 2713. In this manner, a light beam (and/or an optical signal) can be conveyed between the reaction volume 2713 and a region outside of the block 2710 via the first optical member 2831. The first optical member 2831 can be any suitable structure, device and/or mechanism through which or from which a light beam can be conveyed, of the types shown and described herein. In some embodiments, the first optical member 2831 can be any suitable optical fiber to convey a light beam, such as, for example, a multi-mode fiber or a single-mode fiber.

The second optical member 2832 is disposed at least partially within the block 2710 such that the second optical member 2832 defines a second light path 2807 and is in optical communication with the reaction volume 2713. In this manner, a light beam (and/or an optical signal) can be conveyed between the reaction volume 2713 and a region outside of the block 2710 via the second optical member 2832. The second optical member 2832 can be any suitable structure, device and/or mechanism through which or from which a light beam can be conveyed, of the types shown and described herein. In some embodiments, the second optical member 2832 can be any suitable optical fiber to convey a light beam, such as, for example, a multi-mode fiber or a single-mode fiber.

As described above, the first optical member 2831 and the second optical member 2832 are coupled to the optics assembly (not shown in FIG. 35). The optics assembly can produce one or more excitation light beams, and can detect one or more emission light beams. Thus, one or more excitation light beams can be conveyed into the reaction volume 2713 and/or the reaction container 260, and one or more emission light beams can be received from the reaction volume 2713 and/or the portion 261 of the reaction container 260. More particularly, the first optical member 2831 can convey an excitation light beam from the optics assembly into the reaction volume 2713 to excite a portion of the sample S contained within the reaction container 260. Similarly, the second optical member 2832 can convey an emission light beam produced by an analyte or other target within the sample S from the reaction volume 2713 to the optics assembly. In this manner, the optics assembly can monitor a reaction occurring within the reaction container 260.

As shown in FIG. 35, the portion of first optical member 2831 and the first light path 2806 are disposed substantially within a first plane $P_{XY}$. The first plane $P_{XY}$ is substantially parallel to and/or includes the longitudinal axis $L_A$ of the reaction volume 2713. In other embodiments, however, the first plane $P_{YX}$ need not be substantially parallel to and/or include the longitudinal axis $L_A$ of the reaction volume 2713. The portion of second optical member 2832 and the second light path 2807 are disposed substantially within a second plane $P_{YZ}$. The second plane $P_{YZ}$ is substantially parallel to and/or includes the longitudinal axis $L_A$ of the reaction volume 2713. In other embodiments, however, the second plane $P_{YZ}$ need not be substantially parallel to and/or include the longitudinal axis $L_A$ of the reaction volume 2713. Moreover, as shown in FIG. 35, the first light path 2806 and the second light path 2807 define an offset angle $\Theta$ that is greater than approximately 75 degrees. More particularly, the first light path 2806 and the second light path 2807 define an offset angle Θ, when viewed in a direction substantially parallel to the longitudinal axis $L_A$ of the reaction volume 2713 (i.e., that is within a plane substantially normal to the first plane $P_{ZY}$ and the second plane $P_{YZ}$) that is greater than approximately 75 degrees. In a similar manner, the first optical member 2831 and the second optical member 2832 define an offset angle Θ that is greater than approximately 75 degrees. This arrangement minimizes the amount of the excitation light beam that is received by the second optical member 2832 (i.e., the "detection" optical member), thereby improving the accuracy and/or sensitivity of the optical detection and/or monitoring.

In some embodiments, the portion of the instrument 2002 can produce the first light path 2806 and the second light path 2807 within the reaction volume 2713 such that the offset angle Θ is between approximately 75 degrees and approximately 105 degrees. In some embodiments, the portion of the instrument 2002 can produce the first light path 2806 and the second light path 2807 within the reaction volume 2713 such that the offset angle Θ is approximately 90 degrees.

Although the portion of the instrument 2002 is shown as producing the first light path 2806 and the second light path 2807 that are substantially parallel and that intersect in the reaction volume 2713 at a point PT, in other embodiments, the block 2713, the first optical member 2831 and/or the second optical member 2832 can be configured such that the first light path 2806 is non parallel to and/or does not intersect the second light path 2807. For example, in some embodiments, the first light path 2806 and/or the first optical member 2831 can be parallel to and offset from (i.e., skewed from) the second light path 2807 and/or the second optical member 2831. Similarly stated, in some embodiments, the first optical member 2831 and the second optical member 1832 can be spaced apart from a reference plane defined by the block 2710 by a distance $Y_1$ and $Y_2$, respectively, wherein $Y_1$ is different than $Y_2$. Thus, the position along the longitudinal axis $L_A$ at which the first optical member 2831 and/or the first light path 2806 intersects the reaction volume 2713 is different from the position along the longitudinal axis $L_A$ at which the second optical member 2832 and/or the second light path 2807 intersects the reaction volume 2713. In this manner, the first light path 2806 and/or the first optical member 2831 can be skewed from the second light path 2807 and/or the second optical member 2831.

In other embodiments, an angle $\gamma_1$ defined by the longitudinal axis $L_A$ and the first light path 2806 and/or the first optical member 2831 can be different than an angle $\gamma_2$ defined by the longitudinal axis $L_A$ and the second light path 2807 and/or the second optical member 2832 (i.e., the first light path 2806 can be non parallel to the second light path 2807). In yet other embodiments, the block 2713, the first optical member 2831 and/or the second optical member 2832 can be configured such that the first light path 2806 intersects the second light path 2807 at a location outside of the reaction volume 2713.

The distance $Y_1$ and the distance $Y_2$ can be any suitable distance such that the first optical member 2831 and the second optical member 1832 are configured to produce and/or define the first light path 2806 and the second light path 2807, respectively, in the desired portion of the reaction container 260. For example, in some embodiments, the distance $Y_1$ can be such that the first optical member 2831 and/or the first light path 2806 enter and/or intersect the reaction volume 2713 at a location below the location of fill line FL of the sample S when the reaction container 260 is disposed within the block 2710. In this manner the excitation light beam conveyed by the first optical member 2831 will enter the sample S below the fill line. This arrangement can improve the optical detection of analytes within the sample by reducing attenuation of the excitation light beam that may occur by transmitting the excitation light beam through the head space of the reaction container (i.e., the portion of the reaction container 260 above the fill line LF that is substantially devoid of the sample S). In other embodiments, however, the distance $Y_1$ can be such that the first optical member 2831 and/or the first light path 2806 enter the reaction volume 2713 at a location above the location of fill line FL of the sample S when the reaction container 260 is disposed within the block 2710.

Similarly, in some embodiments, the distance $Y_2$ can be such that the second optical member 2832 and/or the second light path 2807 enter and/or intersect the reaction volume 2713 at a location below the location of fill line FL of the sample S when the reaction container 260 is disposed within the block 2710. In this manner the emission light beam received by the second optical member 2832 will exit the sample S below the fill line. This arrangement can improve the optical detection of analytes within the sample by reducing attenuation of the emission light beam that may occur by receiving the emission light beam through the head space of the reaction container. In other embodiments, however, the distance $Y_2$ can be such that the second optical member 2832 and/or the second light path 2807 enter and/or intersect the reaction volume 2713 at a location above the location of fill line FL of the sample S when the reaction container 260 is disposed within the block 2710.

Figure 47:
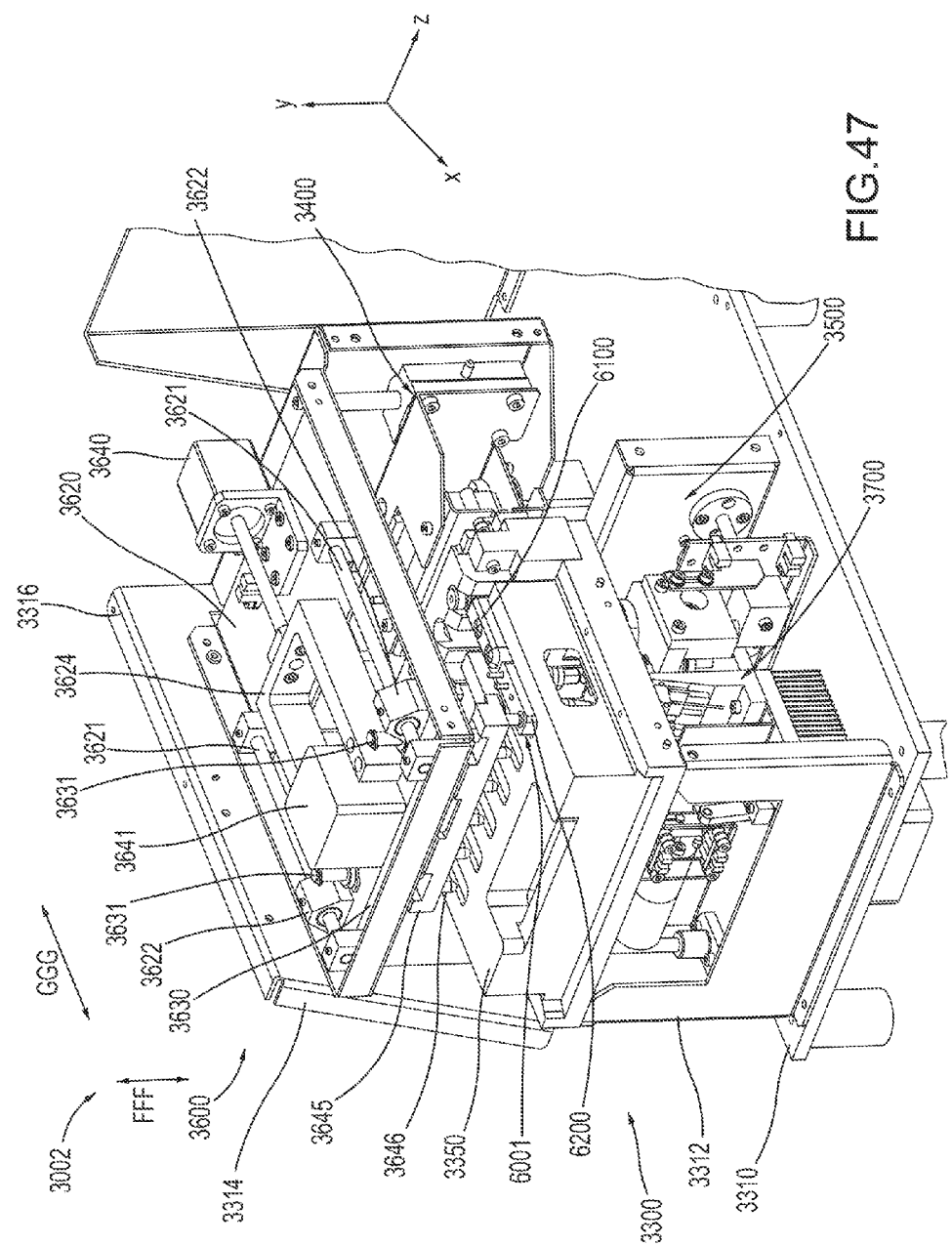
FIG. 47 is a top perspective view of a second actuator assembly of the instrument shown in FIG. 36.

FIGS. 36-70 show various views of an instrument 3002 and/or portions of an instrument configured to manipulate, actuate and/or interact with a series of cartridges to perform a nucleic acid isolation and amplification process on test samples within the cartridges. The cartridges can include any of the cartridges shown and described herein, such as for example, the cartridge 6001. This system can be used for many different assays, such as, for example, the rapid detection of influenza (Flu) A, Flu B, and respiratory syncytial virus (RSV) from nasopharyngeal specimens. The instrument 3002 is shown without the casing 3002 and/or certain portions of the instrument 3002 to more clearly show the components therein. For example, FIG. 47 shows the instrument 3002 without the optics assembly 3800.

Figure 36:
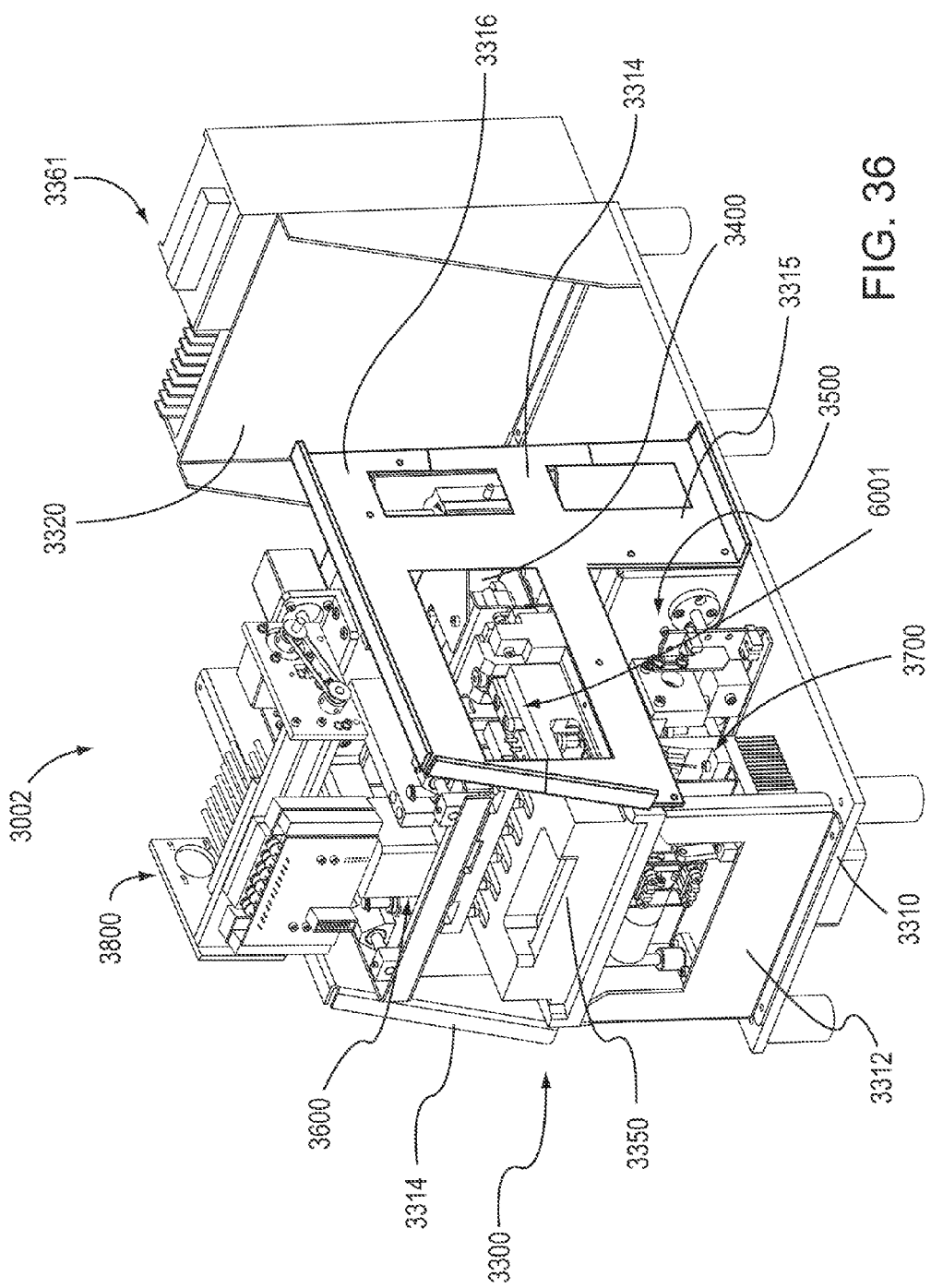
FIG. 36 is a perspective view of an instrument according to an embodiment.

As shown in FIG. 36, the instrument 3002 includes a chassis and/or frame 3300, a first actuator assembly 3400, a sample transfer assembly 3500, a second actuator assembly 3600, a heater assembly 3700 and an optics assembly 3800. The frame 3300 is configured to house, contain and/or provide mounting for each of the components and/or assemblies of the instrument 3002 as described herein. The first actuator assembly 3400 is configured to actuate an actuator or transfer mechanism (e.g., the actuator or transfer mechanism 6166) of the isolation module (e.g., isolation module 6100) of a cartridge to convey one or more reagents and/or substances into a lysing chamber within the isolation module. The transfer actuator assembly 3500 is configured to actuate a transfer assembly (e.g. the transfer assembly 6140a) to transfer a portion of the sample between various chambers and/or volumes within an isolation module (e.g., isolation module 7100). The second actuator assembly 3600 is configured to actuate a mixing mechanism (e.g., mixing mechanism 6130a) and/or a wash buffer module (e.g., wash buffer module 7130a) of the isolation module (e.g., isolation module 6100) and/or the PCR module (e.g., PCR module 6200) to convey into and/or mix one or more reagents and/or substances within a chamber within the isolation module and/or the PCR module. The heater assembly 3700 is configured to heat one or more portions of a cartridge (e.g., the PCR vial 7260, the substrate 7220 and/or a region of the housing 7110 adjacent the lysing chamber 7114) to promote and/or facilitate a process within the cartridge (e.g., to promote, facilitate and/or produce a "hot start" process, a heated lysing process and/or a PCR process). The optics assembly 3800 is configured to monitor a reaction occurring with the cartridge. More specifically, the optics assembly 3800 is configured to detect one or more different analytes and/or targets within a test sample in the cartridge. Each of these assemblies is discussed separately below, followed by a description various methods that can be performed by the instrument 3002.

As shown in FIG. 36 the frame 3300 includes a base frame 3310, a front member 3312, two side members 3314 and a rear member 3320. The base member 3310 supports the functional assemblies described herein, and includes six mounting or support legs. In some embodiments, the support legs can be adjustable to allow the instrument 3302 to be horizontally leveled when mounted and/or installed on a laboratory bench. The rear member 3320 is coupled to the base member 3310 and is configured to support and or retain the power supply assembly 3361. The rear member 3320 can also provide mounting support for any other components related to the operation of the instrument 3302, such as, for example, a processor, control elements (e.g., motor controllers, heating system controllers or the like), a communications interface, a cooling system or the like. FIGS. 71A, 71B, 72A, 72B and 73 are block diagrams of a control and computer system of the instrument 3002.

Each of the side member 3314 includes an upper portion 3316 and a lower portion 3315. The front member 3312 is coupled to each side member 3314 and defines an opening within which a magazine 3350 containing multiple assay cartridges can be disposed for processing. In some embodiments, the magazine 3350 can be configured to contain six cartridges of the types shown and described herein (shown in FIG. 36, for example, as cartridge 6001). In use, the magazine 3350 containing multiple cartridges is disposed within the instrument 3002 and is maintained in a fixed position relative to the chassis 3300 during the isolation and/or amplification process. Thus, the cartridges containing the samples are not moved between various stations to conduct the analysis. Rather, as described herein, the samples, reagents and/or other substances are conveyed, processed and/or manipulated within the various portions of the cartridge by the instrument 3002, as described herein. Although the instrument 3002 is shown as being configured to receive one magazine 3350 containing six cartridges, in other embodiments, an instrument can be configured to receive any number of magazines 3350 containing any number of cartridges.

FIGS. 37-40 show various views of the first actuator assembly 3400 of the instrument 3002. The first actuator assembly 3400 is configured to actuate and/or manipulate a transfer mechanism and/or reagent actuator (e.g., the reagent actuators 6166a, 6166b, 6166c and 6166d) of an isolation module (e.g., isolation module 6100) of a cartridge to convey one or more reagents and/or substances into a lysing chamber within the isolation module. In particular, the first actuator assembly 3400 can actuate a first one of the reagent actuators (e.g. reagent actuator 6166d) from each of the cartridges disposed within the magazine 3350, and then, at a different time, actuate a second one of the reagent actuators (e.g. reagent actuator 6166c) from each of the cartridges.

Figure 38:
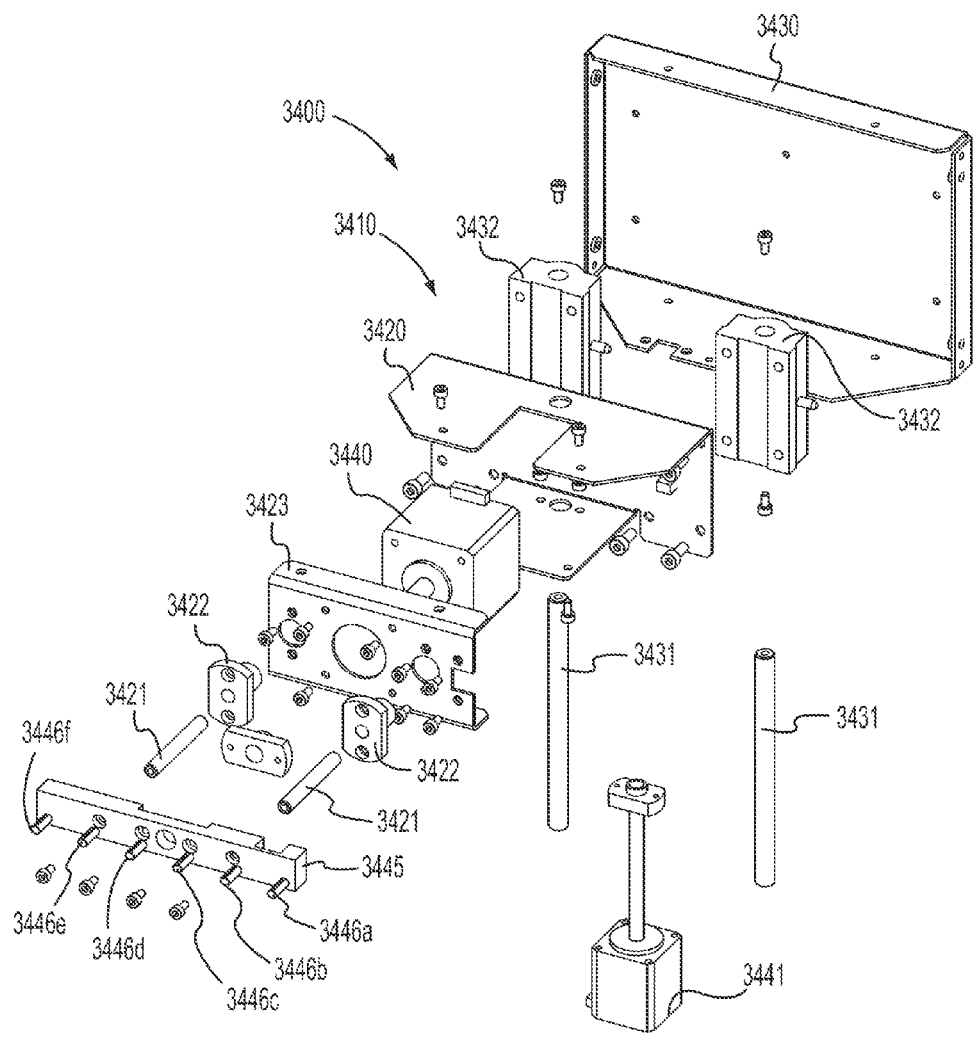
FIG. 38 is an exploded perspective view of the first actuator assembly shown in FIG. 37.
Figure 39:
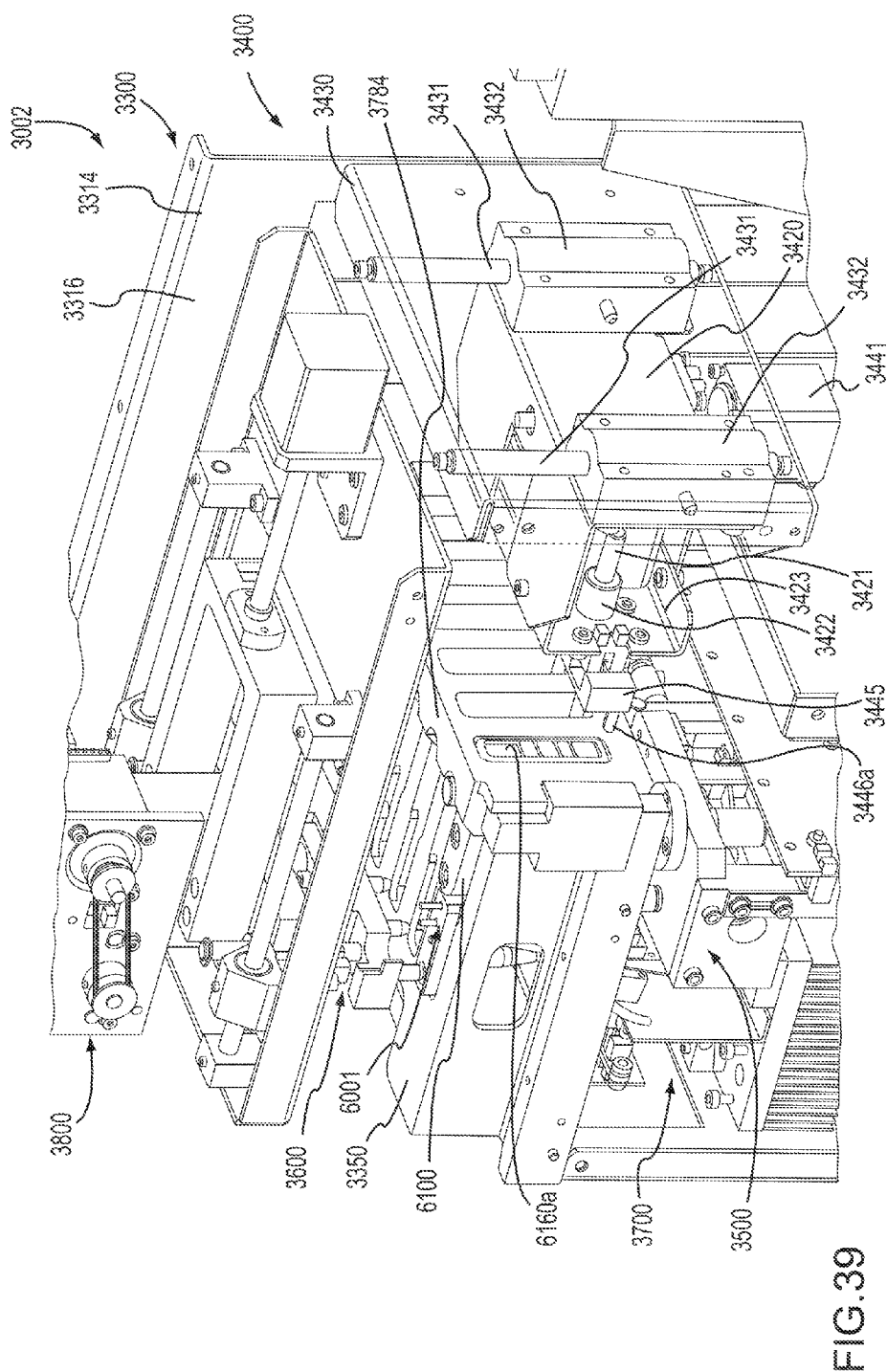
FIG. 39 is a rear perspective view of the first actuator assembly shown in FIG. 37.
Figure 40:
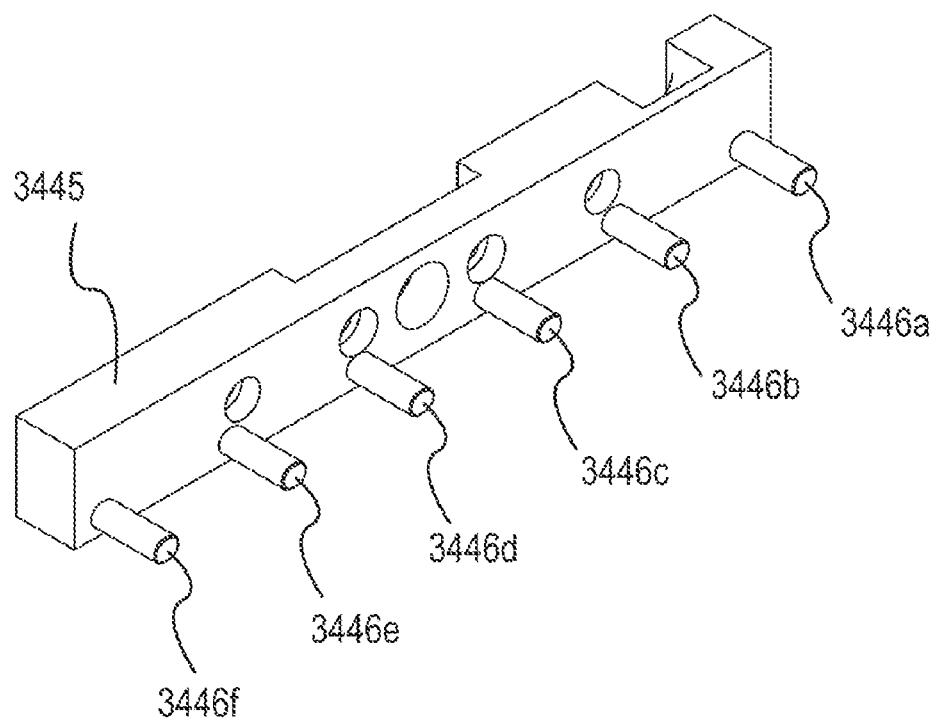
FIG. 40 is a perspective view of a portion of the first actuator assembly shown in FIG. 37.

The first actuator assembly includes an engagement bar 3445, a first (or x-axis) motor 3440 and a second (or y-axis) motor 3441 supported by a frame assembly 3410. As shown in FIGS. 38 and 40, the engagement bar 3445 includes a series of protrusions 3346a, 3346b, 3346c, 3346d, 3346e and 3346f.

Each of the protrusions is configured to engage, be disposed within and/or actuate one or more reagent actuators (e.g., reagent actuator 6166a) of an isolation module (e.g., isolation module 6100) disposed within the instrument 3002. In some embodiments, the engagement bar 3445 and/or the protrusions (e.g., protrusion 3346a) can include a retention mechanism (e.g., a protrusion, a snap ring or the like) configured to retain a protrusion and/or an opening of an actuator (e.g., reagent actuator 6166a) to facilitate reciprocal movement of the reagent actuator within the isolation module.

The frame assembly 3410 includes a first axis (or x-axis) mount frame 3420 that is movably coupled to a second axis (or y-axis) mount frame 3430. In particular, the first axis mount frame 3420 can be moved relative to the second axis mount frame 3430 along the y-axis, as shown by the arrow AAA in FIG. 37. Similarly stated, the first axis mount frame 3420 can be moved relative to the second axis mount frame 3430 in an "alignment direction" (i.e., along the y-axis) to facilitate alignment of the engagement bar 3445 and/or the protrusions (e.g., protrusion 3346a) with the desired series of actuators and/or transfer mechanisms.

Figure 37:
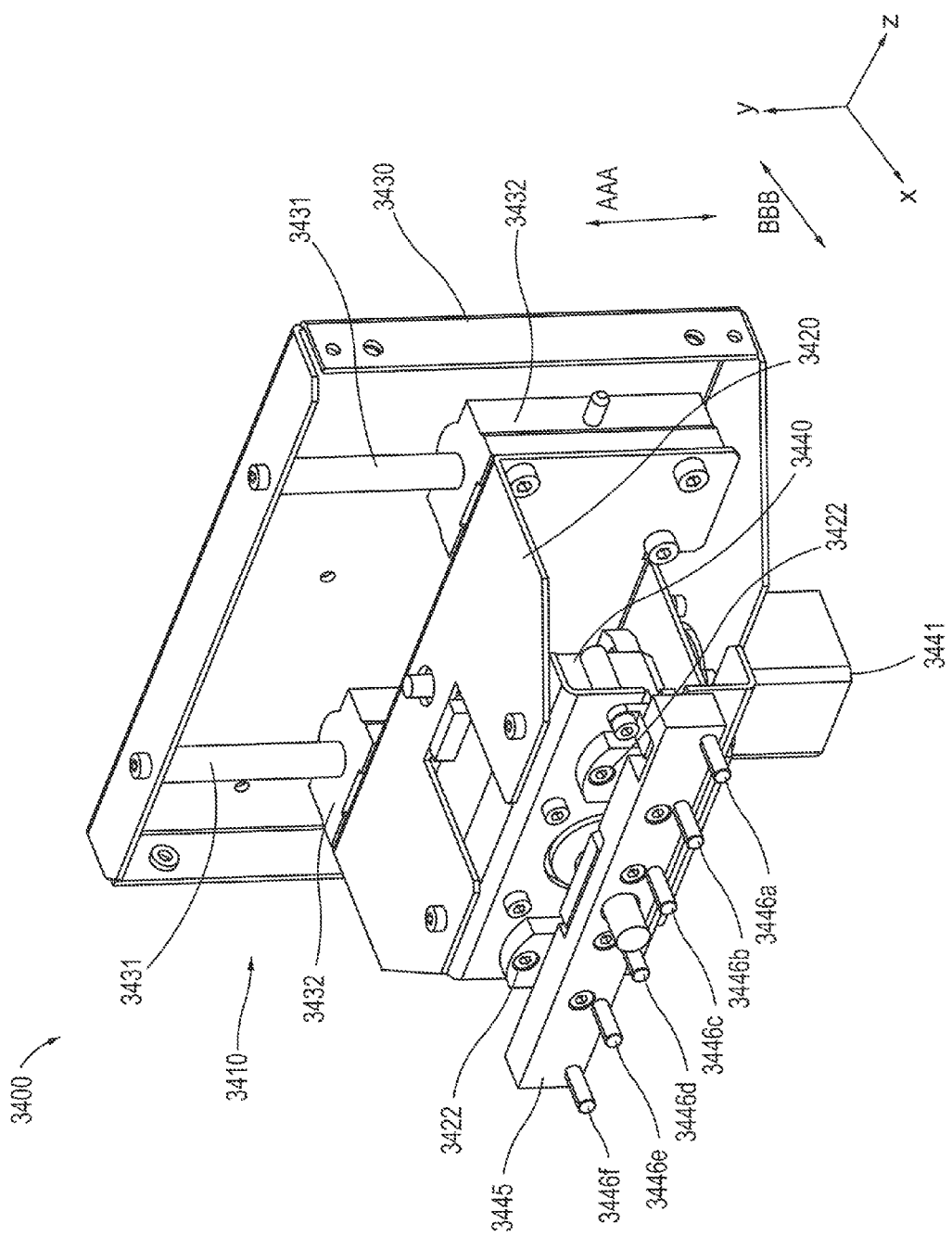
FIG. 37 is a perspective view of a first actuator assembly of the instrument shown in FIG. 36.

The first axis mount frame 3420 provides support for the first (or x-axis) motor 3440, which is configured to move the engagement bar 3445 and/or the protrusions (e.g., protrusion 3346a) along the x-axis, as shown by the arrow BBB in FIG. 37. Similarly stated, the first axis motor 3440 is coupled to the first axis mount frame 3420, and is configured to move the engagement bar 3445 and/or the protrusions (e.g., protrusion 3346a) in an "actuation direction" (i.e., along the x-axis) to actuate the desired series of actuators and/or transfer mechanisms. Movement of the engagement bar 3445 is guided by two x-axis guide shafts 3421, each of which is movably disposed within a corresponding bearing 3422. The bearings 3422 are positioned relative to the first axis mount frame 3420 and/or the first motor 3440 by a bearing mount member 3423.

The second axis mount frame 3430 is coupled to and between the two side frame members 3314 of the frame assembly 3300. The second axis mount frame 3430 provides support for the second (or y-axis) motor 3441 and the first axis mount frame 3420. The second motor 3441 is configured to move the first axis mount frame 3420, and therefore the engagement bar 3445 along the y-axis (or in an alignment direction), as shown by the arrow BBB in FIG. 37. In this manner, the engagement bar 3445 and/or the protrusions (e.g., protrusion 3346a) can be aligned with the desired series of actuators and/or transfer mechanisms prior to actuation of the actuators and/or transfer mechanisms. The first axis mount frame 3420 is coupled to the second axis mount frame 3430 by a pair of bearing blocks 3432 that are slidably disposed about a corresponding pair of y-axis guide shafts 3431.

In use, the first actuator assembly 3400 can sequentially actuate a series of transfer mechanisms and/or reagent actuators (e.g., actuators 6166a, 6166b, 6166c and 6166d) of a set of cartridges (e.g., cartridge 6001) disposed within the instrument 3001. First, the engagement bar 3445 can be aligned with the desired transfer mechanism and/or reagent actuator (e.g., actuator 6166d) by moving the first frame member 3420 in the alignment direction (i.e., along the y-axis). The engagement bar 3445 can then be moved in the actuation direction (i.e., along the x-axis) to actuate the desired transfer mechanism and/or reagent actuator (e.g., actuator 6166d) from each cartridge. In this manner, the first actuator assembly 3400 can actuate and/or manipulate a reagent actuator from each of the cartridges disposed within the instrument 3002 in a parallel (or simultaneous) manner. In other embodiments, however, the actuator assembly 3400 and/or the engagement bar 3445 can be configured to sequentially actuate the corresponding reagent actuators of the each of the cartridges disposed within the instrument 3002 in a sequential (or serial) manner.

The first actuator assembly 3400 can actuate the desired transfer mechanism and/or reagent actuator by moving the engagement bar 3445 in a first direction along the x-axis. In other embodiments, however, the first actuator assembly 3400 can actuate the desired transfer mechanism and/or reagent actuator by reciprocating the engagement bar 3445 (i.e., alternatively moving the engagement bar 3445 in a first direction and a second direction) along the x-axis. When the desired transfer mechanism and/or reagent actuator has been actuated, the first actuator assembly 3400 can actuate another transfer mechanism and/or reagent actuator (e.g., actuators 6166*c*), in a similar manner as described above.

Although the first actuator assembly 3400 is shown and described as actuating a transfer mechanism and/or a reagent actuator, in other embodiments, the first actuator assembly 3400 can actuate any suitable portion of any of the cartridges described herein. For example, in some embodiments, the first actuator assembly 3400 can actuate, manipulate and or move an ultrasonic transducer to facilitate ultrasonic lysing.

FIGS. 41-46 show various views of the transfer actuator assembly 3500 of the instrument 3002. The transfer actuator assembly 3500 is configured to actuate and/or manipulate a transfer assembly or mechanism, such as, for example, the transfer assembly 6140 shown and described above with reference to FIGS. 20 and 21. In particular, the transfer actuator assembly 3500 can actuate a first one of the transfer assemblies (e.g. transfer assembly 6140*a*) from each of the cartridges disposed within the magazine 3350, and then, at a different time, actuate a second one of the transfer assemblies (e.g., transfer assembly 6140*b*) from each of the cartridges.

Figure 41:
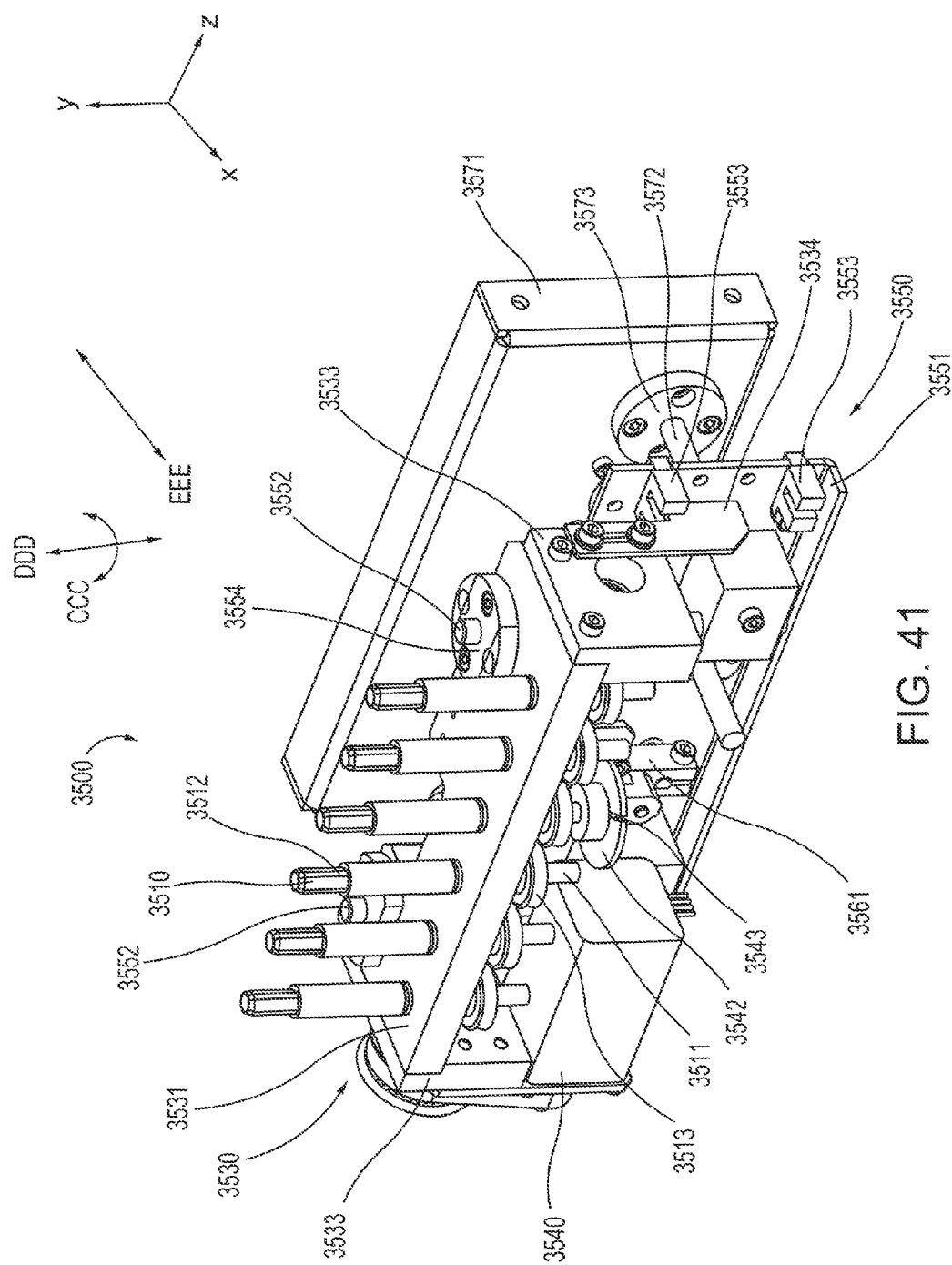
FIG. 41 is a top perspective view of a transfer actuator assembly of the instrument shown in FIG. 36.
Figure 42:
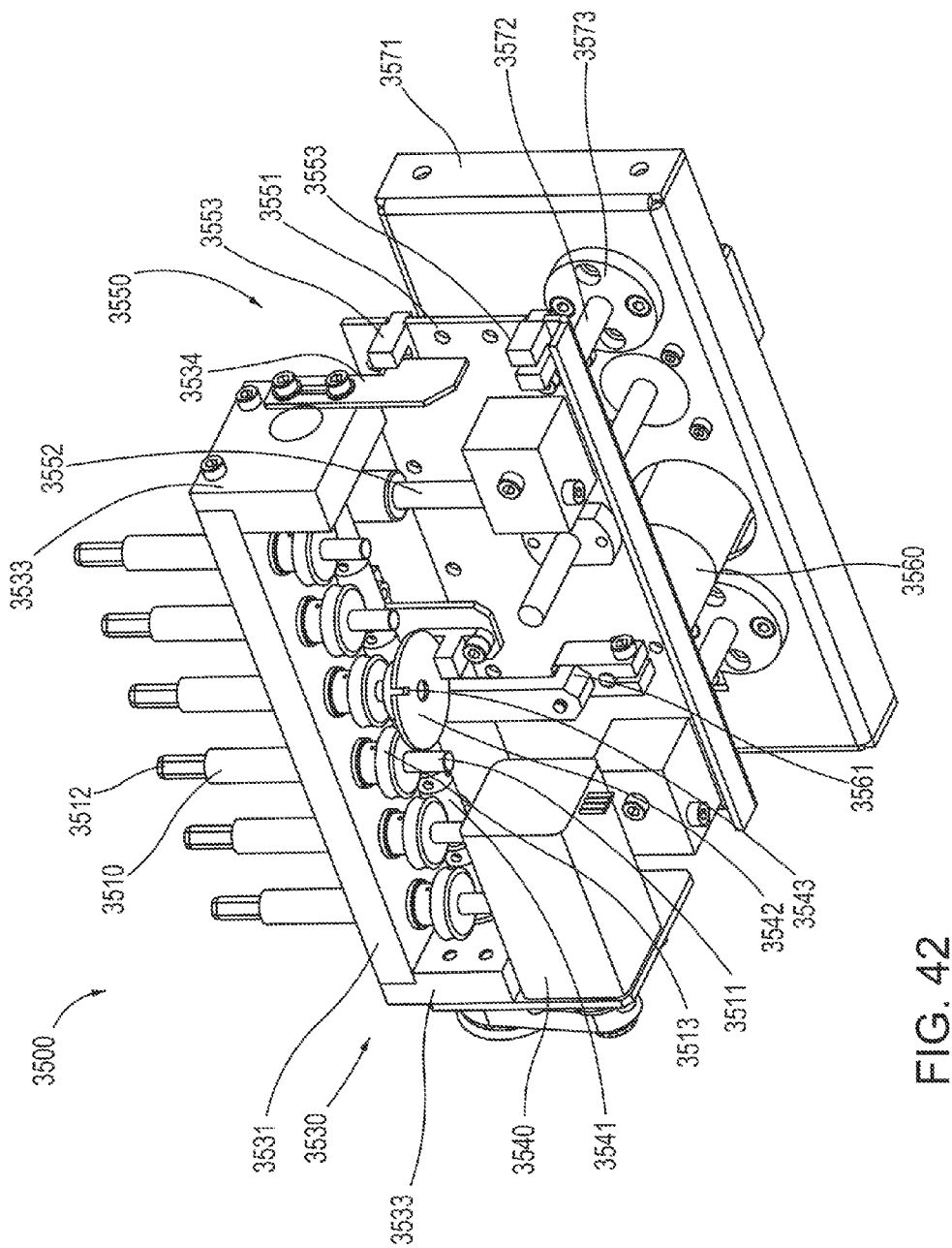
FIG. 42 is a bottom perspective view of the transfer actuator assembly shown in FIG. 41.
Figure 43:
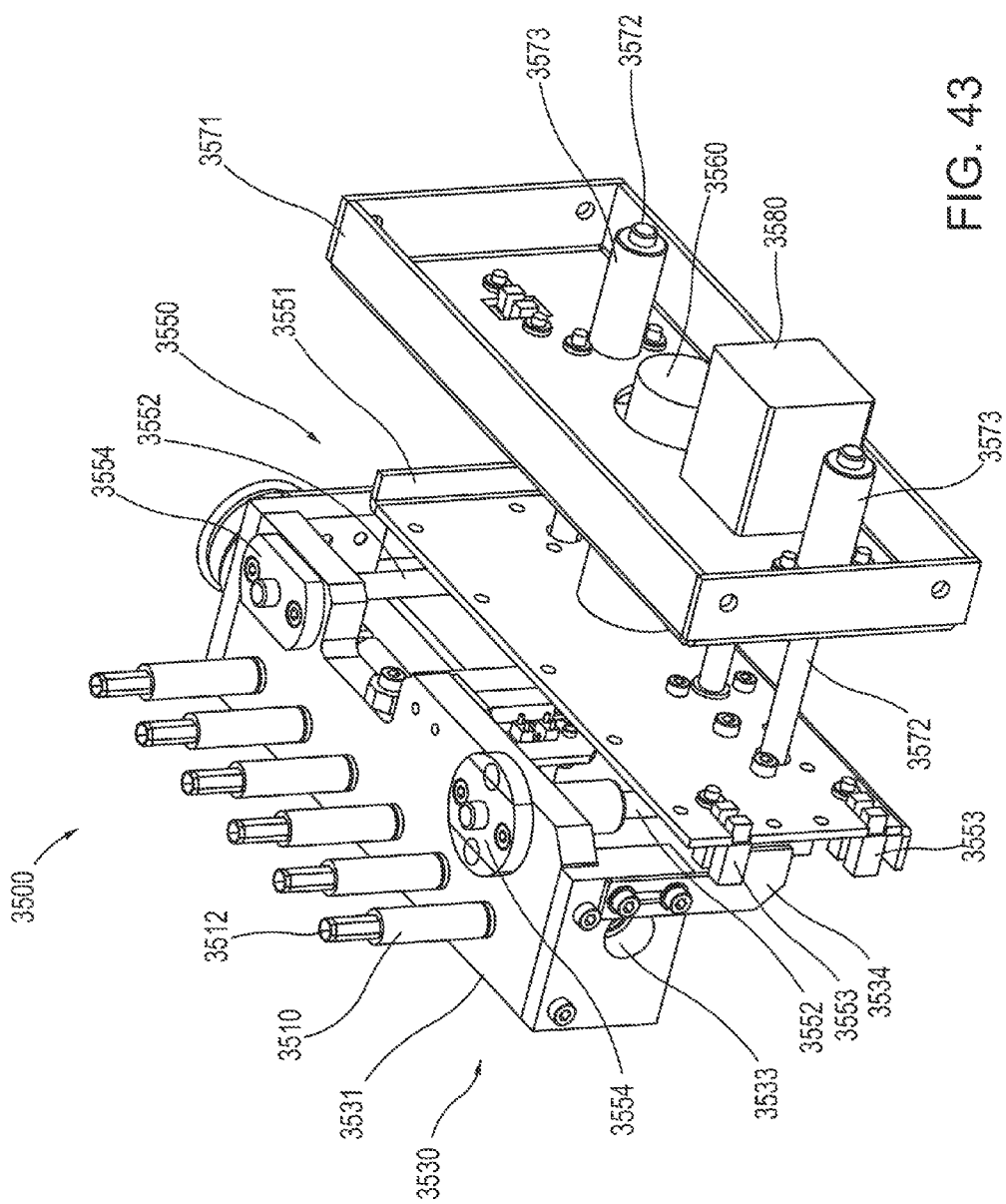
FIG. 43 is a rear perspective view of the transfer actuator assembly shown in FIG. 41.
Figure 44:
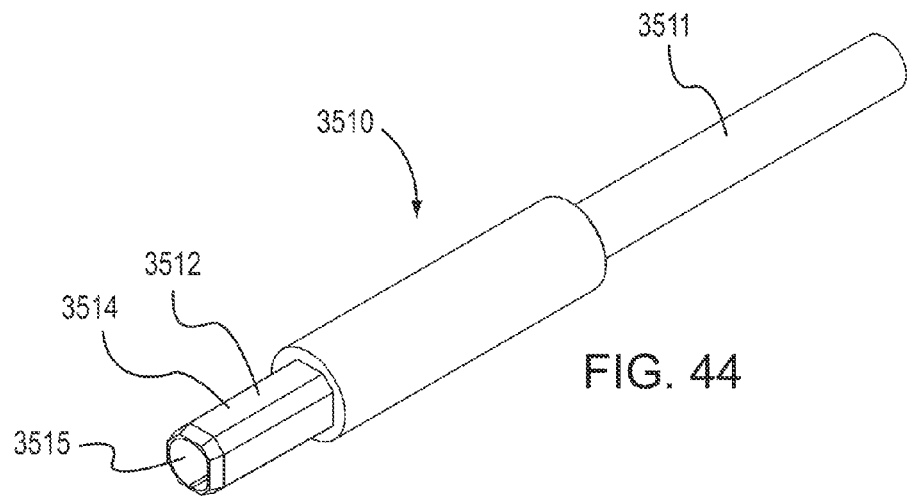
FIG. 44 is a perspective view of a portion of the transfer actuator assembly shown in FIG. 41.
Figure 45:
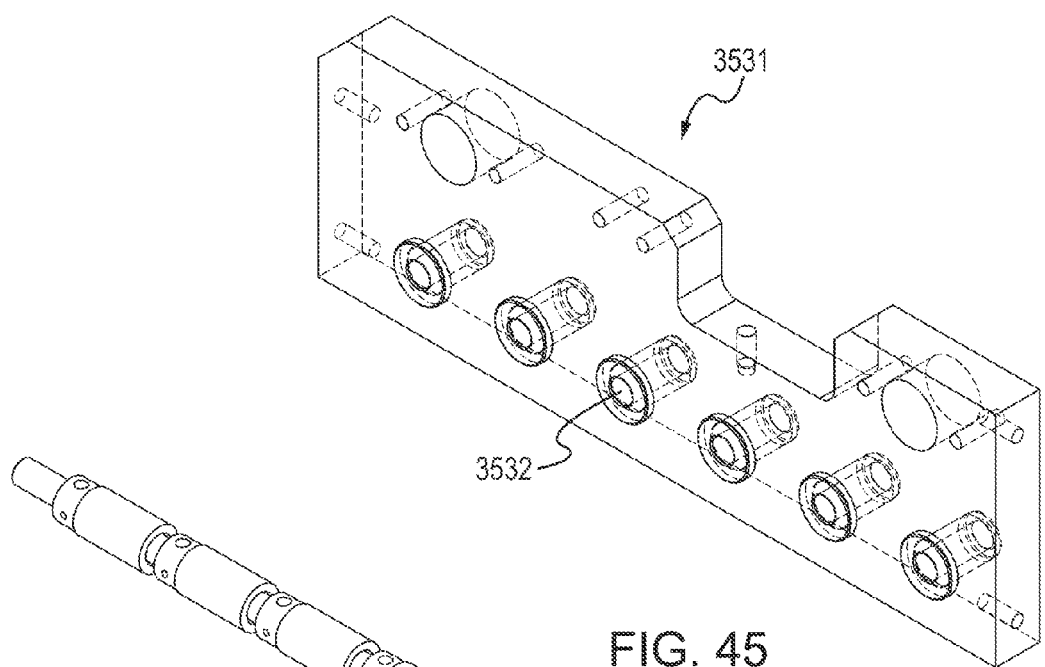
FIG. 45 is a perspective view of a portion of the transfer actuator assembly shown in FIG. 41.
Figure 46:
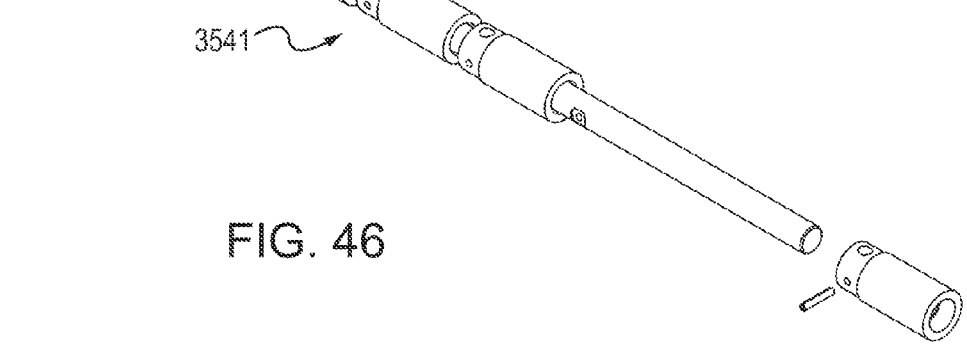
FIG. 46 is a perspective view of a worm drive shaft of the transfer actuator assembly shown in FIG. 41.

The transfer actuator assembly 3500 includes a series of actuator shafts 3510. Although the transfer actuator assembly 3500 includes six actuator shafts, only one is identified in FIGS. 41-46. Each of the actuator shafts 3510 is configured to engage, be disposed within and/or actuate one or more transfer assemblies (e.g., transfer assembly 6140*a*) of an isolation module (e.g., isolation module 6100) disposed within the instrument 3002. As shown in FIG. 44, each actuator shaft 3510 has a first end portion 3511 and a second end portion 3512. The first end portion 3511 is coupled to a drive gear 3513 (see FIGS. 41-42), which is, in turn, driven by a worm drive shaft 3541. As shown in FIGS. 41 and 42, a rotational position indicator 3542 is coupled to the first end portion 3511 of one of the actuator shafts 3510. The rotational position indicator 3542 defines a slot and/or opening 3543, the rotational position of which can be sensed (e.g., via an optical sensing mechanism) to provide feedback regarding the rotational position of the actuator shafts 3510.

The second end portion 3512 of each shaft 3510 includes an engagement portion 3514 configured to be received within and/or engage a transfer assembly (e.g., transfer assembly 6140*a*) of a cartridge (e.g., cartridge 6001) disposed within the instrument 3002. In this manner, the engagement portion 3514 can manipulate and/or actuate the transfer assembly to facilitate the transfer of portions of a sample within the cartridge, as described above. The engagement portion 3514 has a shape that correspond to a shape of a portion of the transfer assembly (e.g., the lumen 6149 defined by the movable member 6146) such that rotation of the actuator shaft 3510 results in rotation of a portion of the transfer assembly. In particular, as shown in FIG. 44, the engagement portion has an octagonal shape. In some embodiments, the engagement portion 3514 can include a retention mechanism (e.g., a protrusion, a snap ring or the like) configured to retain a protrusion and/or an opening of a transfer assembly to facilitate reciprocal movement of a portion of the transfer assembly within the isolation module.

The engagement portion 3514 defines a lumen 3515 within which a magnet (not shown) can be disposed. In this manner, the actuator shaft 3510 can produce and/or exert a force (i.e., a magnetic force) on a portion of the contents (i.e., the magnetic beads) disposed within the cartridge (e.g., cartridge 6001) to facilitate transfer of a portion of the sample via the transfer assembly, as described above.

The actuator shafts 3510 are moved by a first (or x-axis) motor 3580, a second (or y-axis) motor 3560, and a third (or rotational) motor 3540. As described in more detail below, the x-axis motor 3580 is supported by the support frame 3571, the y-axis motor 3560 is supported by the engagement frame assembly 3550, and the rotational motor 3540 is supported by the rotation frame assembly 3530.

The rotation frame assembly 3530 provides support for the rotational motor 3540, which is configured to rotate the actuator shafts 3510 about the y-axis, as shown by the arrow CCC in FIG. 41. Similarly stated, the rotational motor 3540 is coupled to the rotational frame assembly 3530, and is configured to rotate the actuator shafts 3510 in an "actuation direction" (i.e., about the y-axis) to actuate the desired series of transfer assemblies. The rotation frame assembly 3530 includes a rotation plate 3531, a pair of worm drive bearing blocks 3533, and a worm drive shaft 3541. The worm drive shaft 3541 is coupled to the rotational motor 3540 by a pulley assembly, and is supported by the two worm drive bearing blocks 3533. The worm drive shaft 3541 is engage with the drive gear 3513 of each actuator shaft 3510. Accordingly, when the worm drive shaft 3541 is rotated in a first direction (i.e., about the z-axis), each actuator shaft 3510 is rotated in a second direction (i.e., about the y-axis, as shown by the arrow CCC in FIG. 41).

The rotation frame assembly 3530 also includes a y-axis position indicator 3534 that can be slidably disposed within a pair of corresponding slide members 3553 on the engagement frame assembly 3550. In this manner, when the rotation frame assembly 3530 is translated along the y-axis (e.g., in an "engagement direction"), as shown by the arrow DDD in FIG. 41, the y-axis position indicator 3534 and the corresponding slide members 3553 can guide the linear movement and/or provide feedback regarding the position of the rotation frame assembly 3530.

The engagement frame assembly 3550 provides support for the y-axis motor 3560, which is configured to move the rotation frame assembly 3530, and therefore the actuator shafts 3510, along the y-axis, as shown by the arrow DDD in FIG. 41. Similarly stated, the y-axis motor 3560 is coupled to the engagement frame assembly 3550, and is configured to move the actuation shafts 3510 in the "engagement direction" (i.e., along the y-axis) to actuate the desired series of transfer mechanisms. The engagement frame assembly 3550 includes a support frame 3551 that provides support for the drive linkage 3561 (that converts the rotational motion of the y-axis motor to a linear motion of the rotation frame assembly 3530. Movement of the rotation frame assembly 3530 is guided by two y-axis guide shafts 3552, each of which is movably disposed within a corresponding bearing 3554. The bearings 3554 are coupled to the rotation plate 3531, as shown in FIG. 43.

The support frame 3571 is coupled to and between the lower end portion 3315 of the two side frame members 3314 of the frame assembly 3300. The support frame 3571 provides support for the x-axis motor 3580 and the engagement frame assembly 3550. The x-axis motor 3580 is configured to move the engagement frame assembly 3550, and therefore the actuation shafts 3510 along the x-axis (or in an alignment direction), as shown by the arrow EEE in FIG. 41. In this manner, the actuator shafts 3510 can be aligned with the desired series of transfer mechanisms prior to actuation of the transfer mechanisms. The support frame 3571 is coupled to the engagement frame assembly 3550 by a pair of bearing blocks 3573 that are slidably disposed about a corresponding pair of x-axis guide shafts 3572.

In use, the transfer actuator assembly 3500 can sequentially actuate a series of transfer mechanisms (e.g., transfer assemblies 6140a, 6140b and 6166c) of a set of cartridges (e.g., cartridge 6001) disposed within the instrument 3001. First, the actuator shafts 3510 can be aligned with the desired transfer mechanism by moving the engagement frame assembly 3550 in the alignment direction (i.e., along the x-axis). The actuator shafts 3510 can then be moved in the engagement direction (i.e., along the y-axis) to engage the desired transfer mechanism (e.g., transfer assembly 6140a) from each cartridge. The actuator shafts 3510 can then be moved in the actuation direction (i.e., rotation about the y-axis) to actuate the desired transfer mechanism (e.g., transfer assembly 6140a) from each cartridge. In this manner, the transfer actuator assembly 3500 can actuate and/or manipulate a transfer mechanism from each of the cartridges disposed within the instrument 3002 in a parallel (or simultaneous) manner. In other embodiments, however, the transfer actuator assembly 3500 and/or the actuation shafts 3510 can be configured to sequentially actuate the corresponding transfer mechanism of the each of the cartridges disposed within the instrument 3002 in a sequential (or serial) manner.

FIGS. 47-51 show various views of the second actuator assembly 3600 of the instrument 3002. The second actuator assembly 3600 is configured to actuate and/or manipulate a transfer mechanism (e.g., transfer mechanism 7235), wash buffer module (e.g., wash buffer module 7130a), a mixing mechanism (e.g., mixing mechanism 6130a) and/or a reagent module (e.g., the reagent module 7270a) of any of the cartridges shown or described herein. In particular, the second actuator assembly 3600 can actuate a first one of the transfer mechanisms, mixing mechanisms or the like (e.g. the mixing mechanism 6130a) from each of the cartridges disposed within the magazine 3350, and then, at a different time, actuate a second one of the transfer mechanisms, mixing mechanisms or the like (e.g. the mixing mechanism 6130b) from each of the cartridges.

Figure 48:
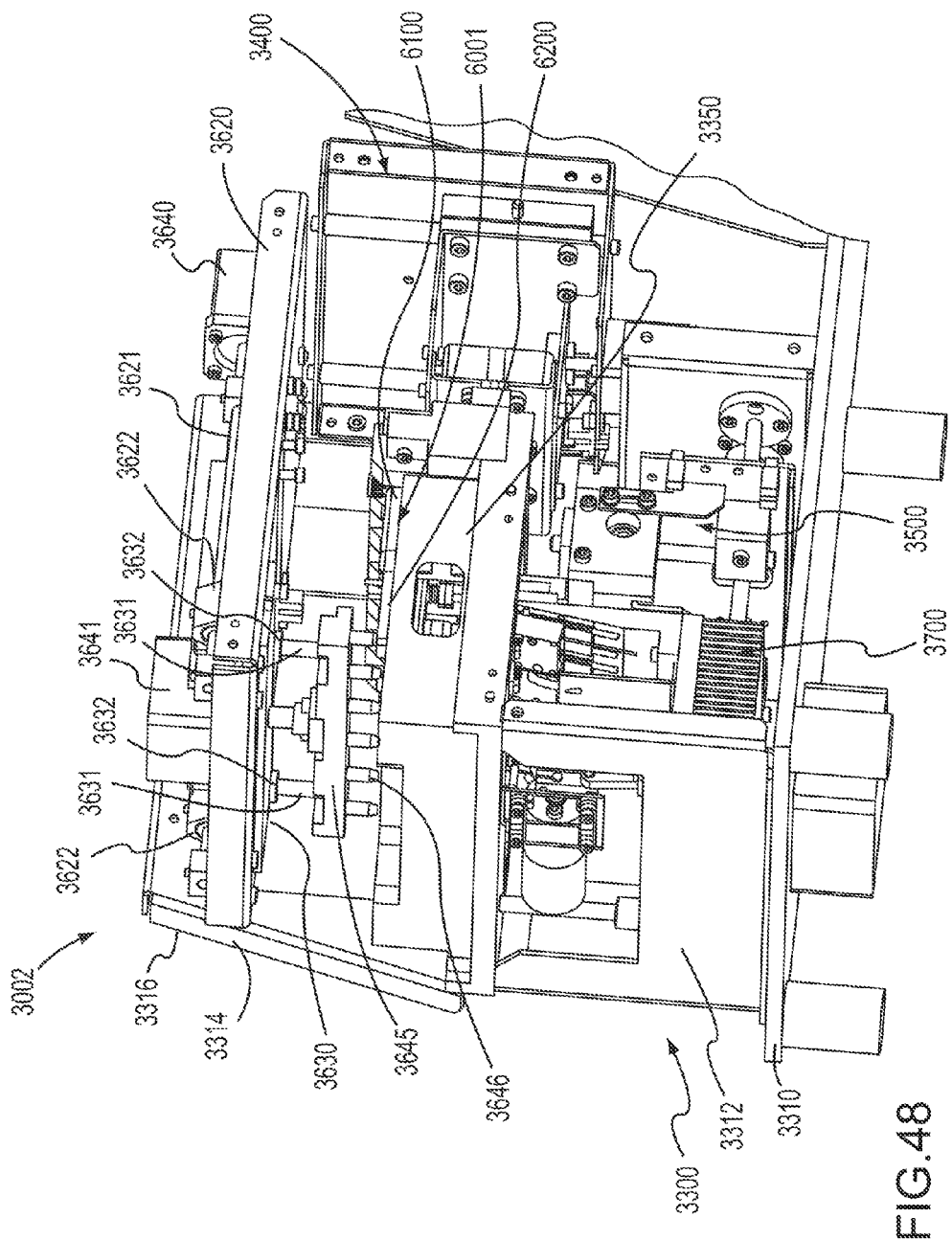
FIG. 48 is a side perspective view of the second actuator assembly shown in FIG. 47.
Figure 49:
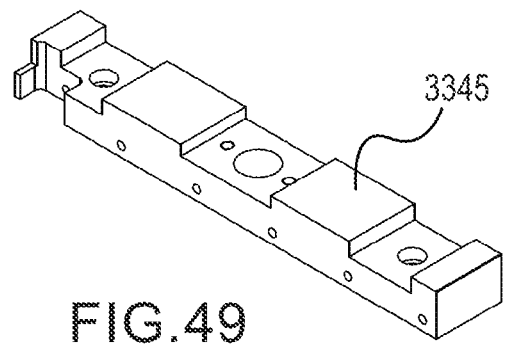
FIGS. 49-51 are perspective views of portions of the second actuator assembly shown in FIG. 47.
Figure 50:
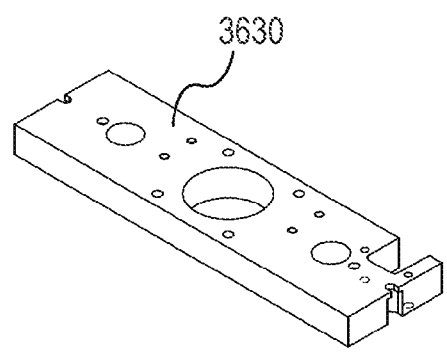
Figure 51:
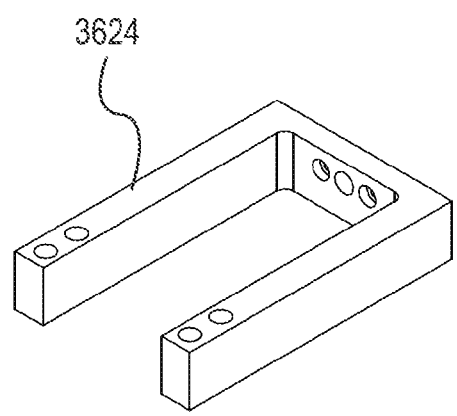

The second actuator assembly 3600 includes an engagement bar 3645, a first (or x-axis) motor 3640 and a second (or y-axis) motor 3641 supported by a frame assembly 3610. As shown in FIG. 48, the engagement bar 3645 includes a series of protrusions 3346. Although the engagement bar 3645 includes six protrusions (one corresponding to each cartridge within the magazine 3350), only one protrusion 3346 is labeled. Each of the protrusions is configured to engage, be disposed within, manipulate and/or actuate one or more transfer mechanisms (e.g., transfer mechanism 7235), wash buffer modules (e.g., wash buffer module 7130a), mixing mechanisms (e.g., mixing mechanism 6130a) and/or a reagent modules (e.g., the reagent module 7270a) of a cartridge disposed within the instrument 3002. In some embodiments, the engagement bar 3645 and/or the protrusions 3346 can include a retention mechanism (e.g., a protrusion, a snap ring or the like) configured to retain a portion of an actuator (e.g., the engagement portion 7153a of the actuator 7150a, shown and described above with reference to FIGS. 27 and 28) to facilitate reciprocal movement of the actuator within a portion of the cartridge.

The frame assembly 3610 includes a second axis (or y-axis) mount frame 3630 that is movably coupled to a first axis (or x-axis) mount frame 3620. In particular, the second axis mount frame 3630 can be moved relative to the first axis mount frame 3620 along the x-axis, as shown by the arrow GGG in FIG. 47. Similarly stated, the second axis mount frame 3630 can be moved relative to the first axis mount frame 3620 in an "alignment direction" (i.e., along the x-axis) to facilitate alignment of the engagement bar 3645 and/or the protrusions 3346 with the desired series of transfer mechanisms, mixing mechanisms, reagent modules or the like.

The second axis mount frame 3620 provides support for the second (or y-axis) motor 3641, which is configured to move the engagement bar 3645 and/or the protrusions 3346 along the y-axis, as shown by the arrow FFF in FIG. 47. Similarly stated, the second axis motor 3641 is coupled to the second axis mount frame 3620, and is configured to move the engagement bar 3645 and/or the protrusions 3346 in an "actuation direction" (i.e., along the y-axis) to actuate the desired series of transfer mechanisms, mixing mechanisms, reagent modules or the like. Movement of the engagement bar 3645 is guided by two y-axis guide shafts 3631, each of which is movably disposed within a corresponding bearing coupled to the second axis mount frame 3620.

The first axis mount frame 3630 is coupled to and between the upper portion 3316 of the two side frame members 3314 of the frame assembly 3300. The first axis mount frame 3630 provides support for the first (or x-axis) motor 3640 and the second axis mount frame 3620. The first motor 3640 is configured to move the second axis mount frame 3620, and therefore the engagement bar 3645 along the x-axis (or in an alignment direction), as shown by the arrow GGG in FIG. 47. In this manner, the engagement bar 3645 and/or the protrusions 3346a can be aligned with the desired series of transfer mechanisms, mixing mechanisms, reagent modules or the like prior to actuation of the such mechanisms. The second axis mount frame 3620 is coupled to the first axis mount frame 3630 by a pair of bearing blocks 3622 that are slidably disposed about a corresponding pair of x-axis guide shafts 3631. The first (or x-axis) motor 3640 is coupled to the to second axis mount frame 3620 via the mounting member 3624 (see e.g., FIG. 51).

In use, the second actuator assembly 3600 can sequentially actuate a series of transfer mechanisms (e.g., transfer mechanism 7235), wash buffer modules (e.g., wash buffer module 7130a), mixing mechanisms (e.g., mixing mechanism 6130a) and/or a reagent modules (e.g., the reagent module 7270a) of a set of cartridges (e.g., cartridge 6001) disposed within the instrument 3001. First, the engagement bar 3645 can be aligned with the desired mechanism (e.g., mixing mechanism 6130a) by moving the second frame member 3630 in the alignment direction (i.e., along the x-axis). The engagement bar 3645 can then be moved in the actuation direction (i.e., along the y-axis) to actuate the desired mechanism (e.g., mixing mechanism 6130a) from each cartridge. In this manner, the second actuator assembly 3600 can actuate and/or manipulate a transfer mechanism, a wash buffer module, a mixing mechanism and/or a reagent module from each of the cartridges disposed within the instrument 3002 in a parallel (or simultaneous) manner. In other embodiments, however, the second actuator assembly 3600 and/or the engagement bar 3645 can be configured to sequentially actuate the corresponding mechanisms of the each of the cartridges disposed within the instrument 3002 in a sequential (or serial) manner.

The second actuator assembly 3600 can actuate the desired mechanism by moving the engagement bar 3645 in a first direction along the y-axis. In other embodiments, however, the second actuator assembly 3600 can actuate the desired transfer mechanism and/or reagent actuator by reciprocating the engagement bar 3645 (i.e., alternatively moving the engagement bar 3645 in a first direction and a second direction) along the y-axis. When the desired mechanism has been actuated, the second actuator assembly 3600 can actuate another mechanism and/or actuator (e.g., mixing mechanism 6130*b*), in a similar manner as described above.

Although the second actuator assembly 3600 is shown and described as actuating a transfer mechanism and/or a reagent actuator, in other embodiments, the second actuator assembly 3600 can actuate any suitable portion of any of the cartridges described herein. For example, in some embodiments, the second actuator assembly 3600 can actuate, manipulate and or move an ultrasonic transducer to facilitate the transmission of acoustic energy into a portion of the cartridge.

FIGS. 52-63 show various views of the heater assembly 3700 of the instrument 3002. The heater assembly 3700 is configured to heat one or more portions of a cartridge (e.g., the PCR vial 7260, the substrate 7220 and/or a region of the housing 7110 adjacent the lysing chamber 7114) to promote and/or facilitate a process within the cartridge (e.g., to promote, facilitate and/or produce a "hot start" process, a heated lysing process and/or a thermal-cycle process for PCR). In particular, the heater assembly 3700 can actuate and/or heat a first portion (e.g. the PCR vial 6260) of each of the cartridges disposed within the magazine 3350, and then, at a different time, actuate and/or heat a second portion (e.g. the portion of the isolation module 6100 adjacent the lysing chamber 6114) from each of the cartridges.

Figure 54:
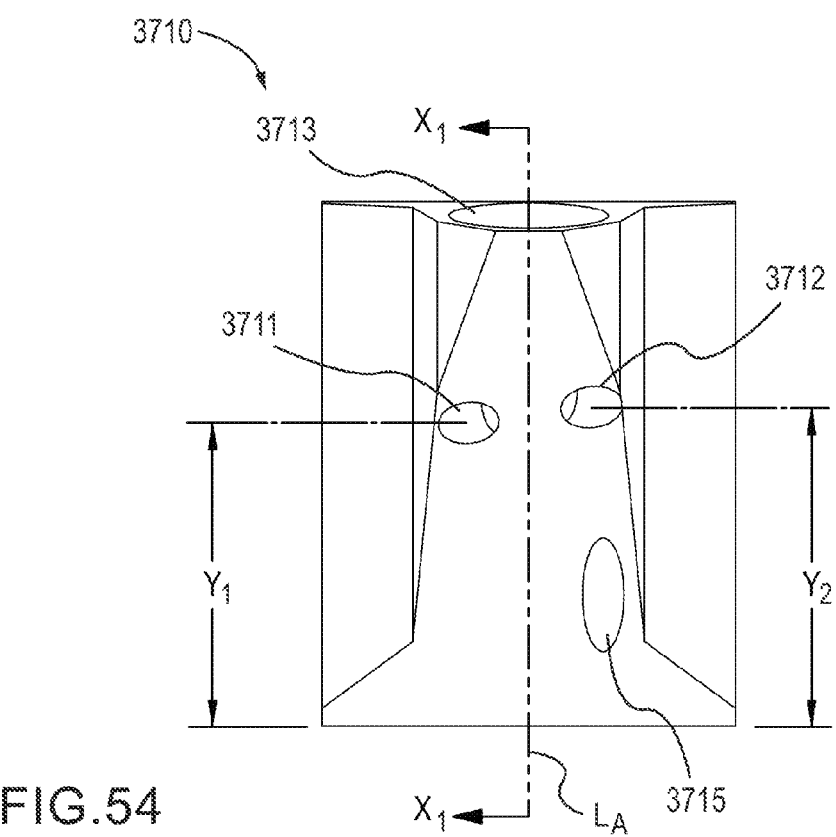
Figure 59:
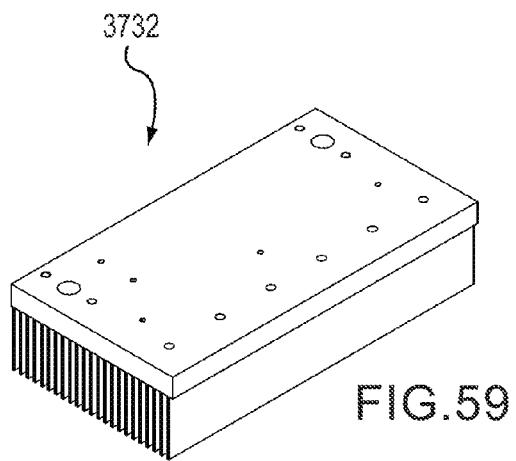
FIG. 59 is a perspective view of a heat sink of the heater assembly shown in FIG. 52.

The heater assembly 3700 includes a series of receiving blocks 3710 (one corresponding to each of the cartridges within the magazine 3350), a positioning assembly 3770, a first heating module 3730, a second heating module 3750 and a third heating module 3780. The receiving block 3710 is configured to receive at least a portion of a reaction chamber of a cartridge, such as the PCR vial 6260 of the cartridge 6001. As shown in FIGS. 53-56, the receiving block 3710 includes a mounting surface 3714 and defines a reaction volume 3713. The reaction volume 3713 has a size and/or shape that substantially corresponds to a size and/or shape of the PCR vial 6260 of the cartridge 6001. As shown in FIGS. 54 and 56, the reaction volume 3713 defines a longitudinal axis $L_A$ and substantially surrounds the portion of the PCR vial 6260 when the PCR vial 6260 is disposed within the reaction volume 3713. In this manner, any stimulus (e.g., heating or cooling) provided to the sample within the PCR vial 6260 by the heater assembly 3700 can be provided in a substantially spatially uniform manner. Moreover, as shown in FIG. 56, the side wall of the portion of the receiving block 3710 that defines the reaction volume 3713 has a substantially uniform wall thickness. This arrangement allows the heat transfer between the reaction volume 3713 and the remaining portions of the heater assembly 3700 to occur in a substantially spatially uniform manner.

The receiving block 3710 is coupled to a mounting block 3734 (see e.g., FIG. 58) by a clamp block 3733 (see, e.g., FIG. 57) such that a thermo-electric device 3731 is in contact with the mounting surface 3714. In this manner, the reaction volume 3713 and the sample contained therein can be cyclically heated to produce a thermally-induced reaction of the sample S, such as, for example, a PCR process.

Figure 52:
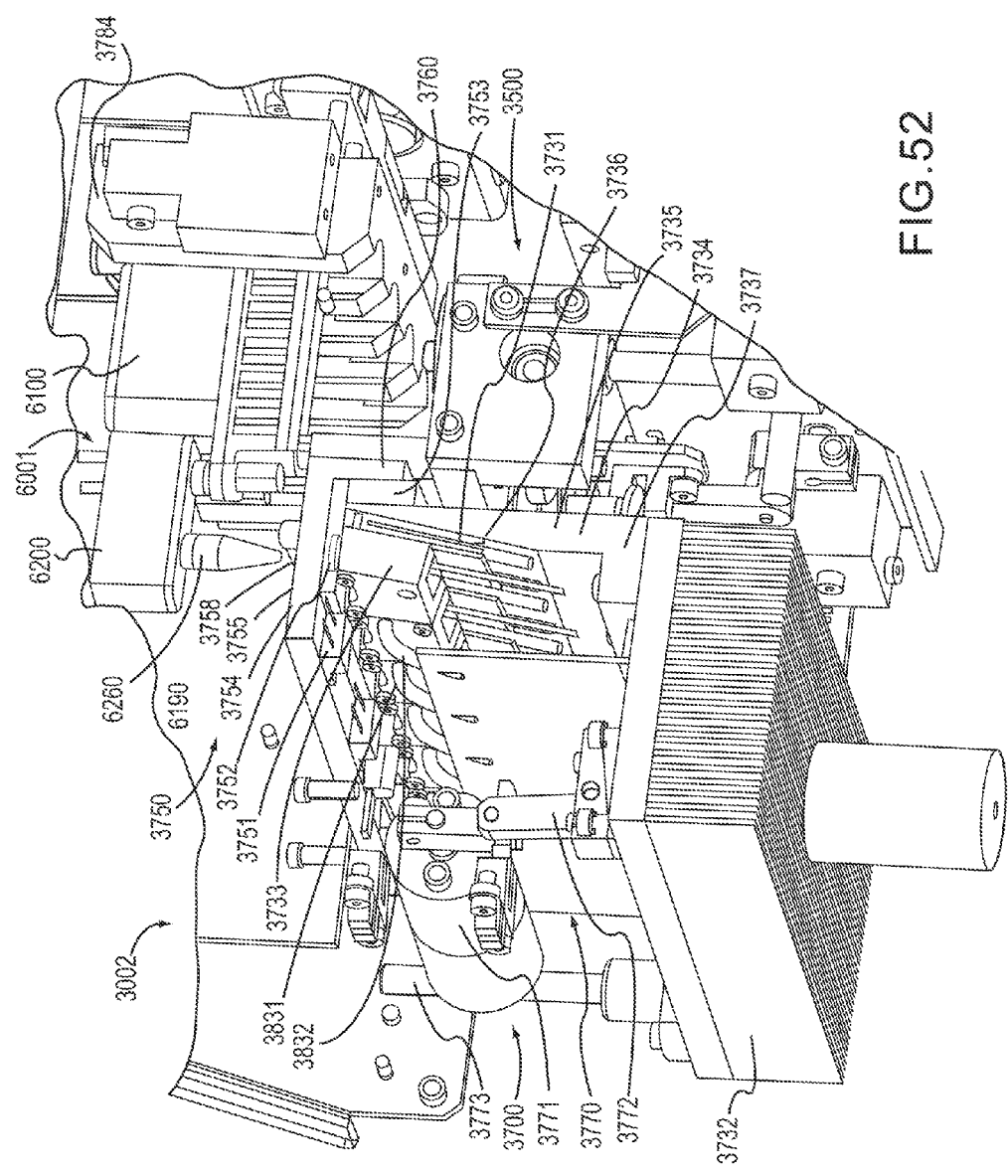
FIG. 52 is a side perspective view of a heater assembly of the instrument shown in FIG. 36.
Figure 53:
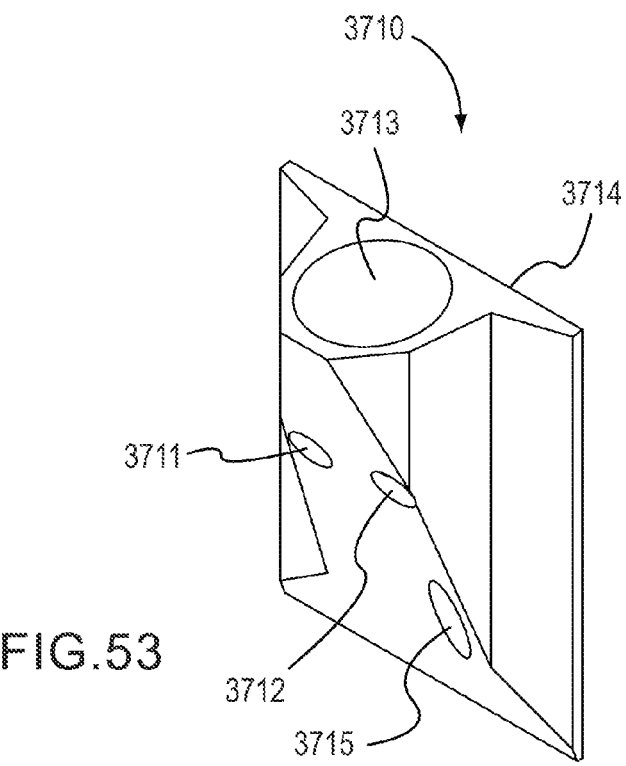
FIG. 53 is a perspective view of a receiving block of the heater assembly shown in FIG. 52.

Each receiving block 3710 defines a first (or excitation) lumen 3711, a second (or emission) lumen 3712 and a third (or temperature monitoring) lumen 3715. A thermocouple or other suitable temperature measuring device can be disposed adjacent the PCR vial via the third lumen 3715. As shown in FIG. 52, an excitation fiber 3831 is disposed at least partially within the first lumen 3711 such that the excitation fiber 3831 and/or the first lumen 3711 defines a first light path 3806 and is in optical communication with the reaction volume 3713. In this manner, a light beam (and/or an optical signal) can be conveyed between the reaction volume 3713 and a region outside of the block 3710 via the excitation fiber 3831 and/or the first lumen 3711. The excitation fiber 3831 can be any suitable structure, device and/or mechanism through which or from which a light beam can be conveyed, of the types shown and described herein. In some embodiments, the excitation fiber 3831 can be any suitable optical fiber to convey a light beam, such as, for example, a multi-mode fiber or a single-mode fiber.

A detection fiber 3832 is disposed at least partially within the second lumen 3712 such that the detection fiber 3832 and/or the second lumen 3712 defines a second light path 3807 and is in optical communication with the reaction volume 3713. In this manner, a light beam (and/or an optical signal) can be conveyed between the reaction volume 3713 and a region outside of the block 3710 via the detection fiber 3832 and/or the second lumen 3712. The detection fiber 3832 can be any suitable structure, device and/or mechanism through which or from which a light beam can be conveyed, of the types shown and described herein. In some embodiments, the detection fiber 3832 can be any suitable optical fiber to convey a light beam, such as, for example, a multi-mode fiber or a single-mode fiber.

As described below, the excitation fiber 3831 and the detection fiber 3832 are coupled to the optics assembly 3800. The optics assembly 3800 can produce one or more excitation light beams, and can detect one or more emission light beams. Thus, the excitation fiber 3831 can convey an excitation light beam from the optics assembly into the reaction volume 3713 to excite a portion of the sample S contained within the PCR vial 6260. Similarly, the detection fiber 3832 can convey an emission light beam produced by an analyte or other target within the sample S from the PCR vial 6260 to the optics assembly 3800.

As shown in FIG. 55, the first lumen 3711 and the second lumen 3712 define an offset angle Θ that is approximately 90 degrees. Similarly stated, the first light path 3806 and the second light path 3807 define an offset angle Θ that is approximately 90 degrees. More particularly, the first light path 3806 and the second light path 3807 define an offset angle Θ, when viewed in a direction substantially parallel to the longitudinal axis $L_A$ of the reaction volume 3713 that is approximately 90 degrees. In a similar manner, the excitation fiber 3831 and the detection fiber 3832, which are disposed within the first lumen 3711 and the second lumen 3712, respectively, define the offset angle Θ that is approximately 90 degrees. This arrangement minimizes the amount of the excitation light beam that is received by the detection fiber 3832, thereby improving the accuracy and/or sensitivity of the optical detection and/or monitoring.

In some embodiments, the first lumen 3711 and the second lumen 3712 can be positioned such that the offset angle Θ is greater than approximately 75 degrees. In other embodiments, the first lumen 3711 and the second lumen 3712 can be positioned such that the offset angle Θ is between approximately 75 degrees and approximately 105 degrees.

As shown in FIG. 54, a center line of the first lumen 3711 is substantially parallel to and offset from (i.e., skewed from) a center line of the second lumen 3712. Similarly stated, the excitation fiber 3831 (and therefore the first light path 3806) is skewed from the detection fiber 3832 (and therefore the second light path 3807). Said another way, the first lumen 3711 (and/or the excitation fiber 3831) and the second lumen 3712 (and/or the detection fiber 3832) are spaced apart from a reference plane defined by the receiving block 3710 by a distance $Y_1$ and $Y_2$, respectively, wherein $Y_1$ is different than $Y_2$. Thus, the position along the longitudinal axis $L_A$ at which the excitation fiber 3831 and/or the first light path 3806 intersects the reaction volume 3713 is different from the position along the longitudinal axis $L_A$ at which the detection fiber 3832 and/or the second light path 3807 intersects the reaction volume 3713. In this manner, the first light path 3806 and/or the excitation fiber 3831 can be skewed from the second light path 3807 and/or the second optical member 3831.

The distance $Y_1$ and the distance $Y_2$ can be any suitable distance such that the excitation fiber 3831 and the detection fiber 3832 are configured to produce and/or define the first light path 3806 and the second light path 3807, respectively, in the desired portion of the PCR vial 6260. For example, in some embodiments, the distance $Y_1$ can be such that the first lumen 3711, the excitation fiber 3831 and/or the first light path 3806 enters and/or intersects the reaction volume 3713 at a location below the location of a fill line of a sample within the PCR vial 6260 disposed within the receiving block 3710. In this manner the excitation light beam conveyed by the excitation fiber 3831 will enter the sample below the fill line. In other embodiments, however, the distance $Y_1$ can be such that the first lumen 3711, the excitation fiber 3831 and/or the first light path 3806 enters the reaction volume 3713 at a location above the location of the fill line of the sample within the PCR vial 6260.

Similarly, in some embodiments, the distance $Y_2$ can be such that the second lumen 3712, the detection fiber 3832 and/or the second light path 3807 enter and/or intersect the reaction volume 3713 at a location below the location of the fill line of a sample within the PCR vial 6260 disposed within the receiving block 3710. In other embodiments, however, the distance $Y_2$ can be such that the second lumen 3712, the detection fiber 3832 and/or the second light path 3807 enters and/or intersects the reaction volume 3713 at a location above the location of the fill line of the sample within the PCR vial 6260.

The first heating module 3730 includes a series of thermo-electric devices 3731 (one corresponding to each of the cartridges and/or each of the receiving blocks 3710), a mounting block 3734, a series of clamp blocks 3733, and a heat sink 3732. As shown in FIG. 58, the mounting block 3734 includes a first portion 3735 and a second portion 3737. The first portion 3735 includes an angled surface 3736 to which each of the thermo-electric devices 3731 is coupled. In this manner, each receiving block 3710 is coupled to a mounting block 3734 by the corresponding clamp block 3733 such that the thermo-electric device 3731 is in contact with the mounting surface 3714 of the receiving block 3710.

The second portion 3737 of the mounting block 3734 is coupled to the heat sink 3732. The heat sink (see e.g., FIG. 59) can be any suitable device for facilitating heat transfer between the receiving blocks 3710 and a region exterior to the instrument 3002. In some embodiments the heat sink 3732 can include a device and/or mechanism to actively cool (i.e. remove heat from) the mounting block 3734.

The positioning assembly 3770 is coupled to the heat sink 3732 and a portion of the frame assembly 3300, and is configured to move the heater assembly 3700 linearly in direction along the y-axis. Thus, when actuated, the positioning assembly 3770 can move the heater assembly 3700 relative to the magazine 3350 and/or the cartridges therein such that the PCR vial (e.g. PCR vial 6260) is disposed within the receiving block 3710, as described above. The positioning assembly 3770 includes a motor 3771 and a linkage assembly 3772 configured to convert the rotational motion of the motor 3771 into linear motion. Movement of the heater assembly 3700 is guided by a y-axis guide shaft 3773.

In use, the first heating module 3730 can cyclically heat the PCR vial of each of the cartridges disposed within the instrument 3001 to promote a PCR process and/or mixing of contents contained therein. Moreover, because each of the cartridges is heated by a separate thermo-electric device 3731 via a separate receiving block 3710, in some embodiments, the thermal cycling of a first cartridge can be conducted at a different time than the thermal cycling of a second cartridge. Moreover, because each cartridge can be thermally-cycled independently from the other cartridges in the instrument, in some embodiments the thermal cycle protocol (e.g., the times and temperatures of the thermal cycle events) for a first cartridge can be different than the thermal cycle protocol for a second cartridge. In some embodiments, the first heating module 3730 is not used for thermal cycling, and instead is kept at a constant temperature, for example a temperature to carry out reverse transcription on an RNA sample.

Figure 60:
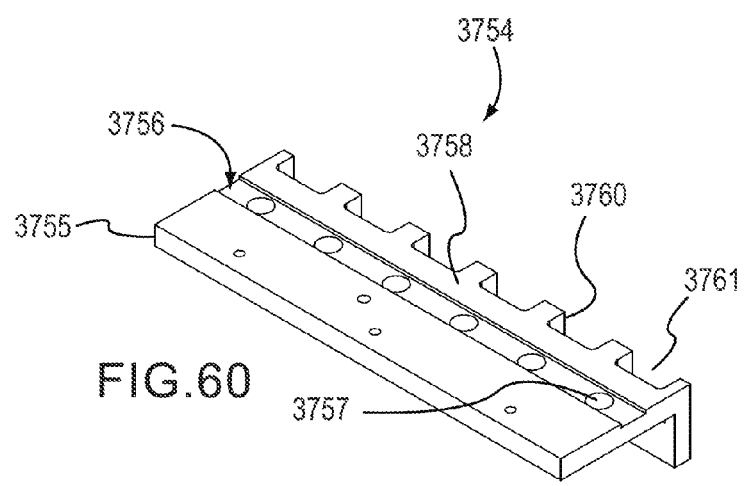
FIG. 60 is a perspective view of a mounting plate of the heater assembly shown in FIG. 52.
Figure 61:
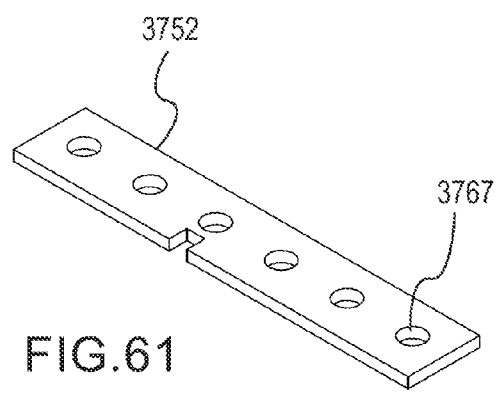
FIGS. 61 and 62 are a perspective view of a first insulating member and a second insulating member, respectively, of the heater assembly shown in FIG. 52.
Figure 62:
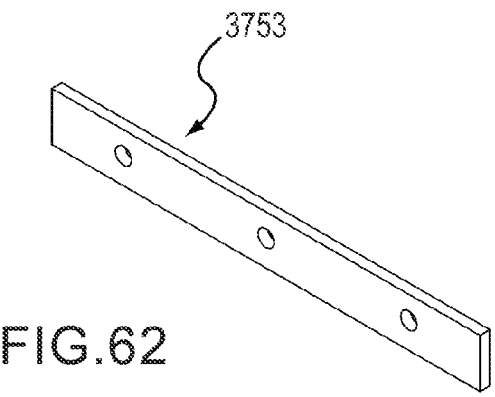

The second heating module 3750 includes a series of resistance heaters 3751 (one corresponding to each of the cartridges and/or each of the receiving blocks 3710), a mounting plate 3754, a first insulation member 3752, and a second insulation member 3753. As shown in FIG. 60, the mounting plate 3754 includes a first portion 3755 and a second portion 3760. The first portion 3755 provides mounting support for each of the resistance heaters 3751. Similarly stated, each of the resistance heaters 3731 is coupled to the mounting plate 3754.

The mounting plate 3754 is coupled to the mounting block 3734 of the first heating module 3730 such that the first insulation member 3752 is disposed between the mounting block 3734 and the first portion 3755 of the mounting plate 3754, and the second insulation member 3753 is disposed between the mounting block 3734 and the second portion 3760 of the mounting plate 3754. In this manner, the second heating module 3750 can function substantially independent of the first heating module 3730. Similarly stated, this arrangement reduces and/or limits heat transfer between the mounting plate 3754 and the mounting block 3734.

The first portion 3755 of the mounting plate 3754 includes a top surface 3758, and defines a recess 3756 and a series of lumens 3757 (one corresponding to each of the cartridges within the magazine 3350). In use, when the heater assembly 3700 is moved into position about each of the cartridges within the instrument 3002, each PCR vial is disposed through the corresponding lumen 3757 and into the reaction volume 3713 defined by the corresponding receiving block 3710. Thus, in some embodiments, when the heater assembly 3700 positioned about each of the cartridges, a side wall of the mounting plate 3754 that defines the lumens 3757 is positioned about and/or substantially surrounds a portion of each PCR vial 6260. In other embodiments, however, the PCR vial 6260 can be spaced apart from and/or not resident within the lumen 3757. For example, in some embodiments, only a transfer port (such as transfer port 7229 of the PCR module 7200, shown and described above with reference to FIGS. 30 and 31) can be disposed within the lumen 3737 of the mounting plate 3754 when the heater assembly 3700 is positioned about each of the cartridges.

As shown in FIG. 60, the second portion 3760 of the mounting plate 3754 defines a series of recesses and/or cavities 3761 (one corresponding to each of the cartridges within the magazine 3350). In use, when the heater assembly 3700 is moved into position about each of the cartridges within the instrument 3002, a portion of the cartridge is disposed within the corresponding recess 3761 of the mounting plate 3754. More particularly, as shown in FIG. 52, a portion of the isolation module (e.g., isolation module 6100) that corresponds to the elution chamber 6190 (not identified in FIG. 52) is disposed within the corresponding recess 3761. Thus, when the heater assembly 3700 positioned about each of the cartridges, a side wall of the second portion 3760 of the mounting plate 3754 that defines the recesses 3761 is positioned about and/or substantially surrounds a portion of the elution chamber 6190. In this manner, the second heating module 3750 can heat and/or thermally cycle a portion of a sample contained within the elution chamber 6190 of each cartridge.

In use, the second heating module 3750 can heat a portion of each of the cartridges disposed within the instrument 3001 to promote, improve and/or facilitate a reaction process occurring within the cartridge. For example, in some embodiments, the second heating module 3750 can heat portion of a substrate of a PCR module (e.g., the substrate 7220 of the PCR module 7200 shown and described above with reference to FIGS. 29-31). Heating by the second heating module 3750, in one embodiment, is done facilitate a reverse transcription reaction, or for a "hot start" PCR.

More particularly, in some embodiments the second heating module 3750 can facilitate a "hot start" method associated with a PCR process. The hot start method involves the use of "hot start enzymes" (polymerase) to reduce nonspecific priming of nucleic acids in an amplification reaction. More particularly, when enzymes are maintained at ambient temperature (e.g., below approximately 50° C.), nonspecific hybridization may occur, which can lead to nonspecific priming in the presence of the polymerase. Thus, hot start enzymes are enzymes that are inactive at ambient temperature, and do not become active until heated to a predetermined temperature. Such a predetermined temperature can be a temperature above approximately 40° C., 50° C., 70° C. or 95° C. To facilitate the "hot start" method, the second heating module 3750 can heat an elution chamber (e.g., elution chamber 7190) to maintain the eluted nucleic acid sample at an elevated temperature (e.g., at a temperature above approximately 40° C., 50° C., 70° C. or 95° C.) prior to the addition of the master mix to the amplification reaction within the PCR vial (e.g., PCR vial 7260). In some embodiments, for example, the second heating module 3750 can maintain the temperature of the sample within the elution chamber 7190 to a temperature of between approximately 50° C. and approximately 95° C. By heating the eluted nucleic acid in this manner, nonspecific hybridization and/or false priming in the presence of polymerase can be eliminated and/or reduced.

Reaction reagents (e.g., the substance R2 contained within the reagent module 7270b shown above in FIGS. 30 and 31) can then be added to the PCR vial (e.g., the PCR vial 7260) to the lyophilized master mix contained therein. The heated nucleic acid sample from the elution chamber (e.g., elution chamber 7190) can then be transferred into the PCR vial, as described above. Moreover, the second heating module 7250 can also heat a flow path between the elution chamber and the PCR vial (e.g., the passageway 7222) such that the contents therein (e.g. the eluted nucleic acid sample that is being transferred from the elution chamber to the PCR vial) can be maintained at an elevated temperature (e.g., at a temperature above approximately 40° C., 50° C., 70° C. or 95° C.). In some embodiments, for example, the second heating module 3750 can maintain the temperature of the sample within the flow passageway to a temperature of between approximately 50° C. and approximately 95° C. After the heated elution sample is conveyed into the PCR vial, the solution is mixed through a temperature cycling (produced by the first heating module 3730), and then the PCR reaction is initiated.

Figure 63:
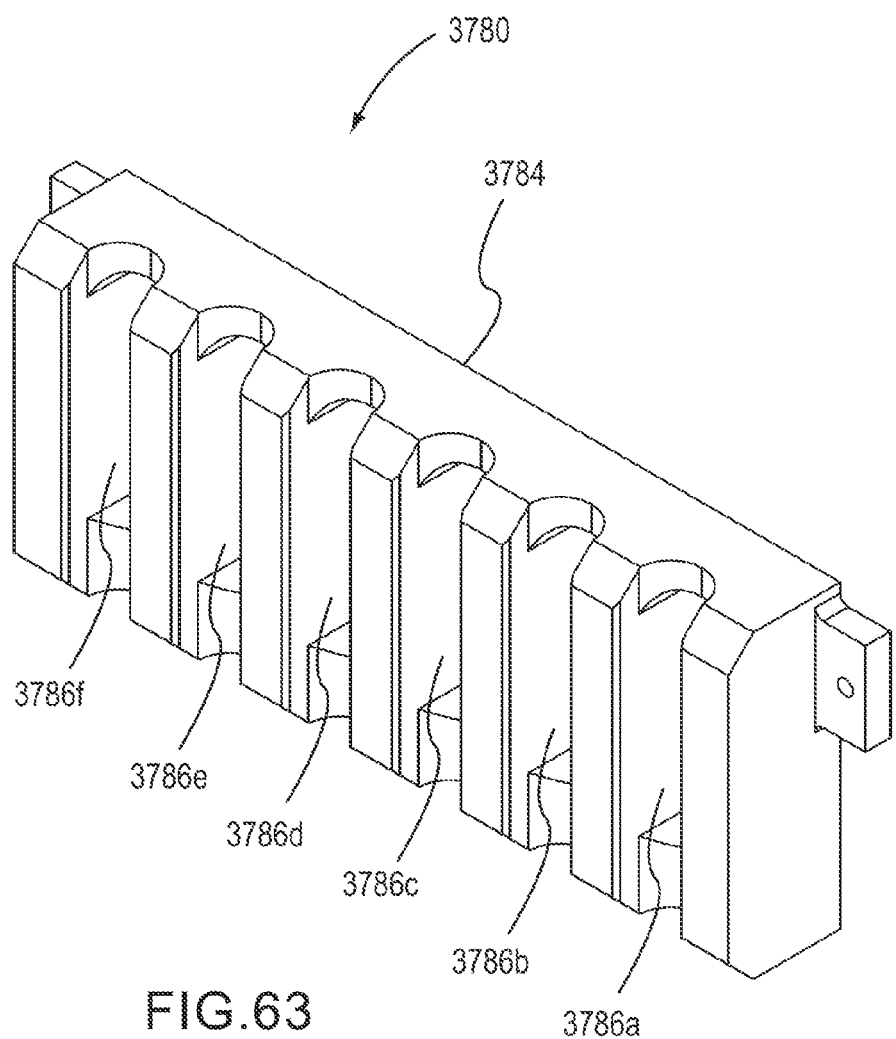
FIG. 63 is a perspective view of a heating block of the heater assembly shown in FIG. 52.

The third heating module 3780 includes at least one heater (not shown) and a heater block 3784. As shown in FIG. 63, the heater block 3784 defines a series of recesses and/or cavities 3786a, 3786b, 3786c, 3786d, 3786e, 3786f, each of which corresponds to each of the cartridges within the magazine 3350). In use, when the heater assembly 3700 is moved into position about each of the cartridges within the instrument 3002, a portion of the cartridge is disposed within the corresponding recess (e.g., recess 3786a) of the heater block 3784. More particularly, as shown in FIG. 52, a portion of the isolation module (e.g., isolation module 6100) that corresponds to the lysing chamber 6114 (not identified in FIG. 52) is disposed within the corresponding recess. Thus, when the heater assembly 3700 positioned about each of the cartridges, a side wall of the heater block 3784 that defines the recesses 3786 is positioned about and/or substantially surrounds a portion of the lysing chamber 6114. In this manner, the third heating module 3780 can heat and/or thermally cycle a portion of a sample contained within the lysing chamber 6114 of each cartridge. In one embodiment, heating by the third heating module 3780 takes place during a reverse transcription and/or PCR reaction.

FIGS. 64-70 show various views of the optics assembly 3800 of the instrument 3002. The optics assembly 3800 is configured to monitor a reaction occurring with a cartridge disposed within the instrument 3002. More specifically, the optics assembly 3800 is configured to detect one or more different analytes and/or targets within a test sample in before during and/or after a PCR reaction occurring within the PCR vial (e.g., PCR vial 6260) of the cartridge. As described herein, the optics assembly 3800 can analyze the samples in a sequential and/or time-phased manner and/or in real-time. The optics assembly 3800 includes an excitation module 3860, a detection module 3850, a slide assembly 3870 and an optical fiber assembly 3830.

For example, in one embodiment, the optics assembly is used to monitor a nucleic acid amplification reaction in real time. In a further embodiment, the amplification reaction is a PCR. In another embodiment, the optics assembly is used to measure the results from binding assays, for example, binding between enzyme and substrate or ligand and receptor.

Figure 64:
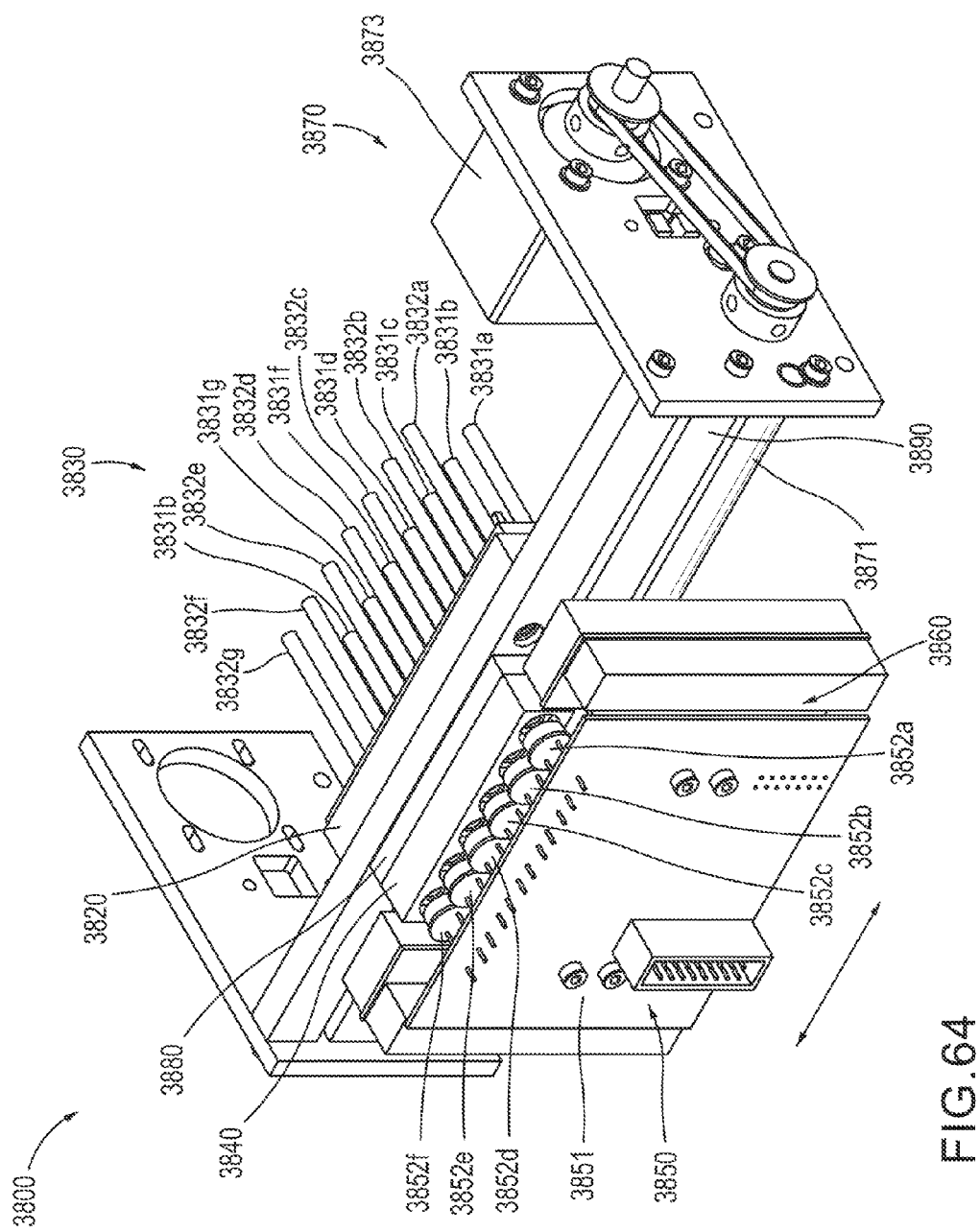
FIGS. 64 and 66 are a front perspective view and a rear perspective view, respectively, of an optics assembly of the instrument shown in FIG. 36.

The optical fiber assembly 3830 includes a series of excitation optical fibers (identified as excitation fibers 3831a, 3831b, 3831c, 3831d, 3831e, 3831f, 3831g in FIG. 64). Each of the excitation fibers 3831a, 3831b, 3831c, 3831d, 3831e and 3831f is configured to convey a light beam and/or optical signal from the excitation module 3860 to the corresponding receiving block 3710. Accordingly, a first end portion of each excitation fiber 3831a, 3831b, 3831c, 3831d, 3831e and 3831f is disposed within the lumen 3711 of the receiving block 3710, as described above. The excitation fiber 3831g is a calibration fiber and is configured to convey a light beam and/or optical signal from the excitation module 3860 to an optical calibration module (not shown). The excitation optical fibers 3831 can be any suitable optical fiber to convey a light beam, such as, for example, a multi-mode fiber or a single-mode fiber.

The optical fiber assembly 3830 includes a series of detection optical fibers (identified as detection fibers 3832a, 3832b, 3832c, 3832d, 3832e, 3832f, 3832g in FIG. 64). Each of the detection fibers 3832a, 3832b, 3832c, 3832d, 3832e and 3832f is configured to convey a light beam and/or optical signal from the receiving block 3710 to the detection module 3850. Accordingly, a first end portion of each detection fiber

3832*a*, 3832*b*, 3832*c*, 3832*d*, 3832*e* and 3832*f* is disposed within the lumen 3712 of the receiving block 3710, as described above. The detection fiber 3832*g* is a calibration fiber and is configured to receive a light beam and/or optical signal from the optical calibration module (not shown). The detection optical fibers 3832 can be any suitable optical fiber to convey a light beam, such as, for example, a multi-mode fiber or a single-mode fiber.

Figure 70:
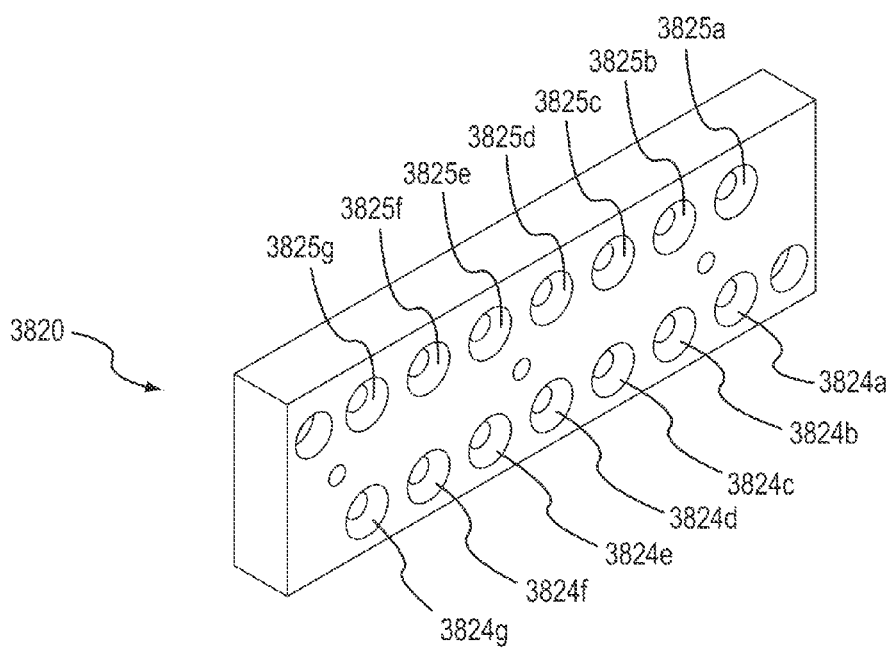
FIG. 70 is a perspective view of a portion of a fiber optics module of the optics assembly shown in FIGS. 64 and 66.
Figure 71A:
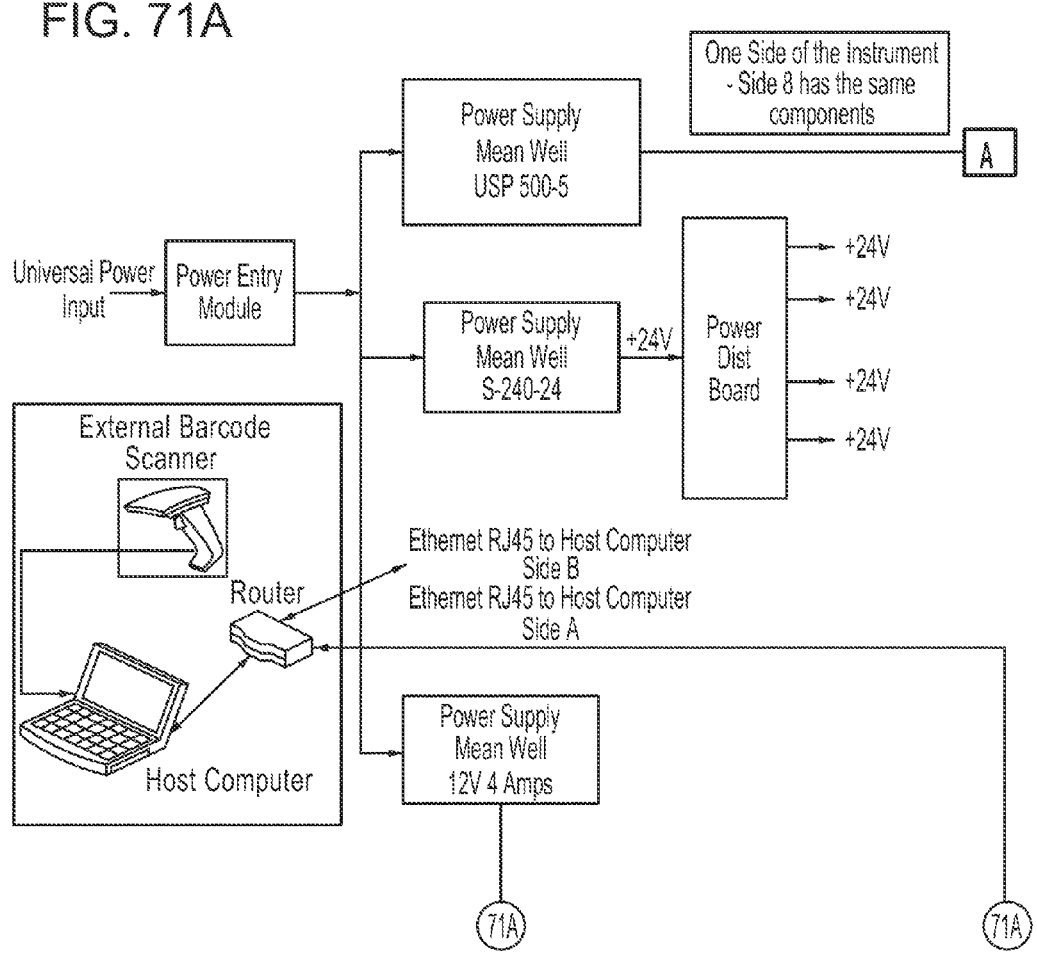
FIGS. 71A, 71B, 72A, 72B and 73 show a block diagram of the electronic control system of the instrument shown in FIG. 36.
Figure 71B:
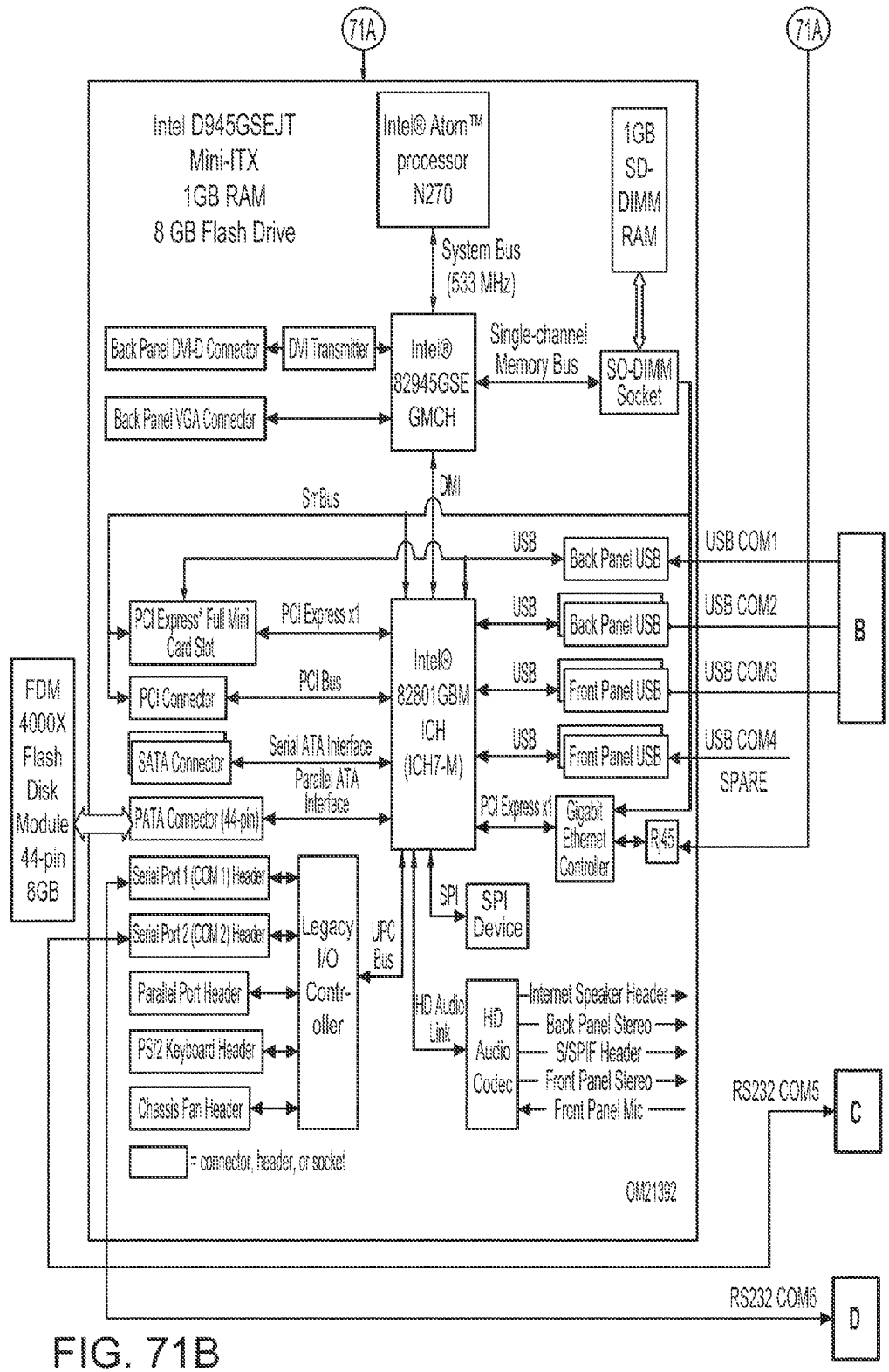
Figure 72A:
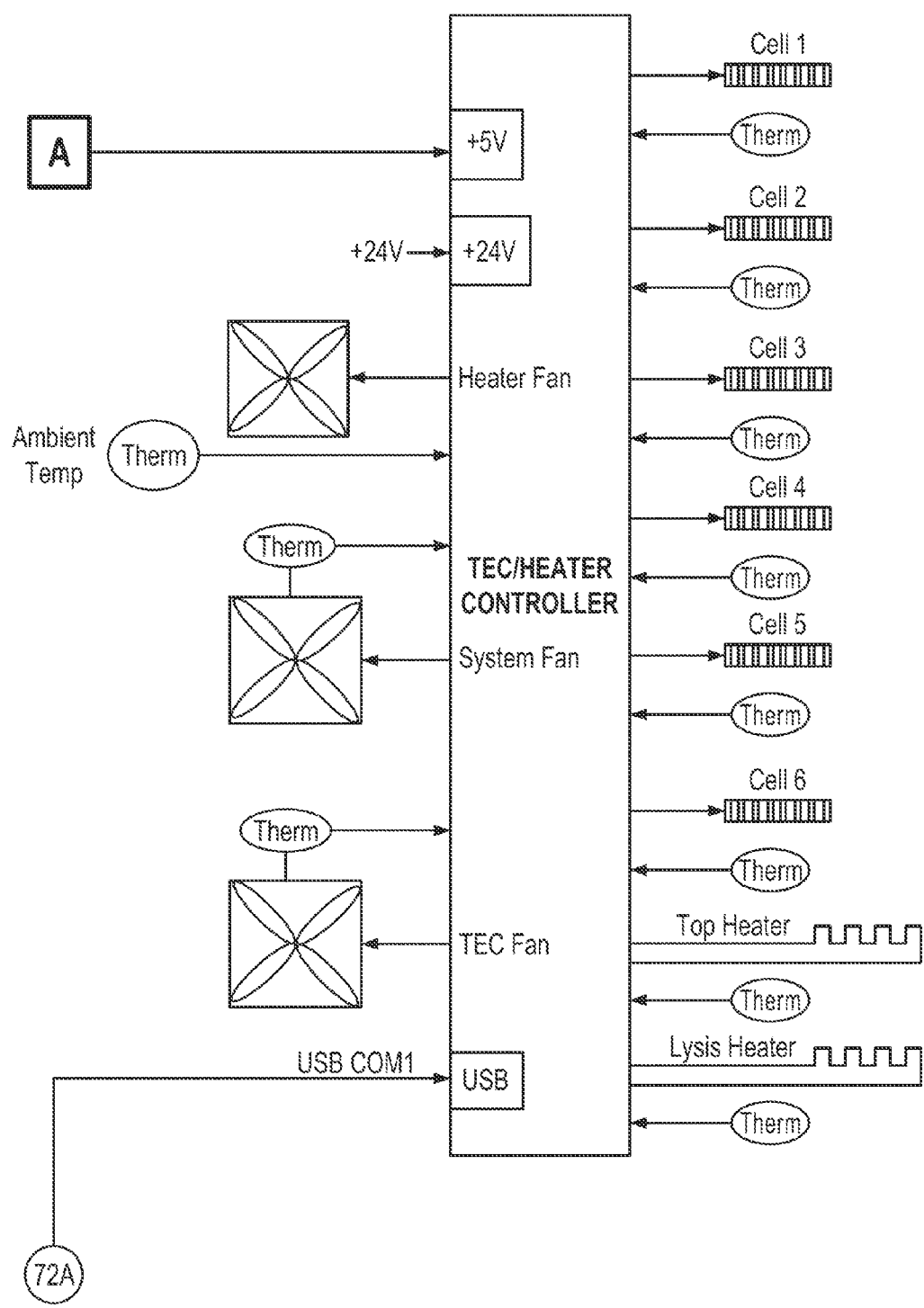
Figure 72B:
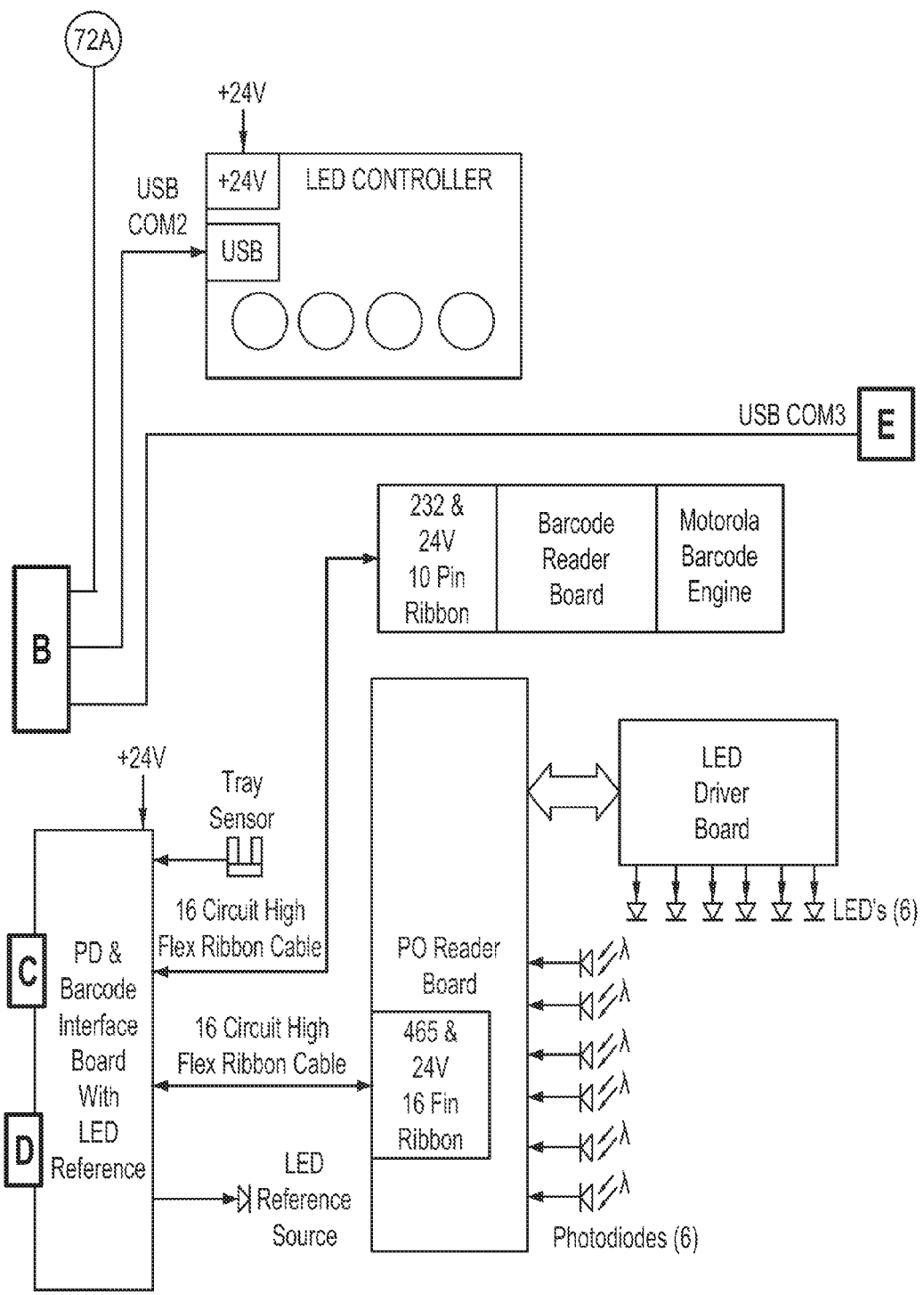
Figure 73:
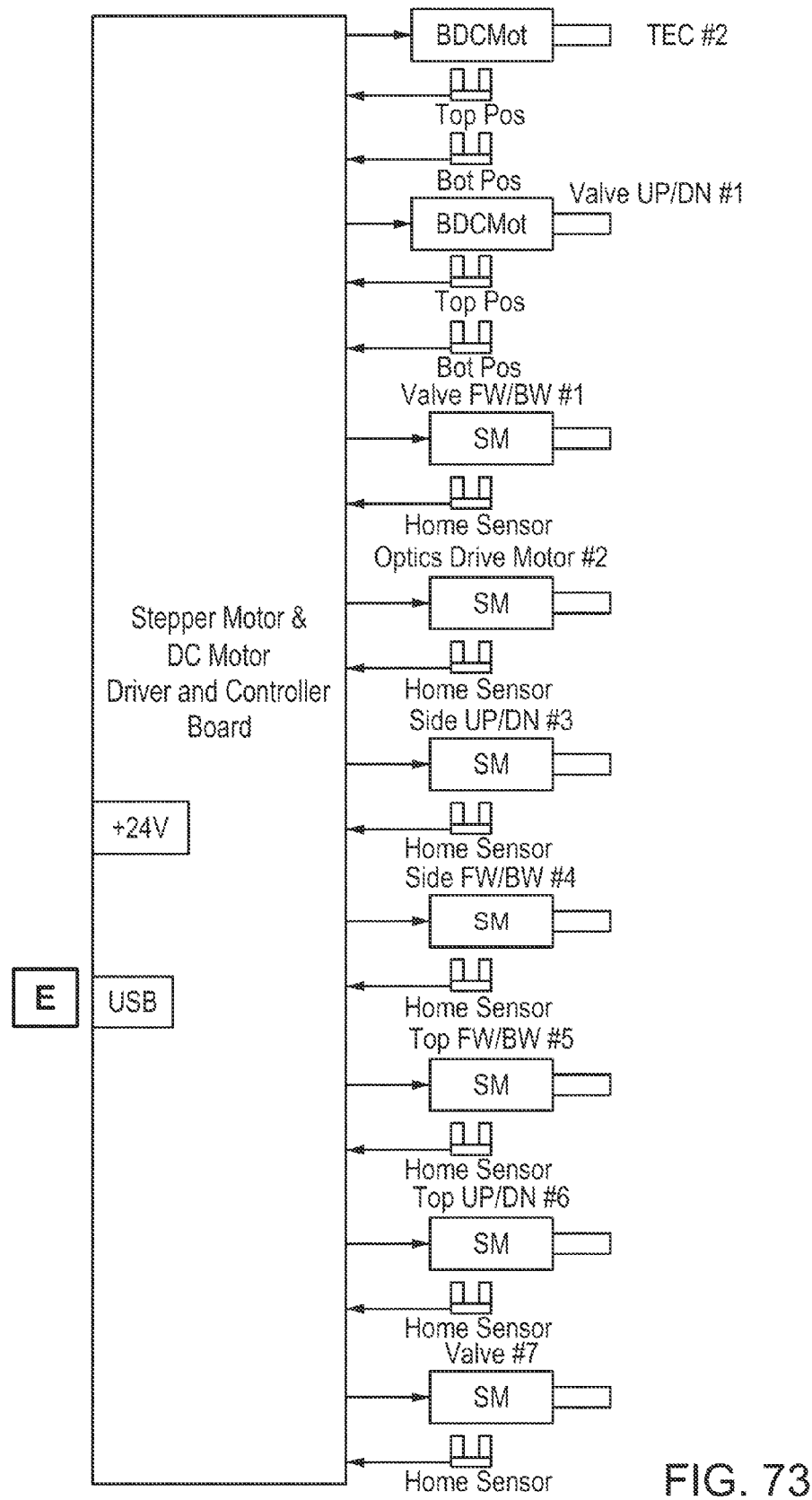

The optical fiber assembly 3830 also includes a fiber mounting block 3820. As shown in FIG. 70, the fiber mounting block 3820 defines a series of lumens 3825*a*-3825*g* and a series of lumens 3824*a*-3824*g*. Each of the lumens 3824 is configured to receive a second end portion of the corresponding excitation optical fiber (e.g., excitation fiber 3831*a*, as identified in FIG. 65). Similarly, each of the lumens 3825 is configured to receive a second end portion of the corresponding detection optical fiber (e.g., detection fiber 3832*a*, as identified in FIG. 65). The fiber mounting block 3820 is coupled to the slide rail 3890 of the slide assembly 3870 to optically couple the excitation fibers 3831 to the excitation module 3860 and optically couple the detection fibers 3832 to the detection module 3850, as described in more detail below.

Figure 65:
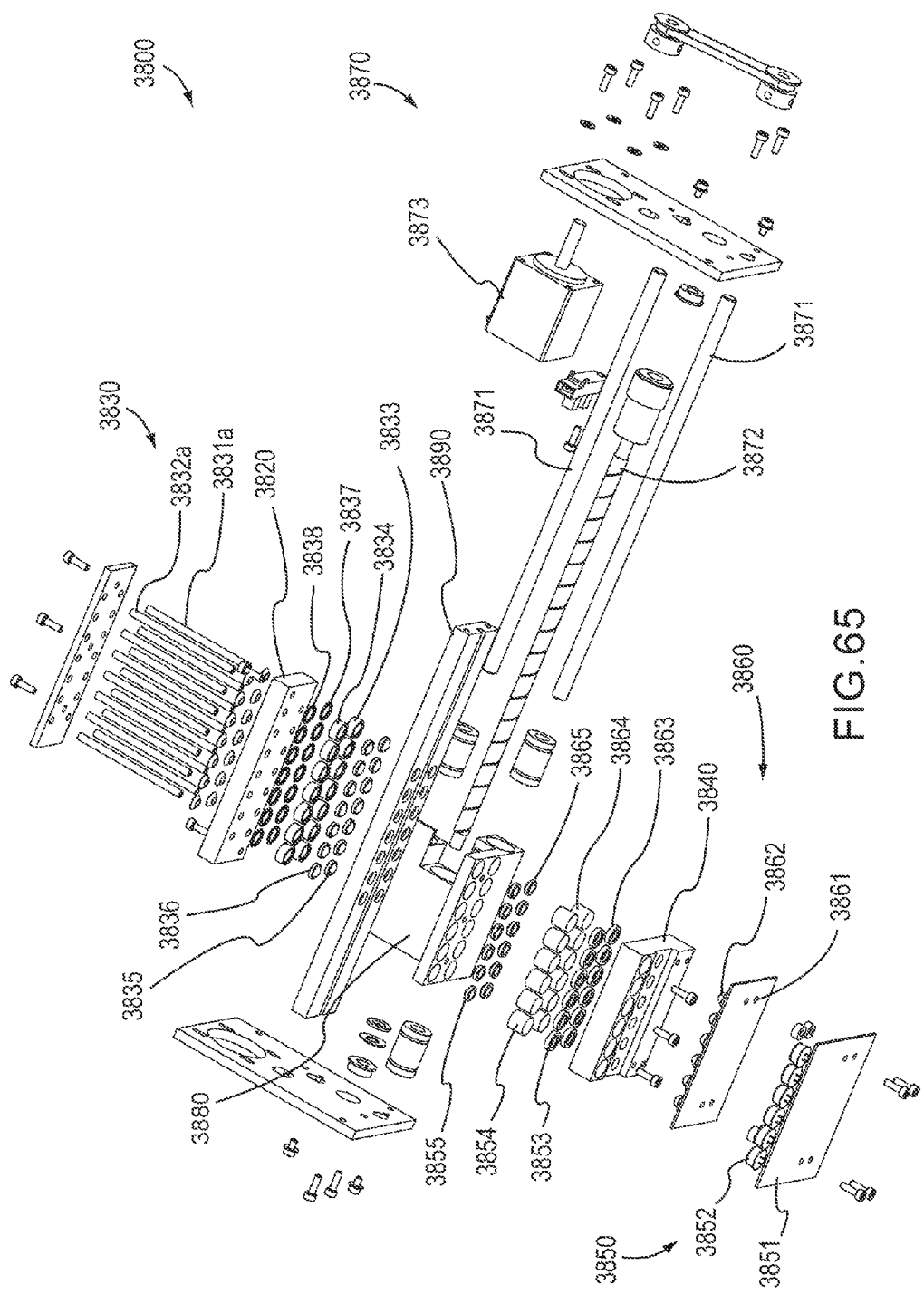
FIG. 65 is an exploded perspective view of the optics assembly shown in FIGS. 64 and 66.

As shown in FIG. 65, the optical fiber assembly 3830 includes a series of spacers, lenses and sealing members to facilitate the optical connections described herein, and/or to modify, condition and/or transform a light beam conveyed by the optical fiber assembly 3830. More particularly, the optical fiber assembly 3830 includes a series of excitation spacers 3833 and detection spacers 3834 configured to be disposed within the fiber mounting block 3820 and/or the slide plate 3890. The optical fiber assembly 3830 also includes a series of excitation lenses 3835 and detection lenses 3836 configured to be disposed within the fiber mounting block 3820 and/or the slide plate 3890. The optical fiber assembly 3830 also includes a series of excitation sealing members 3837 and detection sealing members 3838 configured to be disposed within the fiber mounting block 3820 and/or the slide plate 3890. The excitation sealing members 3837 and detection sealing members 3838 are configured to seal and/or prevent contamination from entering the optical paths defined by the optics assembly 3800.

Figure 66:
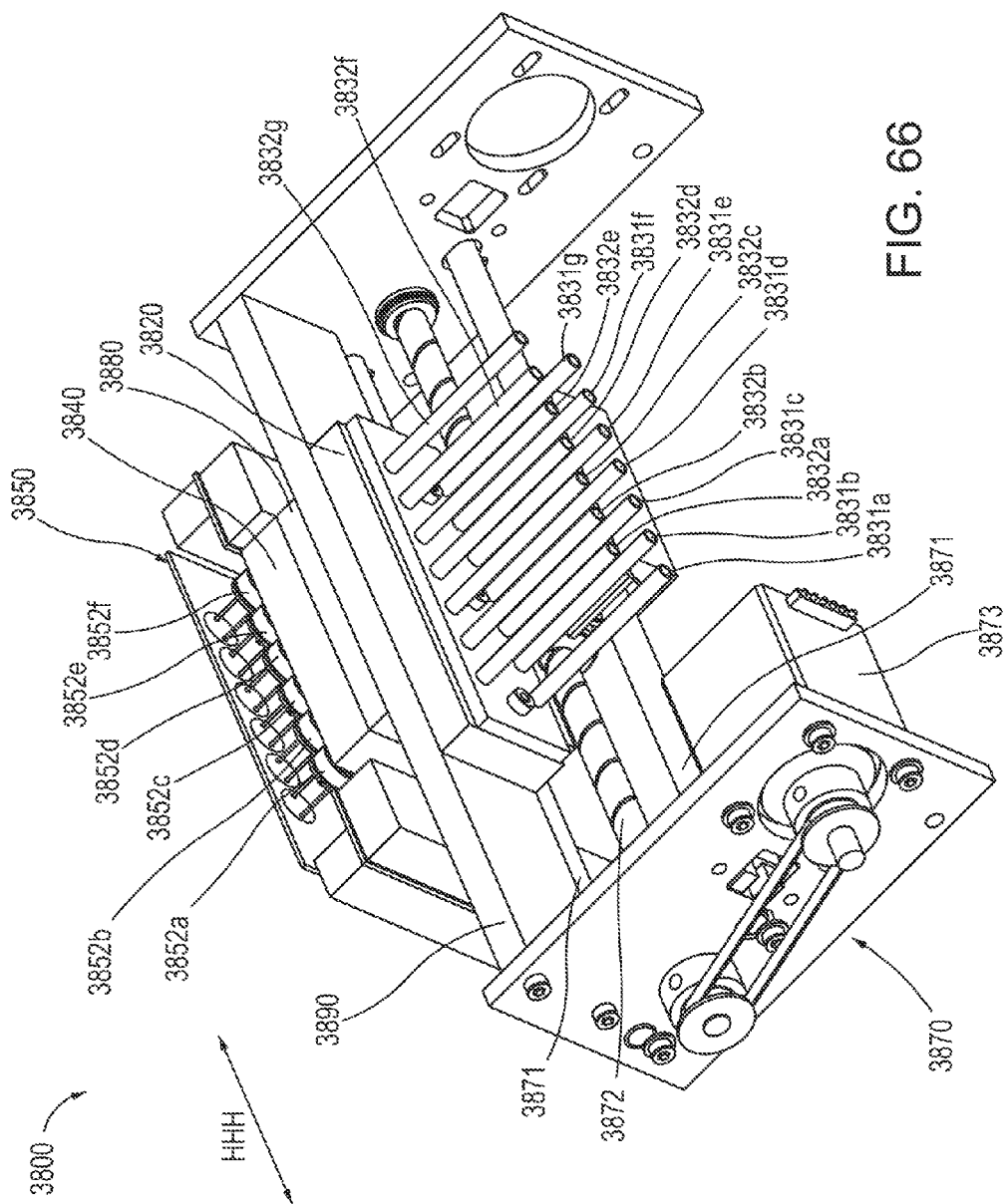

As shown in FIGS. 64-66, the optics assembly 3800 includes an excitation module 3860 configured to produce a series excitation light beams (and/or optical signals, not shown). The excitation module 3860 includes an excitation circuit board 3861 upon which a series of excitation light sources 3862 is mounted. The light sources 3862 can be any suitable device and/or mechanism for producing a series of excitation light beams, such as, for example, a laser, a light-emitting diode (LED), a flash lamp, or the like. In some embodiments, the light beam produced by each of the light sources 3862 can have substantially the same characteristics (e.g., wavelength, amplitude and/or energy) the light beams produced by the other light sources 3862. In other embodiments, however, a first light source 3862 can produce a light beam having a first set of characteristics (e.g., a wavelength associated with a red light beam) and a second light source 3862 can produce a light beam having a second, different set of characteristics (e.g., a wavelength associated with a green light beam). This arrangement allows each of the different light beams (i.e., the beams having different characteristics) to be conveyed to each of the receiving blocks 3710 in a sequential manner, as described in more detail herein. As shown in FIG. 65, the excitation module 3860 includes a series of spacers 3863, filters 3864 and lenses 3865 to facilitate the optical connections described herein, and/or to modify, condition and/or transform a light beam produced by the excitation module 3860 and conveyed by the excitation fibers 3831.

As shown in FIGS. 64-66, the optics assembly 3800 includes a detection module 3850 configured to receive and/or detect a series emission light beams (and/or optical signals, not shown). The detection module 3850 includes a detection circuit board 3851 upon which a series of emission light detectors 3852 is mounted. The emission light detectors 3852 can be any suitable device and/or mechanism for detecting a series of emission light beams, such as for example, an optical detector, a photoresistor, a photovoltaic cell, a photo diode, a phototube, a CCD camera or the like. In some embodiments, each detector 3852 can be configured to selectively receive an emission light beam regardless of the characteristics (e.g., wavelength, amplitude and/or energy) of the emission light beam. In other embodiments, however, the detector 3852 can be configured (or "tuned") to correspond to an emission light beam having a particular set of characteristics (e.g., a wavelength associated with a red light beam). In some embodiments, for example, each of the detectors 3852 can be configured to receive emission light produced by the excitation of a portion of the sample when excited by a corresponding light source 3862 of the excitation module 3860. This arrangement allows each of the different emission light beams (i.e., the beams having different characteristics) to be received from each of the receiving blocks 3710 in a sequential manner, as described in more detail herein. As shown in FIG. 65, the detection module 3850 includes a series of spacers 3853, filters 3854 and lenses 3855 to facilitate the optical connections described herein, and/or to modify, condition and/or transform an emission light beam received by the detection module 3850.

The slide assembly 3870 includes a mounting member 3840, a slide block 3880 and a slide rail 3890. The slide block 3880 is coupled to the mounting member 3840, and is slidably mounted to the slide rail 3890. As described in more detail below, in use, a drive screw 3872, which is rotated by a stepper motor 3873 can rotate within a portion of the slide block 3880 to cause the slide block 3880 (and therefore the mounting member 3840) to move relative to the slide rail 3890, as shown by the arrow HHH in FIGS. 64 and 66. In this manner, the mounting member 3840 can be moved relative to the slide rail 3890 to sequentially move each of the excitation light sources 3862 and emissions light detectors 3852 into optical communication with the second end of each excitation fiber 3831 and emission fiber 3832, respectively. Further detail of the slide assembly 3870 and the operation of the optics module 3800 is provided below.

Figure 67:
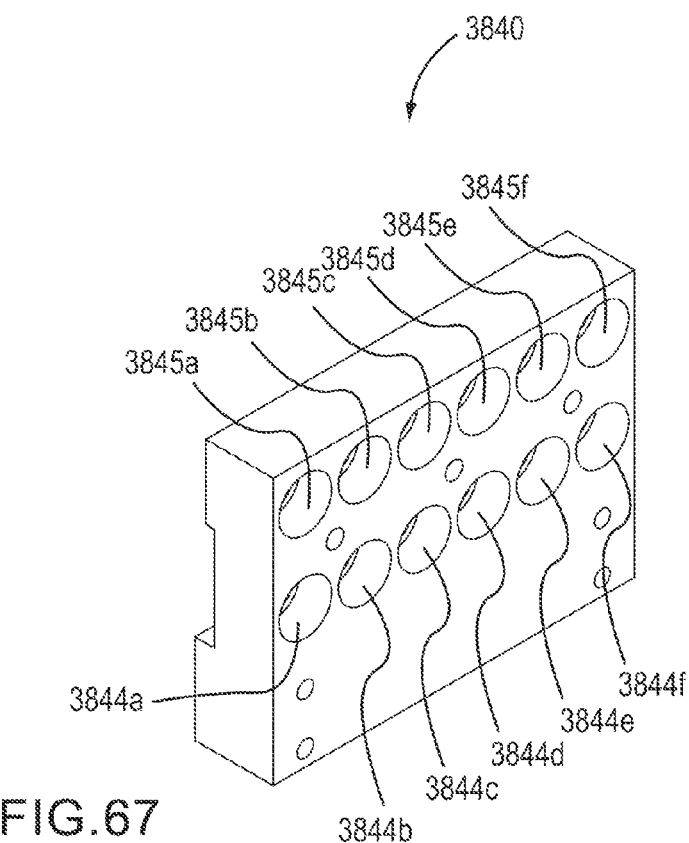
FIG. 67 is a perspective view of a mooting member of the optics assembly shown in FIGS. 64 and 66.

As shown in FIG. 67, the mounting member 3840 defines a series of excitation lumens 3844*a*-3844*f* and a series of emission lumens 3845*a*-3845*f*. As shown in FIG. 65, each excitation light source 3862 is disposed within the corresponding excitation lumen 3844, and each emission light detector 3852 is disposed within the corresponding emission lumen 3845. The mounting member 3840 is coupled to the slide block 3880 such that movement of the slide block 3880 causes movement of the mounting member 3840 (and therefore the excitation light sources 3862 and the emission light detectors 3852).

Figure 68:
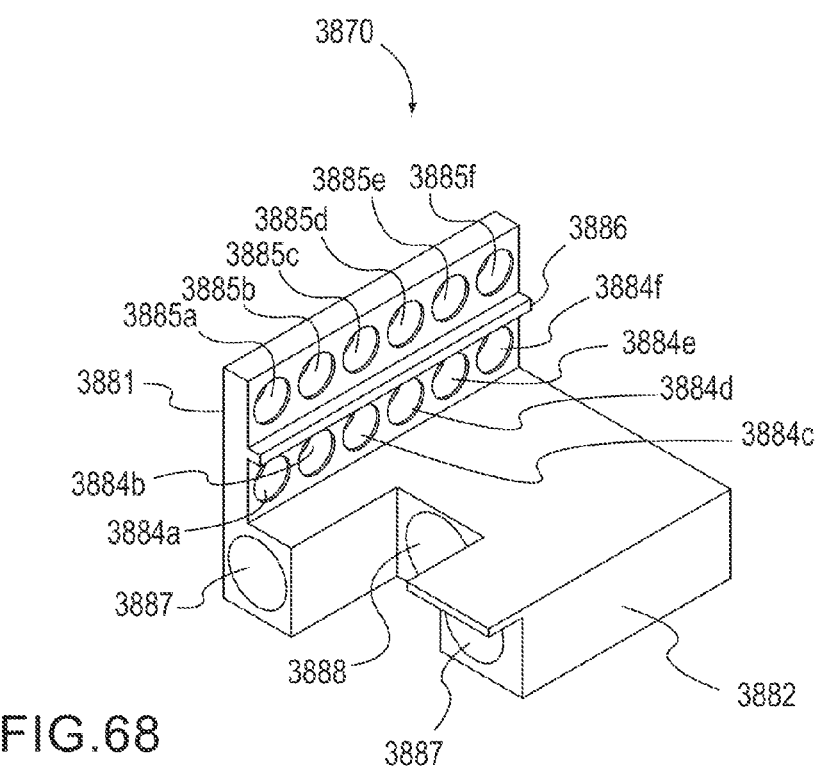
FIG. 68 is a perspective view of a slide block of the optics assembly shown in FIGS. 64 and 66.

As shown in FIG. 68, the slide block 3880 includes a first portion 3881 and a second portion 3882. The first portion 3881 includes a guide protrusion 3886 and defines a series of excitation lumens 3884*a*-3884*f* and a series of emission lumens 3855*a*-3855*f*. When the slide block 3880 is coupled to the mounting member 3840, each of the excitation lumens 3884 of the slide block 3880 is aligned with the corresponding excitation lumen 3844 of the mounting member 3840. Similarly, each of the emission lumens 3885 of the slide block 3880 is aligned with the corresponding emission lumen 3845 of the mounting member 3840. The guide protrusion is configured to be slideably disposed within the corresponding groove 3896 on the slide rail 3890.

The second portion 3882 of the slide block 3880 defines a pair of guide lumens 3887 and a lead screw lumen 3888. In use, the drive screw 3872 is rotated within the lead screw lumen 3888 to move the slide block 3880 relative to the slide rail 3890. Movement of the slide block 3880 is guided by the guide rails 3871, which are slideably disposed within the corresponding guide lumen 3887.

Figure 69:
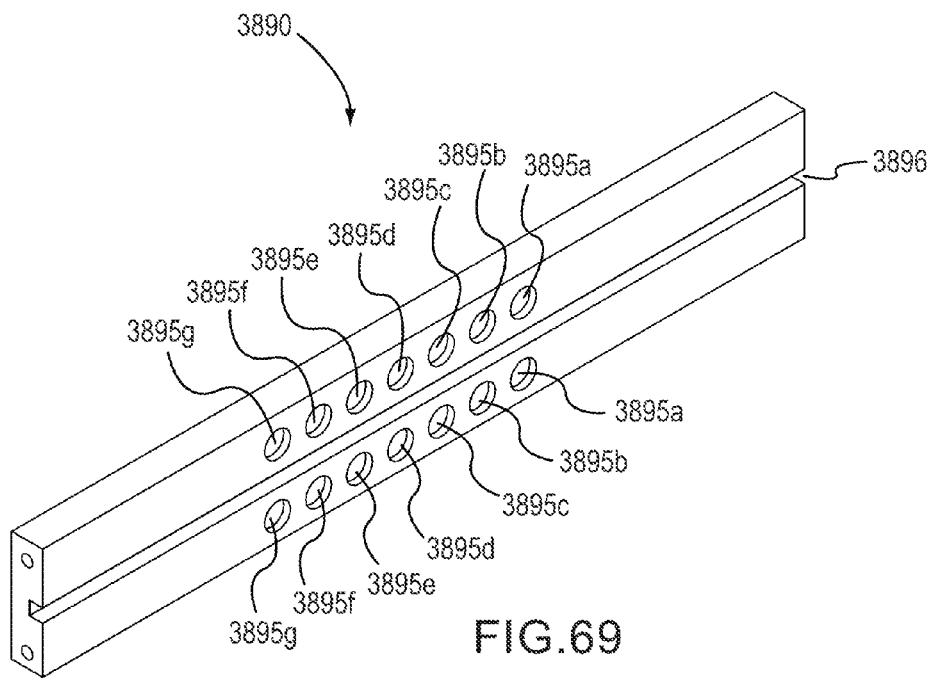
FIG. 69 is a perspective view of a slide rail of the optics assembly shown in FIGS. 64 and 66.

As shown in FIG. 69, the slide rail 3890 defines seven excitation openings 3894a, 3894b, 3894c, 3894d, 3894e, 3894f and 3894g, and seven detection openings 3895a, 3895b, 3895c, 3895d, 3895e, 3895f and 3895g. The fiber mounting block 3820 is coupled to the slide rail 3890 such that the excitation fibers 3831 are in optical communication with each corresponding excitation opening, and the detection fibers 3832 are in optical communication with each corresponding excitation opening. In this manner, when the slide block 3880 and the mounting member 3840 are collectively moved relative to the slide rail 3890, each of the excitation openings and detection openings of the slide block 3880 and mounting member 3840 are sequentially aligned with each of the excitation openings 3894 and detection openings 3895, respectively, of the slide rail 3890.

In use, during or after the amplification process, the slide assembly 3870 can controllably move slide block 3880 such that each light source 3862 and optical detector 3852 pair sequentially passes each pair of excitation fibers 3831 and detection fibers 3832. In this manner, the optical assembly 3800 can analyze the samples within each of the six PCR vials (e.g., PCR vial 6260) in a time-phased and/or multiplexed fashion.

FIGS. 71A, 71B, 72A, 72B and 73 are schematic block diagrams of the electronic control and computer system for the instrument 3002.

Figure 74:
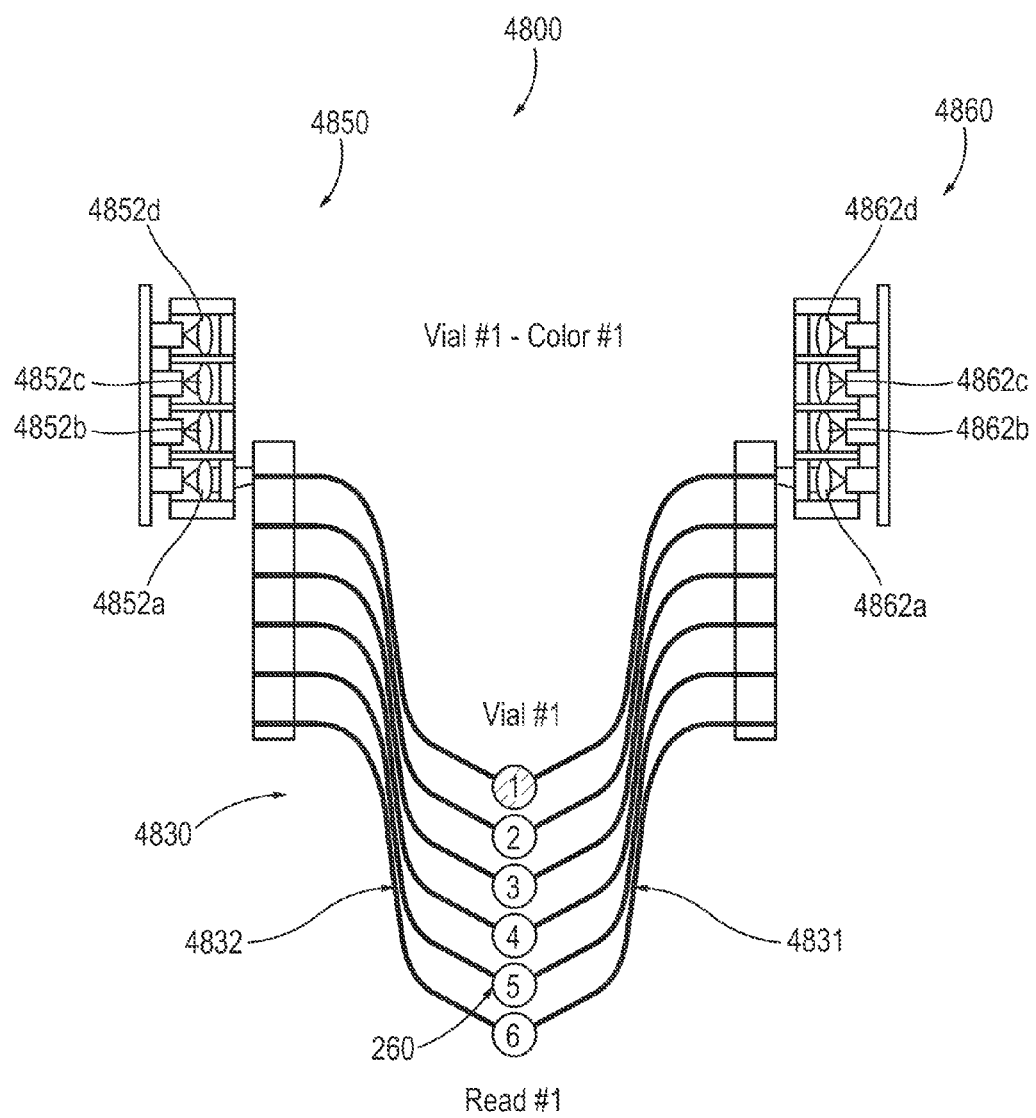
FIGS. 74-76 are schematic illustrations of an optics assembly according to an embodiment, in a first configuration, a second configuration and a third configuration, respectively.
Figure 75:
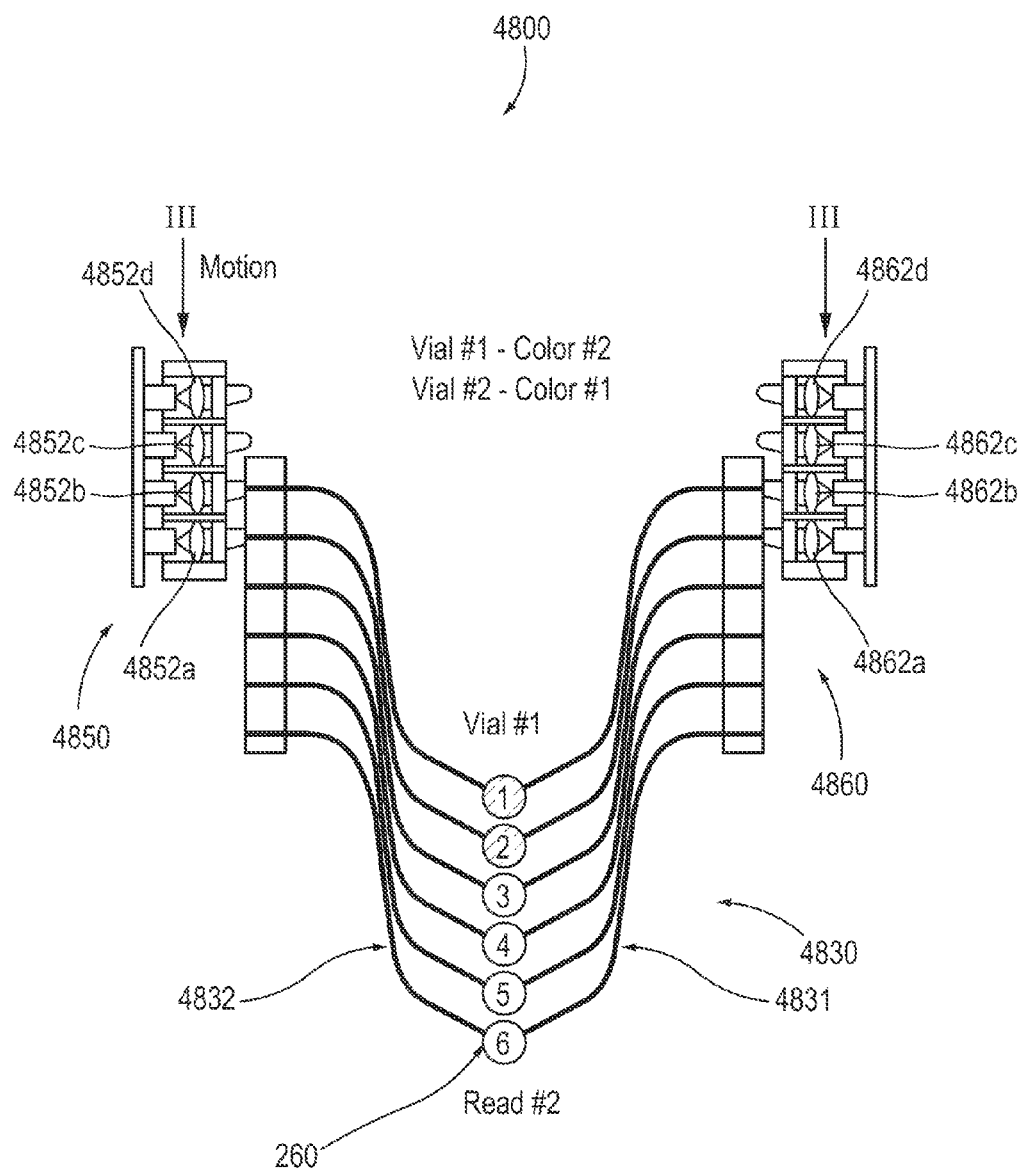
Figure 76:
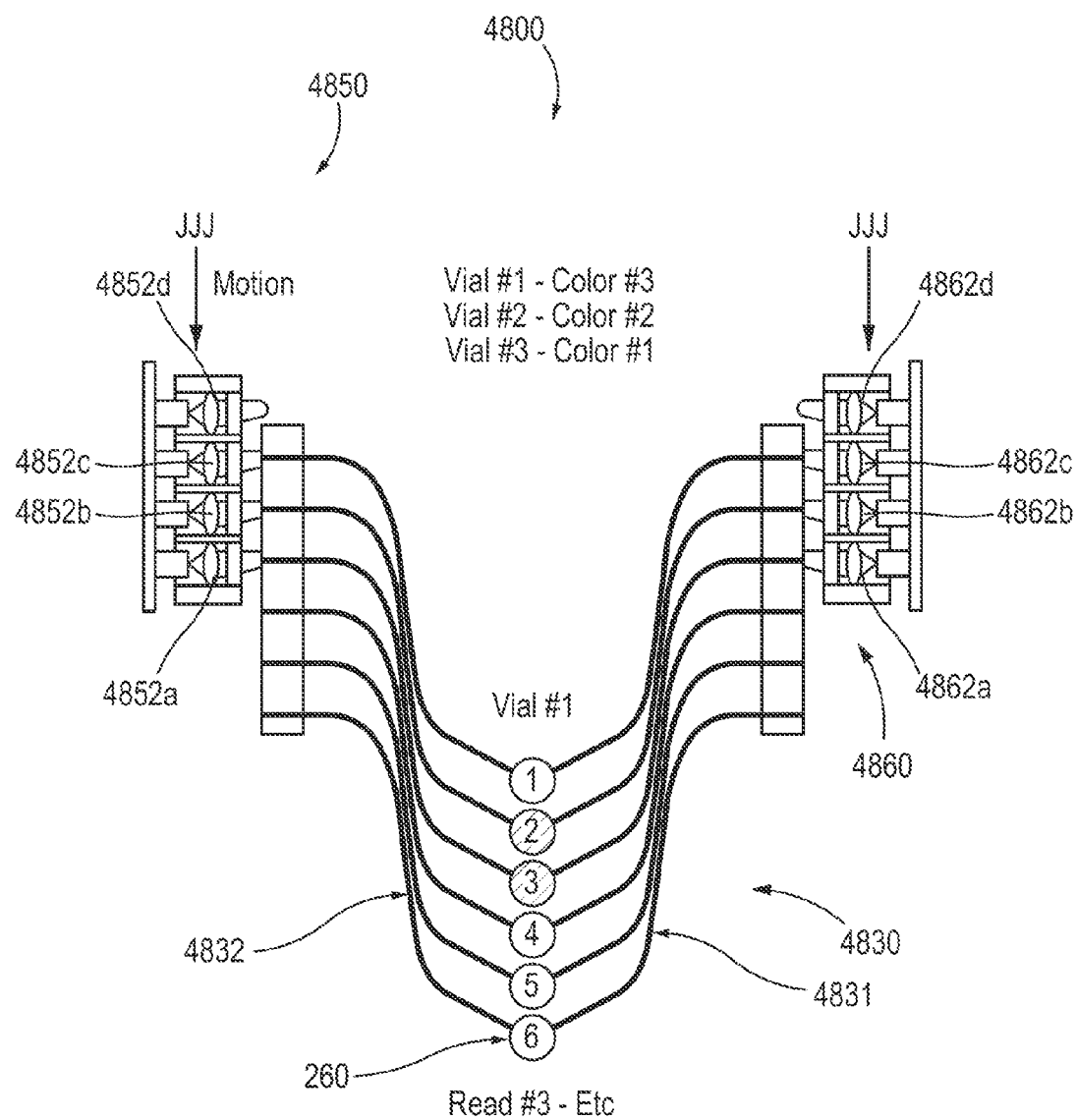

Although the optics assembly 3800 is shown as including the detection module 3850 adjacent the excitation module 3860, in other embodiments, an optics assembly of an instrument can include a detection module located in an position relative to an excitation module. For example, FIGS. 74-76 are schematic illustrations an optics assembly 4800 configured to perform time-phased optical detection of a series of samples, as described above with reference to the optics assembly 3800. The optics assembly 4800 is a portion of an instrument (such as, for example, any of the instruments shown and described herein) that is configured to contain and six reaction vials 260. The optics assembly 4800 includes an excitation module 4860, a detection module 4850 and a fiber assembly 4830. The excitation module 4860 includes four excitation light sources 4862a, 4862b, 4862c and 4862d. Each of the excitation light sources is configured to produce an excitation light beam having a different wavelength. For example, the light source 4862a is configured to produce a light beam having color #1 (e.g., red), the light source 4862b is configured to produce a light beam having color #2 (e.g., green), the light source 4862c is configured to produce a light beam having color #3 (e.g., blue) and the light source 4862d is configured to produce a light beam having color #4 (e.g., yellow).

The detection module 4850 includes four detectors 4852a, 4852b, 4852c and 4865d. Each of the detectors is configured to receive an emission light beam having a different wavelength. For example, the detector 4852a is configured to receive a light beam resulting from the excitation of an analyte with excitation color #1, the detector 4852b is configured to receive a light beam resulting from the excitation of an analyte with excitation color #2, the detector 4852cv is configured to receive a light beam resulting from the excitation of an analyte with excitation color #3 and the detector 4852d is configured to receive a light beam resulting from the excitation of an analyte with excitation color #4.

The fiber assembly 4830 includes a series of excitation fibers 4831 and a series of detection fibers 4832. In particular, one excitation fiber is used to optically couple each reaction vial 260 to the excitation module 4860 and one detection fiber 4832 is used to optically couple each reaction vial 260 to the detection module 4850. The excitation module 4860 and the detection module 4850 are configured to move relative to the fiber assembly 4830. In this manner, each of the light sources and its corresponding detector (e.g., light source 4862a and detector 4852a) can be sequentially aligned with the excitation and detection fiber for a particular reaction vial 260.

In use, when the optics assembly 4800 is in a first configuration, as shown in FIG. 74, the light source 4862a and the detector 4852a are in optical communication with the first reaction vial 260. Thus, the sample contained within the first reaction vial can be analyzed with an excitation light having color #1. The excitation module 4860 and the detection module 4850 are then moved, as shown by the arrows III in FIG. 75 to place the optics assembly in a second configuration. When the optics assembly 4800 is in the second configuration, as shown in FIG. 75, the light source 4862a and the detector 4852a are in optical communication with the second reaction vial 260, and the light source 4862b and the detector 4852b are in optical communication with the first reaction vial 260. Thus, the sample contained within the first reaction vial can be analyzed with an excitation light having color #2 and the sample contained within the second reaction vial can be analyzed with an excitation light having color #1. The excitation module 4860 and the detection module 4850 are then moved, as shown by the arrows JJJ in FIG. 76 to place the optics assembly in a third configuration. When the optics assembly 4800 is in the third configuration, as shown in FIG. 76, the light source 4862a and the detector 4852a are in optical communication with the third reaction vial 260, the light source 4862b and the detector 4852b are in optical communication with the second reaction vial 260, and the light source 4862c and the detector 4852c are in optical communication with the first reaction vial 260. Thus, the sample contained within the first reaction vial can be analyzed with an excitation light having color #3, the sample contained within the second reaction vial can be analyzed with an excitation light having color #2, and the sample contained within the third reaction vial can be analyzed with an excitation light having color #1.

FIG. 75 is a flow chart of a method 100 of detecting nucleic acids in a biological sample according to an embodiment. In particular, the illustrated method is a "one stage target detection" method, which can be performed using any of the cartridges shown and described herein, and any of the instruments shown and described herein. More particularly, the operations of the method 100 described below can be performed in a cartridge without opening the cartridge and/or otherwise exposing the samples, reagents and/or PCR mixture to outside conditions. Similarly stated, the operations of the method 100 described below can be performed in a cartridge without the need for human intervention to transfer the samples and/or reagents. For purposes of the description, the method 100 is described as being performed with the isolation module 7100 and the PCR module 7200 of the cartridge 7001 shown and described above with reference to FIGS. 25-33.

The method includes eluting the nucleic acid from the magnetic capture beads within an elution chamber, 102. This process can occur, for example, within the elution chamber 7190 of the isolation module 7100. More particularly, referring to FIGS. 29-31, an elution buffer can stored within the reagent module 7270*a*, and can be transferred into the elution chamber 7190, as described above, to complete the elution operation. The elution buffer can be any suitable elution buffer described herein and/or that is compatible with nucleic acid amplification (e.g., via PCR and reverse transcription).

The eluted nucleic acid is then transferred from the elution chamber to a PCR chamber, 104. The PCR chamber can be, for example, the PCR vial 7260 shown in FIGS. 29-31. Although elution chamber 7190 and the PCR vial 7260 are shown above as being in different modules and/or housings, in other embodiments, the elution chamber and the PCR chamber can be located within a monolithically constructed housing or structure. As described above, in some embodiments, the PCR chamber can include lyophilized amplification reagents, such that upon transfer of the nucleic acid, the reagents are reconstituted. The eluted nucleic acid is then transferred into the PCR vial 7260 using the transfer mechanism 7235, as described above, or any other suitable mechanism.

The PCR mixture is then thermally cycled and/or heated within the PCR chamber, 106. The PCR mixture can be cycled between any suitable temperature range using the instrument 3002, as shown above. In some embodiments, the PCR mixture can be elevated to a constant temperature to activate the enzymes for amplification.

The amplification reaction is monitored in real time, 108. In some embodiments, the amplification reaction can be monitored by minor groove binders (MGB) with fluorescent tags and/or any other affinity based hybridization interactions) that bind to the product (i.e., the amplicon). The monitoring can be performed using the optical assembly 3800 of the instrument 3002 shown and described above.

Upon completion of the amplification, detection probes (e.g., MGB) can bind to the target amplicons, 110. This provides for an end point detection.

In some embodiments, the method includes performing melt analysis and/or anneal analysis, 112. This operation can be performed to identify or confirm molecular targets of specific or mismatched sequences.

FIG. 76 is a flow chart of a method 200 of detecting nucleic acids in a biological sample according to an embodiment. In particular, the illustrated method is a "two stage target detection" method, which can be performed using any of the cartridges shown and described herein, and any of the instruments shown and described herein. More particularly, the operations of the method 200 described below can be performed in a cartridge without opening the cartridge and/or otherwise exposing the samples, reagents and/or PCR mixture to outside conditions. Similarly stated, the operations of the method 200 described below can be performed in a cartridge without the need for human intervention to transfer the samples and/or reagents. For purposes of the description, the method 200 is described as being performed with the isolation module 6100 and the PCR module 6200 shown and described above with reference to FIGS. 8-24.

The method includes eluting the nucleic acid from the magnetic capture beads within an elution chamber, 202. This process can occur, for example, within the elution chamber 6190 of the isolation module 6100. More particularly, referring to FIGS. 8-10, an elution buffer can stored within the reagent chamber 6213*c*, and can be transferred into the elution chamber, as described above, to complete the elution operation. The elution buffer can be any suitable elution buffer described herein and/or that is compatible with nucleic acid amplification (e.g., via PCR and reverse transcription).

The eluted nucleic acid is then transferred from the elution chamber to a PCR chamber, 204. The PCR chamber can be, for example, the PCR vial 6260 shown in FIG. 8. As described above, in some embodiments, the PCR chamber can include lyophilized amplification reagents, such that upon transfer of the nucleic acid, the reagents are reconstituted. The eluted nucleic acid is then transferred using the transfer mechanism 6235, as described above, or any other suitable mechanism.

The PCR mixture is then thermally cycled and/or heated within the PCR chamber, 206. The PCR mixture can be cycled between any suitable temperature range using the instrument 3002, as shown above. In some embodiments, the PCR mixture can be elevated to a constant temperature to activate the enzymes for amplification.

The amplification reaction is monitored in real time, 208. In some embodiments, the amplification reaction can be monitored by minor groove binders (MGB) with fluorescent tags and/or any other affinity based hybridization interactions) that bind to the product (i.e., the amplicon). The monitoring can be performed using the optical assembly 3800 of the instrument 3002 shown and described above.

Upon completion of the amplification, detection probes (e.g., MGB) can bind to the target amplicons, 210. This provides for an end point detection. The method includes performing melt analysis and/or anneal analysis, 212. This operation can be performed to identify or confirm molecular targets of specific or mismatched sequences. As used herein an MGB can be used per se as a probe, or can be conjugated to another molecule and used as a probe. For example, a MGB in one embodiment is conjugated to the 5'-end of a specific DNA oligonucleotide probe, along with a fluorescent dye. The probe, in this embodiment, comprises a non-fluorescent quencher at the 3'-end. The fluorescence of the 5'-fluorescent dye is quenched when the probe is in solution. However, when the probe binds to its complement, the fluorescence is no longer quenched. Accordingly, the amount of fluorescence generated by the probe is directly proportional to the amount of target generated. These probes can be "multiplexed" in a reaction, by conjugating a different fluorescent dye (i.e., each fluorescent dye will emit a different wavelength of light when excited, or can be excited at a unique wavelength) to each probe.

A second set of probes is then delivered to the PCR chamber, 214. In some embodiments, the second set of probes can include a second set of MGB probes or other general probes formulated to bind to specific or mismatched target sequences that melt (dissociation energy to break the affinity interaction) at a temperature above approximately 70 degrees Celsius. In some embodiments, the second set of MGB probes is formulated to bind to specific or mismatched target sequences that melt at a temperature above approximately 75 degrees Celsius. In other embodiments, the second set of MGB probes is formulated to bind to specific or mismatched target sequences that melt at a temperature above approximately 80 degrees Celsius. In yet other embodiments, the second set of MGB probes is formulated to bind to specific or mismatched target sequences that melt at a temperature above approximately 85 degrees Celsius.

In some embodiments, the second set of probes can be stored within the reagent chamber 6213*b*, and can be transferred into the PCR vial 6260, either directly or via the elution chamber 6190, as described above. In this manner, the second set of probes can be added to the PCR mixture without opening the cartridge or the PCR vial, or otherwise exposing the PCR mixture to contaminants.

The method then includes performing a second melt analysis and/or anneal analysis, 216. This operation can be performed to identify or confirm molecular targets of specific or mismatched sequences.

Figure 77:
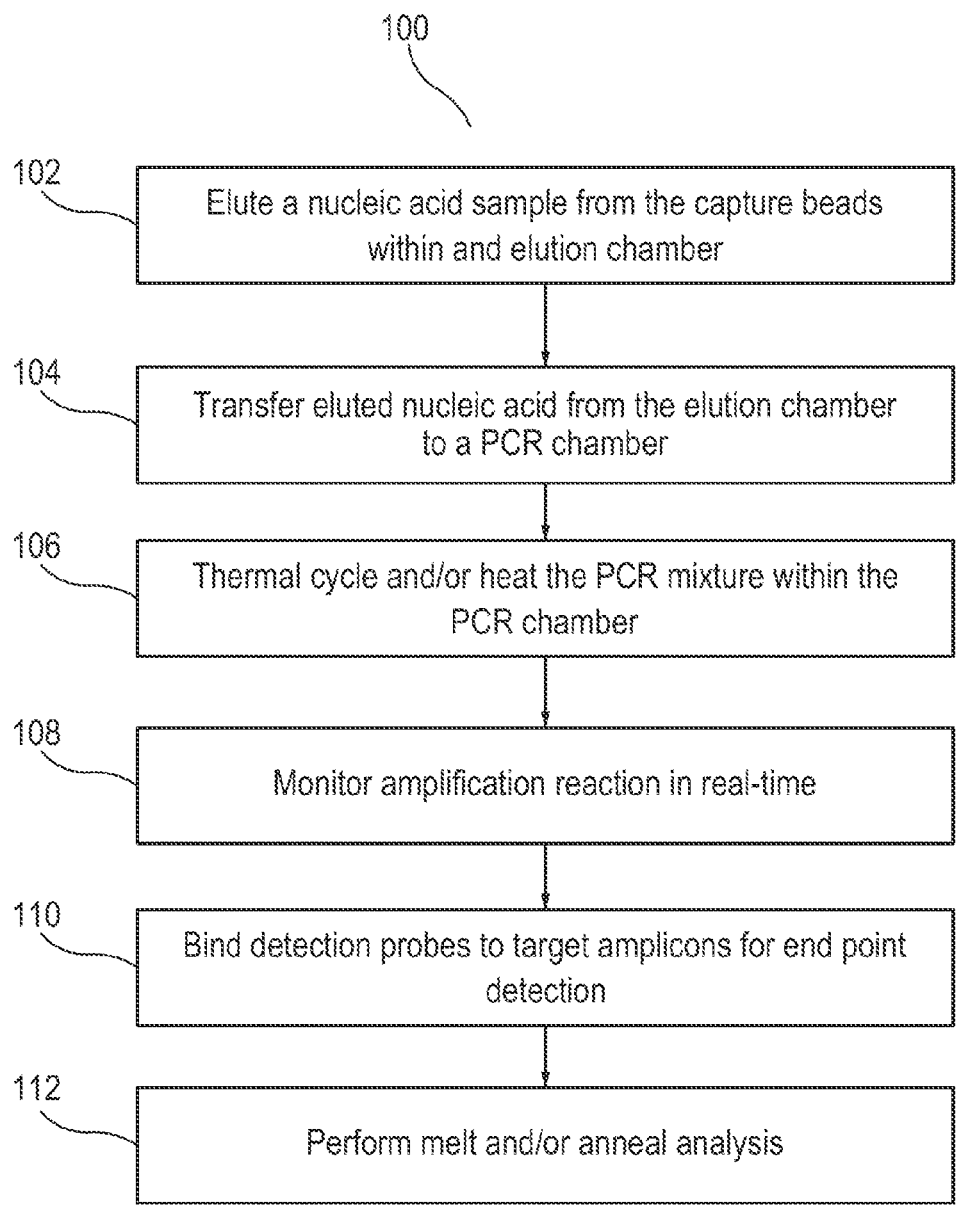
FIGS. 77-80 are flow charts of methods of detecting target analytes in a sample containing a nucleic acid according embodiments.

FIG. 77 is a flow chart of a method 300 of detecting nucleic acids in a biological sample according to an embodiment. In particular, the illustrated method is a "two step reverse transcription PCR (RT-PCR), with a one stage target detection" method, which can be performed using any of the cartridges shown and described herein, and any of the instruments shown and described herein. More particularly, the operations of the method 300 described below can be performed in a cartridge without opening the cartridge and/or otherwise exposing the samples, reagents and/or PCR mixture to outside conditions. Similarly stated, the operations of the method 300 described below can be performed in a cartridge without the need for human intervention to transfer the samples and/or reagents. For purposes of the description, the method 200 is described as being performed with the isolation module 6100 and the PCR module 6200 shown and described above with reference to FIGS. 8-24.

The method includes eluting the nucleic acid from the magnetic capture beads within an elution chamber, 302. This process can occur, for example, within the elution chamber 6190 of the isolation module 600. More particularly, referring to FIGS. 8-10, an elution buffer can stored within the reagent chamber 6213c, and can be transferred into the elution chamber, as described above, to complete the elution operation. The elution buffer can be any suitable elution buffer described herein and/or that is compatible with nucleic acid amplification (e.g., via PCR and reverse transcription).

The eluted nucleic acid is then transferred from the elution chamber to a PCR chamber, 304. The PCR chamber can be, for example, the PCR vial 6260 shown in FIG. 8. As described above, in some embodiments, the PCR chamber can include lyophilized amplification reagents, such that upon transfer of the nucleic acid, the reagents are reconstituted. The eluted nucleic acid is then transferred using a syringe pump, as described above, or any other suitable mechanism.

The mixture is then heated within the PCR chamber to a substantially constant temperature, 306. In this manner, the enzymes for reverse transcription can be activated.

Upon completion of the reverse transcription, the PCR reagents are delivered to the PCR chamber, 308. The PCR reagents can be stored within the reagent chamber 6213b and/or 6213a, and can be transferred into the PCR vial 6260, either directly or via the elution chamber 6190, as described above. In this manner, the PCR reagents can be added to the PCR mixture after completion of the reverse transcription without opening the cartridge or the PCR vial, or otherwise exposing the PCR mixture to contaminants.

The amplification reaction is monitored in real time, 310. In some embodiments, the amplification reaction can be monitored by minor groove binders (MGB) with fluorescent tags and/or any other affinity based hybridization interactions) that bind to the product (i.e., the amplicon). However, any DNA binding agent can be used for real time monitoring a PCR reaction. The monitoring can be performed using the optical assembly 3800 of the instrument 3002 shown and described above.

As used herein, "DNA binding agent" refers to any detectable molecule, e.g., detectable by fluorescence, capable of binding double stranded or single stranded DNA. In one embodiment, the DNA binding agent is a fluorescent dye or other chromophore, enzyme, or agent capable of producing a signal, directly or indirectly, when bound to double-stranded or single stranded DNA. The agent may bind indirectly, i.e., the DNA binding agent may be attached to another agent that binds the DNA directly. It is only necessary that the agent is capable of producing a detectable signal when bound to a double-stranded nucleic acid or single stranded DNA that is distinguishable from the signal produced when that same agent is in solution.

In one embodiment, the DNA binding agent is an intercalating agent. Intercalating agents, such as ethidium bromide and SYBR green, fluoresce more intensely when intercalated into double-stranded DNA than when bound to single-stranded DNA, RNA, or in solution. Other intercalating agents exhibit a change in the fluorescence spectra when bound to double-stranded DNA. For example, actinomycin D fluoresces red when bound to single-stranded nucleic acids, and green when bound to a double-stranded template. Whether the detectable signal increases, decreases or is shifted, as is the case with actinomycin D, any intercalating agent that provides a detectable signal that is distinguishable when the agent is bound to double-stranded DNA or unbound is suitable for practicing the disclosed invention.

In another embodiment, the DNA binding agent is an exonuclease probe that employs fluorescent resonance energy transfer. For example, the DNA binding agent, in one embodiment, is an oligonucleotide probe with a reporter and a quencher dye on the 5' and 3' ends, respectively, and binds specifically to a target nucleic acid molecule. In solution, and when intact, the reporter dye's fluorescence is quenched. However, the exonuclease activity of certain Taq polymerase serves to cut the probe during the PCR, and the reporter is no longer quenched. Therefore, the fluorescence emission is directly proportional to the amount of target generated.

In another embodiment, the DNA binding agent employs a MGB conjugated to the 5' end of an oligonucleotide probe. In addition to the MGB at the 5' end, a reporter dye is also conjugated to the 5' end of the probe, and a quencher dye is positioned at the 3' end. For example, in one embodiment, the DNA probes described by Lukhtanov are employed (Lukhtavon (2007). Nucleic Acids Research 35, p. e30). The MGB, in one embodiment, is conjugated directly to the oligonucleotide probe. In another embodiment, the MGB is conjugated to the reporter dye. The fluorescence of the 5'-fluorescent dye is quenched when the probe is in solution. However, when the probe binds to its complement, the fluorescence is no longer quenched. Accordingly, the amount of fluorescence generated by the probe is directly proportional to the amount of target generated. These probes can be "multiplexed" in a reaction, by conjugating a different fluorescent dye (i.e., each fluorescent dye will emit a different wavelength of light when excited, or can be excited at a unique wavelength) to each probe.

In yet another embodiment, a minor groove binder is used to monitor the PCR reaction in real time. For example, Hoechst 33258 (Searle & Embrey, 1990, Nuc. Acids Res. 18(13):3753-3762) exhibits altered fluorescence with increasing amount of target. Other MGBs for use with the present invention include distamycin and netropsin.

According to the embodiments described herein, a DNA binding agent produces a detectable signal directly or indirectly. The signal is detectable directly, such as by fluorescence or absorbance, or indirectly via a substituted label moiety or binding ligand attached to the DNA binding agent.

According to the embodiments described herein, a DNA binding agent produces a detectable signal directly or indirectly. The signal is detectable directly, such as by fluorescence or absorbance, or indirectly via a substituted label moiety or binding ligand attached to the DNA binding agent. For example, in one embodiment, a DNA probe conjugated to a fluorescent reporter dye is employed. The DNA probe has a quencher dye on the opposite end of the reporter dye, and will only fluoresce when bound to its complementary sequence. In a further embodiment, the DNA probe has both a MGB and a fluorescent dye at the 5' end.

Other non-limiting DNA binding agents for use with the invention include, but are not limited to, Molecular Beacons, Scorpions and FRET probes.

Upon completion of the amplification, detection probes (e.g., MGB) can bind to the target amplicons, 312. This provides for an end point detection. The method includes performing melt analysis and/or anneal analysis, 314. This operation can be performed to identify or confirm molecular targets of specific or mismatched sequences.

Figure 78:
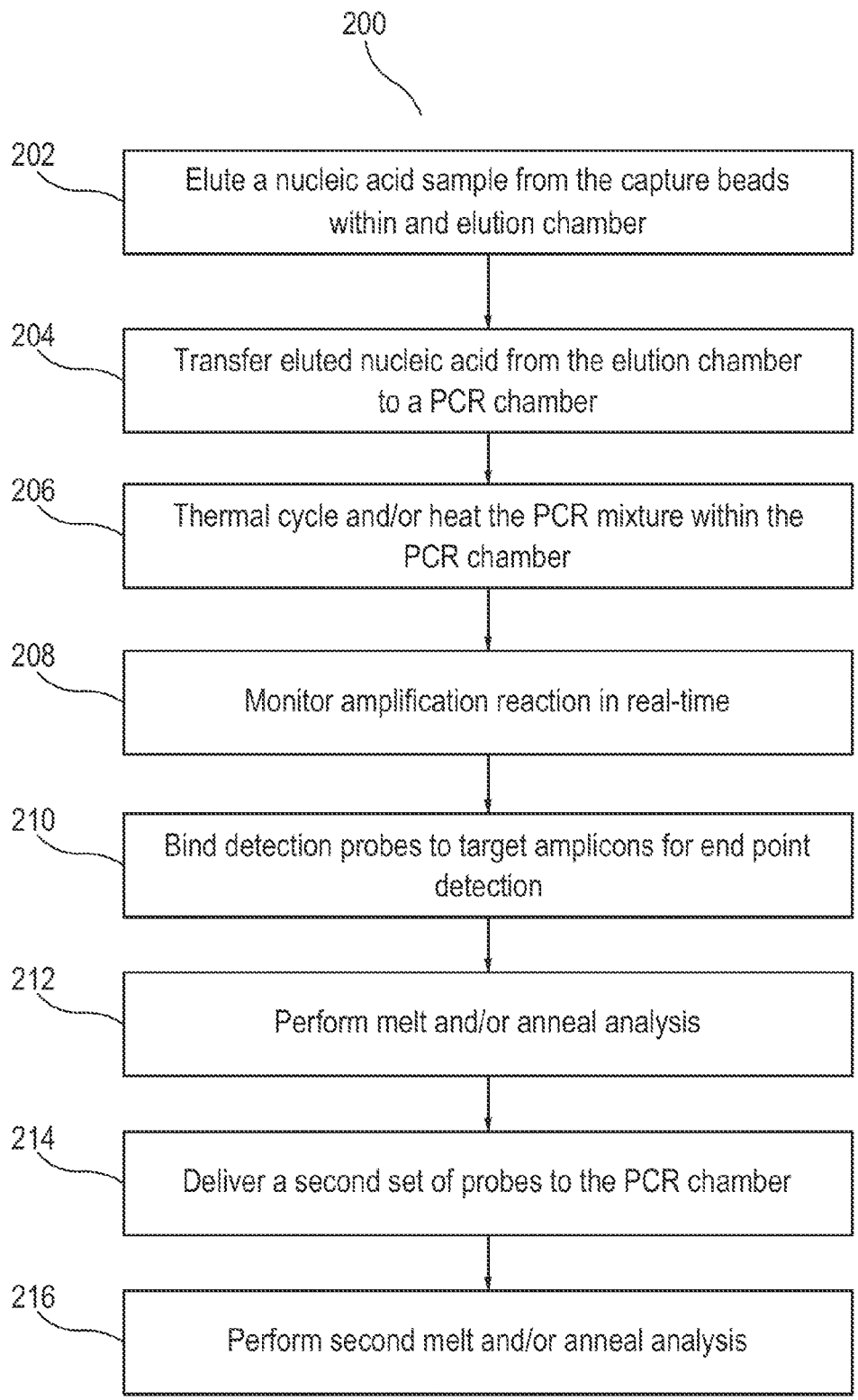
Figure 79:
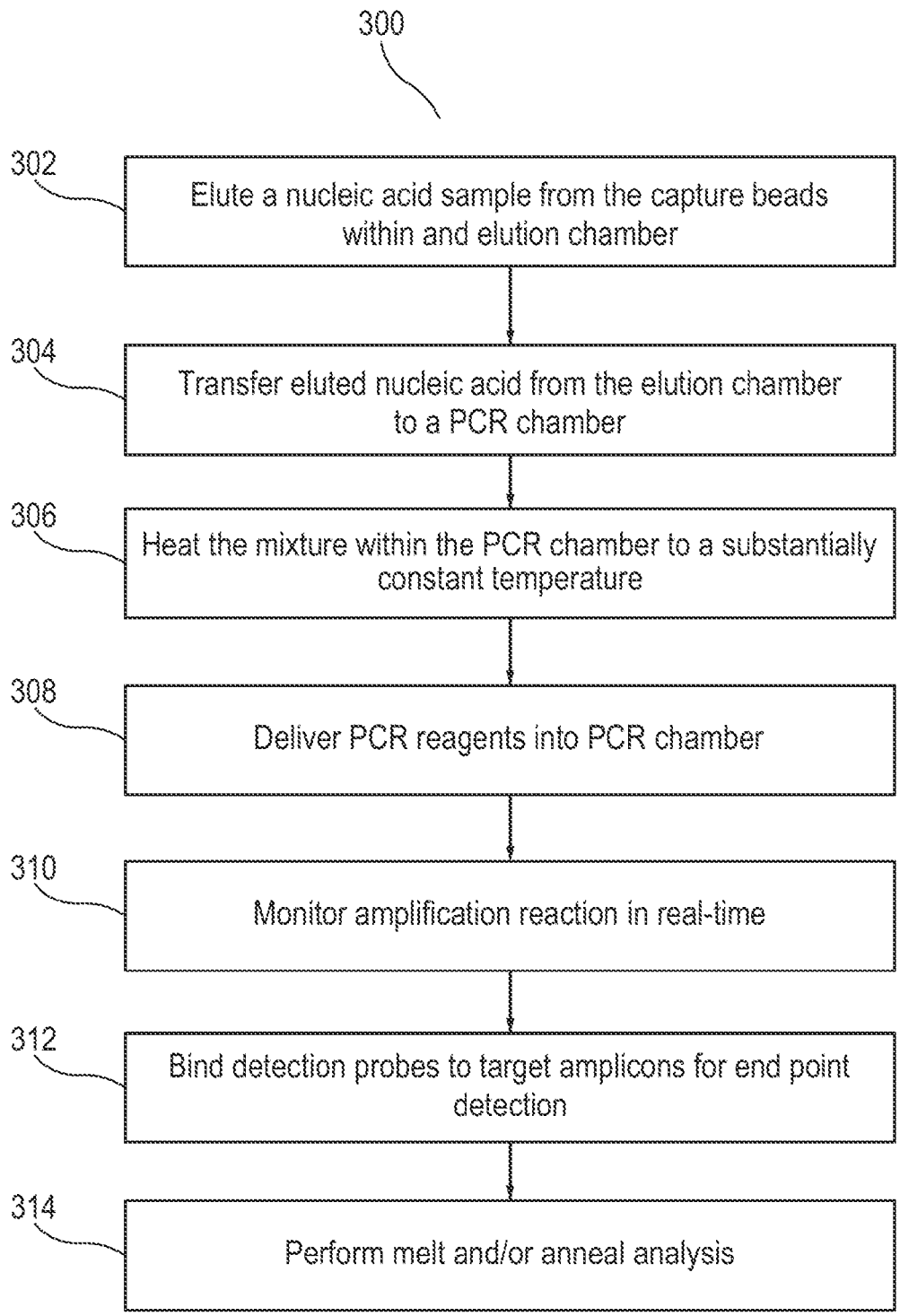
Figure 80:
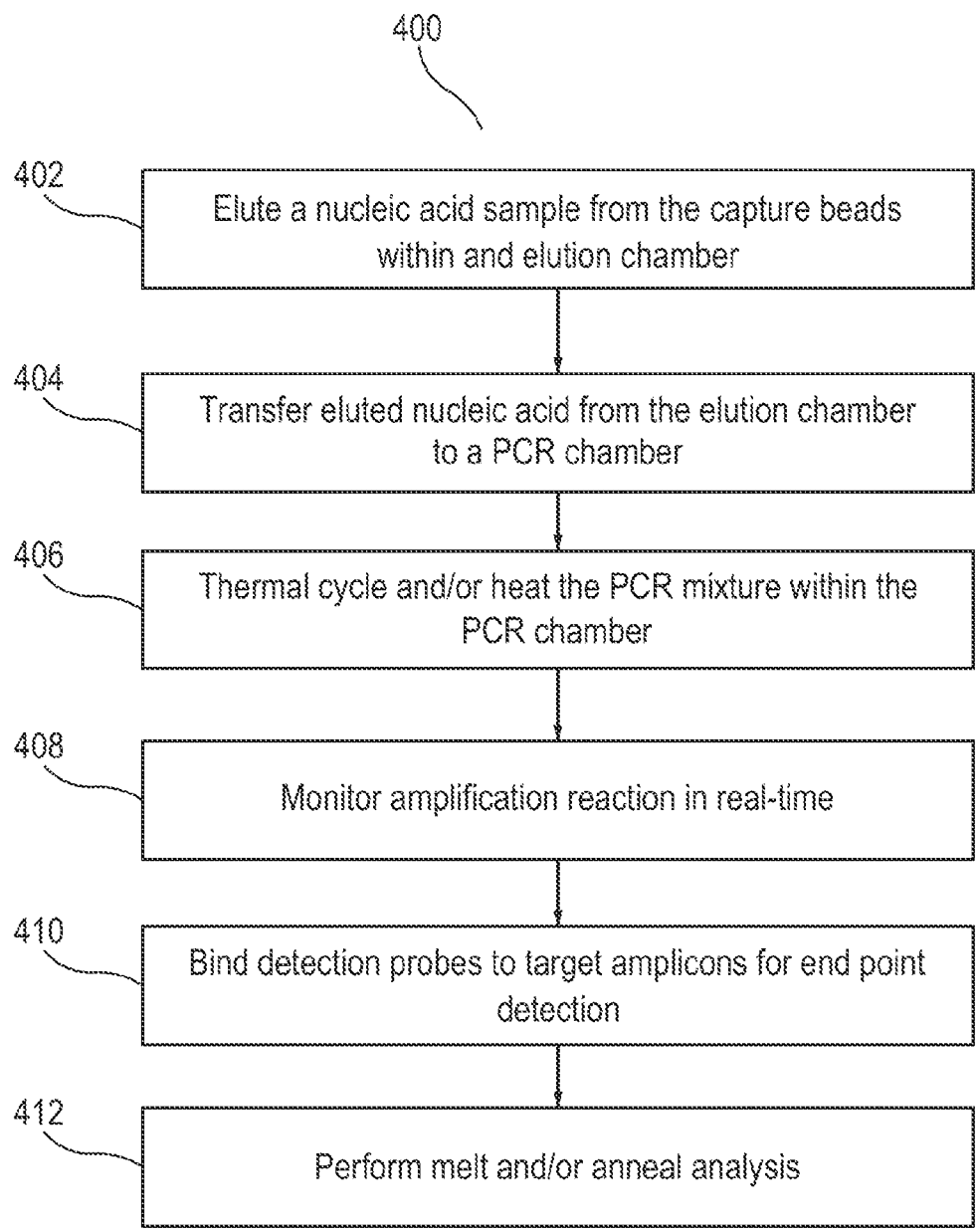

FIG. 78 is a flow chart of a method 400 of detecting nucleic acids in a biological sample according to an embodiment. In particular, the illustrated method is an alternative "one stage target detection" method to the method 100 shown and described above. The method 400 can be performed using any of the cartridges shown and described herein, and any of the instruments shown and described herein. More particularly, the operations of the method 400 described below can be performed in a cartridge without opening the cartridge and/or otherwise exposing the samples, reagents and/or PCR mixture to outside conditions. Similarly stated, the operations of the method 400 described below can be performed in a cartridge without the need for human intervention to transfer the samples and/or reagents. For purposes of the description, the method 400 is described as being performed with the isolation module 10100 and the PCR module 10200 shown and described herein with reference to FIGS. 85-87.

The method 400 differs from the method 100 in that the elution buffer is stored within the elution chamber of the housing, rather than in the reagent chamber 6213c, as described for the method 100. Thus, the method includes eluting the nucleic acid from the magnetic capture beads within an elution chamber, 402. This process occurs within the elution chamber of the isolation module 10100. The elution buffer can be any suitable elution buffer that is compatible with nucleic acid amplification (e.g., via PCR and reverse transcription).

The eluted nucleic acid is then transferred from the elution chamber to a PCR chamber, 404. The PCR chamber can be, for example, the PCR vial 10260 shown in FIGS. 85-87. Although elution chamber 10190 and the PCR vial 10260 are shown as being in different modules and/or housings, in other embodiments, the elution chamber and the PCR chamber can be located within a monolithically constructed housing or structure. As described above, in some embodiments, the PCR chamber can include lyophilized amplification reagents, such that upon transfer of the nucleic acid, the reagents are reconstituted. The eluted nucleic acid is then transferred using a syringe pump, as described above, or any other suitable mechanism.

The PCR mixture is then thermally cycled and/or heated within the PCR chamber, 406. The PCR mixture can be cycled between any suitable temperature range using the instrument 3002, as shown above. In some embodiments, the PCR mixture can be elevated to a constant temperature to activate the enzymes for amplification.

The amplification reaction is monitored in real time, 408. In some embodiments, the amplification reaction can be monitored by minor groove binders (MGB) with fluorescent tags and/or any other affinity based hybridization interactions) that bind to the product (i.e., the amplicon). The monitoring can be performed using the optical assembly 3800 of the instrument 3002 shown and described above.

Upon completion of the amplification, detection probes (e.g., MGB) can bind to the target amplicons, 410. This provides for an end point detection. In some embodiments, the method includes performing melt analysis and/or anneal analysis, 412. This operation can be performed to identify or confirm molecular targets of specific or mismatched sequences.

Figure 81:
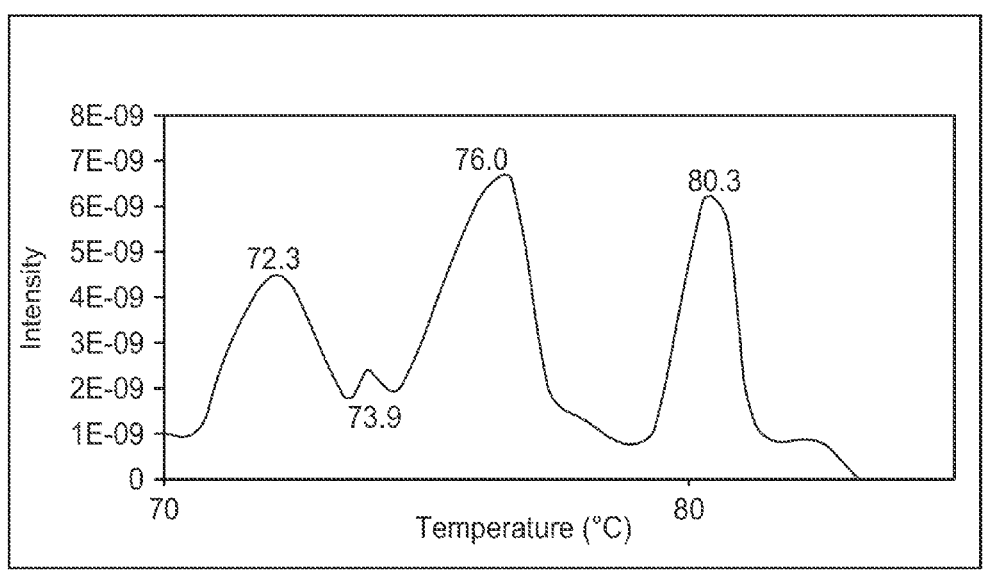
FIG. 81 is a molecular signature produced by using the systems and methods according to an embodiment.

The data produced using the systems and methods described herein can be analyzed using any number of different methods. For example, the data can be analyzed for sequence identification of amplified nucleic acids via melt or anneal analysis using affinity probes. Melt/Anneal Profiling-Molecular Profiling with unique "affinity probes" or molecular tags (consist of modified bases and MGB-fluor with affinity directed binding to target nucleic acid-affinity constant-Kd) indicates/generates spectra of a specific genetic state(s). For example, FIG. 81 is a plot of a spectrum indicating a molecular signature generated from a set of probes binding to an amplified nucleic acid originating from a biological sample. The molecular signature represents a diseased state (or presence of unique nucleic acid sequences) relating back to the biological sample. The molecular signature or profile is dependent on the specific interaction of the molecular tags to the target nucleic acid that can only be generated with the molecular tags inside the cartridge. In other words, the spectrum is a fingerprint trace (i.e., a unique sequence of peaks or "spectral responses" that indicate a diseased state(s) (oncology, infectious disease) or genetic state).

Multiplexing within a spectrum-more than one diseased state-(Multiple Markers)-Multiplexing with temperature and time (within a specific wavelength), with unique "probes" or multi-probes (unique molecular entities-molecular reactants, indicators, tags).

Multichannel Approach: More than one fingerprint trace (sets of fingerprints) can be used in the identification process. Multi-panel fingerprint-Spectral Array of fingerprints can be used to determine result. Variables to generate the multi channel or array data are Wavelength difference fluorescence used, temperature ranges for annealing or dissociation (melting), and data acquisition rate (time dependent domain).

Control of heating and cooling of affinity probes and amplified target can be used yield the fingerprint desired identify the diseased. The temperature range can be within the range of 70-100 degrees Celsius for the data generation (annealing and melt)

Although the isolation module 6001 above is shown as including an isolation module 6100 with a mixing pump 6181 for facilitating the lysing process, in other embodiments, any suitable mechanism for transferring energy into a solution to promote and/or enhance cell lysing can be used. For example, in some embodiments, can use acoustic energy.

Figure 82:
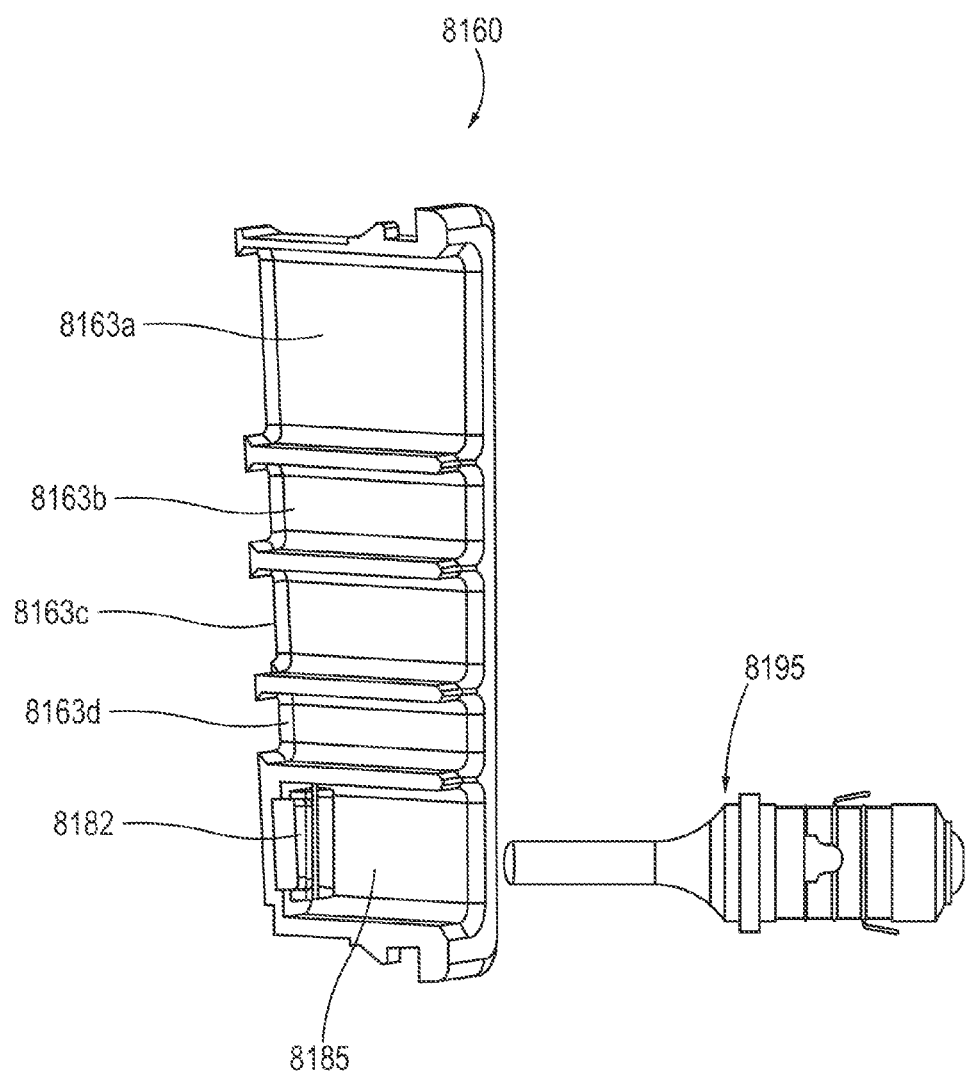
FIG. 82 is a cross-sectional perspective view of a portion of an isolation module according to an embodiment that is configured to receive acoustic energy.

For example, FIG. 82 shows a second housing 8160 of an isolation module according to an embodiment configured to transmit ultrasonic energy into the sample contained within an isolation chamber (not shown) of the isolation module (e.g., the isolation module 6100, the isolation module 7100 or the like) to promote cell lysis and/or isolation of the nucleic acids contained therein. The second housing 8160 can be coupled to and/or disposed within a corresponding first housing (not shown in FIG. 82), in a similar manner to that described above with reference to FIG. 11. More particularly, the second housing 8160 includes a seal (not shown) similar to the seal 6172 shown and described above that substantially acoustically isolates the second housing 8160 from the first housing.

The second housing 8160 defines a series of holding chambers 8163a, 8163b, 8163c and 8163d that contain the reagents and/or other substances used in the isolation process. In particular, the holding chambers can contain a protease (e.g., Proteinase K), a lysis solution to solubilize the bulk material, a binding solution to magnetically charge the nucleic acid, and a solution of magnetic beads that bind to the magnetically charged nucleic acid to assist in the transportation of the nucleic acid within the isolation module and/or the first housing.

The second housing 8160 also defines an opening 8185 within which a portion of an ultrasonic transducer 8195 can be disposed. An acoustic coupling member 8182 is coupled to a portion of the side wall of the second housing 8160 within the opening 8185. Accordingly, in use at least a portion of an acoustic transducer 8195 can be disposed within the opening 8185 and in contact with the acoustic coupling member 8182. In this manner, the acoustic and/or ultrasonic energy produced by the transducer 8195 can be conveyed through the acoustic coupling member 8182 and the side wall of the second housing 8160, and into the solution within the isolation chamber. The acoustic transducer 8195 can be any suitable acoustic transducer, and can be configured to resonate between 20 kHz and 300 kHz.

The ultrasonic transducer 8195 can be moved into the opening 8185 by an actuator of an instrument, such as, instrument 3002 described herein. Such an actuator can include, for example, a stepper-motor configured to move the ultrasonic transducer 8195 by a predetermined distance into contact with the acoustic coupling member 8182. In some embodiments, for example, an instrument can include an actuator assembly that is similar to the first actuator assembly 3400 shown and described above with reference to FIGS. 37-40. In such an embodiment, the first actuator assembly can include a series of ultrasonic transducers that are moved into the opening via an engagement bar similar to the engagement bar 3445.

In some embodiments, the actuator can be configured to vary the force exerted by the ultrasonic transducer 8195 on the acoustic coupling member 8182. This can be accomplished, for example, by moving the ultrasonic transducer 8195 relative to the coupling member 8182 while the ultrasonic transducer is being actuated. This arrangement can allow the transmission of ultrasonic energy through the acoustic coupling member 8182 and/or the heat generated by the transmission of ultrasonic energy through the acoustic coupling member 8182 to be dynamically adjusted.

In some embodiments, the acoustic coupling member 8182 is constructed from a thermally-insulative material. In this manner, transfer of heat from the acoustic coupling member 8182 to the adjacent side wall of the second housing 8160 can be minimized. This arrangement can minimize and/or prevent deformation and/or melting of the side wall of the second housing 8160 when the acoustic transducer 8195 is actuated when in contact with the side wall. Additionally, in some embodiments, the acoustic coupling member 8182 can be configured and/or constructed to have an acoustic impedance to promote the transfer of ultrasonic energy through the acoustic coupling member 8182 and into the isolation chamber.

Figure 83:
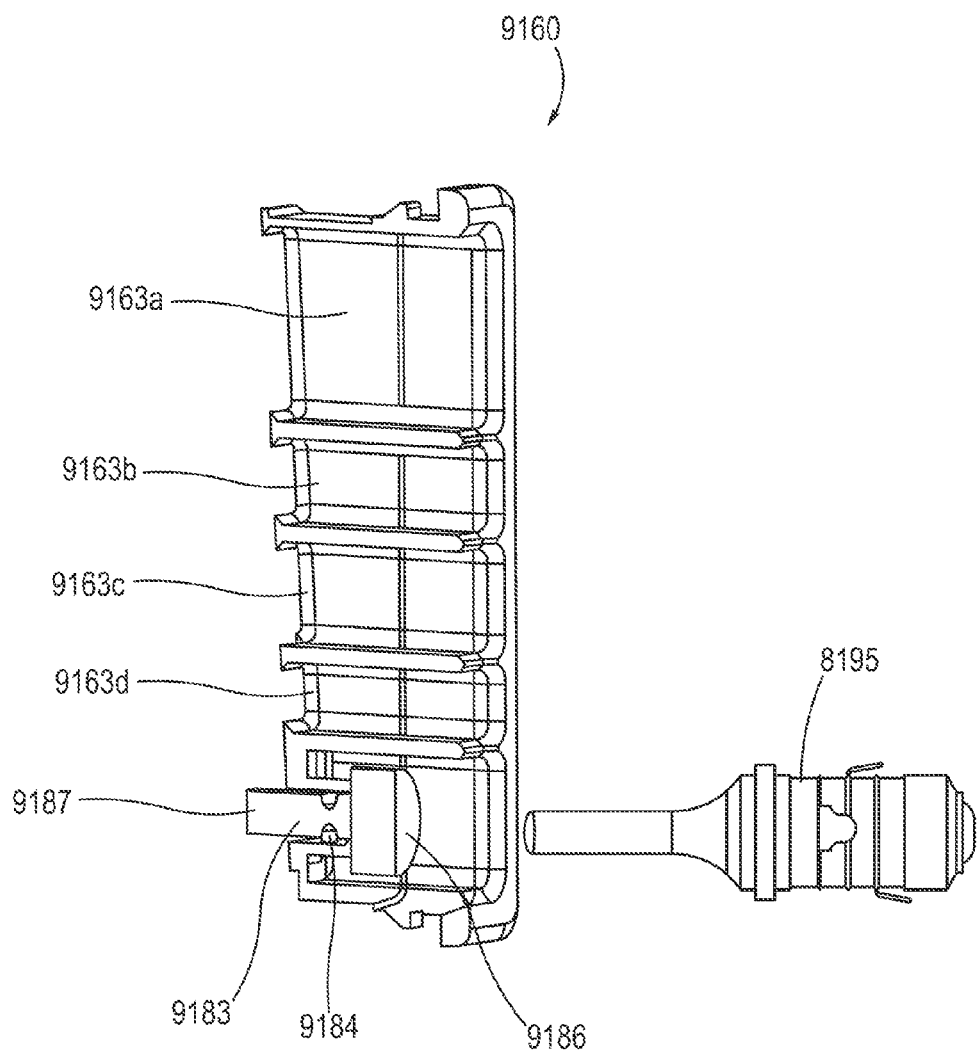
FIG. 83 is a cross-sectional perspective view of a portion of an isolation module according to an embodiment that is configured to receive acoustic energy.

FIG. 83 shows a second housing 9160 of an isolation module according to an embodiment configured to transmit ultrasonic energy into the sample contained within an isolation chamber (not shown) of the isolation module to promote cell lysis and/or isolation of the nucleic acids contained therein. The second housing 9160 can be coupled to and/or disposed within a corresponding first housing (not shown in FIG. 83), in a similar manner as described above. More particularly, the second housing 9160 includes a seal (not shown) similar to the seal 6172 shown and described above that substantially acoustically isolates the second housing 9160 from the first housing.

The second housing 9160 defines a series of holding chambers 9163a, 9163b, 9163c and 9163d that contain the reagents and/or other substances used in the isolation process. The second housing 9160 also defines an opening 9185 within which a portion of an ultrasonic transducer 9195 can be disposed. In contrast to the opening 8185 described above, the opening 9185 is can be in fluid communication with the isolation chamber via an opening in the side wall of the second housing 9160.

An acoustic coupling member 9183 is disposed within the opening 9185 and through a portion of the side wall of the second housing 9160. More particularly, the acoustic coupling member 9183 is coupled to the side wall such that a first portion 9186 of the acoustic coupling member 9183 is within the opening 9185 and a second portion 9187 of the acoustic coupling member 9183 is within the isolation chamber. A seal 9184 is disposed between the side wall of the second housing 9160 and the acoustic coupling member 9183 to substantially fluidically isolate the isolation chamber and/or substantially acoustically isolate the acoustic coupling member 9183 from the second housing.

In use at least a portion of an acoustic transducer 8195 can be disposed within the opening 9185 and in contact with the first portion 9186 of the acoustic coupling member 9183. In this manner, the acoustic and/or ultrasonic energy produced by the transducer 9195 can be conveyed through the acoustic coupling member 9183 into the solution within the isolation chamber.

The ultrasonic transducer 8195 can be moved into the opening 9185 by an actuator of an instrument, such as, instrument 3002 described herein. Such an actuator can include, for example, a stepper-motor configured to move the ultrasonic transducer 9195 by a predetermined distance into contact with the acoustic coupling member 9183. In some embodiments, for example, an instrument can include an actuator assembly that is similar to the first actuator assembly 3400 shown and described above with reference to FIGS. 37-40. In such an embodiment, the first actuator assembly can include a series of ultrasonic transducers that are moved into the opening via an engagement bar similar to the engagement bar 3445.

In some embodiments, the actuator can be configured to vary the force exerted by the ultrasonic transducer 5195 on the acoustic coupling member 5183. This can be accomplished, for example, by moving the ultrasonic transducer 8195 relative to the coupling member 9183 while the ultrasonic transducer is being actuated. This arrangement can allow the transmission of ultrasonic energy through the acoustic coupling member 9183 and/or the heat generated by the transmission of ultrasonic energy through the acoustic coupling member 9183 to be dynamically adjusted.

As described above, in some embodiments, the acoustic coupling member 5183 can be configured to have an acoustic impedance to promote the transfer of ultrasonic energy through the acoustic coupling member 9183 and into the isolation chamber.

Figure 84:
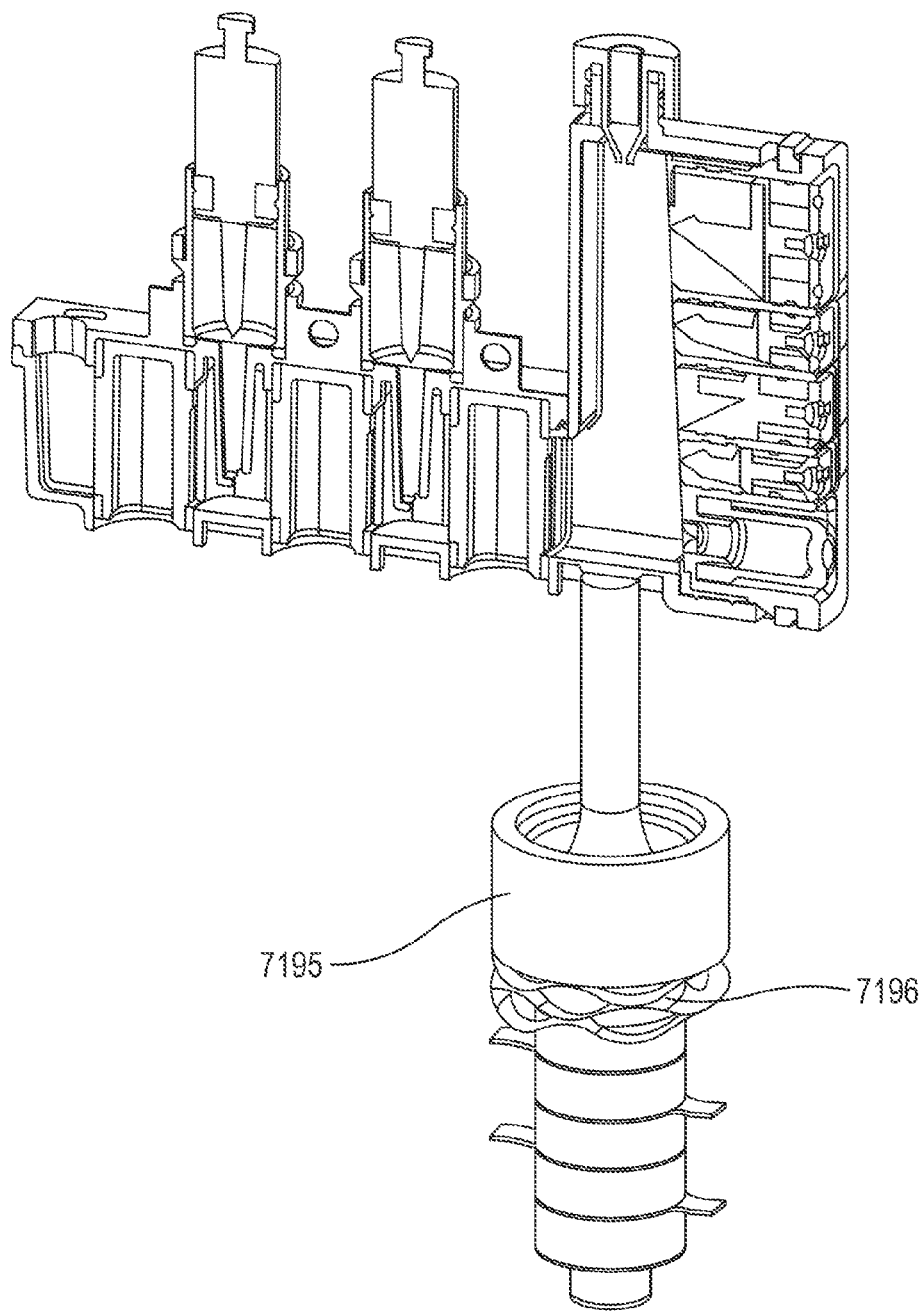
FIG. 84 is a cross-sectional perspective view of a portion of the cartridge shown in FIG. 26 and an acoustic transducer.

Although FIGS. 82 and 83 show the second housing of an isolation module configured to transmit ultrasonic energy into the sample contained within the isolation module, in other embodiments, any portion of a cartridge can be configured to transmit ultrasonic energy into the sample. For example, FIG. 84 shows the isolation module 7100 (see e.g., FIGS. 26-28) and an ultrasonic transducer 7195. In particular, as described above, the housing 7110 includes an acoustic coupling portion 7182. In use, at least a portion of the acoustic transducer 7195 can be disposed in contact with the acoustic coupling portion 7182. In this manner, the acoustic and/or ultrasonic energy produced by the transducer can be conveyed through the acoustic coupling portion 7182 and the side wall of the first housing 7110, and into the solution within the lysing chamber 7114.

The ultrasonic transducer 7195 can be moved into contact with the acoustic coupling portion 7182 by an actuator of an instrument, such as, instrument 3002 described herein. Such an actuator can include, for example, a stepper-motor configured to move the ultrasonic transducer 7195 by a predetermined distance into contact with the acoustic coupling portion 7182. In some embodiments, for example, an instrument can include an actuator assembly that is similar to the first actuator assembly 3400 shown and described above with reference to FIGS. 37-40. In such an embodiment, the first actuator assembly can include a series of ultrasonic transducers that are moved into contact with the acoustic coupling portion 7182 via an engagement bar similar to the engagement bar 3445.

In some embodiments, the actuator can be configured to vary the force exerted by the ultrasonic transducer 7195 on the acoustic coupling portion 7182. This can be accomplished, for example, by moving the ultrasonic transducer 7195 relative to the acoustic coupling portion 7182 while the ultrasonic transducer is being actuated. This arrangement can allow the transmission of ultrasonic energy through the acoustic coupling portion 7182 and/or the heat generated by the transmission of ultrasonic energy through the acoustic coupling portion 7182 to be dynamically adjusted. As shown in FIG. 83, the ultrasonic transducer 7195 can include a spring 7196 or other biasing member configured to maintain and/or bias the ultrasonic transducer relative to the actuator assembly of the instrument.

Figure 85:
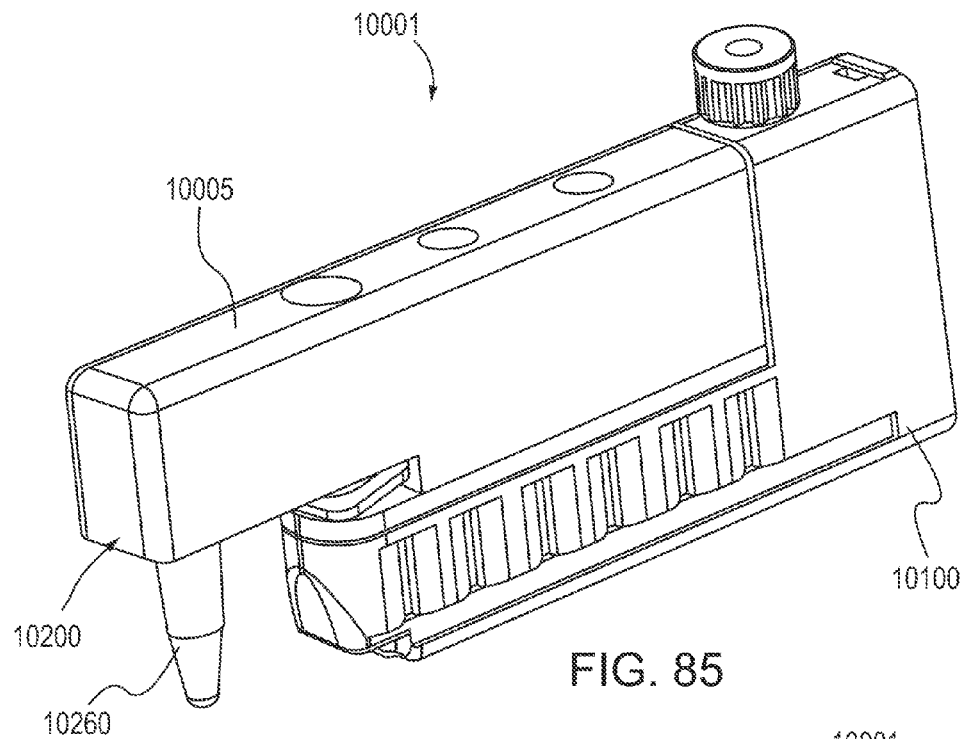
FIG. 85 is a perspective view of a cartridge according to an embodiment.
Figure 86:
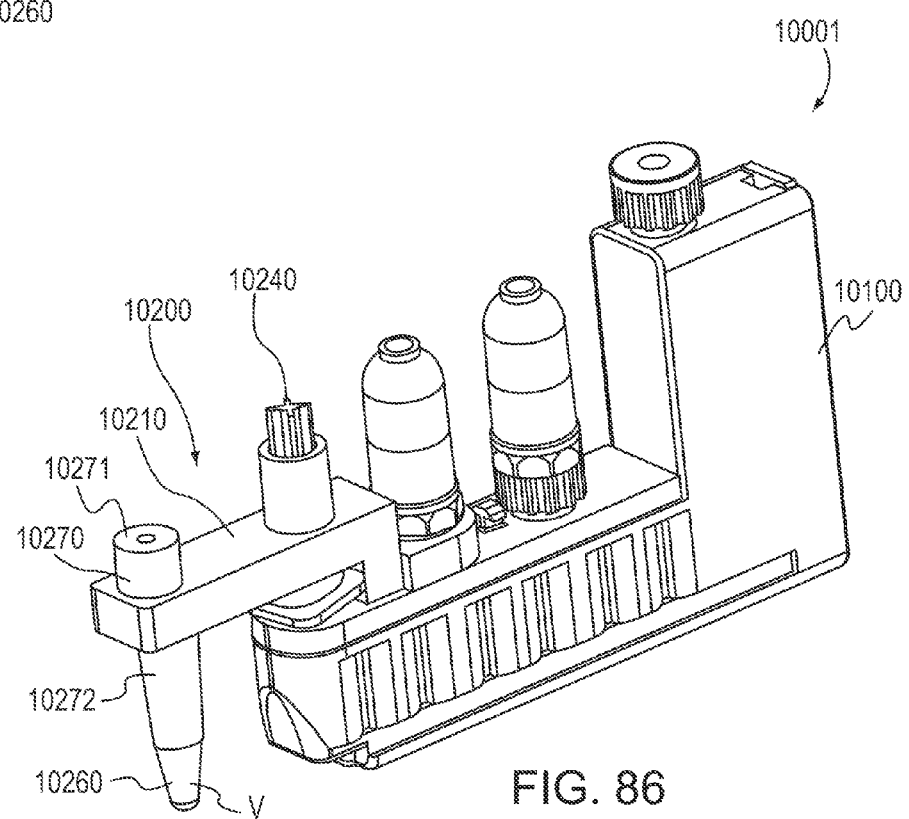
FIG. 86 is a perspective view of the cartridge shown in FIG. 85 without the cover.
Figure 87:
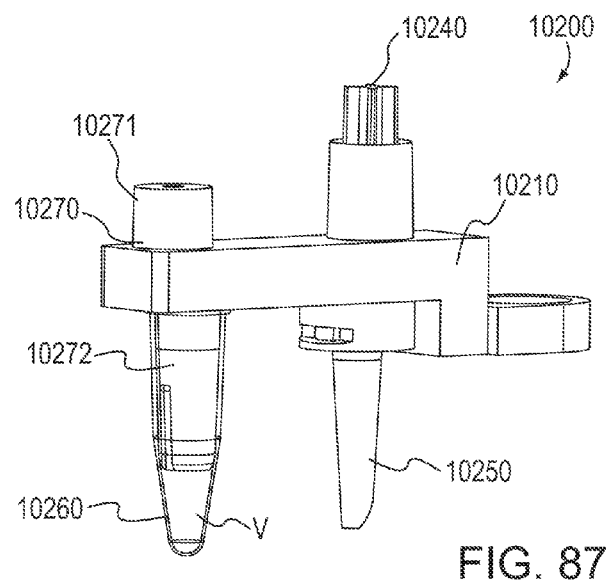
FIG. 87 is a perspective view of a PCR module of the cartridge shown in FIG. 85.

Although the PCR module 6200 is shown and described above as including three reagent chambers 6213*a*, 6213*b* and 1213*c* in which PCR reagents, elution buffers and the like can be stored, in other embodiments, a PCR module can include any number of reagent chambers. In some embodiments, a PCR module can be devoid of any reagent chambers. For example, FIGS. 85-87 show a cartridge 10001 according to an embodiment. The cartridge 10001 includes a nucleic acid isolation module 10100 and an amplification (or PCR) module 10200 coupled together to form the integrated cartridge 10001. The integrated cartridge 10001 is similar in many respects to the cartridge 6001 and/or the cartridge 7001 shown and described above and is therefore not described in detail herein. As shown in FIG. 86, which shows the cartridge without the cover 10005, the PCR module 10200 includes a housing 10210, a PCR vial 10260 and a transfer tube 10250. The amplification module 10200 is coupled to the isolation module 10100 such that at least a portion of the transfer tube is disposed within the elution chamber of the isolation module 10100.

The housing 10210 includes a transfer port 10270. The transfer port 10270 defines one or more lumens and/or passageways through which the isolated nucleic acid and/or other substances or reagents can be conveyed into the PCR vial 10260. The housing 10210 and/or the transfer port 10270 can define one or more vent passageways to fluidically couple the elution chamber and/or the PCR vial 10260 to atmosphere. In some embodiments, any of such vents can include a frit, valve and/or other suitable mechanism to minimize and/or prevent loss of the sample and/or the reagents from the elution chamber and/or the PCR vial 10260.

A first end portion 10271 of the transfer port 10270 is disposed outside of the PCR vial 10260, and a second end portion 10272 of the transfer port 10270 is disposed within the PCR vial. More particularly, the second end portion 10272 is disposed within the PCR vial 10260 such that the volume V of the PCR vial 10260 within which the sample can be disposed is not greater than a predetermined magnitude. In this manner, because there is limited "head space" above the sample within the PCR vial 10260, condensation that can form on the wall of the PCR vial 10260 during the thermal cycling can be minimized and/or eliminated.

The PCR module 10200 includes a transfer piston 10240 configured to produce a pressure and/or a vacuum within the elution chamber and/or the PCR vial 10260 to transfer at least a portion of the sample and/or the reagents within the elution chamber to the PCR vial 10260, as described above.

The elution buffer used with the cartridge 10001 is stored in the elution chamber (not shown in FIGS. 85-87) of the isolation module 10100. The PCR reagents are stored in the PCR vial 10260 in a lyophilized form, as described above. In use, the isolated nucleic acid is eluted from the capture beads in the elution chamber. The eluted nucleic acid is then transferred into the PCR vial 10260, as described above, and is mixed with the PCR reagents within the PCR vial 10260.

Figure 88:
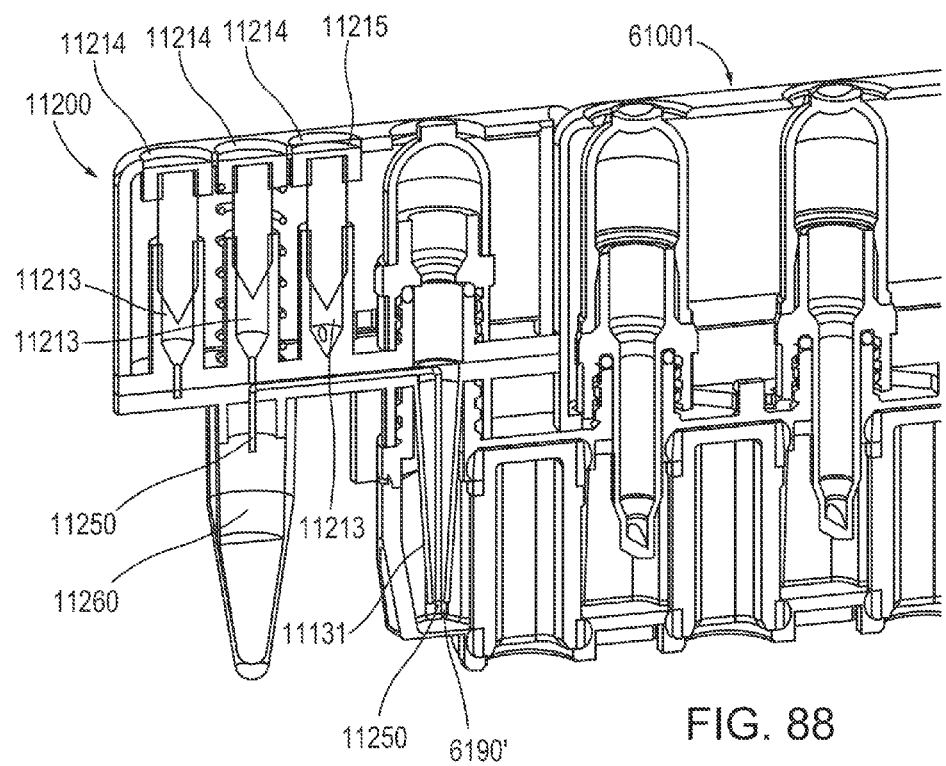
FIG. 88 is a cross-sectional view of a PCR module according to an embodiment.

Although the PCR module 6200 is shown and described as including three reagent chambers 6213*a*, 6213*b* and 6213*c* that are disposed adjacent the first end portion 6211 of the housing 6210 (see e.g., FIG. 8), in other embodiments, a PCR module can include any number of reagent chambers or modules disposed in any position and/or orientation. Moreover, in some embodiments, the reagent plungers (e.g., the plunger 6214*a*) and/or any of the transfer mechanisms described herein can be biased. For example, FIG. 88 is a cross-sectional view of a PCR module 11200 coupled to an isolation module 6100'. The PCR module 11200 includes a housing 11210 that defines three reagent chambers 11213, within which substances and/or reagents of the types described herein can be stored. A plunger 11214 and a spring 11215 (only one is shown and labeled in FIG. 88) are disposed within each of the reagent chambers 11213. In this manner, the plunger (or transfer mechanism) is biased in the non-actuated position. In other embodiments, however, the plunger can be biased in an actuated position and can be held in place by a lock tab or the like. In this manner, actuation of the plunger can be assisted by the spring force.

The PCR module also includes a mixing mechanism (or transfer mechanism) 11130 that is in fluid communication with the elution chamber 6190' via a nozzle 11131. A pipette tube 11250 places the elution chamber 6190 in fluid communication with the PCR vial 11260.

Figure 89:
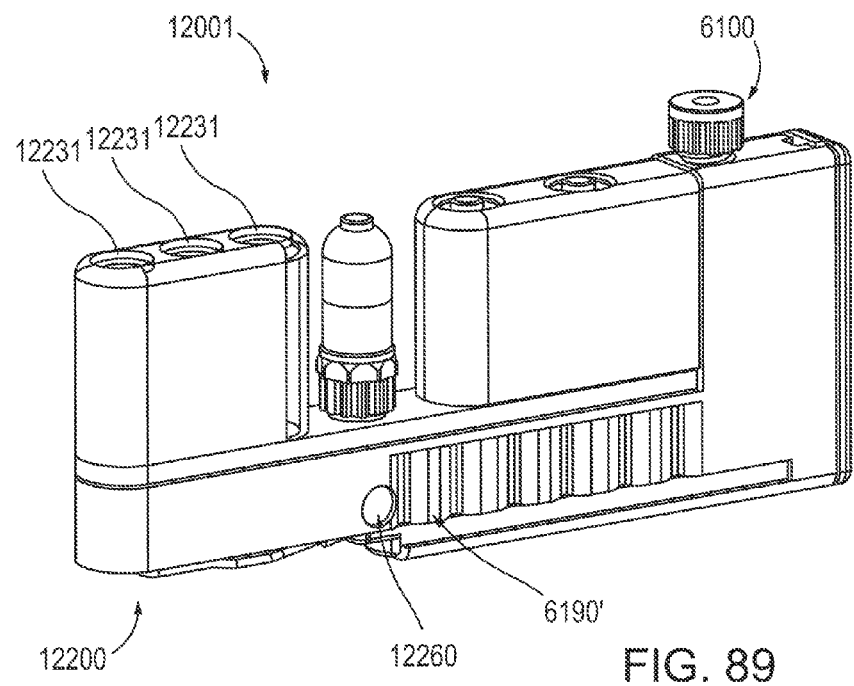
FIG. 89 is a perspective view of a cartridge according to an embodiment.

In some embodiments, a PCR module can include a PCR vial or reaction chamber that is disposed adjacent an elution chamber of an isolation module. For example, FIG. 89 shows a cartridge 12001 having the isolation module 6100' coupled to a PCR module 12200. The PCR module 12200 includes a PCR chamber 12260 that is adjacent the elution chamber 6190'. Similarly stated, when the PCR module 12200 is coupled to the isolation module 6100', the PCR vial 12260 is disposed between the PCR reagent chambers 12231 and the isolation module 6100'.

Figure 90:
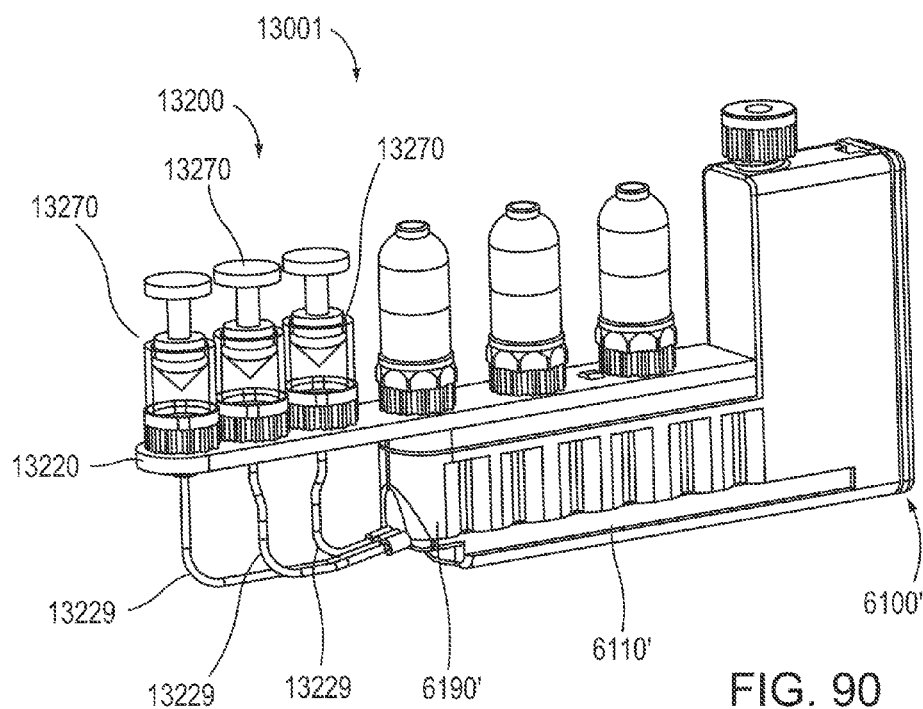
FIG. 90 is a perspective view of a cartridge according to an embodiment.

Although the cartridges shown and described herein include an isolation module include an elution chamber (e.g., the elution chamber 7190) coupled to a PCR module such that in use, a portion of an isolated sample is transferred into a PCR vial (e.g., PCR vial 7260), in other embodiments, a PCR module need not include a PCR vial. For example, in some embodiments, a cartridge can include an elution chamber that is also configured to be the reaction volume in which a PCR can take place. For example, FIG. 90 shows a cartridge 13001 according to an embodiment that includes an isolation module 6100' and a PCR module 13200. The PCR module 13200 includes a substrate 13220 and a series of reagent modules 13270. In use the reagent modules 13270 are configured to transfer one or more reagents and/or substances of the types shown and described herein into the elution chamber 6190' of the isolation module 6100' via the flow tubes 13229. In this manner, the PCR can occur in the elution chamber 6190'. In such embodiments, an instrument similar to the instrument 3002 can be configured to thermally cycle the elution chamber 6190' to facilitate the PCR. Moreover, the instrument can include an optics assembly configured to optically monitor the reaction within the elution chamber 6190'. In some embodiments, the housing 6110' can include an excitation optical member (not shown) and/or a detection optical member (not shown) disposed therein in a position adjacent the elution chamber 6190'.

Figure 91:
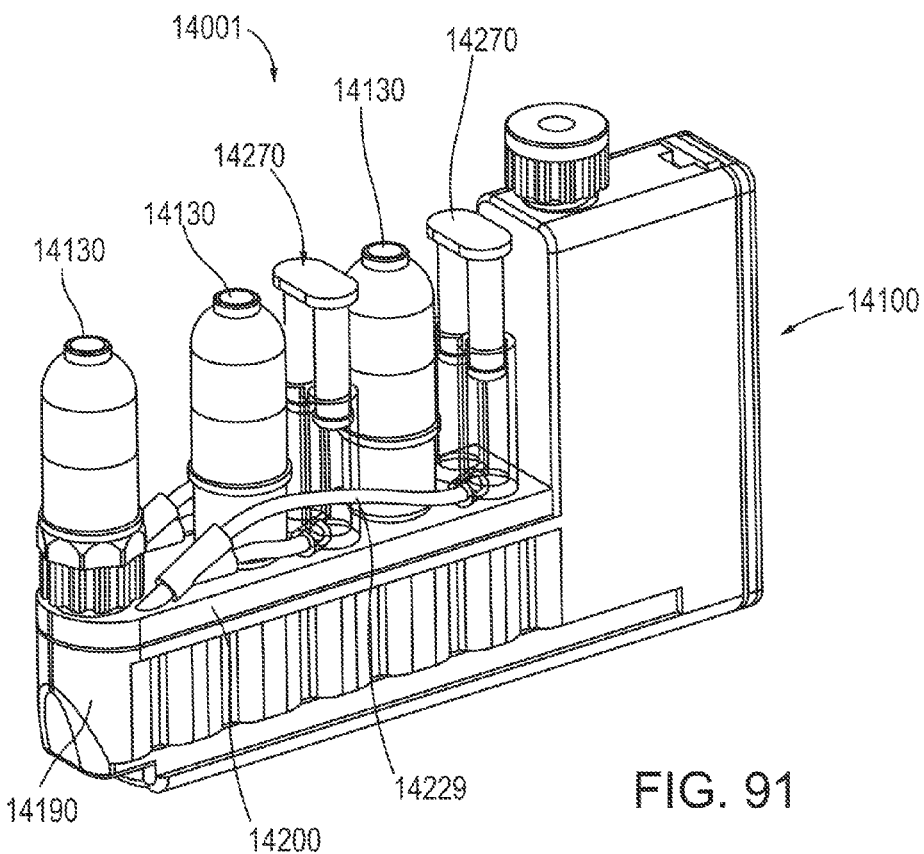
FIG. 91 is a perspective view of a cartridge according to an embodiment.

Although the cartridges shown and described herein generally include a PCR module that is coupled in series with an isolation module, in other embodiments, a cartridge can include a PCR module coupled to an isolation module in any orientation, position and/or location. Similarly stated, although the cartridges are shown and described herein as including a PCR module that is coupled to an end portion of an isolation module, in other embodiments a PCR module can be integrated with and/or coupled to an isolation module in any manner. For example, FIG. 91 shows a cartridge 14001 that includes an isolation module 14100 and a PCR module 14200. The isolation module 14100 includes a series of washing mechanisms 14130, similar to those described above. The PCR module includes a series of reagent modules 14270. The reagent modules 14270 are disposed adjacent to and/or between the washing mechanisms 14130.

In use the reagent modules 14270 are configured to transfer one or more reagents and/or substances of the types shown and described herein into the elution chamber 14190 of the isolation module 14100 via the flow tubes 14229. In this manner, the PCR can occur in the elution chamber 14190.

Figure 92:
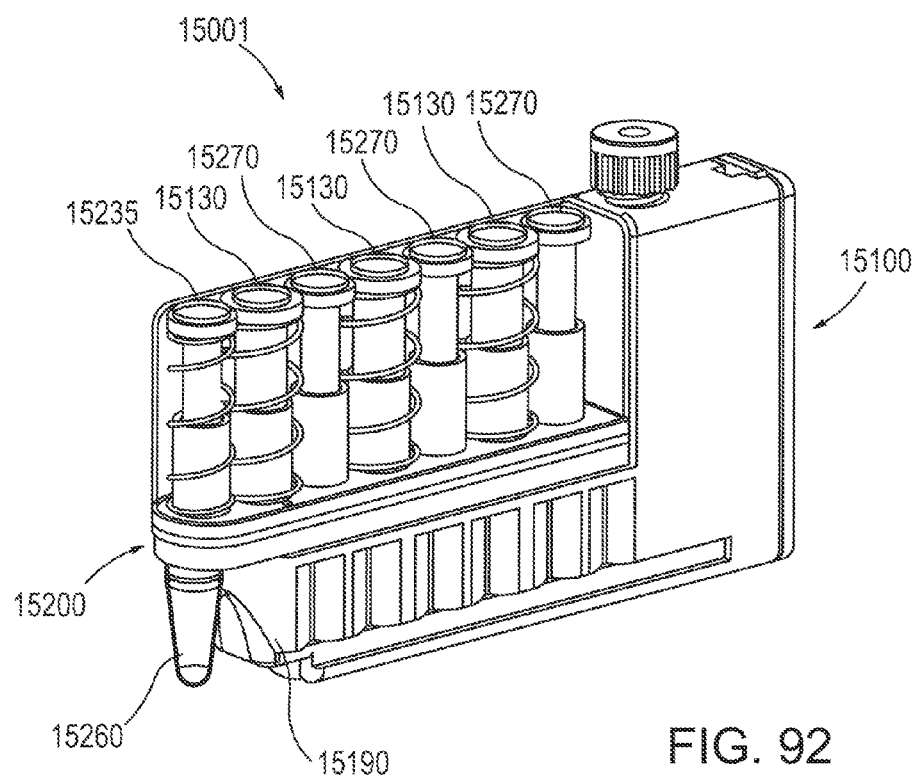
FIG. 92 is a perspective view of a cartridge according to an embodiment.
Figure 93:
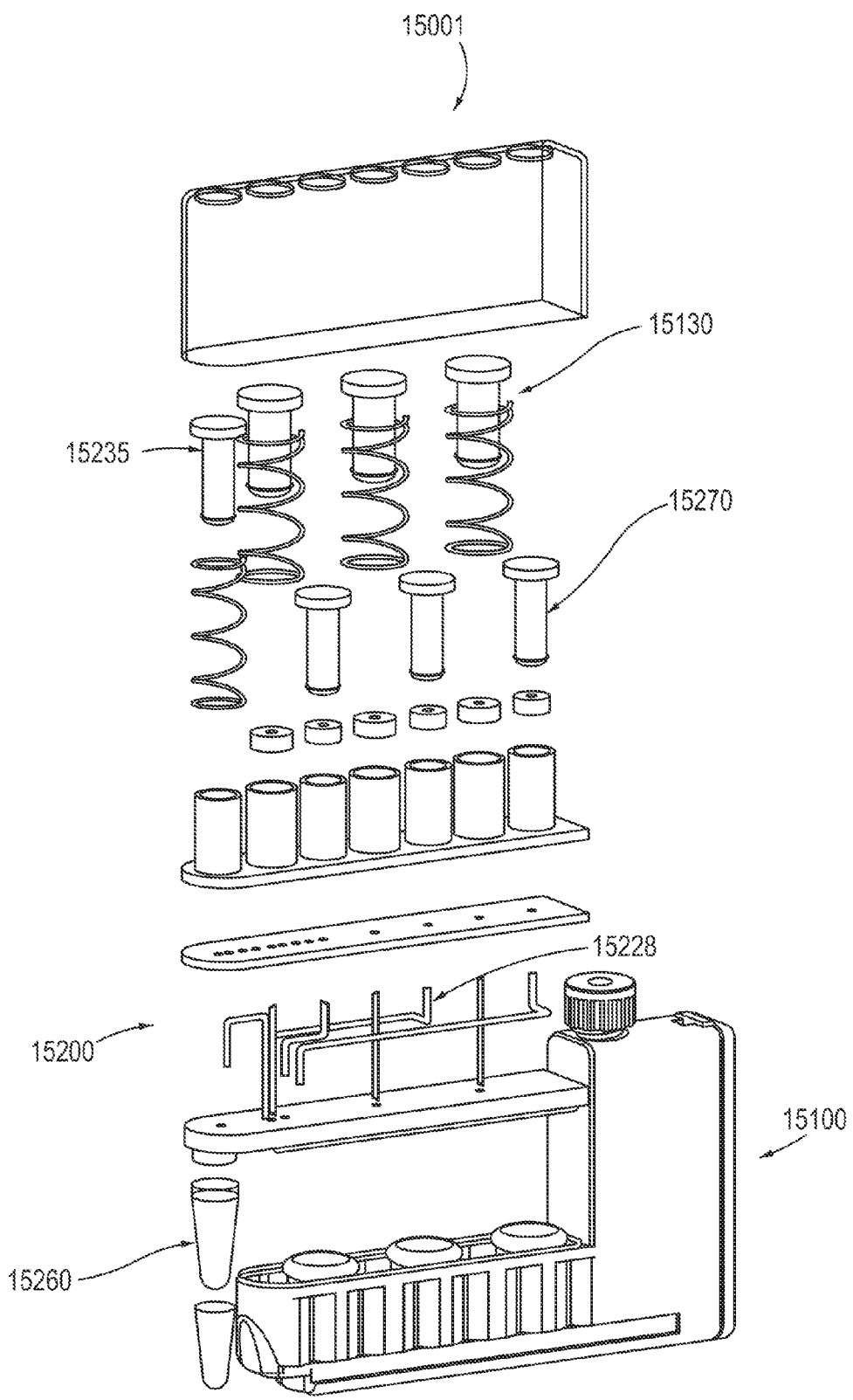
FIG. 93 is an exploded perspective view of the cartridge shown in FIG. 92.

FIGS. 92 and 93 show another embodiment in which the reagent modules 15270 of the PCR module 15200 are disposed adjacent to and/or between the washing mechanisms 15130 of the isolation module 15100. The cartridge 15001 differs from the cartridge 14001 in that the substances contained within the reagent modules 15270 are transferred into the PCR vial 15260 via a series of internal flow paths 15228. The PCR module includes a transfer mechanism 15235 to transfer a portion of the isolated sample from the elution chamber 15190 into the PCR vial 15260.

Figure 94:
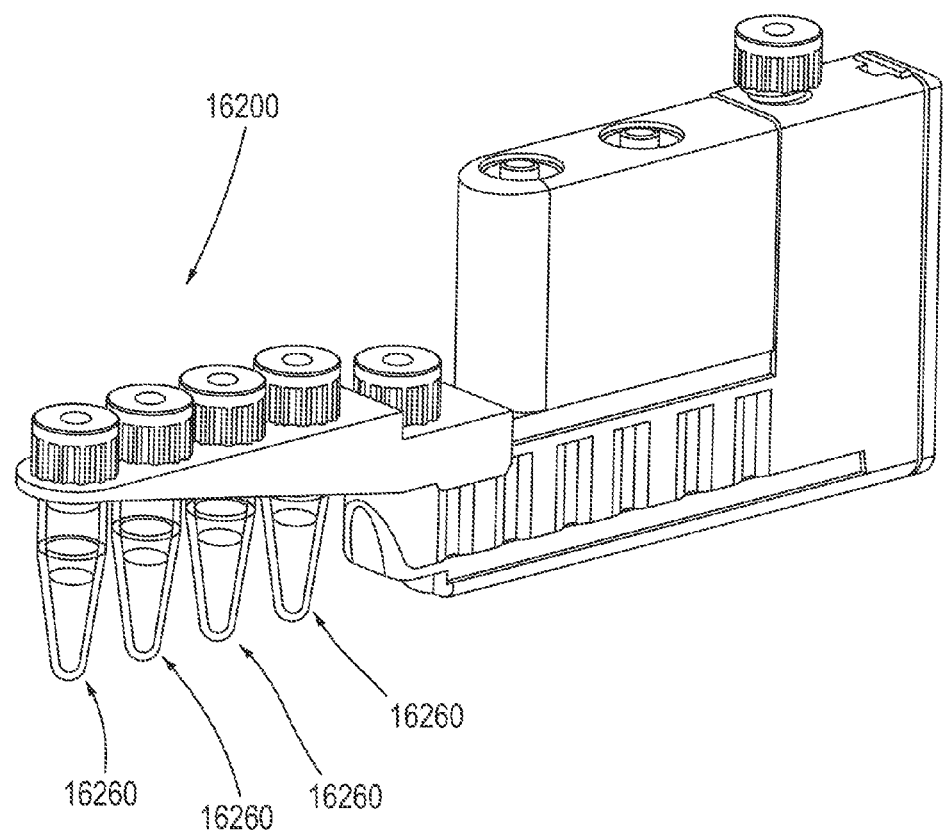
FIG. 94 is a perspective view of a cartridge having multiple PCR vials according to an embodiment.

Although the PCR modules shown and described herein include a single PCR vial, in other embodiments, a PCR module can include any number of PCR vials. One example, is shown in FIG. 94, which shows a PCR module 16200 having four PCR vials 16260.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

While the embodiments have been particularly shown and described, it will be understood that various changes in form and details may be made.

Although many of the chambers described herein, such as for example, the chamber 6163a, the wash buffer module 7130a and the reagent module 7270a, are described as containing a substance, sample and/or reagent, that is maintained in fluid isolation by a puncturable member (e.g., the puncturable member 6170, the puncturable member 7135a, and the puncturable member 7275), in some embodiments, any of the chambers herein can be only partially filled with the desired substance, sample and/or reagent. More particularly, any of the chambers described herein can include a first volume of the desired substance (which is generally in a liquid state) and a second volume of a gas, such as air, oxygen, nitrogen or the like. This arrangement reduces the force for moving a transfer mechanism or piercing member (e.g., the piercing portion 6168 of the actuator 6166) within the chamber prior to rupturing the puncturable member. More particularly, by including a portion of the volume of the chamber as a gas, when the transfer mechanism moves within the chamber the gas is compressed to reduce the volume of the chamber, thereby allowing the piercing member to contact the puncturable member. In some embodiments, any of the chambers described herein can include approximately ten percent of the volume therein as a gas.

Although the isolation module 6100 is shown and described above as including a transfer assembly 6140a configured to transfer substances between the lysing chamber 6114 and the wash chamber 6121 while maintaining the lysing chamber 6114 substantially fluidically isolated from the wash chamber 6121, in other embodiments, any of the modules described herein can include a transfer mechanism that transfers substances between chambers while allowing fluid communication between those chambers. For example, in some embodiments, a module can include a transfer mechanism configured to selectively control the flow of a substance between a first chamber and second chamber. Such a transfer mechanism can include, for example, a valve.

Although the cartridges are shown and described herein as including multiple modules (e.g., an isolation module and a reaction module) that are coupled together before being disposed within an instrument that manipulates the cartridge, in other embodiments, a cartridge can include multiple modules, at least one of which is configured to be couple to another of the modules within and/or by an instrument. Similarly, in some embodiments an instrument can be configured to couple one module (e.g., a reagent module) to another module (e.g., a reaction module, an isolation module or the like) as a part of the processing of the cartridge.

Although the transfer mechanisms, such as the transfer assembly 6140, are shown and described herein as using magnetic force to facilitate movement of a target portion of the sample within a cartridge, in other embodiments, any of the transfer mechanisms shown and described herein can employ any suitable type of force to facilitate movement of a target portion of the sample within a cartridge. For example, in some embodiments, a transfer mechanism can include a pump. In other embodiments, a transfer mechanism can produce peristaltic movement of the target portion of the sample.

Although the cartridges and/or portions thereof have been described primarily for use with nucleic acid isolation and amplification reactions, and for use with particular instruments described herein, the cartridge is not limited thereto. Although the instruments and/or portions thereof have been described primarily for use with nucleic acid isolation and amplification reactions, and for use with particular cartridges described herein, the instrument is not limited thereto.

For example, the cartridge, instrument and/or portions thereof provided herein can be used in a next generation sequencing (NGS) platform. NGS technologies have been reported to generate three to four orders of magnitude more sequence than the Sanger method, and are also less expensive to carry out (Harismendy et al. (2009). Genome Biology 10, pp. R32.1-R32.13). NGS applications include, but are not limited to, genomic shotgun sequencing, bacterial artificial chromosome (BAC) end sequencing, single nucleotide polymorphism discovery and resequencing, other mutation discovery, chromatin immunoprecipitation (ChIP), micro RNA discovery, large-scale expressed sequence tag sequencing, primer walking, or serial analysis of gene expression (SAGE).

In one embodiment, a module is used to fit a cartridge of the present invention into an NGS platform instrument, for nucleic acid sequence analysis. Alternatively, a sample transfer module (e.g., an automated liquid handling instrument) can transfer the nucleic acid amplification product to a flow cell of an NGS instrument.

In one embodiment, a module is provided so that a cartridge of the present invention is amenable for use with one of the following NGS platforms: Roche 454 GS-FLX platform, Illumina Sequencing Platforms (e.g., HiSeq 2000, HiSeq 1000, MiSeq, Genome Analyzer IIx), Illumina Solexa IG Genome Analyzer, Applied Biosystems 3730xl platform, ABI SOLiD™ (e.g., 5500xl or 5500 SOLiD™ System). The module can fit into one of the aforementioned devices, or can be a sample transfer module, which moves the product of the nucleic acid amplification reaction to the NGS instrument.

In one embodiment, the cartridge of the present invention is used for genomic shotgun sequencing, bacterial artificial chromosome (BAC) end sequencing, single nucleotide polymorphism discovery and resequencing, other mutation discovery, chromatin immunoprecipitation (ChIP), micro RNA discovery, large-scale expressed sequence tag sequencing, primer walking, or serial analysis of gene expression (SAGE).

In one embodiment, nucleic acid isolation and/or amplification (e.g., PCR), is carried out in a cartridge and instrument of the invention, as described herein. In a further embodiment, upon completion of the amplification reaction, a sample transfer module transfers the amplification product to the flow cell of the respective NGS instrument, for library preparation, and subsequent sequencing.

In another embodiment, nucleic acid isolation and/or amplification (e.g., PCR), is carried out in a cartridge and/or instrument of the invention, as described herein. In a further embodiment, upon completion of the amplification reaction, the cartridge is transferred to a module amenable for use with one of the NGS instruments provided above. The nucleic acid amplification product is then transferred to the flow cell of the respective NGS instrument, for library preparation, and subsequent sequencing.

In some embodiments, an apparatus includes a first module, a second module and a third module. The first module defines a first chamber and a second chamber, at least the first chamber configured to contain a sample. The second module defines a first volume configured to contain a first substance. A portion of the second module is configured to be disposed within the first chamber of the first module when the second module is coupled to the first module such that the first volume is configured to be selectively placed in fluid communication with the first chamber. The third module defines a reaction chamber and a second volume configured to contain a second substance. A portion of the third module is disposed within the second chamber of the first module when the third module is coupled to the first module such that the reaction chamber and the second volume are each in fluid communication with the second chamber of the first module.

In some embodiments, any of the modules described herein can include an acoustic coupling member configured to convey acoustic energy into a chamber defined by the module.

In some embodiments, any of the modules described herein can include a transfer mechanism configured to transfer a sample between a first chamber within the module and a second chamber within the module. Such transfer mechanisms can use any suitable mechanism for transferring substances, including flow of a solution, a magnetic force or the like.

In some embodiments, any of the modules described herein can include a valve configured to transfer a sample between a first chamber within the module and a second chamber within the module. In some embodiments, such a valve can be configured to maintain fluid isolation between the first chamber and the second chamber.

In some embodiments, an apparatus includes a first module, a second module and a third module. The first module defines a first chamber and a second chamber. The first module including a first transfer mechanism configured to transfer a sample between the first chamber and the second chamber while maintaining fluid isolation between the first chamber and the second chamber. The second module defines a volume configured to contain a substance. A portion of the second module is configured to be disposed within the first chamber of the first module when the second module is coupled to the first module such that the volume is configured to be selectively placed in fluid communication with the first chamber. The third module defines a reaction chamber, the third module configured to be coupled to the first module such that the reaction chamber is in fluid communication with the second chamber. The third module includes a second transfer mechanism configured to transfer a portion of the sample between the second chamber and the reaction chamber.

In some embodiments, an apparatus includes a first module and a second module. The first module includes a reaction vial, a substrate and a first transfer mechanism. The reaction vial defines a reaction chamber. The first transfer mechanism includes a plunger movably disposed within a housing such that the housing and the plunger define a first volume, the first volume containing a first substance. The substrate defines at least a portion of a first flow path and a second flow path. The first flow path is configured to be in fluid communication with the reaction chamber. The first volume and an isolation chamber of an isolation module, the second flow path configured to be in fluid communication with the isolation chamber. A portion of the plunger is disposed within the first flow pathway such that the first volume is fluidically isolated from the reaction chamber when the plunger is in a first position within the housing. The portion of the plunger is disposed apart from the first flow pathway such that the first volume is in fluid communication with the reaction chamber when the plunger is in a second position within the housing. The plunger is configured to produce a vacuum within the reaction chamber to transfer a sample from the isolation chamber to the reaction chamber when the plunger is moved from the first position to the second position. The second module includes a second transfer mechanism and defines a second volume configured to contain a second substance. The second module is configured to be coupled to the first module such that the second volume can be selectively placed in fluid communication with the isolation chamber via the second flow path. The second transfer mechanism is configured to transfer the second substance from the second volume to the isolation chamber when the second transfer mechanism is actuated.

In some embodiments, an instrument includes a bloc, a first optical member, a second optical member and an optics assembly. The block defines a reaction volume configured to receive at least a portion of a reaction container. The first optical member is disposed at least partially within the block such that the first optical member defines a first light path and is in optical communication with the reaction volume. The second optical member is disposed at least partially within the block such that the second optical member defines a second light path and is in optical communication with the reaction volume. A first plane including the first light path and a second plane including the second light path defining an angle of greater than about 75 degrees. The optics assembly is coupled to the first optical member and the second optical member such that an excitation light beam can be conveyed into the reaction volume and an emission light beam can be received from the reaction volume.

Although various embodiments have been described as having particular features and/or combinations of components, other embodiments are possible having a combination of any features and/or components from any of embodiments as discussed above.

What is claimed is:

1. An apparatus, comprising:
  an isolation module including a first housing and a second housing, the first housing defining a first chamber and a second chamber, at least the first chamber configured to contain a sample, the second housing including a side wall and a puncturable member, the side wall and the puncturable member collectively defining a first volume configured to contain a first substance, a portion of the second housing configured to be disposed within the first housing such that the first volume is in fluid communication with the first chamber when a portion of the puncturable member is punctured; and
  a reaction module defining a reaction chamber and a second volume configured to contain a second substance, the reaction module configured to be coupled to the isolation module such that the reaction chamber and the second volume are each in fluid communication with the second chamber of the first housing,
  the reaction module including a plunger at least partially disposed within the second volume, the plunger configured exert a force on the second substance to transfer the second substance from the second volume into at least one of the reaction chamber or the second chamber when the plunger is moved within the second volume.

2. The apparatus of claim 1, wherein the reaction module is configured to be removably coupled to the isolation module.

3. The apparatus of claim 1, wherein a portion of the reaction module is disposed within the second chamber of the first housing when the reaction module is coupled to the isolation module.

4. The apparatus of claim 1, wherein:
  the reaction module includes a substrate that at least partially defines a first flow path and a second flow path, the first flow path configured to be in fluid communication with the reaction chamber and the second chamber of the first housing, the second flow path configured to be in fluid communication with the second volume and the second chamber of the first housing.

5. The apparatus of claim 1, wherein the isolation module includes a transfer mechanism configured to transfer the sample between the first chamber and the second chamber.

6. The apparatus of claim 1, wherein the isolation module includes a valve at least partially disposed within the first housing, the valve configured to transfer the sample between the first chamber and the second chamber while maintaining fluid isolation between the first chamber and the second chamber.

7. The apparatus of claim 1, wherein the isolation module includes a plunger at least partially disposed within the first volume of the second housing, the plunger of the isolation module configured to puncture the portion of the puncturable member when moved within the first volume.

8. The apparatus of claim 1, wherein the isolation module includes an acoustic coupling member configured to convey ultrasonic energy into the first chamber.

9. The apparatus of claim 1, wherein the first volume contains a first substance comprising a lysis buffer, nucleic acid isolation reagent or a combination thereof.

10. The apparatus of claim 1, wherein the second volume comprises second substance comprising reagents to carry out a PCR.

11. The apparatus of claim 10, wherein the second substance further comprises a reverse transcriptase enzyme.

12. The apparatus of claim 1, wherein the reaction chamber comprises a lyophilized PCR master mix.

13. The apparatus of claim 12, wherein the reaction chamber further comprises a reverse transcriptase enzyme.

14. An apparatus, comprising:
  a first module defining a first chamber and a second chamber, the first module including a first transfer mechanism configured to transfer a sample between the first chamber and the second chamber while maintaining fluid isolation between the first chamber and the second chamber;
  a second module defining a first volume configured to contain a first substance, a portion of the second module configured to be disposed within the first chamber of the first module when the second module is coupled to the first module such that the first volume is configured to be selectively placed in fluid communication with the first chamber; and
  a third module defining a reaction chamber and a second volume, the second volume configured to contain a second substance, the third module configured to be coupled to the first module such that the reaction chamber is in fluid communication with the second chamber and such that the second volume is in fluid communication with the reaction chamber, the third module including a second transfer mechanism and a third transfer mechanism, the second transfer mechanism configured to transfer a portion of the sample between the second chamber and the reaction chamber, the third transfer mechanism configured to transfer a portion of the second substance between the second volume and the reaction chamber.

15. The apparatus of claim 14, wherein a portion of the third module is disposed within the second chamber of the first module when the third module is coupled to the first module.

16. The apparatus of claim 14, wherein the second module includes a puncturable member that defines, at least in part, the first volume, the puncturable member further defining a portion of a boundary of the first chamber of the first module when the second module is coupled to the first module.

17. The apparatus of claim 14, wherein the second module includes a fourth transfer mechanism at least partially disposed within the first volume, the fourth transfer mechanism configured to transfer the first substance from the first volume into the first chamber when the fourth transfer mechanism is actuated.

18. The apparatus of claim 14, wherein:
the first module defines a third chamber between the first chamber and the second chamber; and
the first transfer mechanism includes a valve housing and a valve member, the valve housing defining a first opening in fluid communication with the first chamber and a second opening in fluid communication with the third chamber, the valve member defining a cavity in fluid communication with the first opening when the valve member is in a first position, the cavity in fluid communication with the second opening when the valve member is in a second position.

19. The apparatus of claim 14, wherein the second transfer mechanism includes a plunger disposed within a cylinder in fluid communication with the reaction chamber, the plunger configured to produce a vacuum within the reaction chamber when the plunger is moved within the cylinder.

20. An apparatus, comprising:
a first module including a reaction vial, a substrate and a first transfer mechanism, the reaction vial defining a reaction chamber, the substrate defining at least a portion of a first flow path and a second flow path, the first flow path configured to be in fluid communication with the reaction chamber and an isolation chamber of an isolation module, the first transfer mechanism configured to transfer a sample from the isolation chamber to the reaction chamber when the first transfer mechanism is actuated, the first transfer mechanism including a plunger movably disposed within a housing such that the housing and the plunger define a first volume, the first volume containing a first substance, a portion of the plunger disposed within the first flow path such that the first volume is fluidically isolated from the reaction chamber when the plunger is in a first position within the housing, the portion of the plunger disposed apart from the first flow path such that the first volume is in fluid communication with the reaction chamber when the plunger is in a second position within the housing, the plunger configured to produce a vacuum within the reaction chamber when the plunger is moved from the first position to the second position; and
a second module including a second transfer mechanism and defining a second volume configured to contain a second substance, the second module configured to be coupled to the first module such that the second volume can be selectively placed in fluid communication with the reaction chamber via the second flow path, the second transfer mechanism configured to transfer the second substance from the second volume to the reaction chamber when the second transfer mechanism is actuated.

21. The apparatus of claim 20, wherein:
a portion of the first module is disposed within the isolation chamber of the isolation module when the first module is coupled to the isolation module.

22. The apparatus of claim 20, wherein the plunger is configured to produce the vacuum in the reaction chamber to produce a flow of the sample from the isolation chamber to the reaction chamber.

23. The apparatus of claim 20, wherein the second module includes a puncturable member that defines, at least in part, the second volume, the second volume being placed in fluid communication with the reaction chamber when a portion of the puncturable member is punctured.

24. The apparatus of claim 20, wherein the second transfer mechanism includes a plunger disposed within the second volume of the second module, the plunger of the second transfer mechanism configured to exert a force on the second substance to transfer the second substance from the volume into the reaction chamber when the plunger of the second transfer mechanism is moved within the volume.

* * * * *

UNITED STATES PATENT AND TRADEMARK OFFICE
CERTIFICATE OF CORRECTION

PATENT NO. : 8,372,340 B2  
APPLICATION NO. : 13/033129  
DATED : February 12, 2013  
INVENTOR(S) : Dylan Hilmer Bird et al.

Page 1 of 1

It is certified that error appears in the above-identified patent and that said Letters Patent is hereby corrected as shown below:

In Claim 1, column 83, line 47, delete "configured exert" and insert --configured to exert-- therefor.

Signed and Sealed this
Twenty-sixth Day of March, 2013

Teresa Stanek Rea
*Acting Director of the United States Patent and Trademark Office*